US012661401B2

(12) United States Patent
Siurala et al.

(10) Patent No.: US 12,661,401 B2
(45) Date of Patent: Jun. 23, 2026

(54) SELECTIVE STIMULATION OF T CELLS IN SOLID TUMORS USING ONCOLYTIC VIRAL DELIVERY OF ORTHOGONAL IL-2

(71) Applicants: THE TRUSTEES OF THE UNIVERSITY OF PENNSYLVANIA, Philadelphia, PA (US); THE REGENTS OF THE UNIVERSITY OF CALIFORNIA, Oakland, CA (US)

(72) Inventors: Mikko Siurala, Philadelphia, PA (US); Carl H. June, Merion Station, PA (US); Avery Posey, Philadelphia, PA (US); Antoni Ribas, Los Angeles, CA (US); Anusha Kalbasi, Beverly Hills, CA (US)

(73) Assignees: The Trustees of the University of Pennsylvania, Philadelphia, PA (US); The Regents of the University of California, Oakland, CA (US)

( * ) Notice: Subject to any disclaimer, the term of this patent is extended or adjusted under 35 U.S.C. 154(b) by 488 days.

(21) Appl. No.: 18/549,503

(22) PCT Filed: Mar. 9, 2022

(86) PCT No.: PCT/US2022/019479
§ 371 (c)(1),
(2) Date: Sep. 7, 2023

(87) PCT Pub. No.: WO2022/192346
PCT Pub. Date: Sep. 15, 2022

(65) Prior Publication Data
US 2024/0299541 A1    Sep. 12, 2024

Related U.S. Application Data

(60) Provisional application No. 63/158,671, filed on Mar. 9, 2021.

(51) Int. Cl.
*A61K 40/42* (2025.01)
*A61K 35/761* (2015.01)
(Continued)

(52) U.S. Cl.
CPC ........ *A61K 40/4255* (2025.01); *A61K 35/761* (2013.01); *A61K 40/11* (2025.01);
(Continued)

(58) Field of Classification Search
None
See application file for complete search history.

(56) References Cited

U.S. PATENT DOCUMENTS 10,869,887 B2 * 12/2020 Garcia ............... A61K 38/1793
11,439,664 B2 * 9/2022 Garcia ............... A61K 38/1793
(Continued)

FOREIGN PATENT DOCUMENTS

WO      2017044464      3/2017
WO      2019152660      8/2019
(Continued)

OTHER PUBLICATIONS

Burbridge, S., et al., "Development of adoptive-T-cell therapy for prostate cancer incorporating a novel chimeric cytokine receptor", Molecular Cancer Therapeutics, Dec. 1, 2009 (Dec. 1, 2009), pp. C242-C242.

(Continued)

*Primary Examiner* — Misook Yu
(74) *Attorney, Agent, or Firm* — Saul Ewing LLP; Kathryn Doyle; Valerie O'Shea Murray

(57) ABSTRACT

The present disclosure provides orthogonal chimeric cytokine receptor/orthogonal cytokine pairs and compositions and methods for modified immune cells or precursors thereof (e.g., modified T cells) comprising an orthogonal chimeric cytokine receptor (e.g., an oIL2R-IL9R chimeric
(Continued)

receptor) and a chimeric antigen receptor (CAR) or a T cell receptor (TCR). The present disclosure further provides an oncolytic adenoviral vector comprising a nucleic acid sequence encoding an orthogonal cytokine (e.g., oIL2), as well as methods of using the modified cells and the vector for treating cancer in a subject in need thereof.

20 Claims, 68 Drawing Sheets

Specification includes a Sequence Listing.

(51) Int. Cl.

| | |
|---|---|
| *A61K 40/11* | (2025.01) |
| *A61K 40/30* | (2025.01) |
| *A61K 40/31* | (2025.01) |
| *A61K 40/32* | (2025.01) |
| *A61K 48/00* | (2006.01) |
| *A61P 35/00* | (2006.01) |
| *C07K 14/55* | (2006.01) |
| *C07K 14/715* | (2006.01) |
| *C12N 5/0783* | (2010.01) |
| *C12N 15/86* | (2006.01) |

(52) U.S. Cl.
CPC .............. *A61K 40/30* (2025.01); *A61K 40/31* (2025.01); *A61K 40/32* (2025.01); *A61K 40/4217* (2025.01); *A61K 40/4269* (2025.01); *A61K 40/4276* (2025.01); *A61K 48/0075* (2013.01); *A61P 35/00* (2018.01); *C07K 14/55* (2013.01); *C07K 14/7155* (2013.01); *C12N 5/0636* (2013.01); *C12N 15/86* (2013.01); *A61K 2239/31* (2023.05); *A61K 2239/38* (2023.05); *A61K 2239/57* (2023.05); *C07K 2319/03* (2013.01); *C07K 2319/75* (2013.01); *C12N 2510/00* (2013.01); *C12N 2710/10032* (2013.01); *C12N 2710/10043* (2013.01)

(56) References Cited

U.S. PATENT DOCUMENTS

| | | | | |
|---|---|---|---|---|
| 12,005,079 | B2 * | 6/2024 | Garcia | ............... A61K 38/1793 |
| 2018/0228842 | A1 | 8/2018 | Garcia | |
| 2023/0374454 | A1 * | 11/2023 | Penaflor Aspuria ... | C12N 15/86 |

FOREIGN PATENT DOCUMENTS

| | | |
|---|---|---|
| WO | 2019173773 | 9/2019 |
| WO | 2020163634 | 8/2020 |
| WO | 2021050752 | 3/2021 |
| WO | 2021207274 | 10/2021 |

OTHER PUBLICATIONS

Extended European Search Report issued Feb. 17, 2025 in European Patent Application No. 22767860.4.

Weimin, S., et al., "Chimeric cytokine 1-15 receptor enhancing PSMA-CAR-T cell-mediated prostate cancer regression", Cancer Biology & Therapy, Jun. 2, 2020 (Jun. 2, 2020), pp. 570-580.

Andtbacka, Robert H.I., et al. "Talimogene laherparepvec improves durable response rate in patients with advanced melanoma." Journal of clinical oncology 33.25 (2015):2780-2788, 13 pages.

Bauer, Johannes H., et al. "Heteromerization of the γc chain with the interleukin-9 receptor α subunit leads to STAT activation and prevention of apoptosis." Journal of Biological Chemistry 273.15 (1998): 9255-9260.

Chen, Joyce, et al. "NR4A transcription factors limit CAR T cell function in solid tumours." Nature 567.7749 (2019): 530-534.

Cosmi, Lorenzo, et al. "Th2 cells are less susceptible than Th1 cells to the suppressive activity of CD25+ regulatory thymocytes because of their responsiveness to different cytokines." Blood 103.8 (2004): 3117-3121.

de Heusch, Magali, et al. "IL-9 exerts biological function on antigen-experienced murine T cells and exacerbates colitis induced by adoptive transfer." European journal of immunology 50.7 (2020): 1034-1043.

Demoulin, et al., "A single tyrosine of the interleukin-9 (IL-9) receptor is required for STAT activation, antiapoptotic activity, and growth regulation by IL-9" Mol Cell Biol., 1996, 16:4710-4716.

Demoulin, Jean-Baptiste, et al. "Distinct roles for STAT1, STAT3, and STAT5 in differentiation gene induction and apoptosis inhibition by interleukin-9." Journal of Biological Chemistry 274.36 (1999): 25855-25861.

Druez, Catherine, et al. "Functional and biochemical characterization of mouse P40/IL-9 receptors." Journal of immunology (Baltimore, Md.: 1950) 145.8 (1990): 2494-2499.

Dwyer, Connor J., et al. "Fueling cancer immunotherapy with common gamma chain cytokines." Frontiers in immunology 10 (2019): 263. 18 pages.

Elyaman, Wassim, et al. "IL-9 induces differentiation of TH17 cells and enhances function of FoxP3+ natural regulatory T cells." Proceedings of the National Academy of Sciences 106.31 (2009): 12885-12890.

Evans, Robert K., et al. "Development of stable liquid formulations for adenovirus-based vaccines." Journal of pharmaceutical sciences 93.10 (2004): 2458-2475.

Gattinoni, Luca, Christopher A. Klebanoff, and Nicholas P. Restifo. "Paths to stemness: building the ultimate antitumour T cell." Nature Reviews Cancer 12.10 (2012): 671-684.

Gattinoni, Luca, et al. "Acquisition of full effector function in vitro paradoxically impairs the in vivo antitumor efficacy of adoptively transferred CD8+ T cells." The Journal of clinical investigation 115.6 (2005): 1616-1626.

Hinrichs, Christian S., et al. "Adoptively transferred effector cells derived from naive rather than central memory CD8+ T cells mediate superior antitumor immunity." Proceedings of the National Academy of Sciences 106.41 (2009): 17469-17474.

Houssiau, F. A., et al. "Human T cell lines and clones respond to IL-9." Journal of immunology (Baltimore, Md.: 1950) 150.7 (1993): 2634-2640.

International Search Report and Written Opinion for International Application No. PCT/US22/19479, dated Jul. 27, 2022, 14 pages.

Kalbasi, Anusha, et al. "Abstract NG11: Orthogonal IL-9 receptor signaling reprograms T cells to obviate conditioning chemotherapy before adoptive cell therapy." Cancer Research 81.13_Supplement (2021): NG11-NG11.

Kalbasi, Anusha, et al. "Uncoupling interferon signaling and antigen presentation to overcome immunotherapy resistance due to JAK1 loss in melanoma." Science translational medicine 12.565 (2020): eabb0152.

Khan, Omar, et al. "TOX transcriptionally and epigenetically programs CD8+ T cell exhaustion." Nature 571.7764 (2019): 211-218.

Kim, Kenneth H., et al. "A phase I clinical trial of Ad5/3-Δ24, a novel serotype-chimeric, infectivity-enhanced, conditionally-replicative adenovirus (CRAd), in patients with recurrent ovarian cancer." Gynecologic oncology 130.3 (2013): 518-524.

Klebanoff, Christopher A., et al. "Central memory self/tumor-reactive CD8+ T cells confer superior antitumor immunity compared with effector memory T cells." Proceedings of the national academy of sciences 102.27 (2005): 9571-9576.

Knoops, Laurent, and Jean-Christophe Renauld. "IL-9 and its receptor: from signal transduction to tumorigenesis." Growth factors 22.4 (2004): 207-215.

Krishna, Sri, et al. "Stem-like CD8 T cells mediate response of adoptive cell immunotherapy against human cancer." Science 370. 6522 (2020): 1328-1334.

Lehrnbecher, Thomas, et al. "Interleukin 7 as interleukin 9 drives phythohemagglutinin-activated T cells through several cell cycles; no synergism between interleukin 7, interleukin 9 and interleukin 4." Cytokine 6.3 (1994): 279-284.

(56) References Cited

OTHER PUBLICATIONS

Leonard, Warren J., Jian-Xin Lin, and John J. O'Shea. "The γc family of cytokines: basic biology to therapeutic ramifications." Immunity 50.4 (2019): 832-850.

Li, Hongmei, et al. "IL-9 is important for T-cell activation and differentiation in autoimmune inflammation of the central nervous system." European journal of immunology 41.8 (2011): 2197-2206.

Lichty, Brian D., et al. "Going viral with cancer immunotherapy." Nature Reviews Cancer 14.8 (2014): 559-567.

Liu, Lintao, et al. "Enhanced CAR-T activity against established tumors by polarizing human T cells to secrete interleukin-9." Nature communications 11.1 (2020): 5902.

Louahed, Jamila, et al. "IL-9 induces expression of granzymes and high-affinity IgE receptor in murine T helper clones." Journal of immunology (Baltimore, Md.: 1950) 154.10 (1995): 5061-5070.

Lu, Yong, et al. "Th9 cells promote antitumor immune responses in vivo." The Journal of clinical investigation 122.11 (2012): 4160-4171.

Lu, Yong, et al. "Tumor-specific IL-9-producing CD8+ Tc9 cells are superior effector than type-I cytotoxic Tc1 cells for adoptive immunotherapy of cancers." Proceedings of the National Academy of Sciences 111.6 (2014): 2265-2270.

Lynn, Rachel C., et al. "c-Jun overexpression in CAR T cells induces exhaustion resistance." Nature 576.7786 (2019): 293-300.

Nishio, Nobuhiro, et al. "Armed oncolytic virus enhances immune functions of chimeric antigen receptor-modified T cells in solid tumors." Cancer research 74.18 (2014): 5195-5205.

Nowak, Elizabeth C., et al. "IL-9 as a mediator of Th17-driven inflammatory disease." The Journal of experimental medicine 206.8 (2009): 1653-1660.

Overwijk, Willem W., et al. "Tumor regression and autoimmunity after reversal of a functionally tolerant state of self-reactive CD8+ T cells." The Journal of experimental medicine 198.4 (2003): 569.

Purwar, Rahul, et al. "Robust tumor immunity to melanoma mediated by interleukin-9-producing T cells." Nature medicine 18.8 (2012): 1248-1253.

Ranki, Tuuli, et al. "Phase I study with ONCOS-102 for the treatment of solid tumors—an evaluation of clinical response and exploratory analyses of immune markers." Journal for immunotherapy of cancer 4 (2016): 1-18.

Robbins, Paul F., et al. "Single and dual amino acid substitutions in TCR CDRs can enhance antigen-specific T cell functions." The Journal of Immunology 180.9 (2008): 6116-6131.

Schanz, Oliver, et al. "Tumor rejection in Cblb−/− mice depends on IL-9 and Th9 cells." Journal for Immunotherapy of Cancer 9.7 (2021).

Scott, Andrew C., et al. "TOX is a critical regulator of tumour-specific T cell differentiation." Nature 571.7764 (2019): 270-274.

Seo, Hyungseok, et al. "TOX and TOX2 transcription factors cooperate with NR4A transcription factors to impose CD8 + T cell exhaustion." Proceedings of the National Academy of Sciences 116.25 (2019): 12410-12415.

Shaw, Amanda Rosewell, et al. "Adenovirotherapy delivering cytokine and checkpoint inhibitor augments CAR T cells against metastatic head and neck cancer." Molecular Therapy 25.11 (2017): 2440-2451.

Siurala et al., "Adenoviral Delivery of Tumor Necrosis Factor-a and Interleukin-2 Enables Successful Adoptive Cell Therapy of Immunosuppressive Melanoma", Molecular Therapy, vol. 24, No. 8, Aug. 2016, 1435-1443.

Sockolosky, Jonathan T., et al. "Selective targeting of engineered T cells using orthogonal IL-2 cytokine-receptor complexes." Science 359.6379 (2018): 1037-1042.

Surh, Charles D., and Jonathan Sprent. "Homeostasis of naive and memory T cells." Immunity 29.6 (2008): 848-862.

Takatsuka, Shogo, et al. "IL-9 receptor signaling in memory B cells regulates humoral recall responses." Nature immunology 19.9 (2018): 1025-1034.

Tanoue, Kiyonori, et al. "Armed oncolytic adenovirus-expressing PD-L1 mini-body enhances antitumor effects of chimeric antigen receptor T cells in solid tumors." Cancer research 77.8 (2017): 2040-2051.

Townsend, Michael J., et al. "IL-9-deficient mice establish fundamental roles for IL-9 in pulmonary mastocytosis and goblet cell hyperplasia but not T cell development." Immunity 13.4 (2000): 573-583.

Turner, Jan-Eric, et al. "IL-9-mediated survival of type 2 innate lymphoid cells promotes damage control in helminth-induced lung inflammation." The Journal of experimental medicine 210.13 (2013): 2951-2965.

Watanabe, Keisuke, et al. "Pancreatic cancer therapy with combined mesothelin-redirected chimeric antigen receptor T cells and cytokine-armed oncolytic adenoviruses." JCI insight 3.7 (2018).

Williams, Douglas E., et al. "T-cell growth factor P40 promotes the proliferation of myeloid cell lines and enhances erythroid burst formation by normal murine bone marrow cells in vitro." Blood 76.5 (1990): 906-911.

* cited by examiner

FIG. 5B

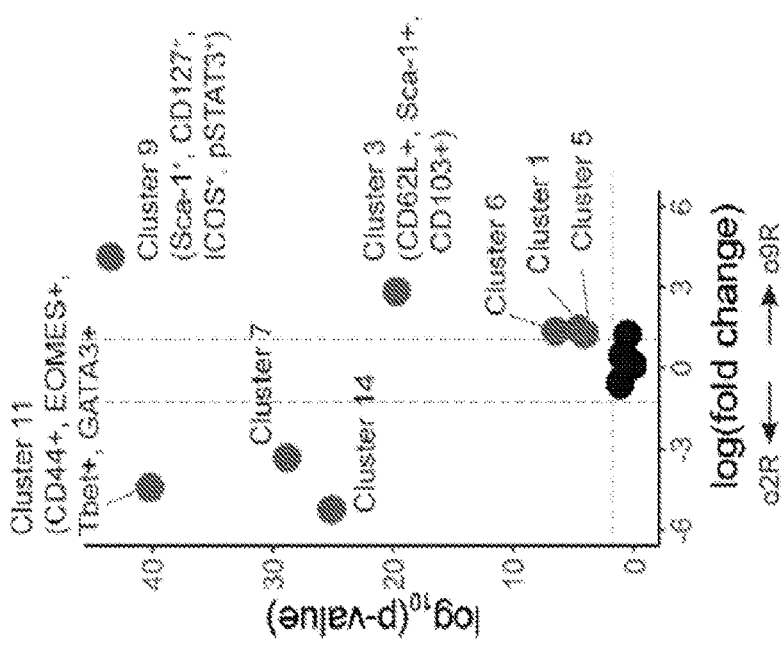
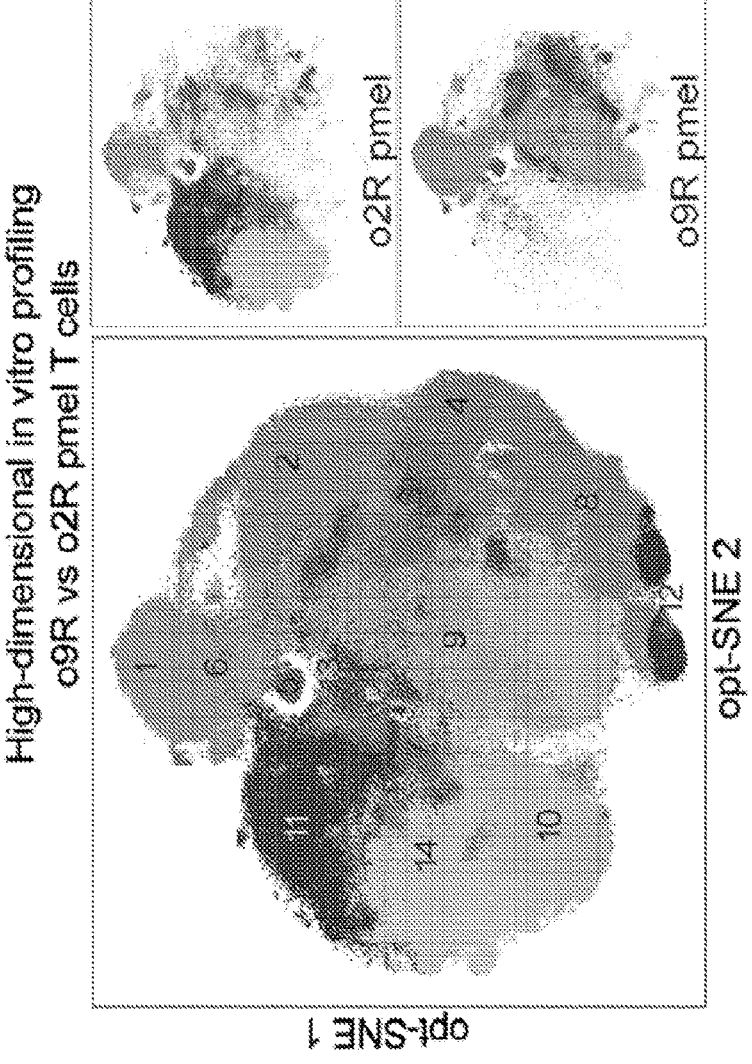
FIG. 7G

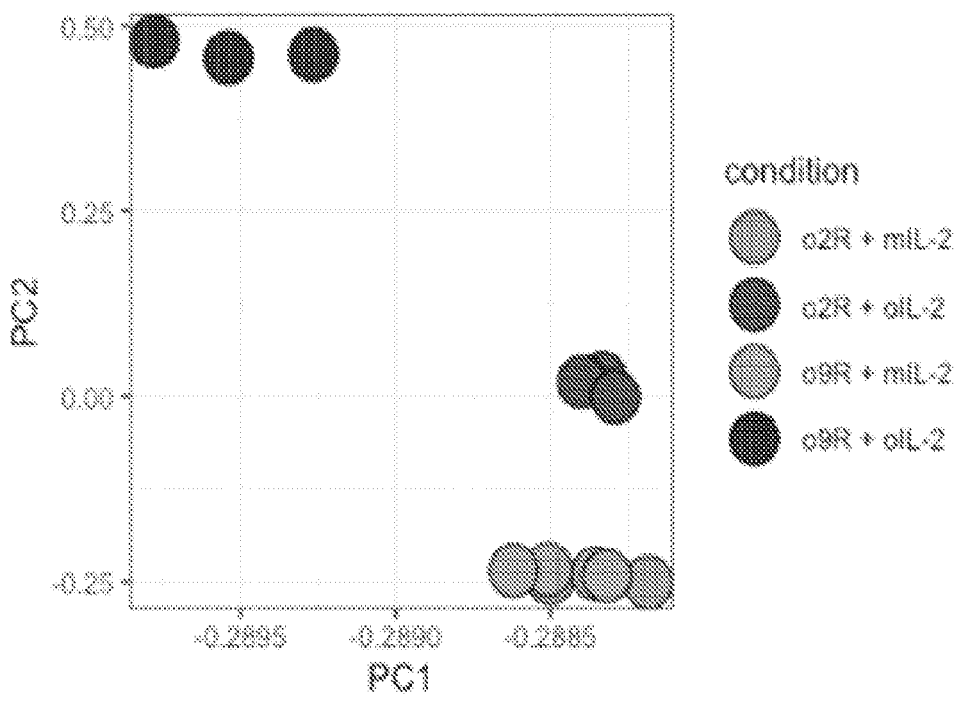
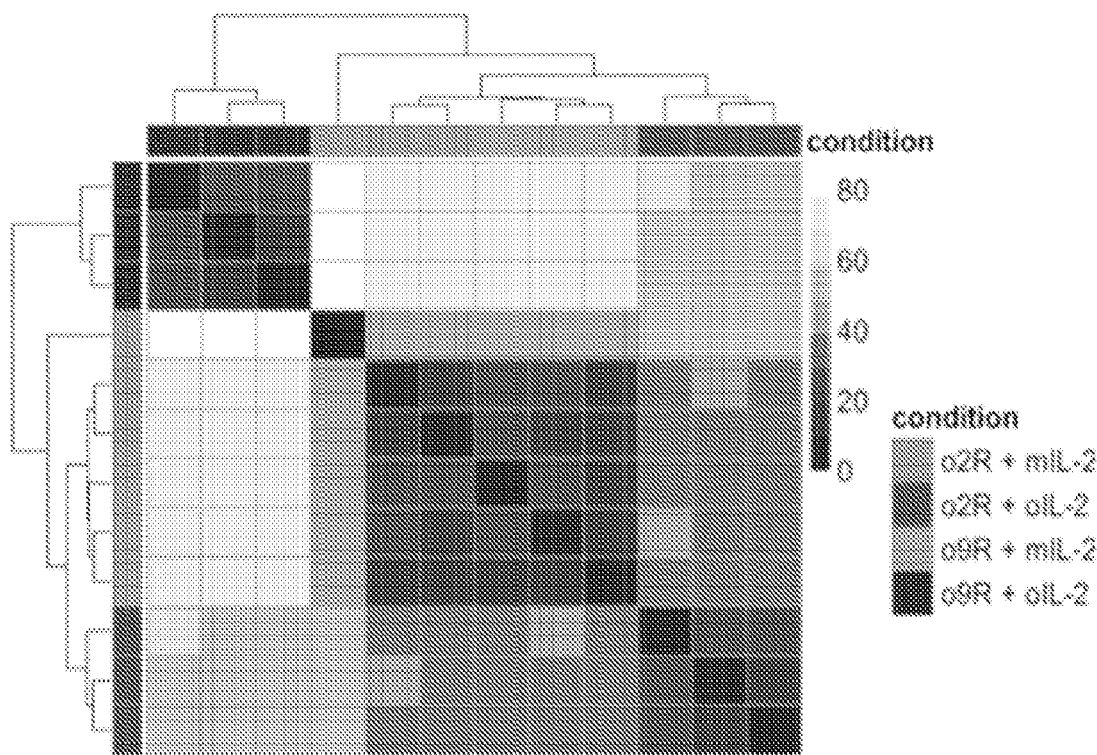
FIG. 11

FIG. 13F ho2R/NYESO1-TCR
ho9R/NYESO1-TCR

| Type | Reagent | Company | Catalog # |
|---|---|---|---|
| Antibody | Anti-mouse CD45 (89Y), clone 30-F11 | Biolegend | 103129 |
| Antibody | Anti-mouse CD11c (209Bi), clone N418 | Biolegend | 117302 |
| Antibody | Anti-mouse CD69 (143Nd), clone H1.2F23 | Biolegend | 104502 |
| Antibody | Anti-mouse F4/80 (146Nd), clone BM8 | DVS | 31460008B |
| Antibody | Anti-mouse CD11b (148Nd), clone M1/70 | Biolegend | 101214 |
| Antibody | Anti-mouse CD19 (149Nd), clone 6D5 | Biolegend | 115514 |
| Antibody | Anti-mouse Ly6C (150Nd or 162Dy), clone HK1.4 | Biolegend | 128002 |
| Antibody | Anti-mouse Ly6G (151Eu), clone 1A8 | Biolegend | 127602 |
| Antibody | Anti-mouse CD3e (152Sm), clone 145-2C11 | Biolegend | 100314 |
| Antibody | Anti-mouse CD28, clone 37.41 | BioXCell | BE0015-1 |
| Antibody | Anti-mouse CD274 (153Eu), clone 10F.9G2 | DVS | 31530018B |
| Antibody | Anti-mouse CD25 (150Nd or 155Gd or 151Eu), clone | Biolegend | 101906 |
| Antibody | Anti-mouse CD279 (159Tb), clone 29F.1A12 | Biolegend | 135202 |
| Antibody | Anti-mouse CD335 (167Er), clone 29A1.4 | DVS | 31670088B |
| Antibody | Anti-mouse CD8a (168Er), clone 53-6.7 | Biolegend | 100716 |
| Antibody | Anti-mouse CD161 (170Er), clone D13.14.4E | Biolegend | 108712 |
| Antibody | Anti-mouse CD44 (171Yb), clone IM7 | Biolegend | 103014 |
| Antibody | Anti-mouse CD40, clone HM40-3, LEAF Purified | Biolegend | HM40-3 |
| Antibody | Anti-mouse CD4 (112Cd), clone RM4-5 | Biolegend | 100561 |
| Antibody | Anti-mouse MHC II (IA/IE) (174Yb), clone M5/114.15 | Biolegend | 107610 |
| Antibody | Anti-mouse CD103 (175Lu or 155Gd), clone 2E7 | Biolegend | 121402 |
| Antibody | Anti-mouse CD45R/B220 (144Nd), clone RA3-6B2 | DVS | 31760028 |
| Antibody | Anti-mouse CD27 (139La), clone LG.3A10 | Biolegend | 124202 |
| Antibody | Anti-mouse CD39 (142**), clone 24DMS1 | DVS | 3142005B |
| Antibody | Anti-mouse CD69 (143Nd), clone H1.2F3 | DVS | 3143004B |
| Antibody | Anti-mouse CD62L (160Gd), clone MEL-14 | DVS | 31600088B |
| Antibody | Anti-mouse CD197 (164Dy), clone 4B12 | DVS | 3164013A |
| Antibody | Anti-mouse Ly-6A/E (169Tm), clone D7 | DVS | 31690015B |
| Antibody | Anti-mouse CD127 (175Lu), clone A7R34 | Biolegend | 135029 |
| Antibody | Anti-mouse CD278 (176Lu), clone 7E.17G9 | DVS | 3176014B |
| Antibody | Anti-mouse Ki67 (115In), clone SolA15 | eBioscience | 14-5698-82 |
| Antibody | Anti-mouse TNFa (141Pr), clone MP6-XT22 | DVS | 3141013B |
| Antibody | Anti-mouse EOMES (147Sm), clone Dan11mag | ThermoFisher | 14-4875-82 |
| Antibody | Anti-mouse pSTAT5 (150Nd), clone 47 | DVS | 3150005A |
| Antibody | Anti-mouse pSTAT1 (153Eu), clone 58D6 | DVS | 3153003A |
| Antibody | Anti-mouse pSTAT3 (158Gd), clone 4/p-STAT3 | DVS | 3158005A |
| Antibody | Anti-mouse Tbet (161Dy), clone 4B10 | DVS | 3161014B |
| Antibody | Anti-mouse BCL-6 (163Dy), clone K112-91 | DVS | 3163012B |
| Antibody | Anti-mouse IFNg (165Ho), clone XMG1.2 | DVS | 3165003B |
| Antibody | Anti-mouse GATA3 (167Er), clone TWAJ1 | DVS | 3167007A |
| Antibody | Anti-mouse CD73 (154Sm), clone CD73 | DVS | 3154019B |
| Antibody | Anti-mouse Thy1.1 (162Dy), clone OX-7 | Biolegend | 202501 |
| Antibody | Anti-mouse Foxp3 (158Gd), clone FJK-16s | DVS | 3158003A |
| Antibody | Anti-mouse CD45 (BV510), clone 30F11 | BD Biosciences | 563891 |
| Antibody | Anti-mouse CD8 (BV421), clone 53-6.7 | Biolegend | 100738 |
| Antibody | Anti-mouse CD62L (PE-Cy7), clone MEL-14 | ThermoFisher/eBioscie | 25-0621-82 |
| Antibody | Anti-mouse CD44 (APC-Cy7), clone IM7 | BD Biosciences | 560568 |

FIG. 20

| Antibody | Anti-mouse CD44 (FITC), clone IM7 | Biolegend | 103005 |
|---|---|---|---|
| Antibody | Anti-mouse CD95 (BV605), clone SA367H8 | Biolegend | 152612 |
| Antibody | Anti-mouse Thy1.1/CD90.1 (AF700), clone OX-7 | Biolegend | 202528 |
| Antibody | Anti-mouse CD45.1 (PE), clone REA11 | Miltenyi | 130-121- |
| Viability | LIVE/DEAD™ Fixable Aqua Dead Cell Stain | ThermoFisher | L34957 |
| Antibody | Anti-mouse IL9R (CD129) APC, clone S18011E | Biolegend | 158705 |
| Antibody | Anti-mouse IL2Rb (PE) (clone 5H4) | Biolegend | 105906 |
| Antibody | biotinylated F(ab)₂ –fragment specific IgG | Jackson | 109-066- |
| Other | Streptavidin BV785 | Biolegend | 405249 |
| Other | CountBright™ Absolute Counting Beads | ThermoFisher | C36950 |
| Viability | 7-AAD | Beckman Coulter | A07704 |
| Antibody | Anti-mouse GAPDH (clone 14C10 or D16H11) | Cell Signaling | 5174S |
| Antibody | Anti-pSTAT1 Tyr701, clone 58D6 | Cell Signaling | 9167S |
| Antibody | Anti-pSTAT1 Tyr701 (PE) clone 58D6 | Cell Signaling | 8062S |
| Antibody | Anti-pSTAT3 Tyr705, clone EP2147Y | Abcam | ab76315 |
| Antibody | Anti-pSTAT3 pY705 (AF647), clone 4/P-STAT3 | BD Biosciences | 612599 |
| Antibody | Anti-pSTAT5 Tyr694, clone C11C5 | Cell Signaling | 9359S |
| Antibody | Anti-pSTAT5 Tyr694, (AF647) clone 47/STAT5 | BD Biosciences | 612599 |
| Cytometr | Mouse IFNg Flex Set | BD Biosciences | 558296 |
| Antibody | IRDye® 800CW Goat anti-Rabbit IgG (H + L) | LI-COR Biosciences | 926-32211 |
| Antibody | IRDye® 680RD Goat anti-Rabbit IgG Secondary | LI-COR Biosciences | 926-68071 |
| Antibody | Anti-rabbit IgG, HRP-linked Antibody | Cell Signaling | 7074S |
| Antibody | Anti-mouse CD3, Rabbit polyclonal – Opal 480 | DAKO | A0452 |
| Antibody | Anti-mouse CD4, Rabbit clone EPR19514 – Opal 520 | Abcam | AB183685 |
| Antibody | Anti-mouse CD8, Rat clone 4SM15 – Opal 570 | Ebioscience | 14-0808 |
| Antibody | Anti-mouse PD-1, Rabbit – Opal 690 | Abcam | Ab21442 |
| Antibody | Anti-human Vβ13.1 (PE) | Beckman Coulter | IM2292 |
| Antibody | Anti-human CD45RA (APC or BV421), clone HI100 | Biolegend | 304112 |
| Antibody | Anti-human CD27 (PE-CF594 or APC), clone M-T271 | Biolegend | 562297 |
| Antibody | Anti-human CD95 (PE-Cy7), clone DX2 | Biolegend | 305622 |
| Antibody | Anti-human CCR7 (BV711), clone G043H7 | Biolegend | 353229 |
| Antibody | Anti-human CD62L (BV650), clone DREG-56 | Biolegend | 304832 |
| Antibody | Anti-human CXCR3 (PE-CF594), clone 1C6 | BD Biosciences | 560831 |
| Antibody | Anti-human CD4 (BV510), clone OKT4 | Biolegend | 317444 |
| Antibody | Anti-human CD8 (BV605), clone RPA-T8 | Biolegend | 301040 |
| Antibody | Anti-human IFNγ (PE) clone 4S.B3 | BD Biosciences | 559326 |
| Antibody | Anti-human TNFα (PerCP-Cy5.5), clone MAb11 | Biolegend | 502926 |
| Antibody | Anti-human IL-2 (BV711), clone MQI-17H12 | Biolegend | 500346 |
| Other | TransIT Transfection Reagent | Mirus | MIR2705 |
| Other | Brefeldin A | Biolegend | 420601 |
| Other | Monensin | Biolegend | 420701 |

FIG. 20 (continued)

MSLN KO tumor cell line – confirmation by flow and cell killing after sorting

PDA7940b MSLN-

MSLN KO tumor cell line – confirmation by flow and cell killing after sorting

Sec Ab ctrl

PDA7940b<sup>MSLN+</sup>
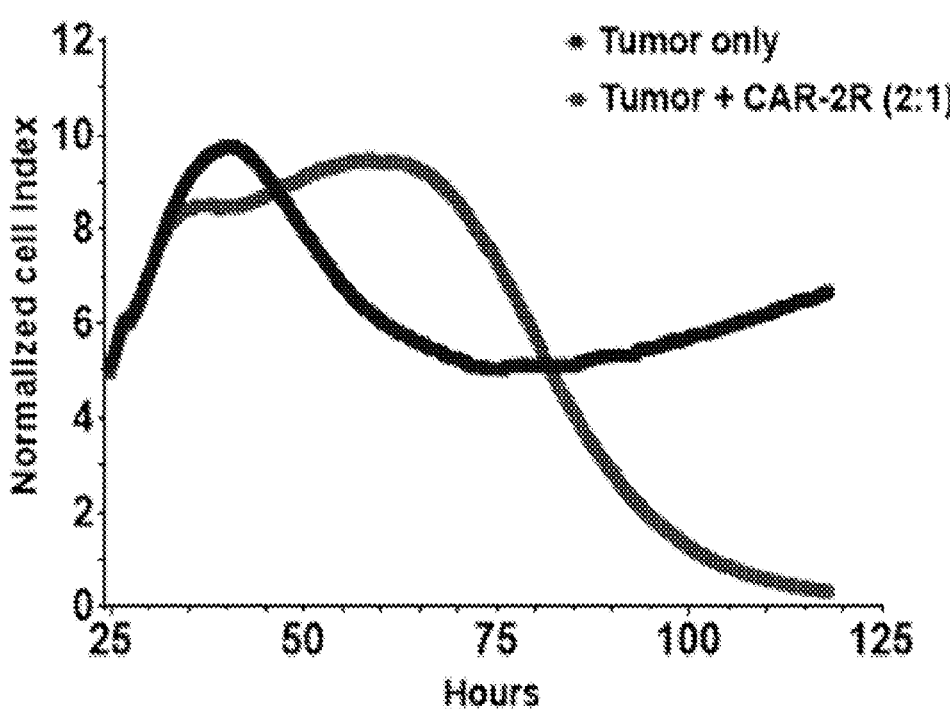
PDA7940b<sup>MSLN-</sup>
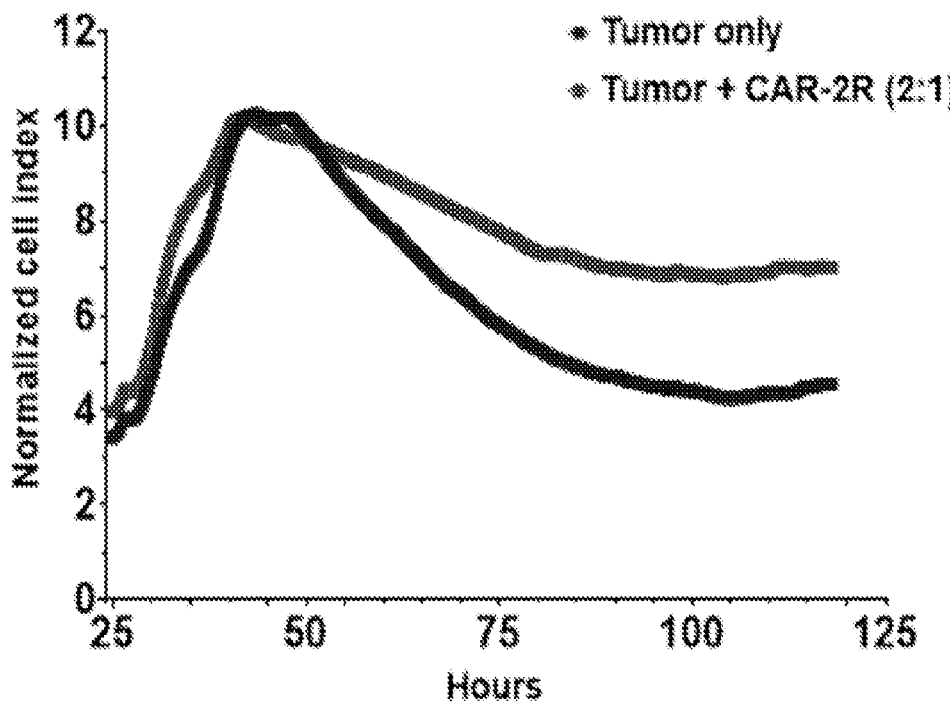
FIG. 21 (Continued)

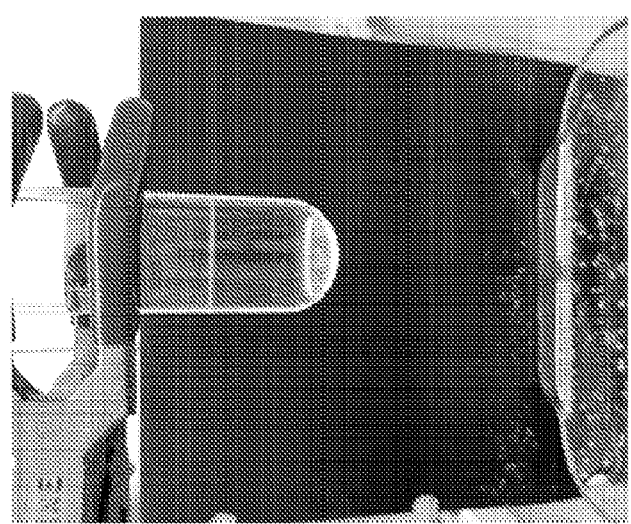
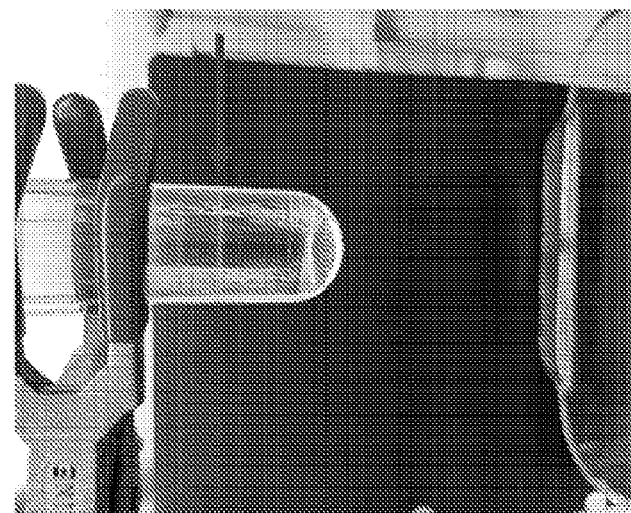
FIG. 23B
FIG. 23A

SEQUENCE LISTING

```
<160> NUMBER OF SEQ ID NOS: 21

<210> SEQ ID NO 1
<211> LENGTH: 462
<212> TYPE: DNA
<213> ORGANISM: Artificial Sequence
<220> FEATURE:
<223> OTHER INFORMATION: Human ortho-IL2 cDNA

<400> SEQUENCE: 1
atgtacagga tgcagctgct gtcttgcatc gccctgagcc tggccctggt gaccaactcc      60
gcccccacaa gctcctctac caagaagaca cagctgcagc tgtctcagct gctggtgctg     120
ctgaaggcca tcctgaacgg catcaacaat tacaagaatc ccaagctgac ccgcatgctg     180
acattcaagt tttatatgcc taagaaggcc accgagctga agcacctgca gtgtctggag     240
gaggagctga agccactgga ggaggtgctg aacctggccc agtccaagaa tttccacctg     300
cggcccagag acctgatctc taacatcaat gtgatcgtgc tggagctgaa gggcagcgag     360
accaccttca tgtgcgagta tgccgatgag accgccacaa tcgtggagtt cctgaatcgg     420
tggatcacat tttgtcagag catcatctcc accctgacat ga                       462

<210> SEQ ID NO 2
<211> LENGTH: 153
<212> TYPE: PRT
<213> ORGANISM: Artificial Sequence
<220> FEATURE:
<223> OTHER INFORMATION: Human ortho-IL2

<400> SEQUENCE: 2

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Ser Gln Leu Leu Val Leu Leu Lys Ala Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125
```

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 3
<211> LENGTH: 1656
<212> TYPE: DNA
<213> ORGANISM: Artificial Sequence
<220> FEATURE:
<223> OTHER INFORMATION: Human orthoIL2Rb cDNA
<400> SEQUENCE: 3

```
atggcggccc ctgctctgtc ctggcgtctg cccctcctca tcctcctcct gcccctggct      60
acctcttggg catctgcagc ggtgaatggc acttcccagt tcacatgctt ctacaactcg     120
agagccaaca tctcctgtgt ctggagccaa gatggggctc tgcaggacac ttcctgccaa     180
gtccatgcct ggccggacag acggcggtgg aaccaaacct gtgagctgct ccccgtgagt     240
caagcatcct gggcctgcaa cctgatcctc ggagccccag attctcagaa actgaccaca     300
gttgacatcg tcaccctgag ggtgctgtgc cgtgaggggg tgcgatggag ggtgatggcc     360
atccaggact tcaagccctt tgagaacctt cgcctgatgg cccccatctc cctccaagtt     420
gtccacgtgg agacccacag atgcaacata agctgggaaa tctcccaagc tccgacttc      480 tttgaaagac acctggagtt cgaggcccgg acgctgtccc aggccacac ctgggaggag      540 gccccctgc tgactctcaa gcagaagcag gaatggatct gcctggagac gctcaccca      600 gacacccagt atgagtttca ggtgcgggtc aagcctctgc aaggcgagtt cacgacctgg     660 agccctgga gccagcccct ggccttcagg acaaagcctg cagcccttgg gaaggacacc      720
attccgtggc tcggccacct cctcgtgggt ctcagcgggg cttttggctt catcatctta     780
gtgtacttgc tgatcaactg caggaacacc gggccatggc tgaagaaggt cctgaagtgt     840 aacacccccag acccctcgaa gttctttttcc cagctgagct cagagcatgg aggagacgtc    900
cagaagtggc tctcttcgcc cttcccctca tcgtccttca gccctggcgg cctggcacct     960
gagatctcgc cactagaagt gctggagagg acaaggtga cgcagctgct cctgcagcag    1020
gacaaggtgc ctgagcccgc atccttaagc agcaaccact cgctgaccag ctgcttcacc    1080
aaccagggtt acttcttctt ccacctcccg gatgccttgg agatagaggc ctgccaggtg    1140
tactttactt acgaccccta ctcagaggaa gaccctgatg agggtgtggc cggggcaccc    1200
acagggtctt cccccaacc cctgcagcct ctgtcagggg aggacgacgc ctactgcacc    1260
ttcccctcca gggatgacct gctgctcttc tcccccagtc tcctcggtgg cccagcccc    1320 ccaagcactg cccctggggg cagtggggcc ggtgaagaga ggatgccccc ttctttgcaa    1380
gaaagagtcc ccagagactg ggaccccag ccctggggc ctcccacccc aggagtccca    1440
gacctggtgg attttcagcc accccctgag ctggtgctgc gagaggctgg ggaggaggtc    1500
cctgacgctg gccccaggga gggagtcagt ttcccctggt ccaggcctcc tgggcagggg    1560
gagttcaggg cccttaatgc tcgcctgccc ctgaacactg atgcctactt gtccctccaa    1620
gaactccagg tcaggaccc aactcacttg gtgtga                               1656
```

<210> SEQ ID NO 4
<211> LENGTH: 551
<212> TYPE: PRT
<213> ORGANISM: Artificial Sequence
<220> FEATURE:

<223> OTHER INFORMATION: Human orthoIL2Rb

<400> SEQUENCE: 4

```
Met Ala Ala Pro Ala Leu Ser Trp Arg Leu Pro Leu Leu Ile Leu Leu
1               5                   10                  15

Leu Pro Leu Ala Thr Ser Trp Ala Ser Ala Ala Val Asn Gly Thr Ser
            20                  25                  30

Gln Phe Thr Cys Phe Tyr Asn Ser Arg Ala Asn Ile Ser Cys Val Trp
        35                  40                  45

Ser Gln Asp Gly Ala Leu Gln Asp Thr Ser Cys Gln Val His Ala Trp
    50                  55                  60

Pro Asp Arg Arg Arg Trp Asn Gln Thr Cys Glu Leu Leu Pro Val Ser
65                  70                  75                  80

Gln Ala Ser Trp Ala Cys Asn Leu Ile Leu Gly Ala Pro Asp Ser Gln
                85                  90                  95

Lys Leu Thr Thr Val Asp Ile Val Thr Leu Arg Val Leu Cys Arg Glu
            100                 105                 110

Gly Val Arg Trp Arg Val Met Ala Ile Gln Asp Phe Lys Pro Phe Glu
            115                 120                 125

Asn Leu Arg Leu Met Ala Pro Ile Ser Leu Gln Val Val His Val Glu
    130                 135                 140

Thr His Arg Cys Asn Ile Ser Trp Glu Ile Ser Gln Ala Ser Asp Phe
145                 150                 155                 160

Phe Glu Arg His Leu Glu Phe Glu Ala Arg Thr Leu Ser Pro Gly His
                165                 170                 175

Thr Trp Glu Glu Ala Pro Leu Leu Thr Leu Lys Gln Lys Gln Glu Trp
            180                 185                 190

Ile Cys Leu Glu Thr Leu Thr Pro Asp Thr Gln Tyr Glu Phe Gln Val
            195                 200                 205

Arg Val Lys Pro Leu Gln Gly Glu Phe Thr Thr Trp Ser Pro Trp Ser
    210                 215                 220

Gln Pro Leu Ala Phe Arg Thr Lys Pro Ala Ala Leu Gly Lys Asp Thr
225                 230                 235                 240

Ile Pro Trp Leu Gly His Leu Leu Val Gly Leu Ser Gly Ala Phe Gly
                245                 250                 255

Phe Ile Ile Leu Val Tyr Leu Leu Ile Asn Cys Arg Asn Thr Gly Pro
            260                 265                 270

Trp Leu Lys Lys Val Leu Lys Cys Asn Thr Pro Asp Pro Ser Lys Phe
            275                 280                 285

Phe Ser Gln Leu Ser Ser Glu His Gly Gly Asp Val Gln Lys Trp Leu
    290                 295                 300

Ser Ser Pro Phe Pro Ser Ser Ser Phe Ser Pro Gly Gly Leu Ala Pro
305                 310                 315                 320

Glu Ile Ser Pro Leu Glu Val Leu Glu Arg Asp Lys Val Thr Gln Leu
            325                 330                 335

Leu Leu Gln Gln Asp Lys Val Pro Glu Pro Ala Ser Leu Ser Ser Asn
            340                 345                 350

His Ser Leu Thr Ser Cys Phe Thr Asn Gln Gly Tyr Phe Phe Phe His
    355                 360                 365

Leu Pro Asp Ala Leu Glu Ile Glu Ala Cys Gln Val Tyr Phe Thr Tyr
    370                 375                 380

Asp Pro Tyr Ser Glu Glu Asp Pro Asp Glu Gly Val Ala Gly Ala Pro
385                 390                 395                 400
```

-continued

```
Thr Gly Ser Ser Pro Gln Pro Leu Gln Pro Leu Ser Gly Glu Asp Asp
            405             410             415

Ala Tyr Cys Thr Phe Pro Ser Arg Asp Asp Leu Leu Leu Phe Ser Pro
            420             425             430

Ser Leu Leu Gly Gly Pro Ser Pro Pro Ser Thr Ala Pro Gly Gly Ser
            435             440             445

Gly Ala Gly Glu Glu Arg Met Pro Pro Ser Leu Gln Glu Arg Val Pro
        450             455             460

Arg Asp Trp Asp Pro Gln Pro Leu Gly Pro Pro Thr Pro Gly Val Pro
465             470             475             480

Asp Leu Val Asp Phe Gln Pro Pro Glu Leu Val Leu Arg Glu Ala
            485             490             495

Gly Glu Glu Val Pro Asp Ala Gly Pro Arg Glu Gly Val Ser Phe Pro
            500             505             510

Trp Ser Arg Pro Pro Gly Gln Gly Glu Phe Arg Ala Leu Asn Ala Arg
            515             520             525

Leu Pro Leu Asn Thr Asp Ala Tyr Leu Ser Leu Gln Glu Leu Gln Gly
        530             535             540

Gln Asp Pro Thr His Leu Val
545             550
```

```
<210> SEQ ID NO 5
<211> LENGTH: 1497
<212> TYPE: DNA
<213> ORGANISM: Artificial Sequence
<220> FEATURE:
<223> OTHER INFORMATION: Human orthoIL2Rb/IL9Ra cDNA

<400> SEQUENCE: 5
atggccgccc ccgccctgtc ttggagactg cccctcctga tcctgctgct gcctctggct        60
acaagctggg cttctgccgc tgtgaacggc accagccaat ttacctgctt ctacaactcc       120
cgggccaaca tctcttgcgt gtggtcccaa gacggcgccc tgcaagatac cagctgtcag       180
gtgcacgcct ggcctgatag acggagatgg aaccagacct gcgagctgct tccagtgtct       240
caggccagct gggcctgtaa tttgatcctg ggcgctcccg cacagccaga actgaccacc       300
gtggacatcg tgaccctgag ggtgctttgt agagagggcg ttagatggcg ggtgatggcc       360
atccaggatt tcaaaccctt cgaaaacctg agactcatgg ccccaatcag cctgcaggtg       420
gtgcatgtgg aaacacacag atgcaacatc agctgggaga tcagccaggc cagcgacttc       480
ttcgagcggc acctggaatt tgaggccaga accctgtccc aggccacac atgggaagag        540 gcccccctgc tgacactgaa gcagaagcag gagtggatct gcctggagac actgacccct       600
gatacacagt acgagtttca ggtcagagtt aagcccctgc agggagaatt caccacctgg       660
tctccttgga gccagcctct ggccttcaga accaagcctg cccagagaca gggtcctctg       720
attcctcctt ggggctggcc cggcaatacc ctggtggccg tgtctatctt tctgctcctg       780
acaggcccca cctacctgct gttcaagctg tcccctagtg tgaagcggat cttctaccag       840
aacgtgccta gcccggccat gttcttccaa cctctgtaca gcgtgcacaa cggcaacttc       900
caaacctgga tggcgcccca cggcgccggc gtgctgctga ccaggactg cgccggcacc        960 cctcagggcg cactggaacc ttgtgtgcag gaggccacag ccctgctgac atgcggccct      1020
gcccgccctt ggaagagcgt ggccctggaa aagagcagg agggccccgg caccagactg       1080 cctgaaatc tgagctctga ggacgtgctg cctgctggct gtaccgagtg gcgggtgcag       1140
acactggctt atctgcccca ggaggactgg gccctacat ctctgactag acctgcccct      1200
```

```
ccagactctg aaggctctag gtctagcagc agcagcagca gcagcaacaa caacaattac   1260
tgcgccctgg gctgctacgg cggatggcac ctgagcgccc tgcctggcaa cacccagagc   1320
agcggcccca tccctgccct ggcttgcggc ctgtcatgcg accaccaggg actggaaacc   1380
cagcagggcg tggcttgggt cctggccggg cactgccagc ggcctggact gcacgaggat   1440
ctgcaaggaa tgctgctgcc cagcgtgctg agcaaggcca gaagctggac cttctaa      1497
```

<210> SEQ ID NO 6
<211> LENGTH: 498
<212> TYPE: PRT
<213> ORGANISM: Artificial Sequence
<220> FEATURE:
<223> OTHER INFORMATION: Human orthoIL2Rb/IL9Ra

<400> SEQUENCE: 6

```
Met Ala Ala Pro Ala Leu Ser Trp Arg Leu Pro Leu Leu Ile Leu Leu
1               5                   10                  15

Leu Pro Leu Ala Thr Ser Trp Ala Ser Ala Ala Val Asn Gly Thr Ser
            20                  25                  30

Gln Phe Thr Cys Phe Tyr Asn Ser Arg Ala Asn Ile Ser Cys Val Trp
        35                  40                  45

Ser Gln Asp Gly Ala Leu Gln Asp Thr Ser Cys Gln Val His Ala Trp
    50                  55                  60

Pro Asp Arg Arg Arg Trp Asn Gln Thr Cys Glu Leu Leu Pro Val Ser
65                  70                  75                  80

Gln Ala Ser Trp Ala Cys Asn Leu Ile Leu Gly Ala Pro Asp Ser Gln
                85                  90                  95

Lys Leu Thr Thr Val Asp Ile Val Thr Leu Arg Val Leu Cys Arg Glu
            100                 105                 110

Gly Val Arg Trp Arg Val Met Ala Ile Gln Asp Phe Lys Pro Phe Glu
            115                 120                 125

Asn Leu Arg Leu Met Ala Pro Ile Ser Leu Gln Val Val His Val Glu
        130                 135                 140

Thr His Arg Cys Asn Ile Ser Trp Glu Ile Ser Gln Ala Ser Asp Phe
145                 150                 155                 160

Phe Glu Arg His Leu Glu Phe Glu Ala Arg Thr Leu Ser Pro Gly His
                165                 170                 175

Thr Trp Glu Glu Ala Pro Leu Leu Thr Leu Lys Gln Lys Gln Glu Trp
            180                 185                 190

Ile Cys Leu Glu Thr Leu Thr Pro Asp Thr Gln Tyr Glu Phe Gln Val
            195                 200                 205

Arg Val Lys Pro Leu Gln Gly Glu Phe Thr Thr Trp Ser Pro Trp Ser
        210                 215                 220

Gln Pro Leu Ala Phe Arg Thr Lys Pro Ala Gln Arg Gln Gly Pro Leu
225                 230                 235                 240

Ile Pro Pro Trp Gly Trp Pro Gly Asn Thr Leu Val Ala Val Ser Ile
                245                 250                 255

Phe Leu Leu Leu Thr Gly Pro Thr Tyr Leu Leu Phe Lys Leu Ser Pro
            260                 265                 270

Arg Val Lys Arg Ile Phe Tyr Gln Asn Val Pro Ser Pro Ala Met Phe
        275                 280                 285

Phe Gln Pro Leu Tyr Ser Val His Asn Gly Asn Phe Gln Thr Trp Met
    290                 295                 300

Gly Ala His Gly Ala Gly Val Leu Leu Ser Gln Asp Cys Ala Gly Thr
```

-continued

```
305                310                315                320

Pro Gln Gly Ala Leu Glu Pro Cys Val Gln Glu Ala Thr Ala Leu Leu
                325                330                335

Thr Cys Gly Pro Ala Arg Pro Trp Lys Ser Val Ala Leu Glu Glu Glu
            340                345                350

Gln Glu Gly Pro Gly Thr Arg Leu Pro Gly Asn Leu Ser Ser Glu Asp
        355                360                365

Val Leu Pro Ala Gly Cys Thr Glu Trp Arg Val Gln Thr Leu Ala Tyr
    370                375                380

Leu Pro Gln Glu Asp Trp Ala Pro Thr Ser Leu Thr Arg Pro Ala Pro
385                390                395                400

Pro Asp Ser Glu Gly Ser Arg Ser Ser Ser Ser Ser Ser Ser Ser Asn
            405                410                415

Asn Asn Asn Tyr Cys Ala Leu Gly Cys Tyr Gly Gly Trp His Leu Ser
            420                425                430

Ala Leu Pro Gly Asn Thr Gln Ser Ser Gly Pro Ile Pro Ala Leu Ala
        435                440                445

Cys Gly Leu Ser Cys Asp His Gln Gly Leu Glu Thr Gln Gln Gly Val
    450                455                460

Ala Trp Val Leu Ala Gly His Cys Gln Arg Pro Gly Leu His Glu Asp
465                470                475                480

Leu Gln Gly Met Leu Leu Pro Ser Val Leu Ser Lys Ala Arg Ser Trp
                485                490                495

Thr Phe
```

```
<210> SEQ ID NO 7
<211> LENGTH: 510
<212> TYPE: DNA
<213> ORGANISM: Artificial Sequence
<220> FEATURE:
<223> OTHER INFORMATION: Mouse ortho-IL2 (clone 3A10) cDNA

<400> SEQUENCE: 7
atgtattcaa tgcagctcgc ctcatgcgtc accctcacac tcgtcctcct cgtcaactca      60
gcccccacct cttcaccaac ttcctcacca accagctcct ctacagccga ggctcagcaa     120
caacagcagc agcagcagca cctggacaac ctgctggtgc tgctgaaggc cctgctgtct     180
aggatggaga actacagaaa cctgaagctg cccaggatgc tgaccttcaa gtttttacctg     240 cctaagcagg ctacagagct gaaggacctg cagtgcctgg aggatgagct gggaccactg     300
aggcacgtgc tggacctgac ccagagcaag tccttccagc tggaggatgc cgagaacttt     360
atctctaaca tccgcgtgac cgtggtgaag ctgaagggaa gcgataacac attcgagtgt     420
cagtttgacg atgagtccgc tacagtggtg gattttctca gacggtggat tgccttttgc     480
cagagcatca tctcaacttc ccctcagtaa                                      510
```

```
<210> SEQ ID NO 8
<211> LENGTH: 169
<212> TYPE: PRT
<213> ORGANISM: Artificial Sequence
<220> FEATURE:
<223> OTHER INFORMATION: Mouse ortho-IL2 (clone 3A10)

<400> SEQUENCE: 8

Met Tyr Ser Met Gln Leu Ala Ser Cys Val Thr Leu Thr Leu Val Leu
1               5                  10                 15

Leu Val Asn Ser Ala Pro Thr Ser Ser Pro Thr Ser Ser Pro Thr Ser
```

-continued

```
              20              25              30
Ser Ser Thr Ala Glu Ala Gln Gln Gln Gln Gln Gln Gln His Leu
        35              40              45

Asp Asn Leu Leu Val Leu Leu Lys Ala Leu Leu Ser Arg Met Glu Asn
    50              55              60

Tyr Arg Asn Leu Lys Leu Pro Arg Met Leu Thr Phe Lys Phe Tyr Leu
65              70              75              80

Pro Lys Gln Ala Thr Glu Leu Lys Asp Leu Gln Cys Leu Glu Asp Glu
            85              90              95

Leu Gly Pro Leu Arg His Val Leu Asp Leu Thr Gln Ser Lys Ser Phe
            100             105             110

Gln Leu Glu Asp Ala Glu Asn Phe Ile Ser Asn Ile Arg Val Thr Val
        115             120             125

Val Lys Leu Lys Gly Ser Asp Asn Thr Phe Glu Cys Gln Phe Asp Asp
        130             135             140

Glu Ser Ala Thr Val Val Asp Phe Leu Arg Arg Trp Ile Ala Phe Cys
145             150             155             160

Gln Ser Ile Ile Ser Thr Ser Pro Gln
                165
```

```
<210> SEQ ID NO 9
<211> LENGTH: 1620
<212> TYPE: DNA
<213> ORGANISM: Artificial Sequence
<220> FEATURE:
<223> OTHER INFORMATION: Mouse orthoIL2Rb (aka o2R) cDNA

<400> SEQUENCE: 9
atggcaacaa tcgctctccc ttggtctctc agtctctatg tctttctcct gctcctcgct      60
actccctggg catctgctgc tgtgaagaac tgctcccacc tggagtgttt ttacaactct     120
cgcgctaacg tgtcttgtat gtggagccac gaggaggccc tgaacgtgac cacatgccac     180
gtgcacgcta agtccaacct gagacactgg aacaagacct gtgagctgac actggtgcgg     240
caggctagct gggcttgcaa cctgatcctg ggatccttcc ctgagagcca gtccctgacc     300
tctgtggacc tgctggatat caacgtggtg tgctgggagg agaagggctg gaggagagtg     360
aagacatgcg actttcaccc tttcgataac ctgaggctgg tggctccaca ctccctgcag     420
gtgctgcaca tcgacaccca gaggtgtaac atctcttgga aggtgtctca ggtgagcgac     480
ttcatcgagc catacctgga gttcgaggct cggcgcaggc tgctgggaca ctcctgggag     540
gacgcctccg tgctgtctct gaagcagagg cagcagtggc tgttcctgga gatgctgatc     600
ccctctacaa gctacgaggt gcaggtgaga gtgaaggctc agcggaacaa caccggaaca     660
tggagcccct ggtcccagcc tctgaccttt agaacacggc ctgccgatcc aatgaaggag     720
atcctgccca tgagctggct gagatacctg ctgctggtgc tgggatgctt ctccggcttc     780
ttttcttgcg tgtacatcct ggtgaagtgc cggtacctgg cccttggct  gaagaccgtg     840 ctgaagtgcc acatccctga cccaagcgag ttctttttcc agctgagctc ccagcacggc     900
ggagatctgc agaagtggct gtctagcccc gtgcctctga gcttctttt  cccctctgga     960 ccagctcccg agatcagccc tctggaggtg ctggacggcg attccaaggc cgtgcagctg    1020
ctgctgctgc agaaggactc cgctcctctg ccaagcccat ccggacactc tcaggccagc    1080 tgtttttacca accagggcta cttcttttt  cacctgccta cgccctggga gatcgagtct    1140
tgtcaggtgt acttcacata cgacccatgc gtggaggagg aggtggagga ggatggatct    1200
```

```
cgcctgccag aggggcagccc ccacccacct ctgctgcctc tggccggaga gcaggacgat   1260
tactgcgctt ttccacccag ggacgatctg ctgctgttct ctcctagcct gtccaccca    1320 aacacagctt acggaggaag ccgcgctcca gaggagaggt ccctctgtc tctgcacgag    1380 ggactgccaa gcctggcttc cagggacctg atgggcctgc agcgcccact ggagaggatg    1440
ccagagggcg atggagaggg cctgtctgcc aactcctctg gcgagcaggc tagcgtgcca    1500
gagggaaacc tgcacggaca ggaccaggat aggggacagg gacccatcct gacactgaat    1560
acagatgctt acctctcact ccaggaactc caggcacagg attcagtcca cctcatttaa    1620
```

<210> SEQ ID NO 10
<211> LENGTH: 539
<212> TYPE: PRT
<213> ORGANISM: Artificial Sequence
<220> FEATURE:
<223> OTHER INFORMATION: Mouse orthoIL2Rb (aka o2R)

<400> SEQUENCE: 10

```
Met Ala Thr Ile Ala Leu Pro Trp Ser Leu Ser Leu Tyr Val Phe Leu
1               5                   10                  15

Leu Leu Leu Ala Thr Pro Trp Ala Ser Ala Ala Val Lys Asn Cys Ser
            20                  25                  30

His Leu Glu Cys Phe Tyr Asn Ser Arg Ala Asn Val Ser Cys Met Trp
        35                  40                  45

Ser His Glu Glu Ala Leu Asn Val Thr Thr Cys His Val His Ala Lys
    50                  55                  60

Ser Asn Leu Arg His Trp Asn Lys Thr Cys Glu Leu Thr Leu Val Arg
65                  70                  75                  80

Gln Ala Ser Trp Ala Cys Asn Leu Ile Leu Gly Ser Phe Pro Glu Ser
                85                  90                  95

Gln Ser Leu Thr Ser Val Asp Leu Leu Asp Ile Asn Val Val Cys Trp
            100                 105                 110

Glu Glu Lys Gly Trp Arg Arg Val Lys Thr Cys Asp Phe His Pro Phe
            115                 120                 125

Asp Asn Leu Arg Leu Val Ala Pro His Ser Leu Gln Val Leu His Ile
        130                 135                 140

Asp Thr Gln Arg Cys Asn Ile Ser Trp Lys Val Ser Gln Val Ser Asp
145                 150                 155                 160

Phe Ile Glu Pro Tyr Leu Glu Phe Glu Ala Arg Arg Arg Leu Leu Gly
                165                 170                 175

His Ser Trp Glu Asp Ala Ser Val Leu Ser Leu Lys Gln Arg Gln Gln
            180                 185                 190

Trp Leu Phe Leu Glu Met Leu Ile Pro Ser Thr Ser Tyr Glu Val Gln
            195                 200                 205

Val Arg Val Lys Ala Gln Arg Asn Asn Thr Gly Thr Trp Ser Pro Trp
        210                 215                 220

Ser Gln Pro Leu Thr Phe Arg Thr Arg Pro Ala Asp Pro Met Lys Glu
225                 230                 235                 240

Ile Leu Pro Met Ser Trp Leu Arg Tyr Leu Leu Leu Val Leu Gly Cys
                245                 250                 255

Phe Ser Gly Phe Phe Ser Cys Val Tyr Ile Leu Val Lys Cys Arg Tyr
            260                 265                 270

Leu Gly Pro Trp Leu Lys Thr Val Leu Lys Cys His Ile Pro Asp Pro
            275                 280                 285

Ser Glu Phe Phe Ser Gln Leu Ser Ser Gln His Gly Gly Asp Leu Gln
```

-continued

```
              290                   295                   300
Lys Trp Leu Ser Ser Pro Val Pro Leu Ser Phe Phe Ser Pro Ser Gly
305                   310                   315                   320

Pro Ala Pro Glu Ile Ser Pro Leu Glu Val Leu Asp Gly Asp Ser Lys
                  325                   330                   335

Ala Val Gln Leu Leu Leu Leu Gln Lys Asp Ser Ala Pro Leu Pro Ser
                  340                   345                   350

Pro Ser Gly His Ser Gln Ala Ser Cys Phe Thr Asn Gln Gly Tyr Phe
                  355                   360                   365

Phe Phe His Leu Pro Asn Ala Leu Glu Ile Glu Ser Cys Gln Val Tyr
                  370                   375                   380

Phe Thr Tyr Asp Pro Cys Val Glu Glu Glu Val Glu Glu Asp Gly Ser
385                   390                   395                   400

Arg Leu Pro Glu Gly Ser Pro His Pro Pro Leu Leu Pro Leu Ala Gly
                  405                   410                   415

Glu Gln Asp Asp Tyr Cys Ala Phe Pro Pro Arg Asp Asp Leu Leu Leu
                  420                   425                   430

Phe Ser Pro Ser Leu Ser Thr Pro Asn Thr Ala Tyr Gly Gly Ser Arg
                  435                   440                   445

Ala Pro Glu Glu Arg Ser Pro Leu Ser Leu His Glu Gly Leu Pro Ser
                  450                   455                   460

Leu Ala Ser Arg Asp Leu Met Gly Leu Gln Arg Pro Leu Glu Arg Met
465                   470                   475                   480

Pro Glu Gly Asp Gly Glu Gly Leu Ser Ala Asn Ser Ser Gly Glu Gln
                  485                   490                   495

Ala Ser Val Pro Glu Gly Asn Leu His Gly Gln Asp Gln Asp Arg Gly
                  500                   505                   510

Gln Gly Pro Ile Leu Thr Leu Asn Thr Asp Ala Tyr Leu Ser Leu Gln
                  515                   520                   525

Glu Leu Gln Ala Gln Asp Ser Val His Leu Ile
                  530                   535
```

```
<210> SEQ ID NO 11
<211> LENGTH: 240
<212> TYPE: PRT
<213> ORGANISM: Artificial Sequence
<220> FEATURE:
<223> OTHER INFORMATION: Mouse orthoIL2Rb (aka o2R) Extracellular Domain

<400> SEQUENCE: 11

Met Ala Thr Ile Ala Leu Pro Trp Ser Leu Ser Leu Tyr Val Phe Leu
1               5                   10                  15

Leu Leu Leu Ala Thr Pro Trp Ala Ser Ala Ala Val Lys Asn Cys Ser
                20                  25                  30

His Leu Glu Cys Phe Tyr Asn Ser Arg Ala Asn Val Ser Cys Met Trp
            35                  40                  45

Ser His Glu Glu Ala Leu Asn Val Thr Thr Cys His Val His Ala Lys
        50                  55                  60

Ser Asn Leu Arg His Trp Asn Lys Thr Cys Glu Leu Thr Leu Val Arg
65                  70                  75                  80

Gln Ala Ser Trp Ala Cys Asn Leu Ile Leu Gly Ser Phe Pro Glu Ser
                85                  90                  95

Gln Ser Leu Thr Ser Val Asp Leu Leu Asp Ile Asn Val Val Cys Trp
            100                 105                 110

Glu Glu Lys Gly Trp Arg Arg Val Lys Thr Cys Asp Phe His Pro Phe
```

```
              115                 120                 125

Asp Asn Leu Arg Leu Val Ala Pro His Ser Leu Gln Val Leu His Ile
    130                 135                 140

Asp Thr Gln Arg Cys Asn Ile Ser Trp Lys Val Ser Gln Val Ser Asp
145                 150                 155                 160

Phe Ile Glu Pro Tyr Leu Glu Phe Glu Ala Arg Arg Arg Leu Leu Gly
                165                 170                 175

His Ser Trp Glu Asp Ala Ser Val Leu Ser Leu Lys Gln Arg Gln Gln
            180                 185                 190

Trp Leu Phe Leu Glu Met Leu Ile Pro Ser Thr Ser Tyr Glu Val Gln
            195                 200                 205

Val Arg Val Lys Ala Gln Arg Asn Asn Thr Gly Thr Trp Ser Pro Trp
    210                 215                 220

Ser Gln Pro Leu Thr Phe Arg Thr Arg Pro Ala Asp Pro Met Lys Glu
225                 230                 235                 240

<210> SEQ ID NO 12
<211> LENGTH: 28
<212> TYPE: PRT
<213> ORGANISM: Artificial Sequence
<220> FEATURE:
<223> OTHER INFORMATION: Mouse orthoIL2Rb (aka o2R) Transmembrane region

<400> SEQUENCE: 12

Ile Leu Pro Met Ser Trp Leu Arg Tyr Leu Leu Leu Val Leu Gly Cys
1                   5                   10                  15

Phe Ser Gly Phe Phe Ser Cys Val Tyr Ile Leu Val
                20                  25

<210> SEQ ID NO 13
<211> LENGTH: 271
<212> TYPE: PRT
<213> ORGANISM: Artificial Sequence
<220> FEATURE:
<223> OTHER INFORMATION: Mouse orthoIL2Rb (aka o2R) Intracellular Domain

<400> SEQUENCE: 13

Lys Cys Arg Tyr Leu Gly Pro Trp Leu Lys Thr Val Leu Lys Cys His
1                   5                   10                  15

Ile Pro Asp Pro Ser Glu Phe Phe Ser Gln Leu Ser Ser Gln His Gly
                20                  25                  30

Gly Asp Leu Gln Lys Trp Leu Ser Ser Pro Val Pro Leu Ser Phe Phe
            35                  40                  45

Ser Pro Ser Gly Pro Ala Pro Glu Ile Ser Pro Leu Glu Val Leu Asp
    50                  55                  60

Gly Asp Ser Lys Ala Val Gln Leu Leu Leu Leu Gln Lys Asp Ser Ala
65                  70                  75                  80

Pro Leu Pro Ser Pro Ser Gly His Ser Gln Ala Ser Cys Phe Thr Asn
                85                  90                  95

Gln Gly Tyr Phe Phe Phe His Leu Pro Asn Ala Leu Glu Ile Glu Ser
                100                 105                 110

Cys Gln Val Tyr Phe Thr Tyr Asp Pro Cys Val Glu Glu Glu Val Glu
            115                 120                 125

Glu Asp Gly Ser Arg Leu Pro Glu Gly Ser Pro His Pro Pro Leu Leu
    130                 135                 140

Pro Leu Ala Gly Glu Gln Asp Asp Tyr Cys Ala Phe Pro Pro Arg Asp
145                 150                 155                 160
```

```
Asp Leu Leu Leu Phe Ser Pro Ser Leu Ser Thr Pro Asn Thr Ala Tyr
            165                 170                 175

Gly Gly Ser Arg Ala Pro Glu Glu Arg Ser Pro Leu Ser Leu His Glu
        180                 185                 190

Gly Leu Pro Ser Leu Ala Ser Arg Asp Leu Met Gly Leu Gln Arg Pro
        195                 200                 205

Leu Glu Arg Met Pro Glu Gly Asp Gly Glu Gly Leu Ser Ala Asn Ser
    210                 215                 220

Ser Gly Glu Gln Ala Ser Val Pro Glu Gly Asn Leu His Gly Gln Asp
225                 230                 235                 240

Gln Asp Arg Gly Gln Gly Pro Ile Leu Thr Leu Asn Thr Asp Ala Tyr
            245                 250                 255

Leu Ser Leu Gln Glu Leu Gln Ala Gln Asp Ser Val His Leu Ile
        260                 265                 270
```

<210> SEQ ID NO 14
<211> LENGTH: 1317
<212> TYPE: DNA
<213> ORGANISM: Artificial Sequence
<220> FEATURE:
<223> OTHER INFORMATION: Mouse orthoIL2Rb/IL9Ra (aka o9R) cDNA

<400> SEQUENCE: 14

```
atggctacta tcgctctgcc ttggtccctc tcactctatg tcttcctgct cctgctggct      60
acaccctggg cttctgctgc cgtcaaaaac tgctcccacc tggagtgttt ctacaactct     120
cgcgccaacg tgagctgcat gtggtcccac gaggaggccc tgaacgtgac cacatgtcac     180
gtgcacgcta agtccaacct gagacactgg aacaagacct cgcagctgac actggtgcgg     240
caggcctctt gggcttgtaa cctgatcctg ggaagctttc ccgagagcca gtccctgacc     300
tccgtggacc tgctggatat caacgtggtg tgctgggagg agaagggctg gaggagagtg     360
aagacatgtg acttccaccc atttgataac ctgaggctgg tggctccaca cagcctgcag     420
gtgctgcaca tcgacaccca gaggtgcaac atctcctgga aggtgagcca ggtgtccgat     480
ttcatcgagc cttacctgga gtttgaggct cggcgcaggc tgctgggaca ctcctgggag     540
gacgcttctg tgctgagcct gaagcagcgg cagcagtggc tgttcctgga gatgctgatc     600
ccatctacca gctacgaggt gcaggtgcgc gtgaaggccc agaggaacaa caccggaaca     660
tggtcccctt ggagccagcc actgaccttc cgcacaaggc ccgccgatcc tatgaaggag     720
gcttctatcc tggtggtggt gcctatcttt ctgctgctga caggcttcgt gcacctgctg     780
tttaagctgt ctccaagact gaagcggatc ttctaccaga acatccctag cccagaggct     840
ttctttcacc ccctgtacag cgtgtaccac ggagactttc agtcctggac cggagctaga     900
agggctggac tcaggctag acagaacgga gtgtctacaa gctccgctgg cagcgagtct     960
agcatctggg aggccgtggc taccctgaca tactctccag cctgccccgt gcagttcgct    1020
tgtctgaagt gggaggccac cgctcctgc tttccaggac tgccaggaag cgagcacgtg    1080
ctgccagctg atgtctgga ctggaggga cagccatccg cttacctgcc tcaggaggat    1140
tgggctccac tgggatctgc tcggcccct ccaccagact ccgattctgg atcctctgac    1200
tactgcatgc tggattgctg tgaggagtgt cacctgagcg ccttccccgg ccacacagaa    1260
agccccgaac tcaccctcgc acagcccgtc gcactccag tctcctccag agcataa       1317
```

<210> SEQ ID NO 15
<211> LENGTH: 438
<212> TYPE: PRT

```
<213> ORGANISM: Artificial Sequence
<220> FEATURE:
<223> OTHER INFORMATION: Mouse orthoIL2Rb/IL9Ra (aka o9R)

<400> SEQUENCE: 15

Met Ala Thr Ile Ala Leu Pro Trp Ser Leu Ser Leu Tyr Val Phe Leu
1               5                   10                  15

Leu Leu Leu Ala Thr Pro Trp Ala Ser Ala Ala Val Lys Asn Cys Ser
            20                  25                  30

His Leu Glu Cys Phe Tyr Asn Ser Arg Ala Asn Val Ser Cys Met Trp
        35                  40                  45

Ser His Glu Glu Ala Leu Asn Val Thr Thr Cys His Val His Ala Lys
    50                  55                  60

Ser Asn Leu Arg His Trp Asn Lys Thr Cys Glu Leu Thr Leu Val Arg
65                  70                  75                  80

Gln Ala Ser Trp Ala Cys Asn Leu Ile Leu Gly Ser Phe Pro Glu Ser
                85                  90                  95

Gln Ser Leu Thr Ser Val Asp Leu Leu Asp Ile Asn Val Val Cys Trp
            100                 105                 110

Glu Glu Lys Gly Trp Arg Arg Val Lys Thr Cys Asp Phe His Pro Phe
        115                 120                 125

Asp Asn Leu Arg Leu Val Ala Pro His Ser Leu Gln Val Leu His Ile
    130                 135                 140

Asp Thr Gln Arg Cys Asn Ile Ser Trp Lys Val Ser Gln Val Ser Asp
145                 150                 155                 160

Phe Ile Glu Pro Tyr Leu Glu Phe Glu Ala Arg Arg Arg Leu Leu Gly
                165                 170                 175

His Ser Trp Glu Asp Ala Ser Val Leu Ser Leu Lys Gln Arg Gln Gln
            180                 185                 190

Trp Leu Phe Leu Glu Met Leu Ile Pro Ser Thr Ser Tyr Glu Val Gln
        195                 200                 205

Val Arg Val Lys Ala Gln Arg Asn Asn Thr Gly Thr Trp Ser Pro Trp
    210                 215                 220

Ser Gln Pro Leu Thr Phe Arg Thr Arg Pro Ala Asp Pro Met Lys Glu
225                 230                 235                 240

Ala Ser Ile Leu Val Val Val Pro Ile Phe Leu Leu Leu Thr Gly Phe
                245                 250                 255

Val His Leu Leu Phe Lys Leu Ser Pro Arg Leu Lys Arg Ile Phe Tyr
            260                 265                 270

Gln Asn Ile Pro Ser Pro Glu Ala Phe Phe His Pro Leu Tyr Ser Val
        275                 280                 285

Tyr His Gly Asp Phe Gln Ser Trp Thr Gly Ala Arg Arg Ala Gly Pro
    290                 295                 300

Gln Ala Arg Gln Asn Gly Val Ser Thr Ser Ser Ala Gly Ser Glu Ser
305                 310                 315                 320

Ser Ile Trp Glu Ala Val Ala Thr Leu Thr Tyr Ser Pro Ala Cys Pro
                325                 330                 335

Val Gln Phe Ala Cys Leu Lys Trp Glu Ala Thr Ala Pro Gly Phe Pro
            340                 345                 350

Gly Leu Pro Gly Ser Glu His Val Leu Pro Ala Gly Cys Leu Glu Leu
        355                 360                 365

Glu Gly Gln Pro Ser Ala Tyr Leu Pro Gln Glu Asp Trp Ala Pro Leu
    370                 375                 380

Gly Ser Ala Arg Pro Pro Pro Pro Asp Ser Asp Ser Gly Ser Ser Asp
```

```
385             390             395             400

Tyr Cys Met Leu Asp Cys Cys Glu Glu Cys His Leu Ser Ala Phe Pro
            405             410             415

Gly His Thr Glu Ser Pro Glu Leu Thr Leu Ala Gln Pro Val Ala Leu
            420             425             430

Pro Val Ser Ser Arg Ala
        435

<210> SEQ ID NO 16
<211> LENGTH: 235
<212> TYPE: PRT
<213> ORGANISM: Artificial Sequence
<220> FEATURE:
<223> OTHER INFORMATION: Mouse orthoIL2Rb/IL9Ra (aka o9R) - orthoIL2Rb
      extracellular domain

<400> SEQUENCE: 16

Met Ala Thr Ile Ala Leu Pro Trp Ser Leu Ser Leu Tyr Val Phe Leu
1               5               10              15

Leu Leu Leu Ala Thr Pro Trp Ala Ser Ala Ala Val Lys Asn Cys Ser
            20              25              30

His Leu Glu Cys Phe Tyr Asn Ser Arg Ala Asn Val Ser Cys Met Trp
        35              40              45

Ser His Glu Glu Ala Leu Asn Val Thr Thr Cys His Val His Ala Lys
    50              55              60

Ser Asn Leu Arg His Trp Asn Lys Thr Cys Glu Leu Thr Leu Val Arg
65              70              75              80

Gln Ala Ser Trp Ala Cys Asn Leu Ile Leu Gly Ser Phe Pro Glu Ser
            85              90              95

Gln Ser Leu Thr Ser Val Asp Leu Leu Asp Ile Asn Val Val Cys Trp
        100             105             110

Glu Glu Lys Gly Trp Arg Arg Val Lys Thr Cys Asp Phe His Pro Phe
        115             120             125

Asp Asn Leu Arg Leu Val Ala Pro His Ser Leu Gln Val Leu His Ile
        130             135             140

Asp Thr Gln Arg Cys Asn Ile Ser Trp Lys Val Ser Gln Val Ser Asp
145             150             155             160

Phe Ile Glu Pro Tyr Leu Glu Phe Glu Ala Arg Arg Arg Leu Leu Gly
            165             170             175

His Ser Trp Glu Asp Ala Ser Val Leu Ser Leu Lys Gln Arg Gln Gln
            180             185             190

Trp Leu Phe Leu Glu Met Leu Ile Pro Ser Thr Ser Tyr Glu Val Gln
        195             200             205

Val Arg Val Lys Ala Gln Arg Asn Asn Thr Gly Thr Trp Ser Pro Trp
    210             215             220

Ser Gln Pro Leu Thr Phe Arg Thr Arg Pro Ala
225             230             235

<210> SEQ ID NO 17
<211> LENGTH: 21
<212> TYPE: PRT
<213> ORGANISM: Artificial Sequence
<220> FEATURE:
<223> OTHER INFORMATION: Mouse orthoIL2Rb/IL9Ra (aka o9R) -
      transmembrane region

<400> SEQUENCE: 17

Ala Ser Ile Leu Val Val Val Pro Ile Phe Leu Leu Leu Thr Gly Phe
```

-continued

```
1           5              10             15

Val His Leu Leu Phe
            20
```

```
<210> SEQ ID NO 18
<211> LENGTH: 212
<212> TYPE: PRT
<213> ORGANISM: Artificial Sequence
<220> FEATURE:
<223> OTHER INFORMATION: Mouse orthoIL2Rb/IL9Ra (aka o9R) - IL9Ra
      intracellular domain with transmembrane region

<400> SEQUENCE: 18

Gln Arg Arg Gln Gly Leu Leu Val Pro Arg Trp Gln Trp Ser Ala Ser
1               5              10             15

Ile Leu Val Val Val Pro Ile Phe Leu Leu Leu Thr Gly Phe Val His
            20             25             30

Leu Leu Phe Lys Leu Ser Pro Arg Leu Lys Arg Ile Phe Tyr Gln Asn
        35             40             45

Ile Pro Ser Pro Glu Ala Phe Phe His Pro Leu Tyr Ser Val Tyr His
    50             55             60

Gly Asp Phe Gln Ser Trp Thr Gly Ala Arg Arg Ala Gly Pro Gln Ala
65             70             75             80

Arg Gln Asn Gly Val Ser Thr Ser Ser Ala Gly Ser Glu Ser Ser Ile
            85             90             95

Trp Glu Ala Val Ala Thr Leu Thr Tyr Ser Pro Ala Cys Pro Val Gln
            100            105            110

Phe Ala Cys Leu Lys Trp Glu Ala Thr Ala Pro Gly Phe Pro Gly Leu
            115            120            125

Pro Gly Ser Glu His Val Leu Pro Ala Gly Cys Leu Glu Leu Glu Gly
        130            135            140

Gln Pro Ser Ala Tyr Leu Pro Gln Glu Asp Trp Ala Pro Leu Gly Ser
145            150            155            160

Ala Arg Pro Pro Pro Asp Ser Asp Ser Gly Ser Ser Asp Tyr Cys
            165            170            175

Met Leu Asp Cys Cys Glu Glu Cys His Leu Ser Ala Phe Pro Gly His
            180            185            190

Thr Glu Ser Pro Glu Leu Thr Leu Ala Gln Pro Val Ala Leu Pro Val
        195            200            205

Ser Ser Arg Ala
    210
```

```
<210> SEQ ID NO 19
<211> LENGTH: 820
<212> TYPE: PRT
<213> ORGANISM: Artificial Sequence
<220> FEATURE:
<223> OTHER INFORMATION: Mouse orthoIL2Rb/IL4R (aka o4R)

<400> SEQUENCE: 19

Met Ala Thr Ile Ala Leu Pro Trp Ser Leu Ser Leu Tyr Val Phe Leu
1               5              10             15

Leu Leu Leu Ala Thr Pro Trp Ala Ser Ala Ala Val Lys Asn Cys Ser
            20             25             30

His Leu Glu Cys Phe Tyr Asn Ser Arg Ala Asn Val Ser Cys Met Trp
        35             40             45

Ser His Glu Glu Ala Leu Asn Val Thr Thr Cys His Val His Ala Lys
    50             55             60
```

```
Ser Asn Leu Arg His Trp Asn Lys Thr Cys Glu Leu Thr Leu Val Arg
65                  70                  75                  80

Gln Ala Ser Trp Ala Cys Asn Leu Ile Leu Gly Ser Phe Pro Glu Ser
                85                  90                  95

Gln Ser Leu Thr Ser Val Asp Leu Leu Asp Ile Asn Val Val Cys Trp
            100                 105                 110

Glu Glu Lys Gly Trp Arg Arg Val Lys Thr Cys Asp Phe His Pro Phe
            115                 120                 125

Asp Asn Leu Arg Leu Val Ala Pro His Ser Leu Gln Val Leu His Ile
        130                 135                 140

Asp Thr Gln Arg Cys Asn Ile Ser Trp Lys Val Ser Gln Val Ser Asp
145                 150                 155                 160

Phe Ile Glu Pro Tyr Leu Glu Phe Glu Ala Arg Arg Arg Leu Leu Gly
                165                 170                 175

His Ser Trp Glu Asp Ala Ser Val Leu Ser Leu Lys Gln Arg Gln Gln
            180                 185                 190

Trp Leu Phe Leu Glu Met Leu Ile Pro Ser Thr Ser Tyr Glu Val Gln
            195                 200                 205

Val Arg Val Lys Ala Gln Arg Asn Asn Thr Gly Thr Trp Ser Pro Trp
    210                 215                 220

Ser Gln Pro Leu Thr Phe Arg Thr Arg Pro Ala Phe Gln Leu Pro Leu
225                 230                 235                 240

Ile Gln Arg Leu Pro Leu Gly Val Thr Ile Ser Cys Leu Cys Ile Pro
                245                 250                 255

Leu Phe Cys Leu Phe Cys Tyr Phe Ser Ile Thr Lys Ile Lys Lys Ile
            260                 265                 270

Trp Trp Asp Gln Ile Pro Thr Pro Ala Arg Ser Pro Leu Val Ala Ile
        275                 280                 285

Ile Ile Gln Asp Ala Gln Val Pro Leu Trp Asp Lys Gln Thr Arg Ser
    290                 295                 300

Gln Glu Ser Thr Lys Tyr Pro His Trp Lys Thr Cys Leu Asp Lys Leu
305                 310                 315                 320

Leu Pro Cys Leu Leu Lys His Arg Val Lys Lys Thr Asp Phe Pro
            325                 330                 335

Lys Ala Ala Pro Thr Lys Ser Leu Gln Ser Pro Gly Lys Ala Gly Trp
            340                 345                 350

Cys Pro Met Glu Val Ser Arg Thr Val Leu Trp Pro Glu Asn Val Ser
            355                 360                 365

Val Ser Val Val Arg Cys Met Glu Leu Phe Glu Ala Pro Val Gln Asn
    370                 375                 380

Val Glu Glu Glu Glu Asp Glu Ile Val Lys Glu Asp Leu Ser Met Ser
385                 390                 395                 400

Pro Glu Asn Ser Gly Gly Cys Gly Phe Gln Glu Ser Gln Ala Asp Ile
                405                 410                 415

Met Ala Arg Leu Thr Glu Asn Leu Phe Ser Asp Leu Leu Glu Ala Glu
            420                 425                 430

Asn Gly Gly Leu Gly Gln Ser Ala Leu Ala Glu Ser Cys Ser Pro Leu
            435                 440                 445

Pro Ser Gly Ser Gly Gln Ala Ser Val Ser Trp Ala Cys Leu Pro Met
    450                 455                 460

Gly Pro Ser Glu Glu Ala Thr Cys Gln Val Thr Glu Gln Pro Ser His
465                 470                 475                 480
```

-continued

```
Pro Gly Pro Leu Ser Gly Ser Pro Ala Gln Ser Ala Pro Thr Leu Ala
            485             490             495

Cys Thr Gln Val Pro Leu Val Leu Ala Asp Asn Pro Ala Tyr Arg Ser
            500             505             510

Phe Ser Asp Cys Cys Ser Pro Ala Pro Asn Pro Gly Glu Leu Ala Pro
            515             520             525

Glu Gln Gln Gln Ala Asp His Leu Glu Glu Glu Glu Pro Pro Ser Pro
        530             535             540

Ala Asp Pro His Ser Ser Gly Pro Pro Met Gln Pro Val Glu Ser Trp
545             550             555             560

Glu Gln Ile Leu His Met Ser Val Leu Gln His Gly Ala Ala Ala Gly
            565             570             575

Ser Thr Pro Ala Pro Ala Gly Gly Tyr Gln Glu Phe Val Gln Ala Val
            580             585             590

Lys Gln Gly Ala Ala Gln Asp Pro Gly Val Pro Gly Val Arg Pro Ser
            595             600             605

Gly Asp Pro Gly Tyr Lys Ala Phe Ser Ser Leu Leu Ser Ser Asn Gly
        610             615             620

Ile Arg Gly Asp Thr Ala Ala Ala Gly Thr Asp Asp Gly His Gly Gly
625             630             635             640

Tyr Lys Pro Phe Gln Asn Pro Val Pro Asn Gln Ser Pro Ser Ser Val
            645             650             655

Pro Leu Phe Thr Phe Gly Leu Asp Thr Glu Leu Ser Pro Ser Pro Leu
            660             665             670

Asn Ser Asp Pro Pro Lys Ser Pro Pro Glu Cys Leu Gly Leu Glu Leu
            675             680             685

Gly Leu Lys Gly Gly Asp Trp Val Lys Ala Pro Pro Pro Ala Asp Gln
        690             695             700

Val Pro Lys Pro Phe Gly Asp Asp Leu Gly Phe Gly Ile Val Tyr Ser
705             710             715             720

Ser Leu Thr Cys His Leu Cys Gly His Leu Lys Gln His His Ser Gln
            725             730             735

Glu Glu Gly Gly Gln Ser Pro Ile Val Ala Ser Pro Gly Cys Gly Cys
            740             745             750

Cys Tyr Asp Asp Arg Ser Pro Ser Leu Gly Ser Leu Ser Gly Ala Leu
            755             760             765

Glu Ser Cys Pro Glu Gly Ile Pro Pro Glu Ala Asn Leu Met Ser Ala
        770             775             780

Pro Lys Thr Pro Ser Asn Leu Ser Gly Glu Gly Lys Gly Pro Gly His
785             790             795             800

Ser Pro Val Pro Ser Gln Thr Thr Glu Val Pro Val Gly Ala Leu Gly
            805             810             815

Ile Ala Val Ser
            820
```

```
<210> SEQ ID NO 20
<211> LENGTH: 462
<212> TYPE: PRT
<213> ORGANISM: Artificial Sequence
<220> FEATURE:
<223> OTHER INFORMATION: Mouse orthoIL2Rb/IL7R (aka o7R)

<400> SEQUENCE: 20

Met Ala Thr Ile Ala Leu Pro Trp Ser Leu Ser Leu Tyr Val Phe Leu
1               5               10              15
```

Leu Leu Leu Ala Thr Pro Trp Ala Ser Ala Ala Val Lys Asn Cys Ser
            20                  25                  30

His Leu Glu Cys Phe Tyr Asn Ser Arg Ala Asn Val Ser Cys Met Trp
        35                  40                  45

Ser His Glu Glu Ala Leu Asn Val Thr Thr Cys His Val His Ala Lys
        50                  55                  60

Ser Asn Leu Arg His Trp Asn Lys Thr Cys Glu Leu Thr Leu Val Arg
65                  70                  75                  80

Gln Ala Ser Trp Ala Cys Asn Leu Ile Leu Gly Ser Phe Pro Glu Ser
                85                  90                  95

Gln Ser Leu Thr Ser Val Asp Leu Leu Asp Ile Asn Val Val Cys Trp
            100                 105                 110

Glu Glu Lys Gly Trp Arg Arg Val Lys Thr Cys Asp Phe His Pro Phe
            115                 120                 125

Asp Asn Leu Arg Leu Val Ala Pro His Ser Leu Gln Val Leu His Ile
        130                 135                 140

Asp Thr Gln Arg Cys Asn Ile Ser Trp Lys Val Ser Gln Val Ser Asp
145                 150                 155                 160

Phe Ile Glu Pro Tyr Leu Glu Phe Glu Ala Arg Arg Arg Leu Leu Gly
                165                 170                 175

His Ser Trp Glu Asp Ala Ser Val Leu Ser Leu Lys Gln Arg Gln Gln
            180                 185                 190

Trp Leu Phe Leu Glu Met Leu Ile Pro Ser Thr Ser Tyr Glu Val Gln
            195                 200                 205

Val Arg Val Lys Ala Gln Arg Asn Asn Thr Gly Thr Trp Ser Pro Trp
        210                 215                 220

Ser Gln Pro Leu Thr Phe Arg Thr Arg Pro Ala Lys Asn Gln Gly Gly
225                 230                 235                 240

Trp Asp Pro Val Leu Pro Ser Val Thr Ile Leu Ser Leu Phe Ser Val
                245                 250                 255

Phe Leu Leu Val Ile Leu Ala His Val Leu Trp Lys Lys Arg Ile Lys
            260                 265                 270

Pro Val Val Trp Pro Ser Leu Pro Asp His Lys Lys Thr Leu Glu Gln
            275                 280                 285

Leu Cys Lys Lys Pro Lys Thr Ser Leu Asn Val Ser Phe Asn Pro Glu
        290                 295                 300

Ser Phe Leu Asp Cys Gln Ile His Glu Val Lys Gly Val Glu Ala Arg
305                 310                 315                 320

Asp Glu Val Glu Ser Phe Leu Pro Asn Asp Leu Pro Ala Gln Pro Glu
                325                 330                 335

Glu Leu Glu Thr Gln Gly His Arg Ala Ala Val His Ser Ala Asn Arg
            340                 345                 350

Ser Pro Glu Thr Ser Val Ser Pro Pro Glu Thr Val Arg Arg Glu Ser
            355                 360                 365

Pro Leu Arg Cys Leu Ala Arg Asn Leu Ser Thr Cys Asn Ala Pro Pro
        370                 375                 380

Leu Leu Ser Ser Arg Ser Pro Asp Tyr Arg Asp Gly Asp Arg Asn Arg
385                 390                 395                 400

Pro Pro Val Tyr Gln Asp Leu Leu Pro Asn Ser Gly Asn Thr Asn Val
                405                 410                 415

Pro Val Pro Val Pro Gln Pro Leu Pro Phe Gln Ser Gly Ile Leu Ile
            420                 425                 430

Pro Val Ser Gln Arg Gln Pro Ile Ser Thr Ser Ser Val Leu Asn Gln

```
            435             440             445
Glu Glu Ala Tyr Val Thr Met Ser Ser Phe Tyr Gln Asn Lys
   450             455             460

<210> SEQ ID NO 21
<211> LENGTH: 537
<212> TYPE: PRT
<213> ORGANISM: Artificial Sequence
<220> FEATURE:
<223> OTHER INFORMATION: Mouse orthoIL2Rb/IL21R (aka o21R)

<400> SEQUENCE: 21

Met Ala Thr Ile Ala Leu Pro Trp Ser Leu Ser Leu Tyr Val Phe Leu
1               5                   10                  15

Leu Leu Leu Ala Thr Pro Trp Ala Ser Ala Ala Val Lys Asn Cys Ser
           20                  25                  30

His Leu Glu Cys Phe Tyr Asn Ser Arg Ala Asn Val Ser Cys Met Trp
       35                  40                  45

Ser His Glu Glu Ala Leu Asn Val Thr Thr Cys His Val His Ala Lys
   50                  55                  60

Ser Asn Leu Arg His Trp Asn Lys Thr Cys Glu Leu Thr Leu Val Arg
65                  70                  75                  80

Gln Ala Ser Trp Ala Cys Asn Leu Ile Leu Gly Ser Phe Pro Glu Ser
           85                  90                  95

Gln Ser Leu Thr Ser Val Asp Leu Leu Asp Ile Asn Val Val Cys Trp
           100                 105                 110

Glu Glu Lys Gly Trp Arg Arg Val Lys Thr Cys Asp Phe His Pro Phe
           115                 120                 125

Asp Asn Leu Arg Leu Val Ala Pro His Ser Leu Gln Val Leu His Ile
       130                 135                 140

Asp Thr Gln Arg Cys Asn Ile Ser Trp Lys Val Ser Gln Val Ser Asp
145                 150                 155                 160

Phe Ile Glu Pro Tyr Leu Glu Phe Glu Ala Arg Arg Arg Leu Leu Gly
               165                 170                 175

His Ser Trp Glu Asp Ala Ser Val Leu Ser Leu Lys Gln Arg Gln Gln
           180                 185                 190

Trp Leu Phe Leu Glu Met Leu Ile Pro Ser Thr Ser Tyr Glu Val Gln
       195                 200                 205

Val Arg Val Lys Ala Gln Arg Asn Asn Thr Gly Thr Trp Ser Pro Trp
   210                 215                 220

Ser Gln Pro Leu Thr Phe Arg Thr Arg Pro Ala Gly Glu Pro Glu Ala
225                 230                 235                 240

Gly Trp Asp Pro His Met Leu Leu Leu Leu Ala Val Leu Ile Ile Val
           245                 250                 255

Leu Val Phe Met Gly Leu Lys Ile His Leu Pro Trp Arg Leu Trp Lys
           260                 265                 270

Lys Ile Trp Ala Pro Val Pro Thr Pro Glu Ser Phe Phe Gln Pro Leu
       275                 280                 285

Tyr Arg Glu His Ser Gly Asn Phe Lys Lys Trp Val Asn Thr Pro Phe
   290                 295                 300

Thr Ala Ser Ser Ile Glu Leu Val Pro Gln Ser Ser Thr Thr Thr Ser
305                 310                 315                 320

Ala Leu His Leu Ser Leu Tyr Pro Ala Lys Glu Lys Lys Phe Pro Gly
           325                 330                 335

Leu Pro Gly Leu Glu Glu Gln Leu Glu Cys Asp Gly Met Ser Glu Pro
```

-continued

```
                340              345              350
Gly His Trp Cys Ile Ile Pro Leu Ala Ala Gly Gln Ala Val Ser Ala
        355              360              365

Tyr Ser Glu Glu Arg Asp Arg Pro Tyr Gly Leu Val Ser Ile Asp Thr
    370              375              380

Val Thr Val Gly Asp Ala Glu Gly Leu Cys Val Trp Pro Cys Ser Cys
385              390              395              400

Glu Asp Asp Gly Tyr Pro Ala Met Asn Leu Asp Ala Gly Arg Glu Ser
                405              410              415

Gly Pro Asn Ser Glu Asp Leu Leu Leu Val Thr Asp Pro Ala Phe Leu
                420              425              430

Ser Cys Gly Cys Val Ser Gly Ser Gly Leu Arg Leu Gly Gly Ser Pro
        435              440              445

Gly Ser Leu Leu Asp Arg Leu Arg Leu Ser Phe Ala Lys Glu Gly Asp
    450              455              460

Trp Thr Ala Asp Pro Thr Trp Arg Thr Gly Ser Pro Gly Gly Gly Ser
465              470              475              480

Glu Ser Glu Ala Gly Ser Pro Pro Gly Leu Asp Met Asp Thr Phe Asp
                485              490              495

Ser Gly Phe Ala Gly Ser Asp Cys Gly Ser Pro Val Glu Thr Asp Glu
                500              505              510

Gly Pro Pro Arg Ser Tyr Leu Arg Gln Trp Val Val Arg Thr Pro Pro
        515              520              525

Pro Val Asp Ser Gly Ala Gln Ser Ser
    530              535
```

SELECTIVE STIMULATION OF T CELLS IN SOLID TUMORS USING ONCOLYTIC VIRAL DELIVERY OF ORTHOGONAL IL-2

CROSS-REFERENCE TO RELATED APPLICATIONS

The present application is a 35 U.S.C. § 371 national phase application of, and claims priority to, International Application No. PCT/US2022/019479, filed Mar. 9, 2022, which is entitled to priority under 35 U.S.C. § 119 (e) to U.S. Provisional Patent Application No. 63/158,671, filed Mar. 9, 2021, each of which is hereby incorporated by reference in its entirety herein.

STATEMENT REGARDING FEDERALLY SPONSORED RESEARCH OR DEVELOPMENT

This invention was made with Government support under CA016042, CA197633, CA245181, CA244118, and CA244711 awarded by the National Institutes of Health. The Government has certain rights in the invention.

BACKGROUND OF THE INVENTION

Current immunotherapy advances have been revolutionary for the treatment of hematologic malignancies as evident by the FDA approvals of CD19-targeting CAR-T cells for the treatment of acute lymphoblastic leukemia and diffuse-large B-cell lymphoma. However, the greatest unmet burden for cancer treatment is solid tumors. CAR-T cells have lacked efficacy in the fight against solid tumors due to a number of challenges, including the lack of tumor-specific antigens, overcoming obstacles of therapeutic resistance, tumor heterogeneity, poor expansion and persistence, and extrinsic dysfunction and physical barriers to T cell infiltration caused by the dense, immunosuppressive tumor microenvironment (TME). One major limitation is the poor in vivo expansion and persistence of adoptively transferred T cells, necessitating lymphodepleting conditioning chemotherapy—a toxic regimen that limits patient eligibility. Even those T cells that do expand and persist become terminally differentiated and dysfunctional. T cells with a stem-like phenotype can overcome these limitations and exhibit superior antitumor activity in mouse models and humans, but therapeutic manipulations to select or expand stem-like T cells are limited to the cell manufacturing phase and cannot be made in vivo. There is a need in the art for novel cell-based therapies that overcome these obstacles and challenges. The present invention addresses this need.

SUMMARY OF THE INVENTION

In some aspects, the invention provides a system for selective activation of a receptor in a cell, the system comprising: (a) a modified immune cell comprising (i) an orthogonal chimeric cytokine receptor, and (ii) at least one chimeric antigen receptor (CAR), and (b) an oncolytic adenoviral vector comprising a nucleic acid sequence encoding an orthogonal IL2 cytokine, wherein the orthogonal chimeric cytokine receptor comprises an extracellular domain of an orthogonal IL2 receptor (oIL2R) and an intracellular signaling domain of a cytokine receptor that is not IL2R.

In some embodiments, the extracellular domain of an oIL2R is an extracellular domain of an orthogonal IL2 receptor beta (oIL2Rb).

In some embodiments, the intracellular signaling domain of the orthogonal chimeric cytokine receptor comprises an IL9R intracellular signaling domain.

In some embodiments, the IL9R intracellular signaling domain is an IL9R-alpha (IL9Ra) intracellular signaling domain.

In some embodiments, the CAR comprises an antigen binding domain, a transmembrane domain, and an intracellular domain.

In some embodiments, the antigen binding domain is selected from the group consisting of a full length antibody or antigen-binding fragment thereof, a Fab, a single-chain variable fragment (scFv), or a single-domain antibody.

In some embodiments, the antigen binding domain targets a tumor antigen.

In some embodiments, the tumor antigen is selected from the group consisting of CD19, CD20, HER2, NY-ESO-1, MUC1, CD123, FLT3, B7-H3, CD33, IL1RAP, CLL1 (CLEC12A)PSA, CEA, VEGF, VEGF-R2, CD22, ROR1, mesothelin, c-Met, Glycolipid F77, FAP, EGFRvIII, MAGE A3, 5T4, WT1, KG2D ligand, a folate receptor (FRa), and Wnt1 antigens.

In some embodiments, the antigen binding domain is an scFv.

In some embodiments, the antigen binding domain is an anti-mesothelin scFv.

In some embodiments, the intracellular domain of the CAR comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lek, TNFR-I, TNFR-II, Fas, CD30, CD40, ICOS, NKG2C, and B7-H3 (CD276), or a variant thereof, or an intracellular domain derived from a killer immunoglobulin-like receptor (KIR).

In some embodiments, the intracellular domain of the CAR comprises an intracellular signaling domain of a protein selected from the group consisting of a human CD3 zeta chain (CD3ζ), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof.

In some embodiments, (a) the orthogonal chimeric cytokine receptor comprises an extracellular domain of an oIL2Rb and an intracellular signaling domain of an IL9Ra, and (b) the CAR comprises an anti-mesothelin antigen binding domain.

In some aspects, the invention provides a method of treating cancer in a subject comprising: (a) administering to the subject an effective amount of a modified immune cell or precursor thereof (a population of modified immune cells) comprising (i) an orthogonal chimeric cytokine receptor, and (ii) at least one CAR, and (b) administering to the subject an oncolytic adenoviral vector comprising a nucleic acid sequence encoding an orthogonal IL2 cytokine; wherein the orthogonal chimeric cytokine receptor comprises an extracellular domain of an orthogonal IL2 receptor (oIL2R) and an intracellular signaling domain of a cytokine receptor that is not IL2R.

In some embodiments, the extracellular domain of an oIL2R is an extracellular domain of an orthogonal IL2 receptor beta (oIL2Rb).

In some embodiments, the intracellular signaling domain of the orthogonal chimeric cytokine receptor comprises an IL9R intracellular signaling domain.

In some embodiments, the IL9R intracellular signaling domain is an IL9R-alpha (IL9Ra) intracellular signaling domain.

In some embodiments, the CAR comprises an antigen binding domain, a transmembrane domain, and an intracellular domain.

In some embodiments, the antigen binding domain is selected from the group consisting of a full length antibody or antigen-binding fragment thereof, a Fab, a single-chain variable fragment (scFv), or a single-domain antibody.

In some embodiments, the antigen binding domain targets a tumor antigen.

In some embodiments, the tumor antigen is selected from the group consisting of CD19, CD20, HER2, NY-ESO-1, MUC1, CD123, FLT3, B7-H3, CD33, IL1RAP, CLL1 (CLEC12A)PSA, CEA, VEGF, VEGF-R2, CD22, ROR1, mesothelin, c-Met, Glycolipid F77, FAP, EGFRvIII, MAGE A3, 5T4, WT1, KG2D ligand, a folate receptor (FRa), and Wnt1 antigens.

In some embodiments, the antigen binding domain is an scFv.

In some embodiments, the antigen binding domain is an anti-mesothelin scFv.

In some embodiments, the intracellular domain of the CAR comprises a costimulatory domain of a protein selected from the group consisting of proteins in the TNFR super-family, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS, NKG2C, and B7-H3 (CD276), or a variant thereof, or an intracellular domain derived from a killer immunoglobulin-like receptor (KIR).

In some embodiments, the intracellular domain of the CAR comprises an intracellular signaling domain of a protein selected from the group consisting of a human CD3 zeta chain (CD3ζ), FcγRIII, FcεRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof.

In some embodiments, (a) the orthogonal chimeric cytokine receptor comprises an extracellular domain of an oIL2Rb and an intracellular signaling domain of an IL9Ra, and (b) the CAR comprises an anti-mesothelin antigen binding domain.

In some embodiments, the population of modified immune cells assume stem cell memory (Tscm) features with improved trafficking and effector function, thereby treating the cancer.

In some embodiments, administering the vector comprises intratumoral injection.

In some embodiments, the cancer is selected from the group consisting of pancreatic cancer and melanoma.

In some embodiments, the pancreatic cancer is pancreatic ductal adenocarcinoma.

In some aspects, the invention provides a system for selective activation of a receptor in a cell, the system comprising: (a) a modified immune cell engineered to express: (i) an orthogonal chimeric cytokine receptor, and (ii) at least one T cell receptor (TCR), and (b) an oncolytic adenoviral vector comprising a nucleic acid sequence encoding an orthogonal IL2 cytokine, wherein the orthogonal chimeric cytokine receptor comprises an extracellular domain of an orthogonal IL2 receptor (oIL2R) and an intracellular signaling domain of a cytokine receptor that is not IL2R.

In some embodiments, the extracellular domain of an oIL2R is an extracellular domain of an orthogonal IL2 receptor beta (oIL2Rb).

In some embodiments, the intracellular signaling domain of the orthogonal chimeric cytokine receptor comprises an IL9R intracellular signaling domain.

In some embodiments, the IL9R intracellular signaling domain is an IL9R-alpha (IL9Ra) intracellular signaling domain.

In some embodiments, the TCR targets a tumor antigen.

In some embodiments, the TCR targets a gp100 melanoma antigen or NYESO1.

In some embodiments, the TCR is a pmel-1 TCR or an NYESO1-specific TCR.

In some embodiments, (a) the orthogonal chimeric cytokine receptor comprises an extracellular domain of an oIL2Rb and an intracellular signaling domain of an IL9Ra, and (b) the TCR is a pmel-1 TCR or an NYESO1-specific TCR.

In some aspects, the invention provides a method of treating cancer in a subject comprising: (a) administering to the subject an effective amount of a modified immune cell or precursor thereof (a population of modified immune cells) modified to express (i) an orthogonal chimeric cytokine receptor, and (ii) at least one T cell receptor (TCR), and (b) administering to the subject an oncolytic adenoviral vector comprising a nucleic acid sequence encoding an orthogonal IL2 cytokine; wherein the orthogonal chimeric cytokine receptor comprises an extracellular domain of an orthogonal IL2 receptor (oIL2R) and an intracellular signaling domain of a cytokine receptor that is not IL2R.

In some embodiments, the extracellular domain of an oIL2R is an extracellular domain of an orthogonal IL2 receptor beta (oIL2Rb).

In some embodiments, the intracellular signaling domain of the orthogonal chimeric cytokine receptor comprises an IL9R intracellular signaling domain.

In some embodiments, the IL9R intracellular signaling domain is an IL9R-alpha (IL9Ra) intracellular signaling domain.

In some embodiments, the TCR targets a tumor antigen.

In some embodiments, the TCR targets a gp100 melanoma antigen or NYESO1.

In some embodiments, the TCR is a pmel-1 TCR or an NYESO1-specific TCR.

In some embodiments, (a) the orthogonal chimeric cytokine receptor comprises an extracellular domain of an oIL2Rb and an intracellular signaling domain of an IL9Ra, and (b) the TCR is a pmel-1 TCR or an NYESO1-specific TCR.

In some embodiments, the population of modified immune cells assume stem cell memory (Tscm) features with improved trafficking and effector function, thereby treating the cancer.

In some embodiments, administering the vector comprises intratumoral injection.

In some embodiments, the cancer is selected from the group consisting of pancreatic cancer and melanoma.

In some embodiments, the pancreatic cancer is pancreatic ductal adenocarcinoma.

BRIEF DESCRIPTION OF THE DRAWINGS

The foregoing and other features and advantages of the present invention will be more fully understood from the following detailed description of illustrative embodiments taken in conjunction with the accompanying drawings.

(FIG. 1A) Schematic of wild-type IL2Rβ receptor, orthogonal IL20 receptor, or γc family orthogonal IL2Rβ chimeric receptor complexes. All vectors containing orthogonal receptors and orthogonal chimeric receptors also contain an IRES-YFP element. (FIG. 1B) Representative histogram and quantification of pSTAT signaling in ortho chimeric receptor expressing (YFP+) or untransduced (UTD) T cells stimulated with MSA-IL2 (100 nM)(unfilled color) or MSA-oIL2 (5 μM)(filled color) for 20'. Data shown as mean fluorescence+/−SEM, n=3. (FIG. 1C) Dose response curves of pSTAT signaling in o2R (red) or o9R (blue) transduced T cells stimulated with MSA-oIL2, MSA-IL2, or IL9 for 20'. Data shown as mean fluorescence+/−SEM; YFP+gated; n=3. (FIG. 1D). Surface marker levels of CD62L of chimeric receptor expressing T cells cultured with MSA-IL2 (100 nM) or MSA-oIL2 (5 μM) for 2 days. (FIG. 1E) Surface marker levels of Fas of chimeric receptor expressing T cells cultured with MSA-IL2 (100 nM) or MSA-oIL2 (5 μM) for 2 days. (FIG. 1F) Surface marker levels of Sca1 of chimeric receptor expressing T cells cultured with MSA-IL2 (100 nM) or MSA-oIL2 (5 μM) for 2 days. Data shown in FIG. 1D-FIG. 1F as mean fluorescence+/−SEM, n=3. ns, not significant; *, p<0.001; **, p<0.0001 (ANOVA). (FIG. 1G) Dose response curves of o2R or o9R cells that have undergone at least one division after 4-day culture in MSA-oIL2 or MSA-IL2. Data shown as percentage divided, calculated in Flowjo; YFP+gated; n=3 biological replicates.

(FIG. 3A) IL9R expression on mock transduced or mIL9R transduced T cells from C57BL6 transgenic mice. (FIG. 3B) IL9R expression on mock transduced or mIL9R transduced T cells from pmel1 TCR transgenic mice. (FIG. 3C) Representative histogram (top) and quantification (bottom) of pSTAT signaling in mIL9R expressing (YFP+) C57BL6 T cells stimulated with MSA-IL2 (100 nM)(unfilled color) or IL9 (1 M)(filled color) for 20'. Data shown as mean fluorescence+/−SEM, n=3. (FIG. 3D) Dose response curves of pSTAT signaling in IL9R transduced or mock transduced pmel T cells stimulated with MSA-IL2 or IL9.

(FIG. 4A) provides the data for pSTAT5 signaling. (FIG. 4B) provides the data for pSTAT3 signaling. (FIG. 4C) provides the data for pSTAT1 signaling.

FIG. 5A-FIG. 5B provide in vitro proliferation data. (FIG. 5A) Dose titration in vitro proliferation curves of orthoIL2Rb ICD chimeric receptor expressing T cells cultured for 4 days in MSA-IL2 (open symbol) or MSA-orthoIL2 (filled symbol). Data represent total live CD8+ YFP(+) cells normalized to the maximal growth of each different chimeric receptor expressing cell cultured in MSA-IL2. n=2+/−SEM. (FIG. 5B) In vitro proliferation of CTV labeled T cells transduced with o2R (red) or o9R (blue) cultured for 4 days in MSA-oIL2 (filled curves) or MSA-IL2 (unfilled curves). YFP(+) gated; 1 of 3 representative plot shown.

(FIG. 6A) STAT1, STAT3 and STAT5 phosphorylation in o2R versus o9R pmel T cells after 30 minute stimulation with MSA-oIL2 (5 M). Shown are MFI and range of biological duplicates, gated on YFP+ cells. *, adjusted p<0.05; **, adjusted p<0.005 (unpaired t test, corrected for multiple comparisons using Holm-Sidak method). (FIG. 6B) Shown are seven replicate experiments measuring in vitro proliferation (measured by fold growth) of o2R or o9R pmel T cells over 48 h in culture with MSA-oIL2, (each data point represents mean+/−SD, n=3). *, p<0.05 (ratio paired t-test).

FIG. 7A-FIG. 7J illustrate the finding that oIL9R signaling alters the phenotype and function of pmel T cells, endowing them with anti-tumor efficacy in the absence of lymphodepletion. (FIG. 7A) Experimental schematic. C57BL/6 mice implanted with B16-F10 melanoma were lymphodepleted (or not) prior to ACT of $5 \times 10^6$ pmel or control C57BL/6 T cells, then treated with MSA-IL2 or MSA-oIL2 ($2.5 \times 10^4$ U/day, intraperitoneal) for 5 days. (FIG. 7B) Peripheral blood quantification of adoptively transferred T cells seven days after ACT (mean+SD, n=5-6 mice/group). , p<0.01 (unpaired t test). (FIG. 7C) Tumor growth (mean SEM, n=5-6 mice/group) in mice treated with o2R pmel ACT and MSA-IL2 or MSA-oIL2. , p<0.01 (ANOVA). Data representative of three independent experiments. (FIG. 7D) Tumor growth (mean+SEM, n=5-6 mice/group) in mice treated with o9R pmel ACT and MSA-IL2 or MSA-oIL2. , p<0.01 (ANOVA). Data representative of three independent experiments. (FIG. 7E) Quantification (CD8+Thy1.1+ T cells/gram) of tumor infiltrating o2R or o9R pmel T cells five days after ACT in mice treated with MSA-oIL2. , p<0.01 (unpaired t-test). (FIG. 7F) In vitro growth (mean±SD, n=3) of nRFP+B16-F10 tumor cells cocultured with o2R or o9R pmel T cells (2:1 effector:target ratio) pretreated with MSA-IL2 (50 nM) or MSA-oIL2 (5 M), measured on Incucyte live cell imaging system *, p<0.05; , p<0.01 (ANOVA). (FIG. 7G) opt-SNE clustering of o2R and o9R pmel T cells (n=3/group) treated with MSA-oIL2 (5 μM) for 48 h in vitro (left), with separate plots for each group illustrating only differentially abundant clusters (middle), and a volcano plot of differentially abundant clusters annotated with distinguishing features (right). (FIG. 7H) Heatmap of genes differentially expressed between o2R and o9R pmel T cells treated with MSA-oIL2 (5 μM); groups treated with MSA-IL2 (50 nM) are also shown. (FIG. 7I) Heatmap of manually curated genes associated with T cell stemness and dysfunction (left) and T cell activation and effector function (right), and differentially expressed between o9R and o2R pmel T cells treated with MSA-oIL2 (5 μM). (FIG. 7J) Normalized enrichment plot (left panel) of transcription factor gene sets comparing o9R and o2R pmel T cells treated with MSA-oIL2. Statistically significant enrichment (adjusted p-value<0.05) shown in red. Ratio of Jun to Fos expression in o9R and o2R pmel T cells treated with MSA-oIL2 (right panel). , p<0.01 (unpaired t-test).

(FIG. 8A) Survival of B16-F10 tumor-bearing mice treated with o2R pmel T cells and mIL-2 or oIL-2. (FIG. 8B) Survival of B16-F10 tumor-bearing mice treated with o9R pmel T cells and mIL-2 or oIL-2. For FIG. 8A-FIG. 8B: BL/6 T cells treated with mIL-2 were used as an off-target T cell control. Untransduced pmel T cells plus mIL-2 in tumor-bearing lymphodepleted and non-lymphodepleted mice served as controls. (FIG. 8C) Effect of o9R pmel T cells in a lymphodepleted host. Tumor growth (mean+/−

SEM, left panel) of B16-F10 tumors in lymphodepleted C57BL/6 mice treated with o9R pmel T cells and mIL-2, oIL-2, or no IL2.

FIG. 9A-FIG. 9D illustrate trafficking, phenotype and function of o9R pmel T cells. (FIG. 9A) opt-SNE clustering of CD45+ tumor-infiltrating leukocytes 7 days after adoptive transfer of o2R (left) and o9R (middle) pmel T cells (n=4 mice/group). Volcano plot of differentially abundant clusters in tumors from mice treated with o9R versus o2R pmel T cells (right panel). (FIG. 9B) opt-SNE clustering of the subset of tumor infiltrating o9R and o2R pmel T cells in non-lymphodepleted hosts treated with oIL-2 (n=4 mice/group, left panel), with separate plots for each treatment group illustrating only differentially abundant clusters (middle panel), and a volcano plot of differentially abundant clusters annotated with distinguishing features (right panel). (FIG. 9C) Tumor-infiltration of CD3+CD8+ T cells and CD8+PD1+ T cells in non-lymphodepleted hosts treated with either o2R and oIL-2 (left panel) or o9R pmel T cells and oIL-2 (right panel) by multiplex IHC (red=CD3, orange=CD8, yellow=PD1, green=CD4, teal=FOXP3). Quantifications shown below. (FIG. 9D) IFNγ secretion by oIL2R and oIL9R pmel T cells cocultured with B16-F10 melanoma in vitro for 24 h. T cells were pretreated with oIL-2 (5 μM) for 48 h in vitro prior to coculture. *, p<0.05; unpaired t-test.

Figure 10:
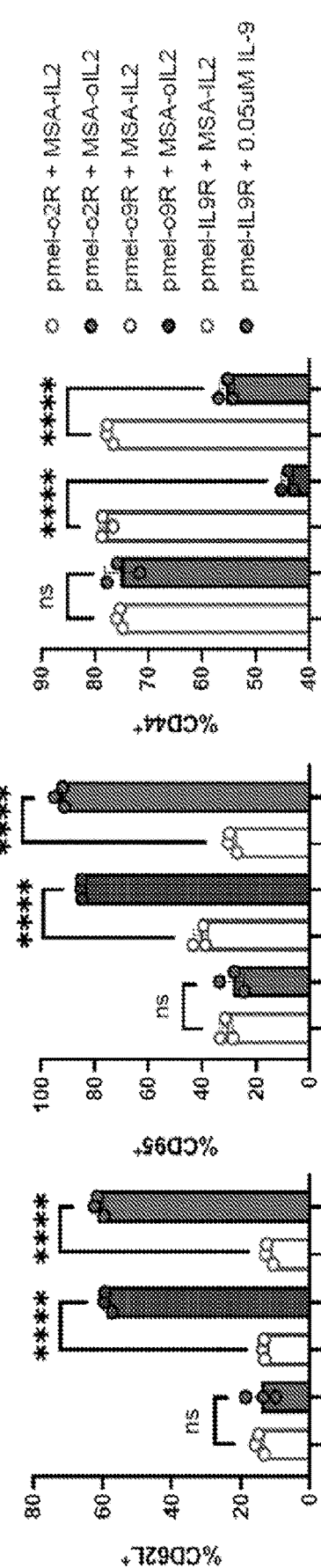

FIG. 10 illustrates the finding that o9R and wildtype IL-9R signaling drive Tscm phenotype. Surface expression of CD62L, CD95 (Fas) and CD44 as percentage of CD8+ Thy1.1+ sorted o9R pmel T cells, o2R pmel T cells, or pmel T cells transduced with wildtype IL-9R (pmel-IL9R) and treated with mIL-2 (0.05 M), oIL-2 (5 μM), or IL-9 (0.05 μM) for 48 h in vitro. ns, not significant; **** p<0.0001; unpaired t-tests.

FIG. 11 illustrates unsupervised transcriptomic analysis (RNA-seq) of sorted pmel-o2R (n=3) and pmel-o9R (n=3) T cells 48 after exposure to oIL-2 or mIL-2 in vitro. Samples separate by treatment group based on principal component analysis (PC1 v PC2, left panel). Samples cluster by treatment group when arranged by sample-sample distances in a heatmap (right panel), with o9R pmel T cells treated with oIL-2 most distinct among the four groups.

Figure 12:
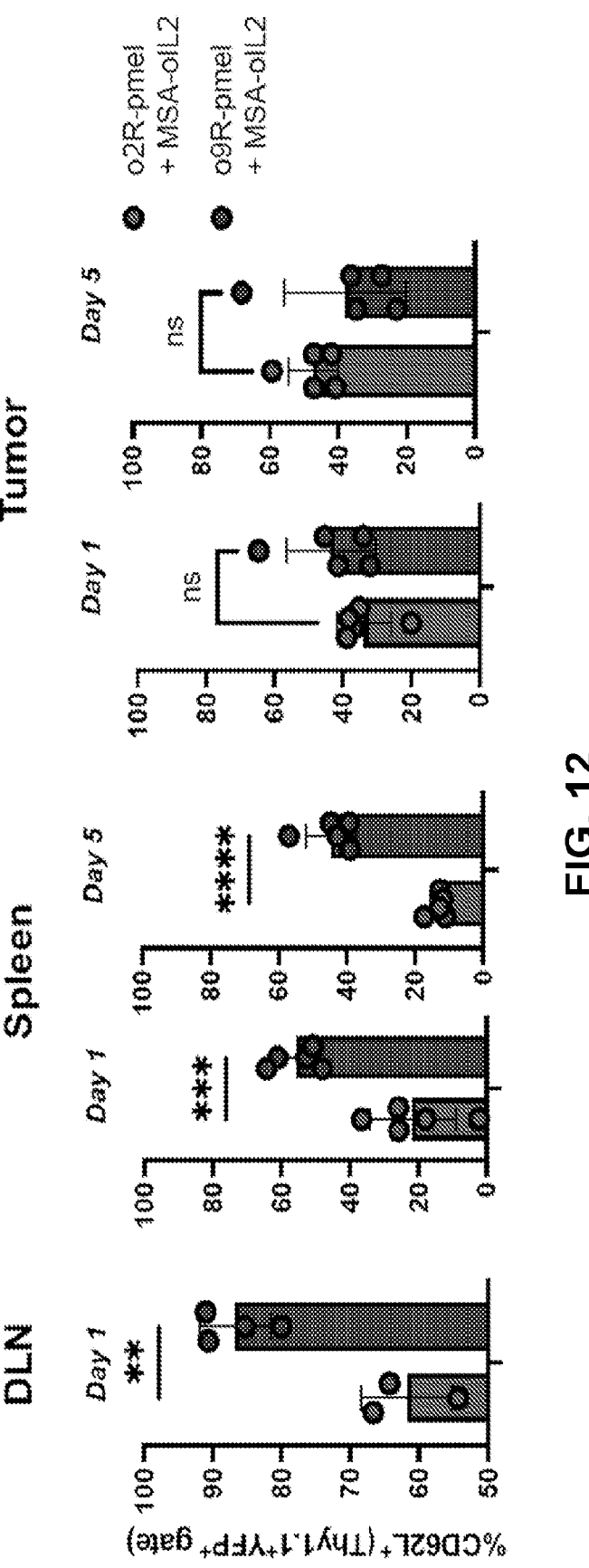

FIG. 12 illustrates frequency of CD62L+o2R or o9R pmel T cells (Thy1.1+ YFP+) from tumor draining lymph nodes (DLN), spleen or tumors of mice treated with MSA-oIL2. Tissues were harvested one or five days after adoptive transfer. Each data point represents one individual mouse, n=3-5 mice per group. , p<0.01; *, p<0.001; ****, <0.0001; unpaired t-test.

Figures 13A, 13B, 13C:
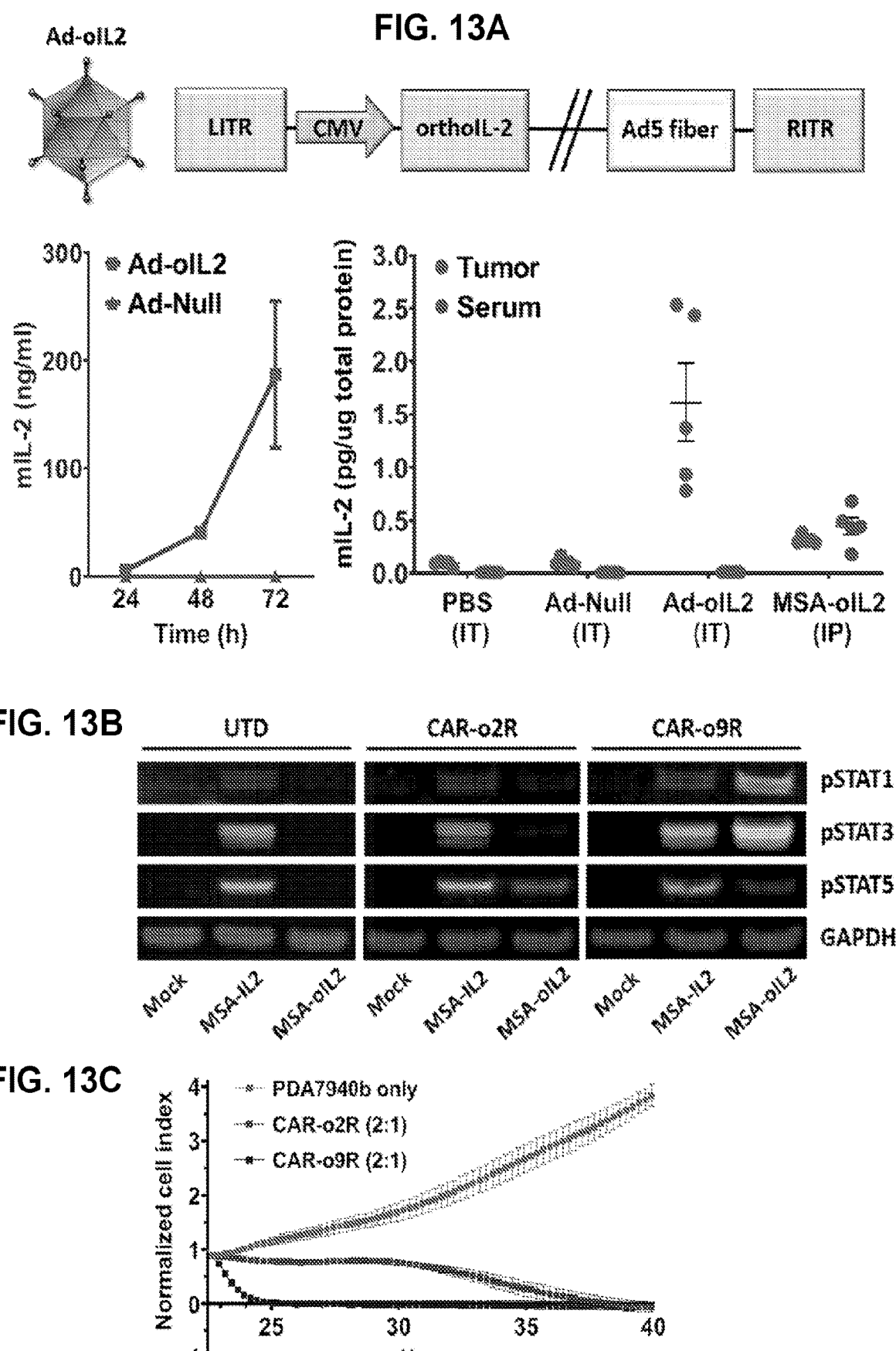
Figures 13D, 13E:
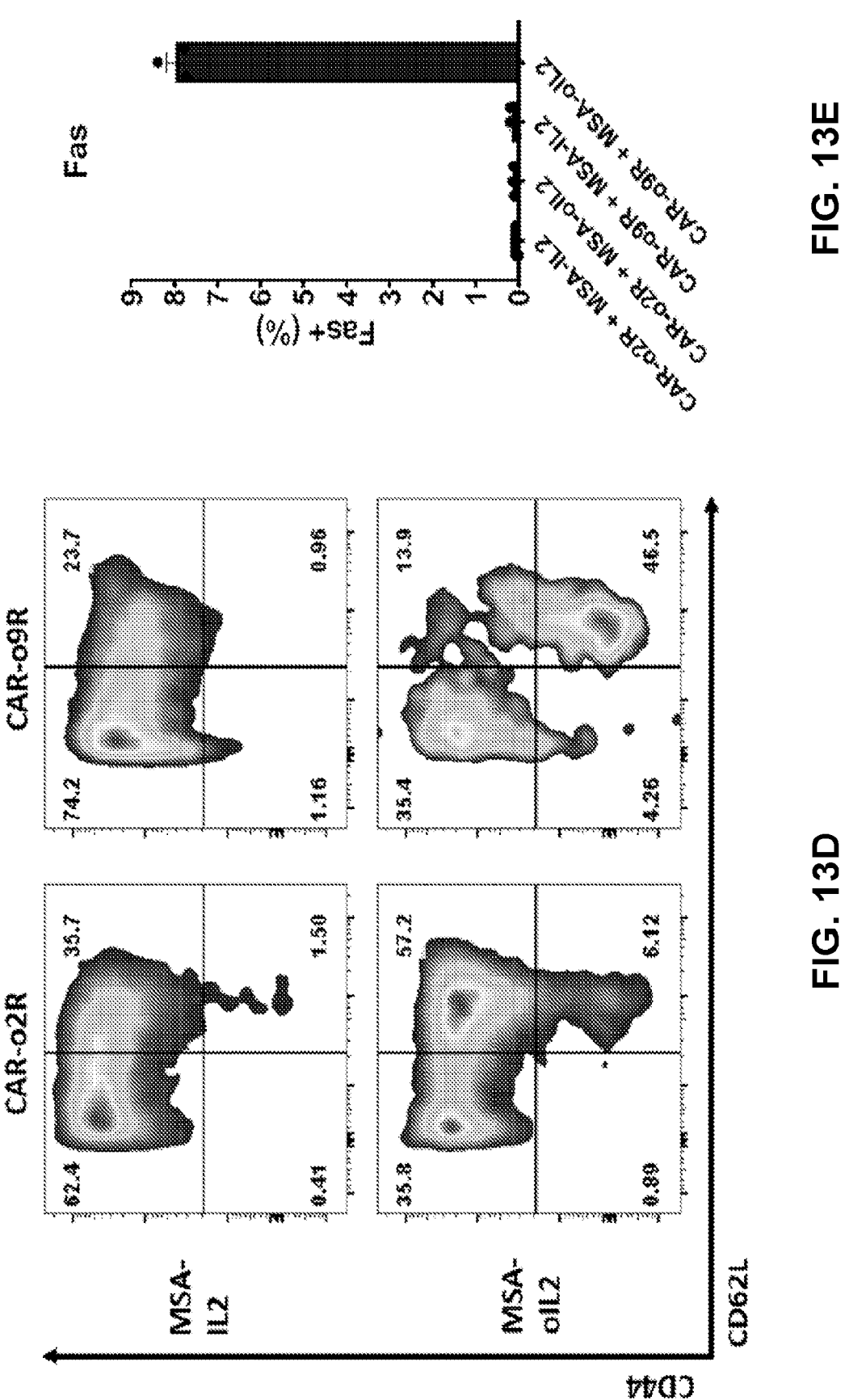
Figure 13F:
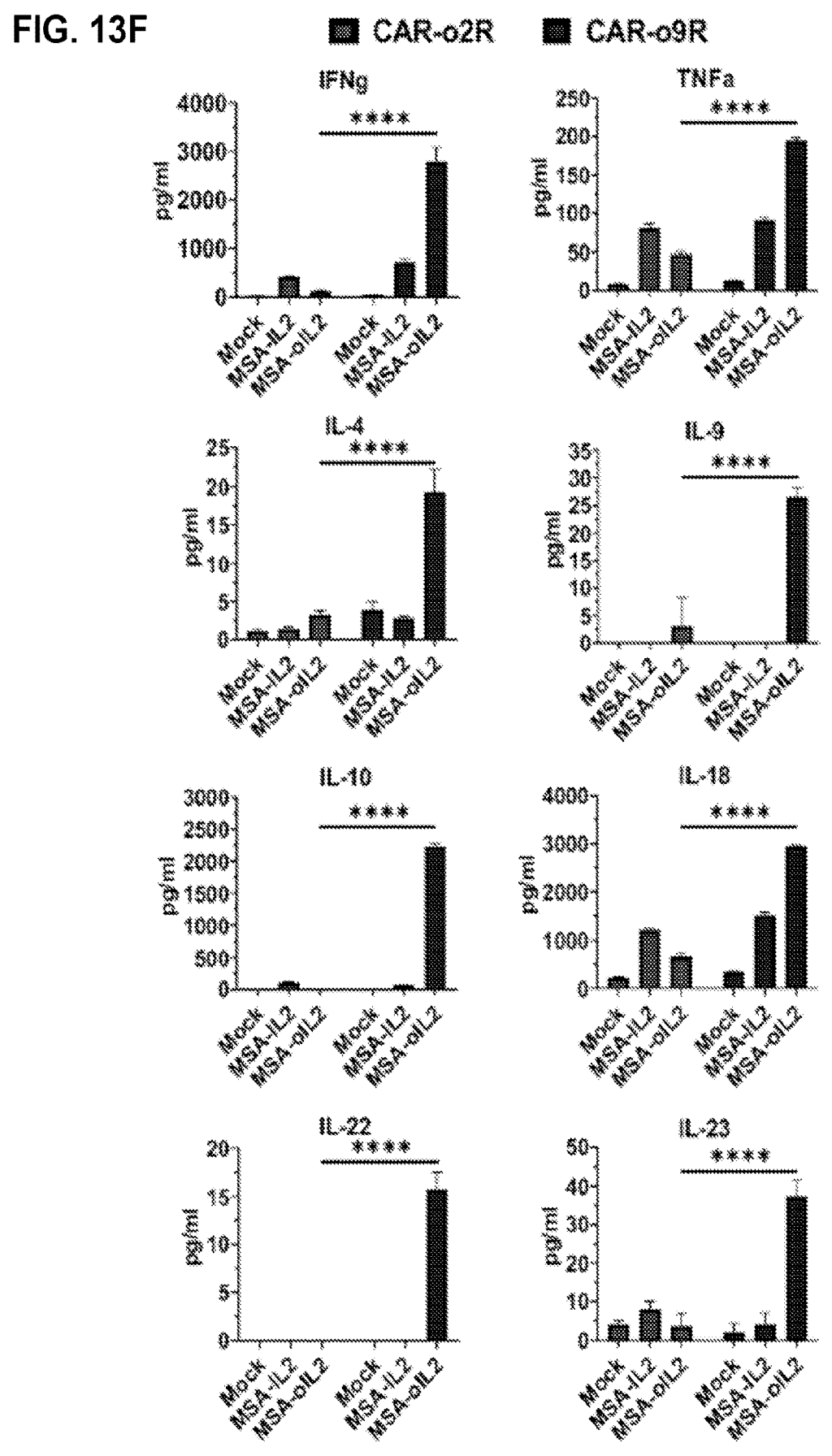

FIG. 13A-FIG. 13M illustrate orthogonal targeting of CAR T cells co-expressing o2R and o9R receptors. (FIG. 13A) Schematic of replication-deficient serotype 5 adenovirus vector Ad-oIL2 encoding oIL-2 under the constitutive cytomegalovirus (CMV) promoter (upper panel). In vitro oIL-2 expression via Ad-oIL2 in cell culture supernatants (lower left panel; means±SEM, n=3). Quantification of oIL-2 expression in tumor homogenates and sera 72 h after intratumoral (IT) injection of $1\times10^9$ viral particles of Ad-oIL2, or daily intraperitoneal (IP) injection of 25,000 units MSA-oIL2 (lower right panel; means±SEM, n=5 mice/group). LITR, left inverted terminal repeat; RITR, right inverted terminal repeat. (FIG. 13B) Representative Western blot analysis of pSTAT1/pSTAT3/pSTAT5 expression in untransduced (UTD), CAR-o2R or CAR-o9R T cells 30 minutes after stimulation with MSA-IL2 (100 nM) or MSA-oIL2 (5 μM). (FIG. 13C) In vitro cell killing of mesothelin-positive PDA7940b tumor cells by CAR-o2R and CAR-o9R T cells (2:1 effector:target ratio) pre-incubated with MSA-oIL2 (5 M) for 48 h, measured on Xcelligence live cell imaging system (means of normalized cell index, n=4). (FIG. 13D) Representative CD44 and CD62L surface co-expression on CAR-o2R/CAR-o9R T cells 4 days after stimulation with MSA-IL2 (100 nM) or MSA-oIL2 (5 μM). (FIG. 13E) Representative Fas expression on CAR-o2R/CAR-o9R T cells 4 days after stimulation with MSA-IL2 (100 nM) or MSA-oIL2 (5 μM). (FIG. 13F) Luminex analysis of secreted cytokines in CAR-o2R and CAR-o9R T cell culture supernatants following 4 days of stimulation with MSA-IL2 (100 nM) or MSA-oIL2 (5 μM) (means±SEM, n=3/group). ****P<0.0001 (ANOVA). (FIG. 13G) Heatmap of genes differentially expressed between o2R and o9R CAR T cells treated with MSA-oIL2 (left panel); groups treated with MSA-IL2 are also shown. Heatmap of manually curated genes associated with T cell stemness and dysfunction and T cell activation and effector function (middle and right panels), and differentially expressed between o9R and o2R CAR T cells in mice treated with MSA-oIL2. (FIG. 13H) Schematic of the syngeneic adoptive CAR T cell therapy mouse model utilizing KPC-derived PDA7940b tumors. Ad-oIL2 dose, $1\times10^9$ VP. CAR T cell dose, $5\times10^6$ cells. CTX dose, 120 mg/kg. SC, subcutaneous; CTX, cyclophosphamide; IP, intraperitoneal; IT, intratumoral; IV, intravenous. (FIG. 13I) Individual growth curves of PDA7940b tumors by indicated treatment group. (FIG. 13J) Individual growth curves of PDA7940b tumors by indicated treatment group. (FIG. 13K) Individual growth curves of PDA7940b tumors by indicated treatment group without cyclophosphamide preconditioning ('No CTX'). For FIG. 13I-FIG. 13K, black lines indicate deaths due to immune effector cell-associated neurotoxicity syndrome (ICANS). n=6-12 mice per group. CR, complete response. Tox, number of deaths due to neurotoxicity. Efficacy experiments were repeated twice. (FIG. 13L) Tumor volumes of cured mice (from FIG. 13J) rechallenged with PDA7940b (left panel) compared to age-matched naïve mice (n=10). Quantification of CD45.1+ lymphocytes in peripheral blood of rechallenged mice (right panel). *P<0.05, **P<0.01 (ANOVA). ns, not significant. (FIG. 13M) Quantification of tumor-infiltrating CAR T cells on Day 9 (8 days after ACT) (left panel). Frequency of IFNγ-positive tumor-infiltrating CAR T cells on Day 9 (right panel). *P<0.05, ****P<0.0001 (ANOVA).

Figure 14A:
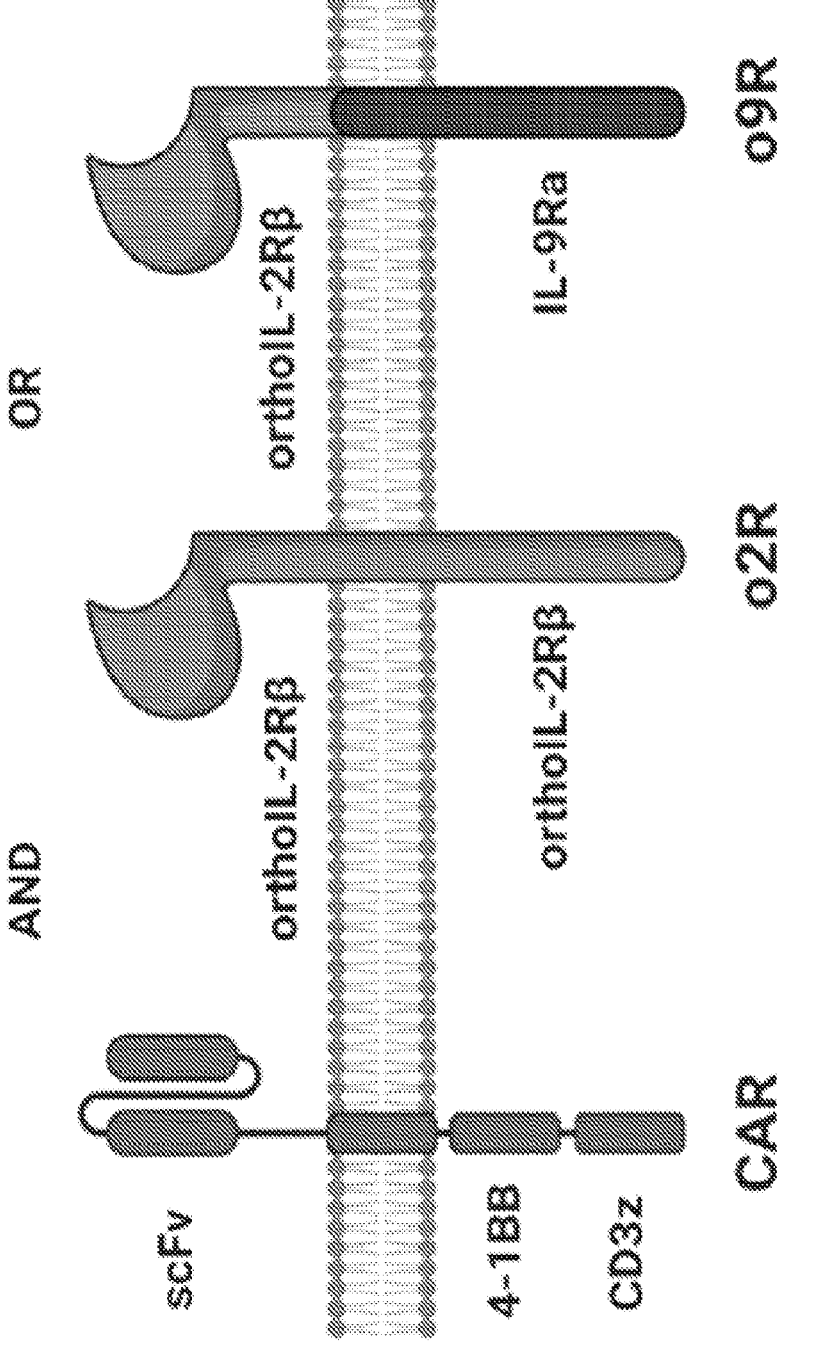
Figure 14B:
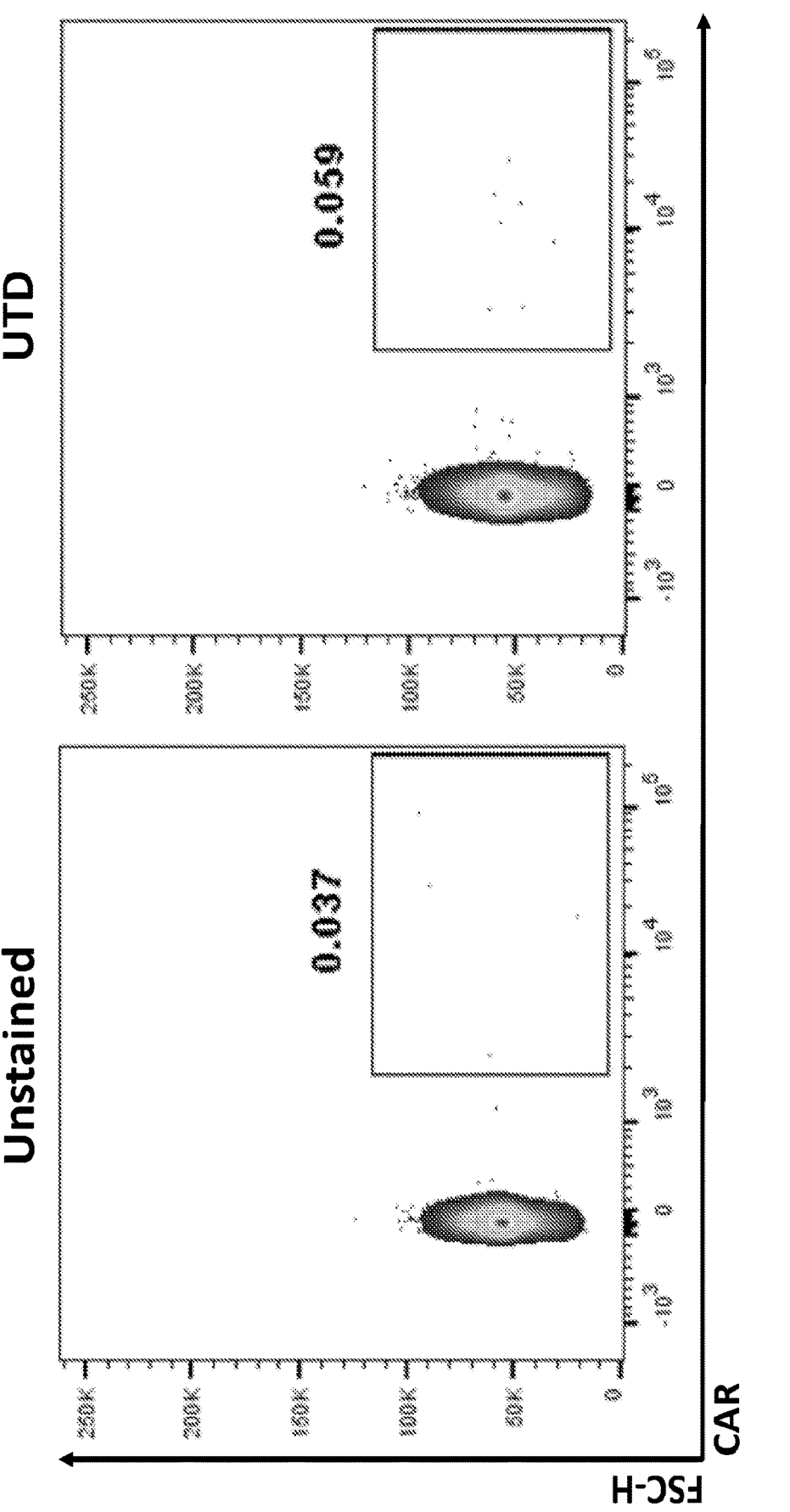
Figure 14B:
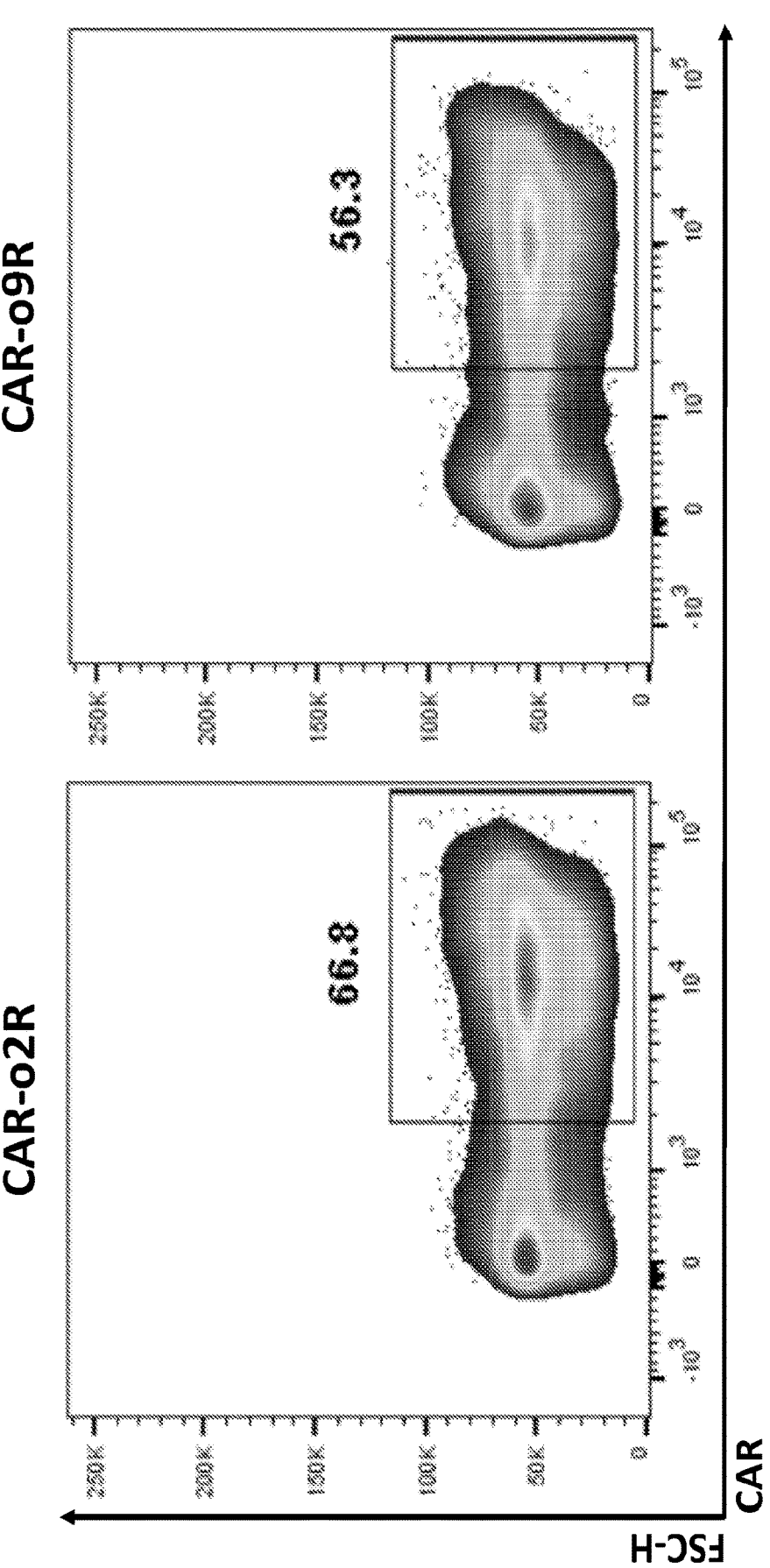
Figure 14B:
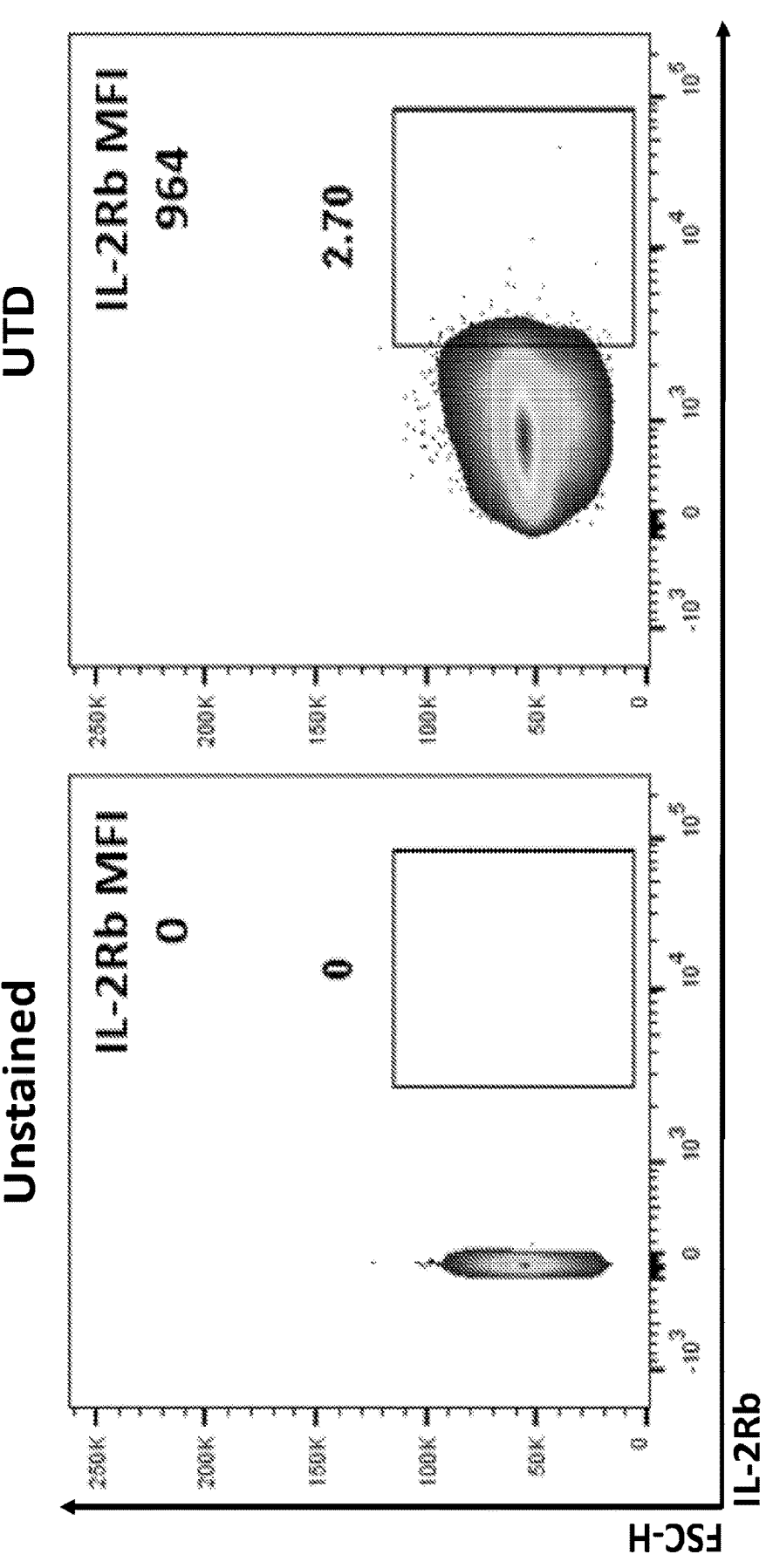
Figure 14B:
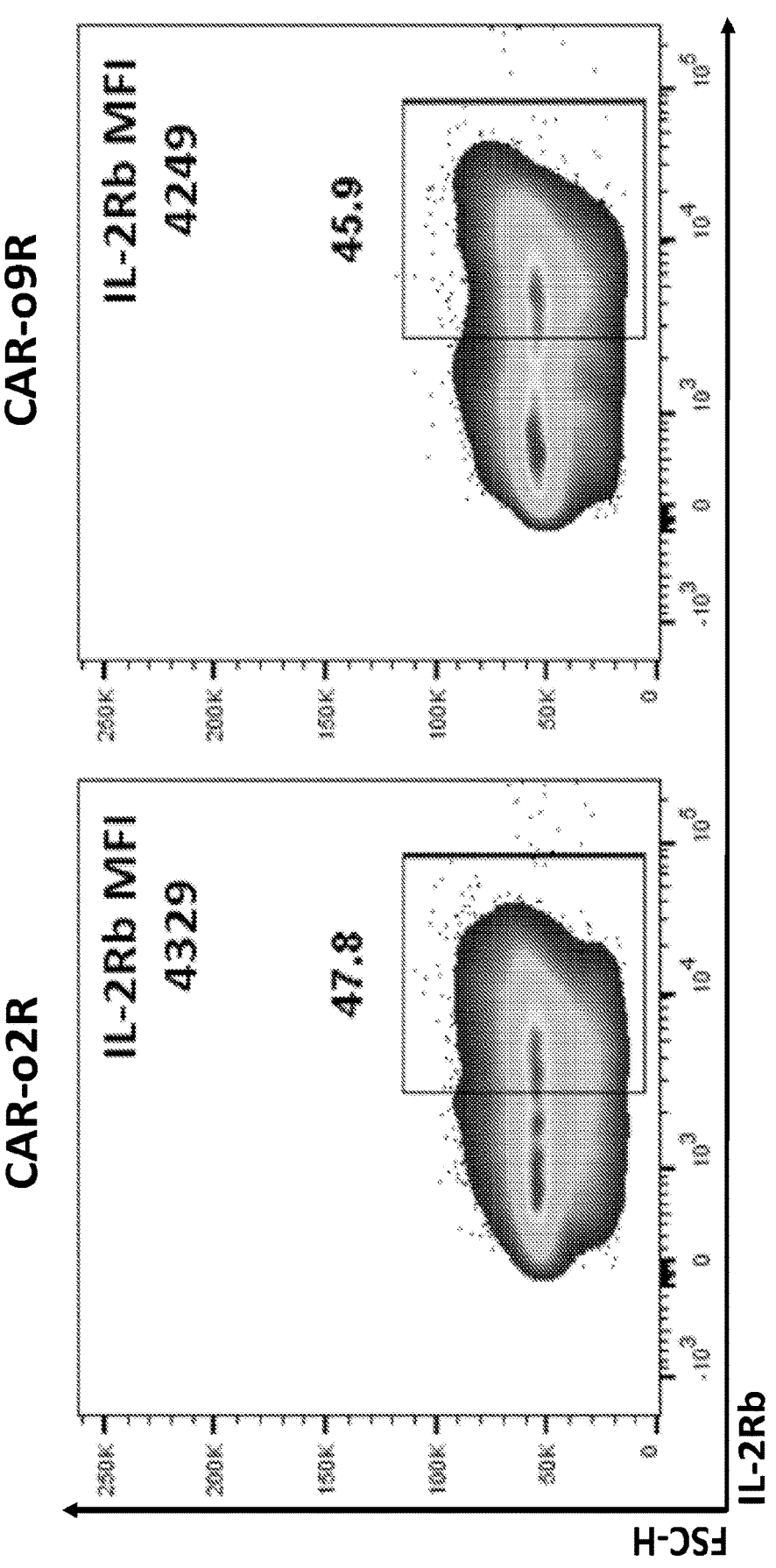
Figure 14B:
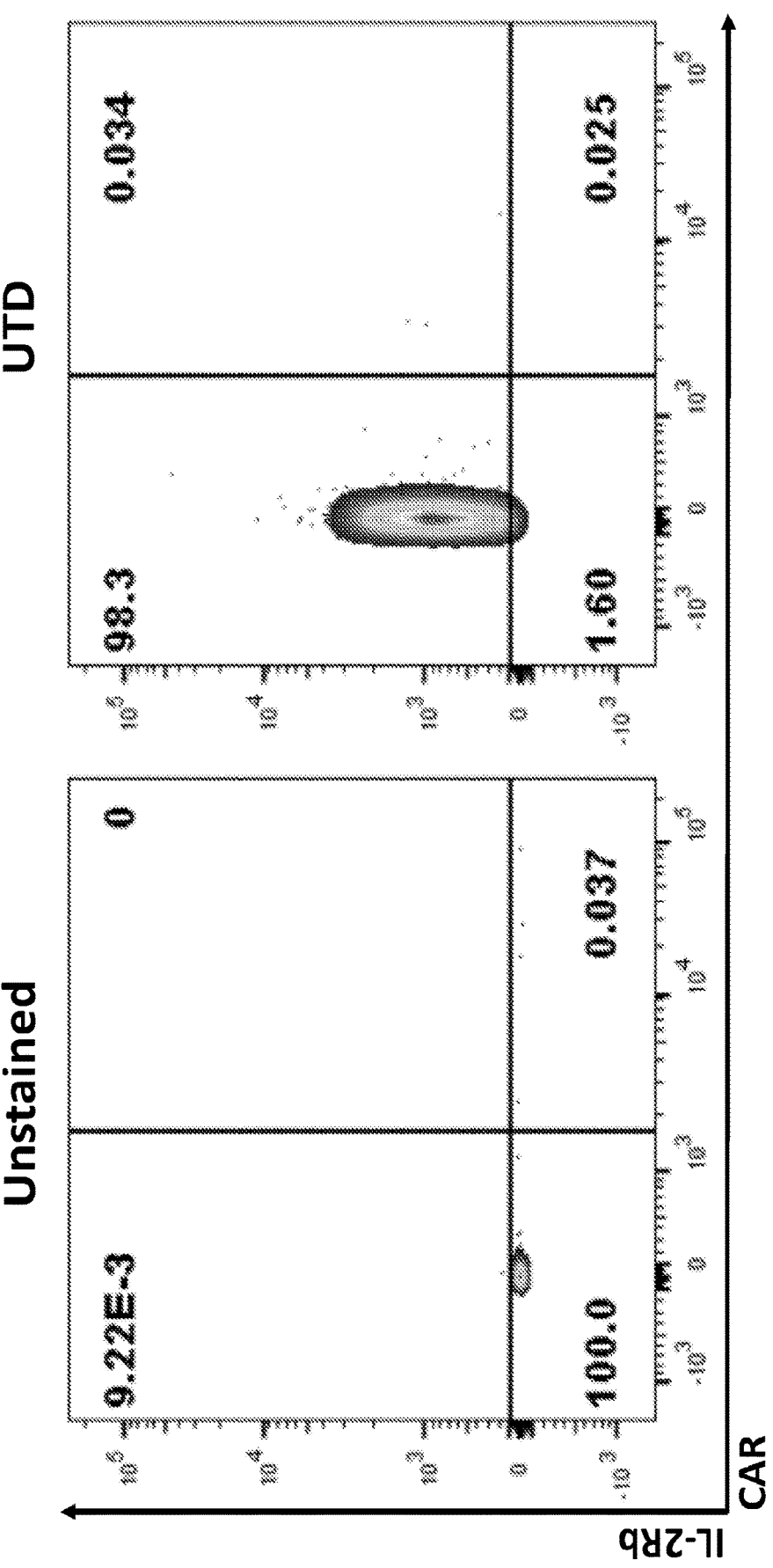
Figure 14B:
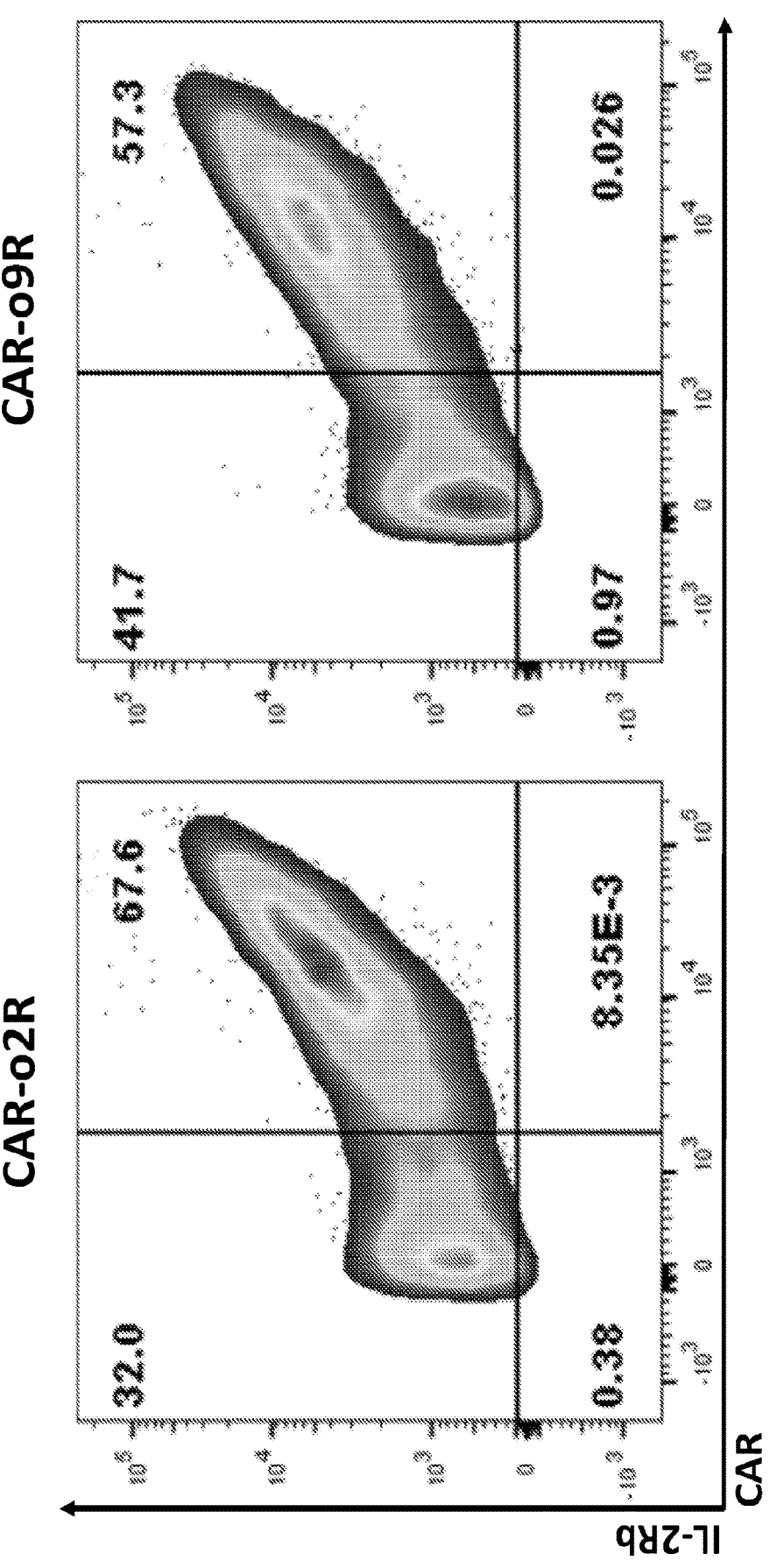

FIG. 14A-FIG. 14B illustrate CAR and orthoIL-2Rβ co-expression in mouse T cells. (FIG. 14A) Schematic of primary mouse CD3+ T cells expressing anti-mesothelin CAR and o2R (CAR-o2R) or o9R (CAR-o9R). (FIG. 14B) Representative mesothelin CAR expression (top panel), IL-2Rβ expression (middle panel) and CAR/IL-2Rβ co-expression (bottom panel) in untransduced (UTD) or retrovirally transduced CAR-o2R and CAR-o9R T cells as determined by flow cytometry. Middle panel inset, mean fluorescence intensity (MFI) of IL-2Rβ in untransduced and transduced T cells.

Figure 15A:
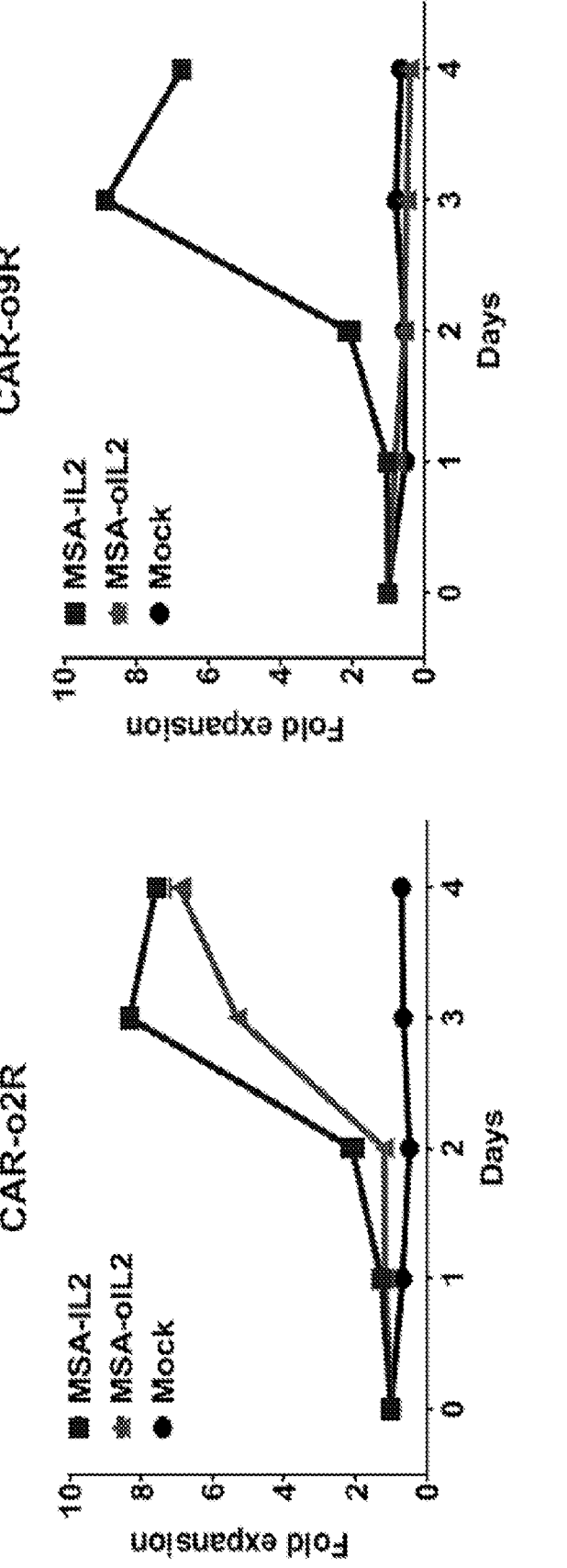
Figure 15B:
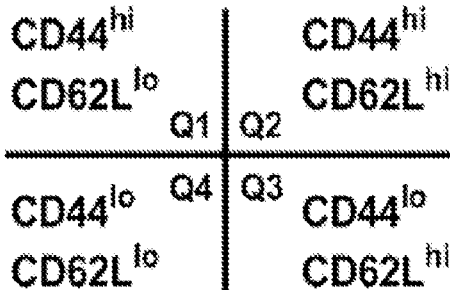

FIG. 15A-FIG. 15B illustrate expansion and phenotype of o2R and o9R CAR T cells. (FIG. 15A) In vitro CAR T cell expansion. CAR-o2R and CAR-o9R cells were incubated in the presence of MSA-IL2 (100 nM) or MSA-oIL2 (5 μM). An aliquot of cells was removed from the plate and stained with Calcein AM viability dye and counted on the Celigo Image Cytometer daily. Mean±SEM, n=3 replicate wells/group. (FIG. 15B) CD44 and CD62L co-expression on CAR T cells. Full data of representative flow plots shown in FIG. 13D. CAR-o2R and CAR-o9R cells were incubated for 4 days in the presence of MSA-IL2 (100 nM) or MSA-oIL2 (5

µM). CD44 and CD62L surface co-expression was determined by flow cytometry on live CAR+ cells. Mean±SEM, n=3/group. ns, not significant. ****P<0.0001 (ANOVA).

FIG. 16A-FIG. 16E illustrate RNA ISH and serum markers of toxicity on Day 11. (FIG. 16A) Ad-oIL2+ CAR-o2R image. (FIG. 16B) Ad-oIL2+ CAR-o9R image. For FIG. 16A-FIG. 16B: Representative images of brain and meningeal sections stained with fluorescent probes specific for mouse CAR (red, Cy3), mouse mesothelin (green, FITC) and counterstained with DAPI (blue). CAR-positive cells (white arrows) and mesothelin-positive meningeal cells (purple arrows) indicated in the pia-arachnoid layer of the meninges. (FIG. 16C) Semi-quantification of CAR T cells in stained brain sections. Mean+SEM, 2 sections/mouse, 3 mice/group. *P<0.05 (t test with Welch's correction). (FIG. 16D) Serum levels of calcium, phosphorus, potassium, and uric acid on Day 11 of treatment. Mean+SEM, n=3 mice/group. (FIG. 16E) Serum levels of CRS-associated cytokines on Day 11 of treatment. Mean+SEM, n=3 mice/group.

Figure 17A:
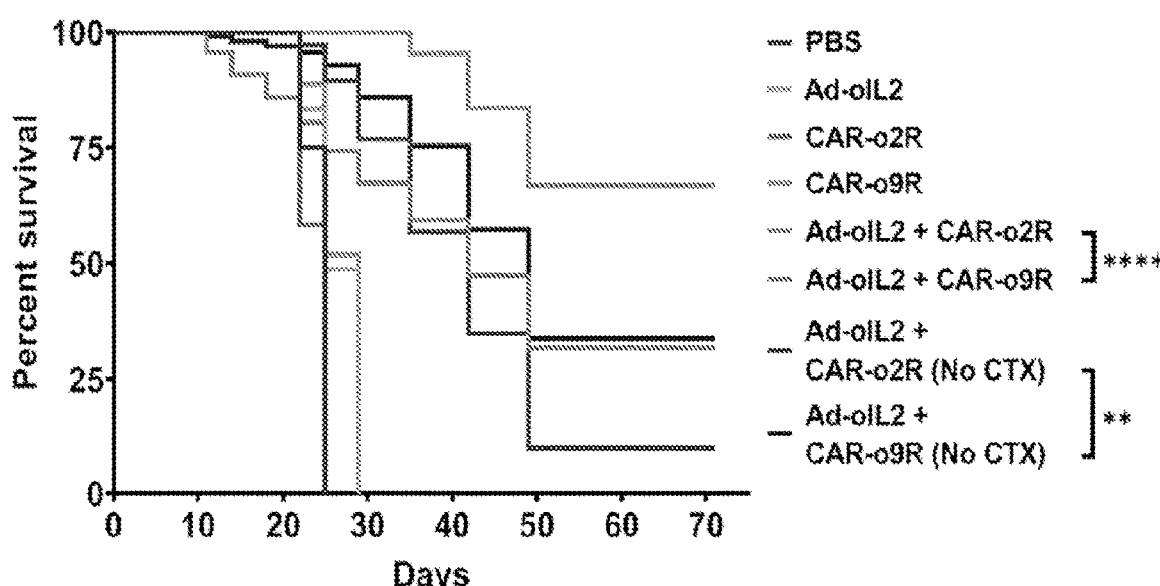
Figure 17B:
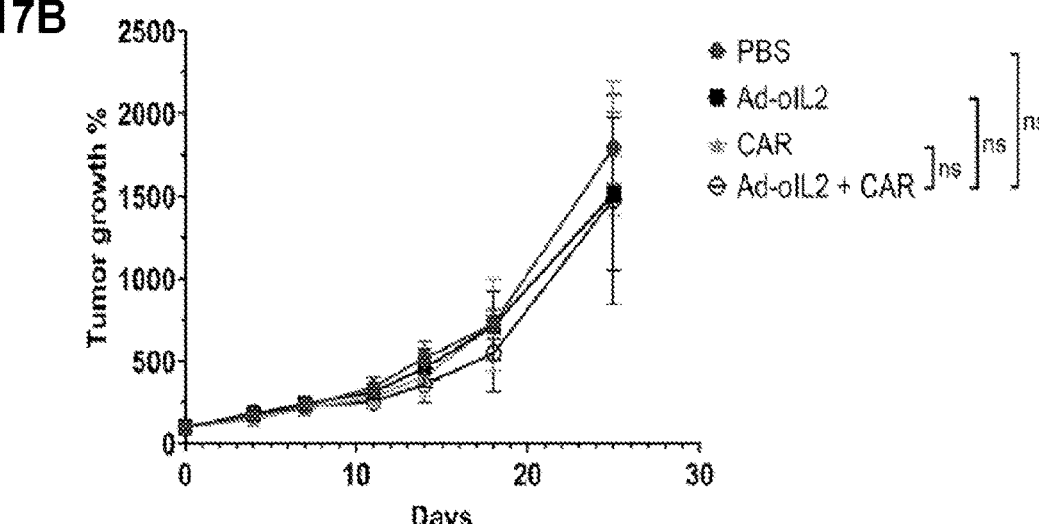
Figure 17C:
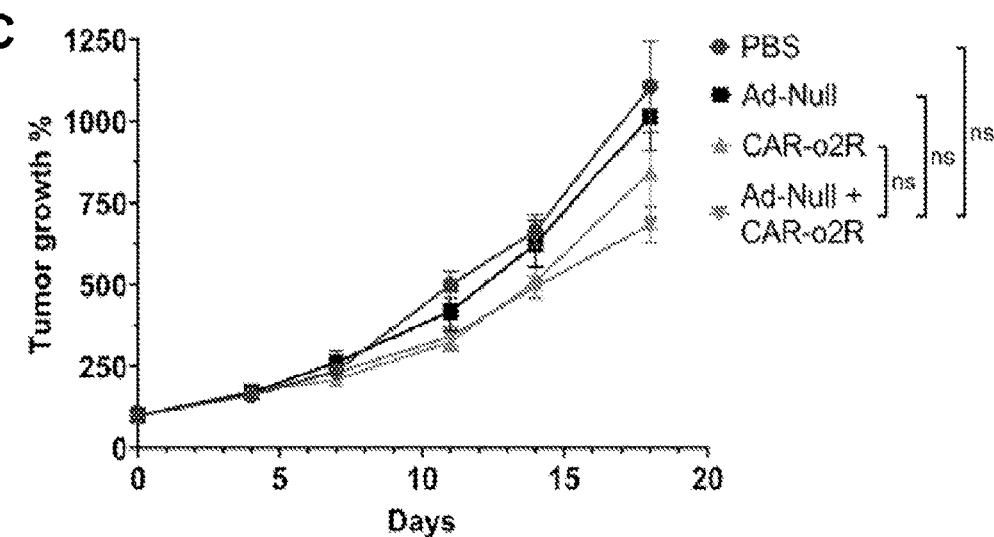

FIG. 17A-FIG. 17C provide data related to survival and anti-tumor efficacy in mice. (FIG. 17A) Survival differences between mice treated with CAR-o2R+Ad-oIL2 and CAR-o9R T cells+Ad-oIL2 with or without conditioning chemotherapy. Kaplan-Meier survival curves of treatment groups in FIGS. 13I-13K. P<0.01, **P<0.0001 (Log rank Mantel-Cox test). (FIG. 17B) Antitumor efficacy in mice treated with Ad-oIL2 and CAR T cells (without orthogonal cytokine receptor). Established subcutaneous PDA7940b tumors were treated with Ad-oIL2 on Days 0 and 4 ($1\times10^9$ VP/tumor) and with CAR T cells on Day 0 ($5\times10^6$). Mean SEM, n=5 mice/group. ns, not significant. (FIG. 17C) Anti-tumor efficacy in mice treated with Ad-Null (no transgene) and CAR-o2R T cells. Established subcutaneous PDA7940b tumors were treated with Ad-Null on Days 0 and 4 ($1\times10^9$ VP/tumor) and with CAR-o2R T cells on Day 0 ($5\times10^6$). Mean+SEM, n=5 mice/group. ns, not significant.

FIG. 18A-FIG. 18G illustrates the finding that human chimeric orthogonal IL-2Rβ/IL-9R drives stemness and polyfunctionality in TCR-engineered T cells. (FIG. 18A) pSTAT signaling in human T cells co-expressing either ho2R or ho9R and the NY-ESO-1 TCR and stimulated with MSA-hoIL2 or MSA-hIL2 for 20'. Data shown as mean fluorescence+/−SEM, n=3. (FIG. 18B) Fold expansion of ho2R/NYESO1-TCR and ho9R/NYESO1-TCR engineered human T cells treated with MSA-hoIL2 (1 µM) or MSA-hIL2 (0.1 µM) over six days. (FIG. 18C) Immunophenotype ho2R/NYESO1-TCR and ho9R/NYESO1-TCR engineered human T cells after six days in culture with MSA-hoIL2 (1 M). Shown are representative plots of CD45RA and CD27 expression gated on YFP+ T cells (top row), and CD95 and CCR7 expression gated on the CD45RA+CD27+ population (indicated by arrow and dotted line). Quantification of CD45RA+CD27+CD95+CCR7+$T_{SCM}$ cells as a percentage of YFP+ population is shown in bar plot to the right. ****, p<0.0001 (unpaired t-test, n=3/group). (FIG. 18D) Fold expansion of $T_{SCM}$ and $T_{CM}$ cells cultured in vitro with MSA-hoIL2 (1 µM) or MSA-hIL2 (0.1 µM), relative to day 2. *, p<0.05; **, p<0.01 (unpaired t-test, n=3/group). (FIG. 18E) T cells co-expressing either ho2R or ho9R and the NY-ESO-1 TCR preincubated with MSA-hoIL2 (1 µM) for 48 h were cocultured at 1:1 E:T ratio with HLA*0201+NY-ESO-1+ melanoma tumor cell line expressing nRFP (nRFP-M407) in the presence of MSA-hoIL2. Untransduced T cells in the presence of MSA-hIL2 (1 nM) were used as a negative control. Tumor cells (105) were reintroduced into coculture every 72 h (light blue arrows); MSA-hoIL2 (1 µM) was added to culture 24 h prior to every tumor challenge. Live cell images were captured every 2 h and percent tumor confluence was measured based on RFP expression. After the fourth tumor challenge, T cells were harvested for phenotypic analysis (see, FIG. 18F) and restimulation and intracellular cytokine staining (ICS)(see, FIG. 18G). (FIG. 18F) Quantification of CD45RA+CD27+ and $T_{SCM}$ cells as a percentage of YFP+ T cells, alongside CD62L and CXCR3 MFI (YFP+ gate). *, p<0.05; , p<0.01; *, p<0.001 (unpaired t-test, n=2/group). (FIG. 18G) T cells after the fourth tumor challenge from FIG. 18E were re-stimulated for 4 h with either αCD3/αCD28 activating antibodies, melanoma cell line M407 (HLA*0201+NY-ESO-1+) or M263 (HLA*0201⁻NY-ESO-1⁻). IFNγ, TNFα, and IL-2 were quantified among CD8+ YFP+ T cells by ICS. Donut charts indicate the proportion of CD8+ YFP+ T cells in each group expressing 0, 1, 2 or 3 of 3 cytokines. ns, not significant; ****, p<0.0001 (two-way ANOVA, n=3/group).

FIG. 19A-FIG. 19D illustrate the finding that human chimeric orthogonal IL-2Rβ/IL-9R drives polyfunctional T cells with stem-like phenotype even after repetitive antigen-specific tumor challenge. (FIG. 19A) Flow plots of normal healthy donor T cells co-transduced with either ho2R and NYESO1-TCR (left) or ho9R and NYESO1-TCR (right), as detected by anti-human Vβ13.1 antibody that recognizes the βchain of the NYESO1-TCR clone 1G4 and YFP (internal marker of the o2R or o9R vectors). Co-transduction efficiencies are shown. (FIG. 19B) Gating strategy for immunophenotyping of YFP+ population of ho2R/NYESO1-TCR and ho9R/NYESO1-TCR T cells shown in FIG. 18C. (FIG. 19C) Immunophenotype of ho2R/NYESO1 TCR and ho9R/NYESO1 TCR engineered human T cells after two days in culture with MSA-hoIL2 (1 µM). Shown is bar plot quantification of $T_{SCM}$ cells as a percentage of the YFP+ population. **, p<0.01 (unpaired t-test, n=3/group). (FIG. 19D) T cells from FIG. 13E were harvested and re-stimulated for 4 h with either αCD3/αCD28 dynabeads, melanoma cell line M407 (HLA*0201+NY-ESO-1+) or M263 (HLA*0201+NY-ESO-1-). IFNγ, TNFα, and IL-2 were quantified among YFP+CD4 T cells (CD8−) by ICS.

FIG. 20 provides a table of reagents used in the experiments described herein.

Figure 21:
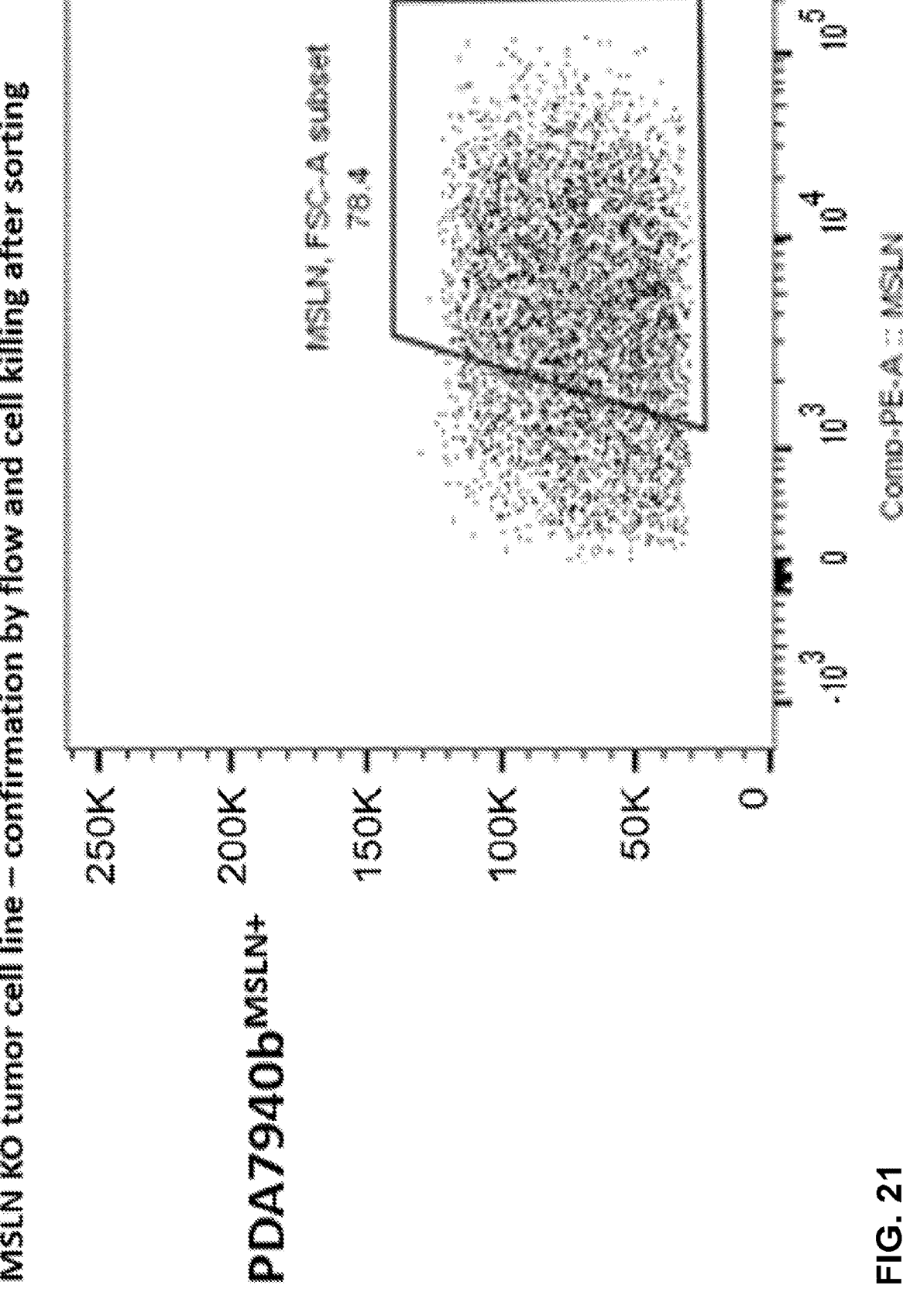
Figure 21:
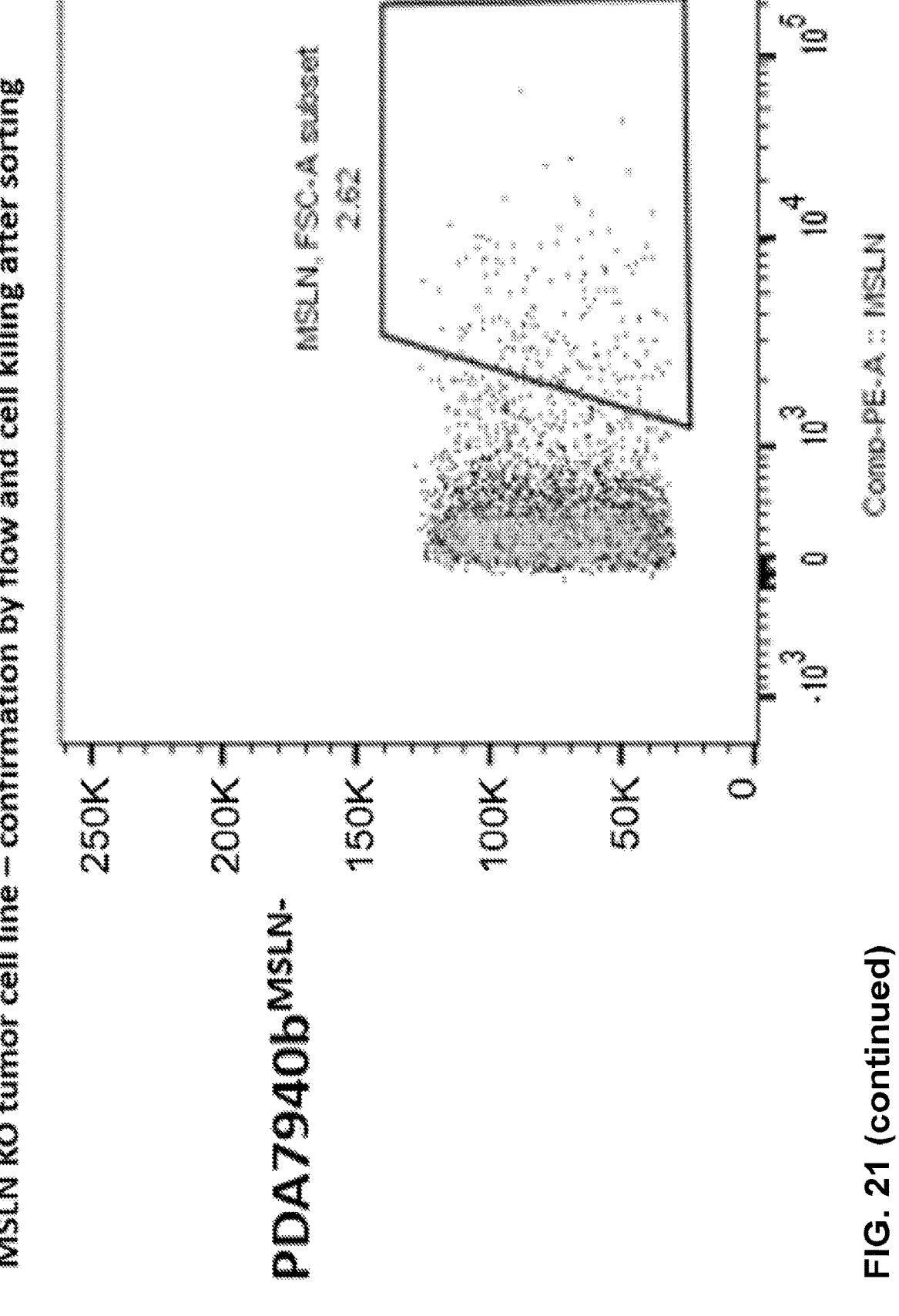
Figure 21:
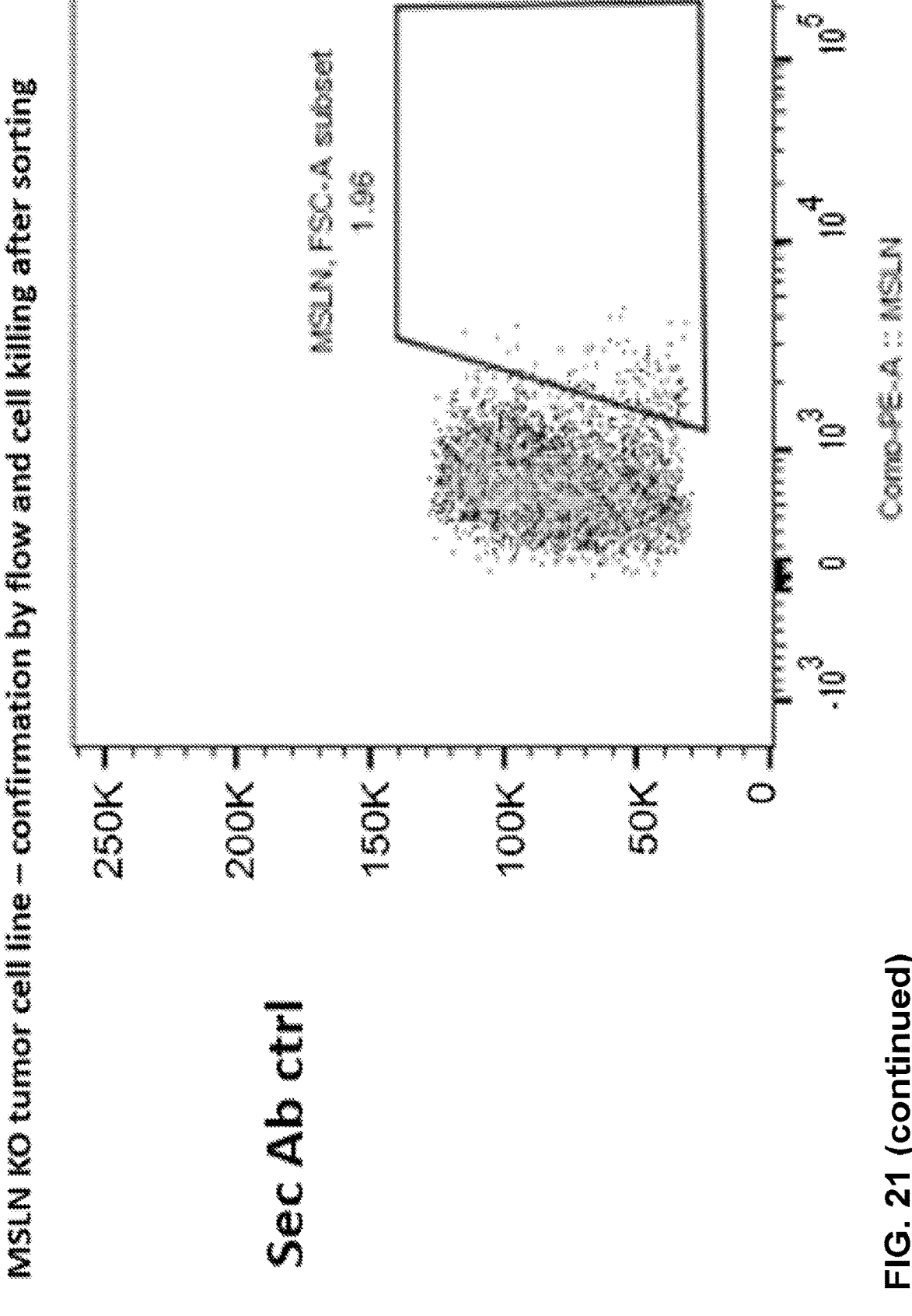

FIG. 21 illustrates generation of mesothelin knockout cell line. Mesothelin-positive PDA7940b tumor cells were edited by CRISPR/Cas9 to knock out mesothelin and sorted to purity by FACS. Anti-mesothelin CAR T cells killed wild-type cells (PDA7940bMSLN+) but not KO cells (PDA7940bMSLN−) in a real-time cell killing assay (RTCA).

Figure 22:
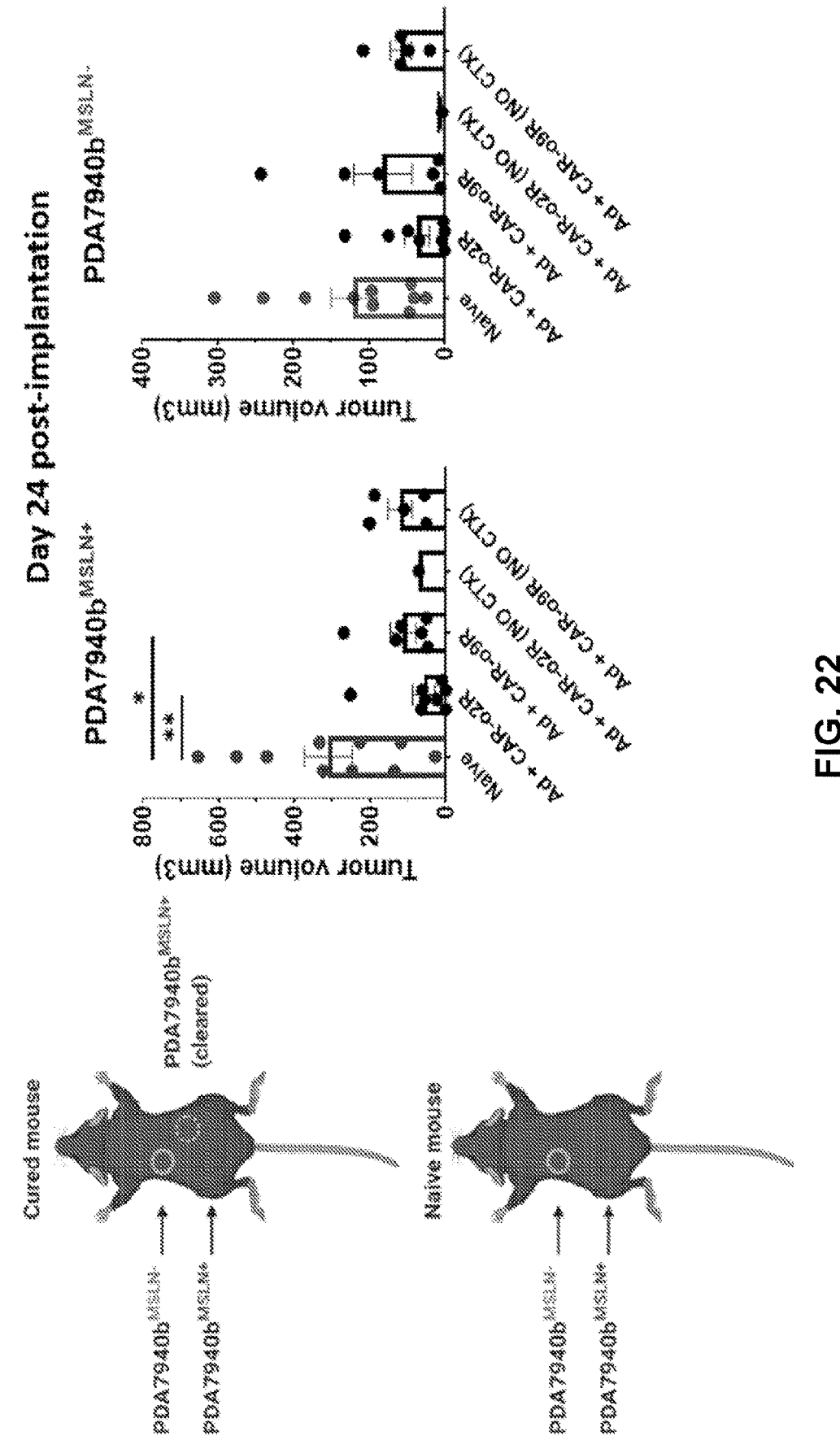

FIG. 22 illustrates tumor antigen spreading. Mice previously cured with combination treatments were re-challenged with mesothelin-positive (PDA7940bMSLN+) and mesothelin-negative (PDA7940bMSLN−) tumor cells. Tumors were allowed to grow for 24 days before tumor size was measured. Age-matched naïve mice served as control for tumor growth.

FIG. 23A-FIG. 23B provide data related to human orthoIL-2. FIG. 23A provides a graph illustrating in vitro expression of human orthoIL-2 via Ad5/3-D24-hoIL2. A549 cells were infected with Ad5/3-D24-hoIL2 or isogenic control virus Ad5/3-D24 or mock-infected. 96 hours post-infection 50 ul of cell culture supernatant was collected and analyzed by human IL-2 ELISA. FIG. 23B provides photographs illustrating purification of fiber-chimeric oncolytic adenovirus Ad5/3-D24-hoIL2 encoding human orthoIL-2 via cesium chloride (CsCl) gradients. Red arrow indicates the band containing intact virus particles that are collected with needle and syringe by puncturing the side of the tube. CsCl was removed by two rounds of buffer exchange.

Figure 24A:
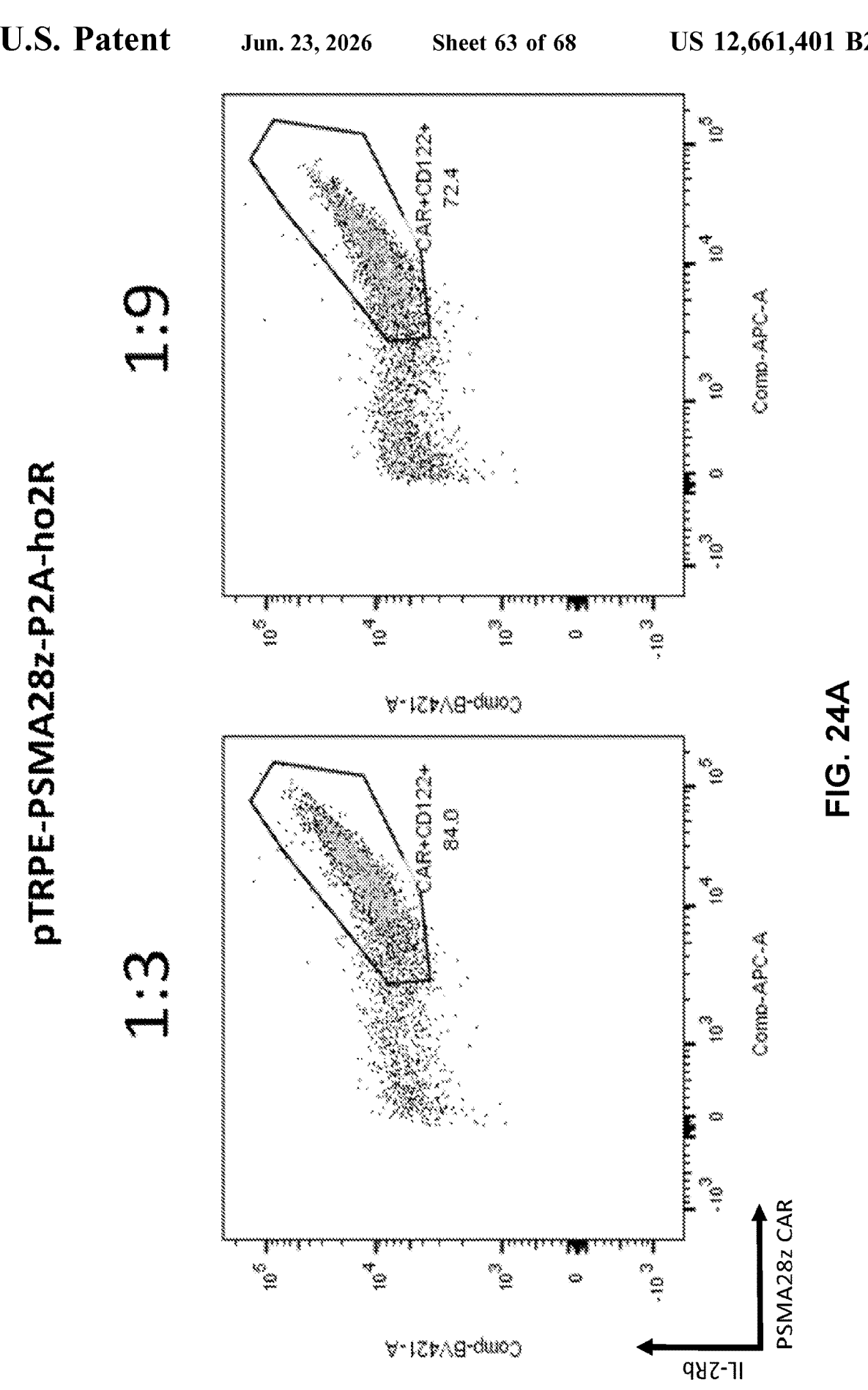
Figure 24A:
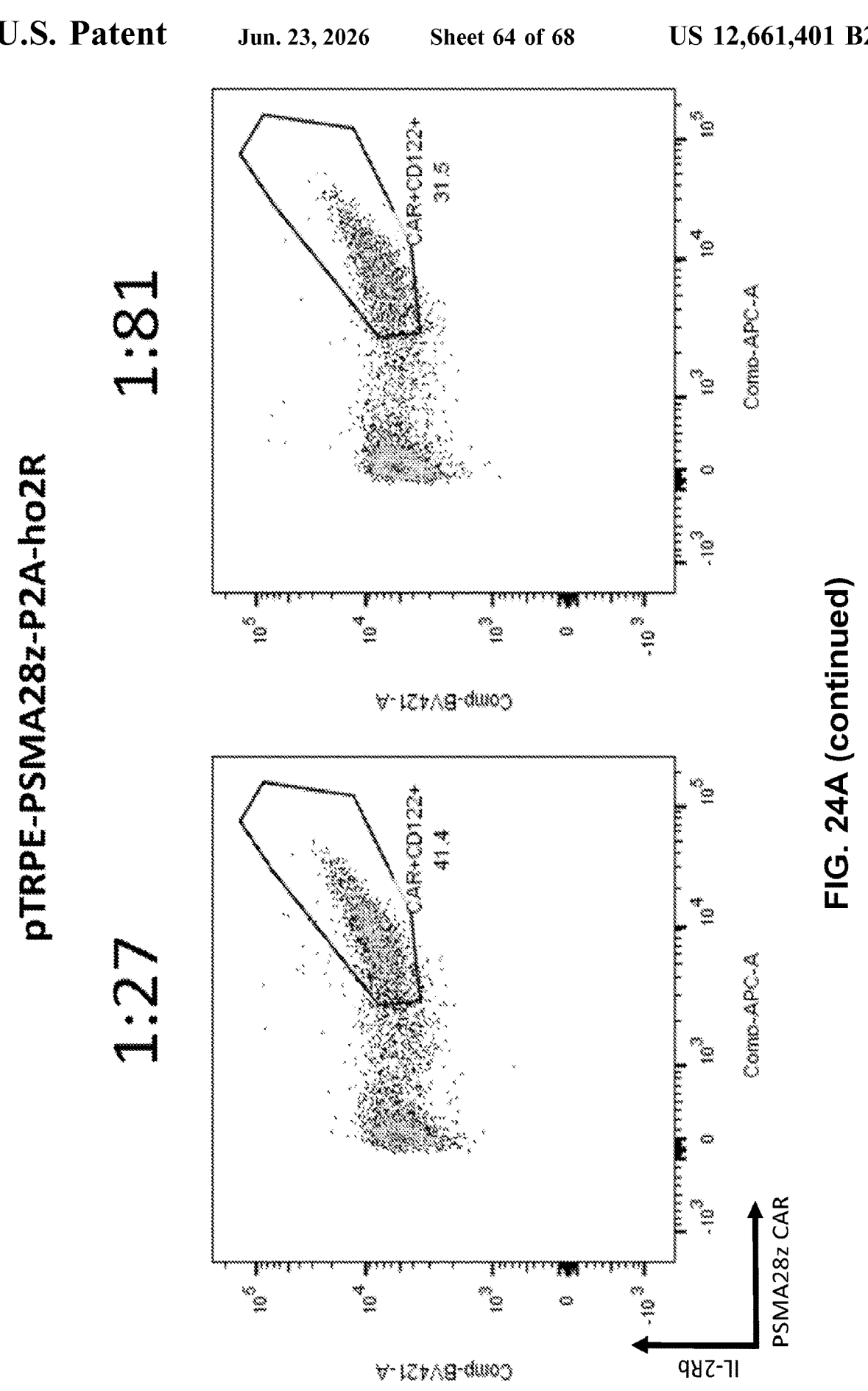
Figure 24A:
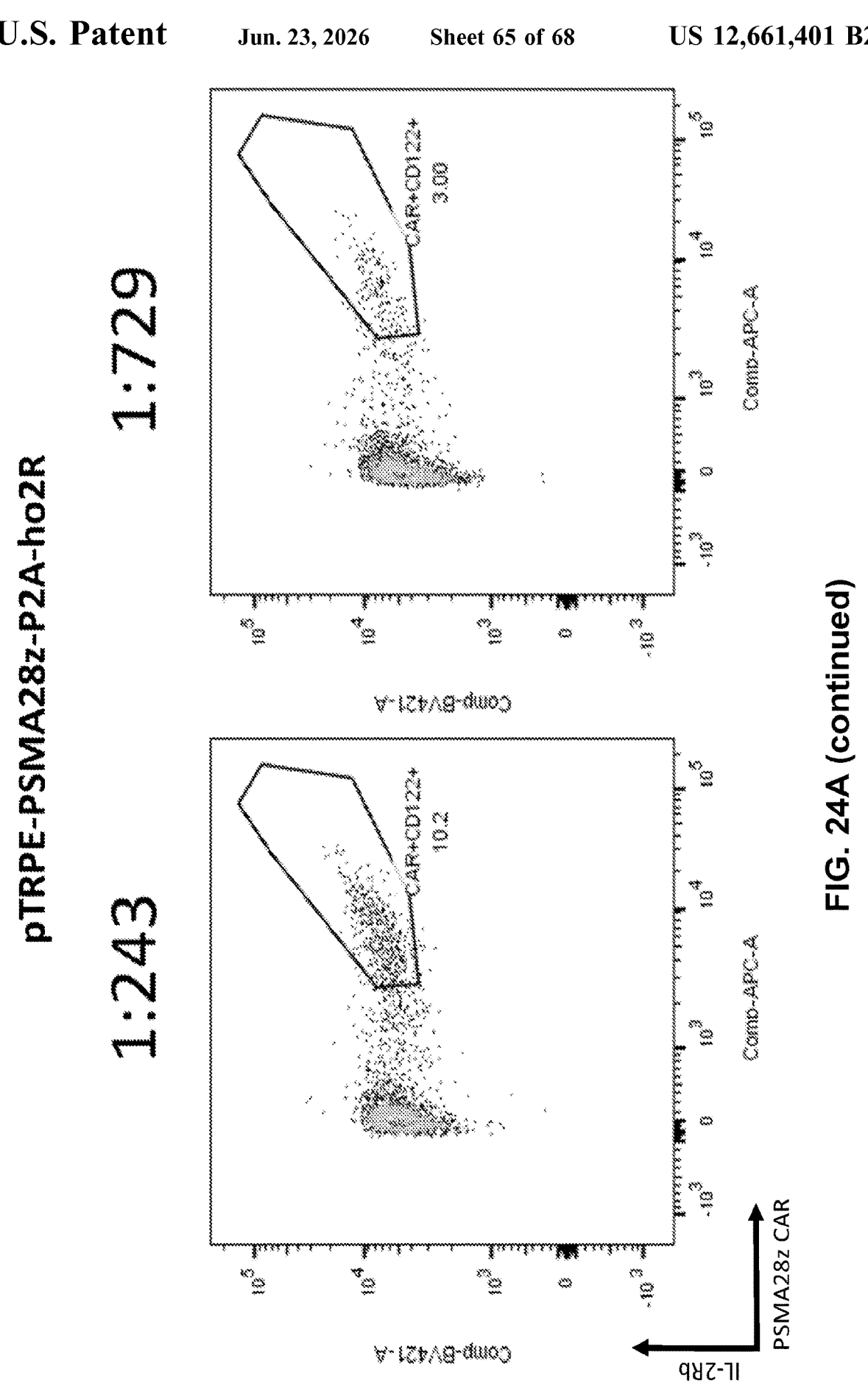
Figure 24B:
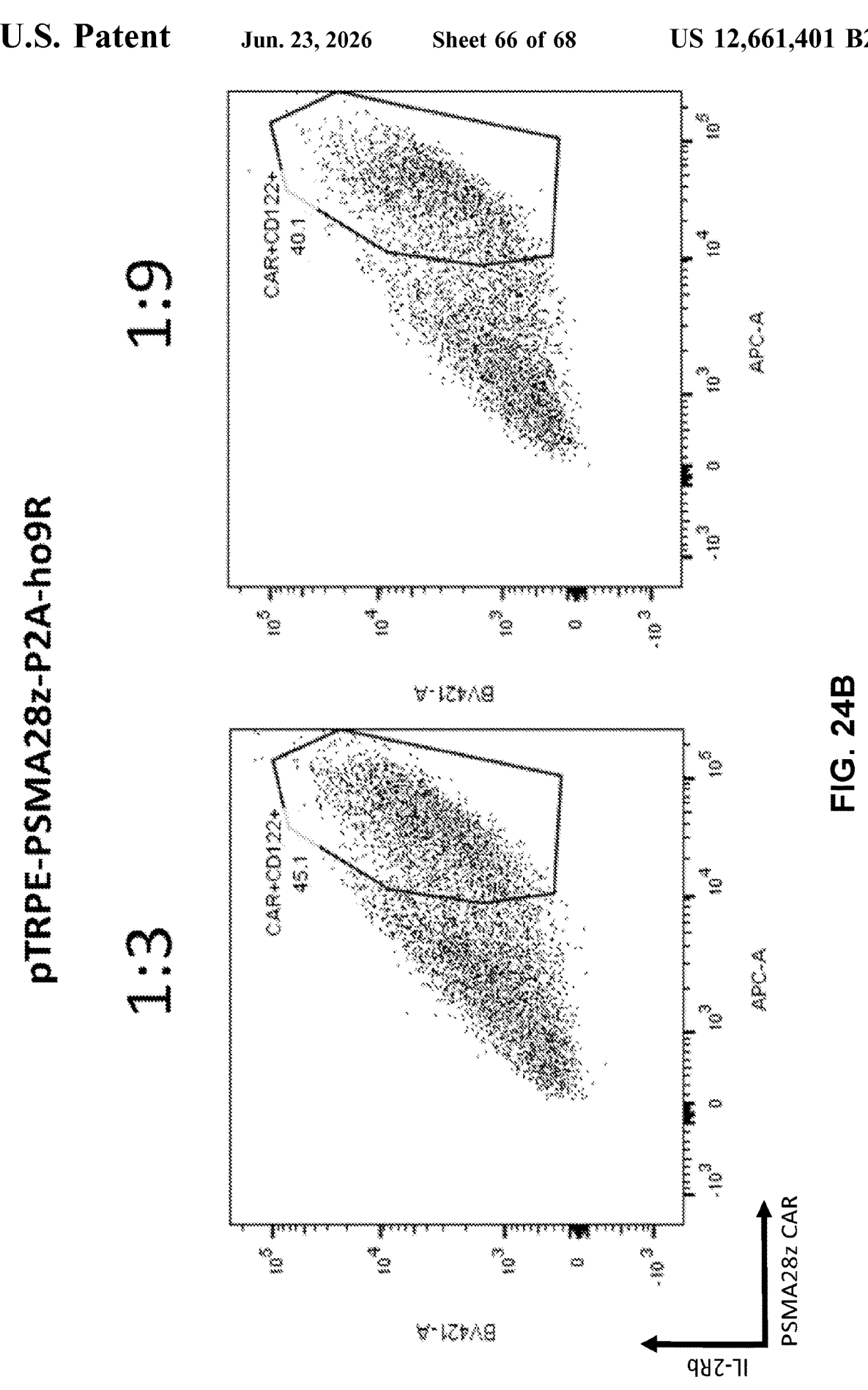
Figure 24B:
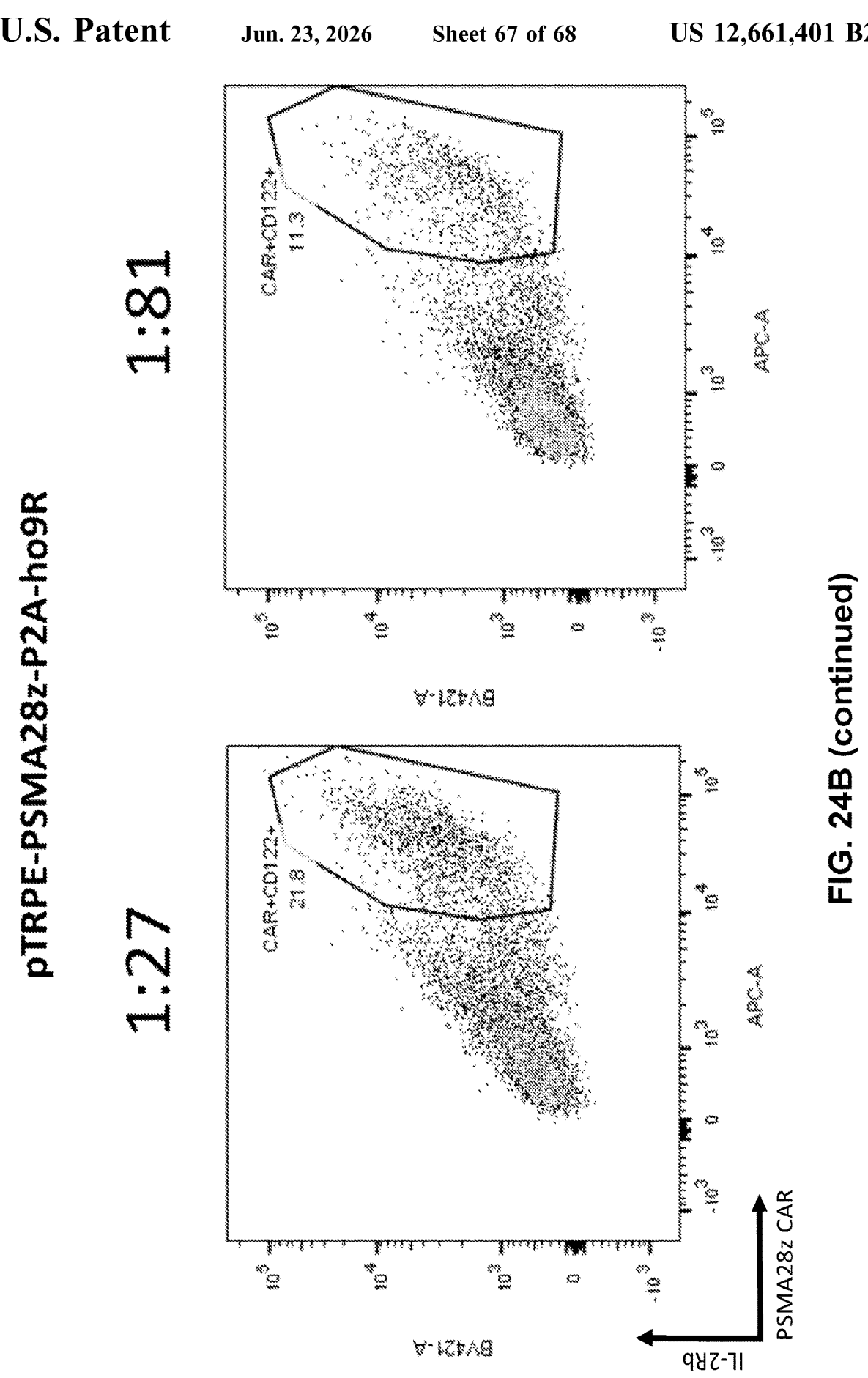
Figure 24B:
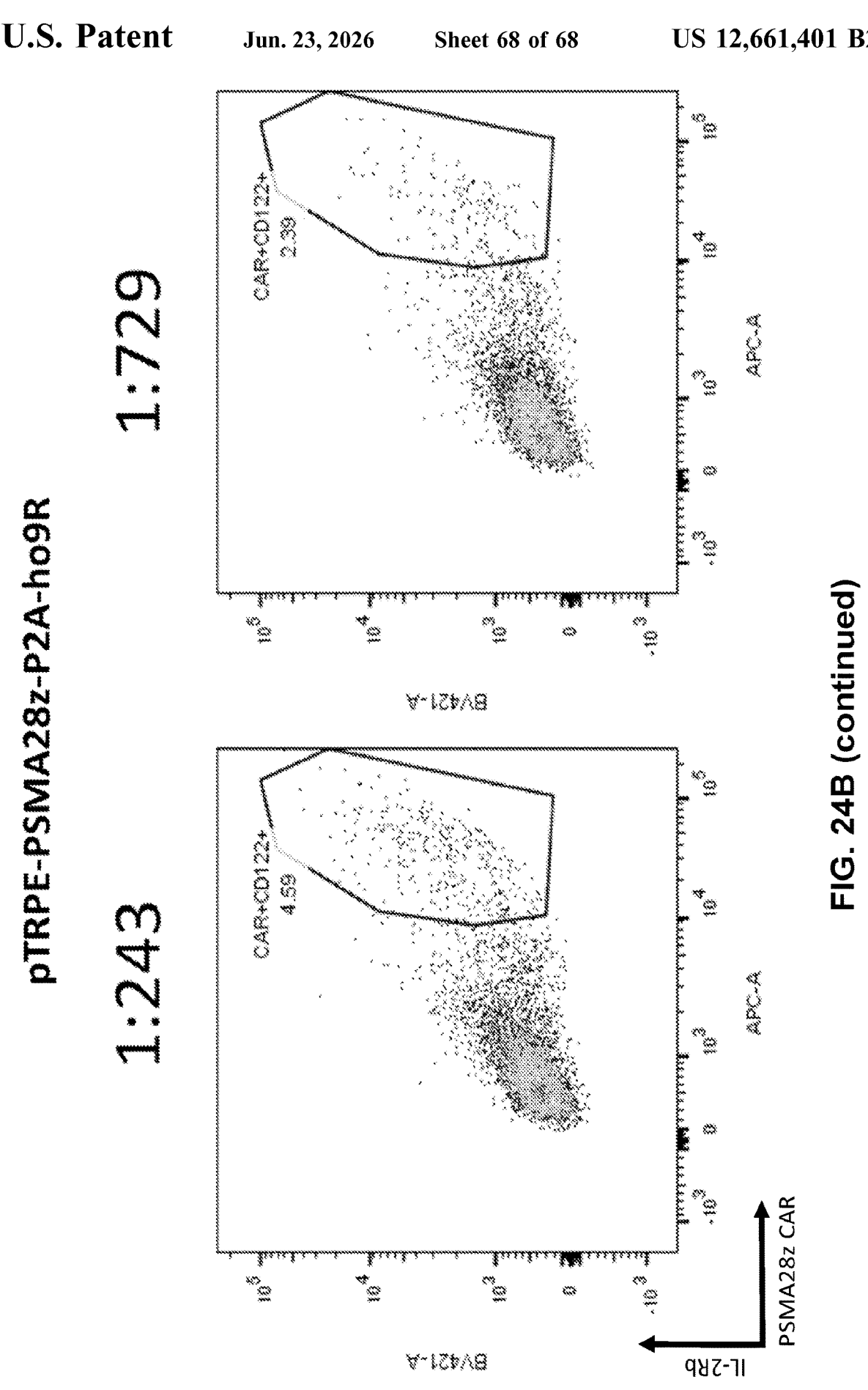

FIG. 24A-FIG. 24B provide data illustrating co-expression of human ortho-receptors and PSMA-retargeted CAR in human T cells. FIG. 24A provides flow cytometry data illustrating co-expression of PSMA28z CAR and full-length human orthoIL2Rb receptor 48 h post-infection. FIG. 24B provides flow cytometry data illustrating co-expression of PSMA28z CAR and chimeric orthoIL2Rb/IL9Ra switch receptor 48 h post-infection.

DETAILED DESCRIPTION

In one aspect, the present invention provides compositions and methods for modified immune cells or precursors thereof (e.g., modified T cells) comprising an orthogonal chimeric cytokine receptor (e.g., an oIL2R-IL9R chimeric receptor) and at least one chimeric antigen receptor (CAR). The present disclosure further provides an oncolytic adenoviral vector comprising a nucleic acid sequence encoding an orthogonal cytokine (e.g., oIL2). Also provided are methods of using the modified cells and vector to treat cancer. In one aspect, the invention provides a method of treating cancer comprising administering (a) modified cells comprising an orthogonal chimeric cytokine receptor and at least one CAR and (b) an oncolytic adenoviral vector comprising a nucleic acid sequence encoding an orthogonal cytokine to a subject having cancer, wherein the modified T cells assume stem cell memory (Tscm) features with improved trafficking and effector function in the subject, thereby treating the caner.

In another aspect, the present invention provides compositions and methods for modified immune cells or precursors thereof (e.g., modified T cells) comprising an orthogonal chimeric cytokine receptor (e.g., an oIL2R-IL9R chimeric receptor) and at least one T cell receptor (TCR). The present disclosure further provides an oncolytic adenoviral vector comprising a nucleic acid sequence encoding an orthogonal cytokine (e.g., oIL2). Also provided are methods of using the modified cells and vector to treat cancer. In one aspect, the invention provides a method of treating cancer comprising administering (a) modified cells comprising an orthogonal chimeric cytokine receptor and at least one TCR and (b) an oncolytic adenoviral vector comprising a nucleic acid sequence encoding an orthogonal cytokine to a subject having cancer, wherein the modified T cells assume stem cell memory (Tscm) features with improved trafficking and effector function in the subject, thereby treating the caner.

It is to be understood that the methods described in this disclosure are not limited to particular methods and experimental conditions disclosed herein as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2nd edition).

A. Definitions

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±110%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, to "alleviate" a disease means reducing the severity of one or more symptoms of the disease.

The term "antigen" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen.

Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly about 10 amino acids and/or sugars in size. Preferably, the epitope is about 4-18 amino acids, more preferably about 5-16 amino acids, and even more most preferably 6-14 amino acids, more preferably about 7-12, and most preferably about 8-10 amino acids. One skilled in the art understands that generally the overall three-dimensional structure, rather than the specific linear sequence of the molecule, is the main criterion of antigenic specificity and therefore distinguishes one epitope from another. Based on the present disclosure, a peptide used in the present invention can be an epitope.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immune response" as used herein is defined as a cellular response to an antigen that occurs when lymphocytes identify antigenic molecules as foreign and induce the formation of antibodies and/or activate lymphocytes to remove the antigen.

The term "immunosuppressive" is used herein to refer to reducing overall immune response.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "oligonucleotide" typically refers to short polynucleotides. It will be understood that when a nucleotide sequence is represented by a DNA sequence (i.e., A, T, C, G), this also includes an RNA sequence (i.e., A, U, C, G) in which "U" replaces "T."

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Parenteral" administration of an immunogenic composition includes, e.g., subcutaneous (s.c.), intravenous (i.v.), intramuscular (i.m.), or intraosteal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used herein, may be a human or non-human mammal. Non-human mammals include, for example, livestock and pets, such as ovine, bovine, porcine, canine, feline and murine mammals, as well as simian and non-human primate mammals. Preferably, the subject is human.

A "target site" or "target sequence" refers to a nucleic acid sequence that defines a portion of a nucleic acid to which a binding molecule may specifically bind under conditions sufficient for binding to occur. In some embodiments, a target sequence refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (α) and beta (β) chain, although in some cells the TCR consists of gamma and delta (γ/δ) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

An "ortholog", or "orthogonal cytokine/receptor pair" refers to a genetically engineered pair of proteins that are modified by amino acid changes to (a) exhibit significantly reduced affinity to the native cytokine or cognate receptor; and (b) to specifically bind to the counterpart engineered (orthogonal) cytokine or receptor. Upon binding of the orthogonal cytokine, the orthogonal cytokine receptor activates signaling that is transduced through native cellular elements to provide for a biological activity that mimics that native response, but which is specific to an engineered cell expressing the orthogonal receptor. Engineered orthogonal cytokine/receptor pairs are described, e.g., in WO 2017/044464 and WO 2019/173773, which are incorporated herein by reference. Orthogonal cytokine/receptor pairs are used to direct the activity of a promiscuous cytokine to a T cell subset of interest, thereby enabling precise control over T cell function though genetic engineering.

An "orthogonal chimeric cytokine receptor" refers to a cytokine receptor comprising an extracellular domain of an orthogonal cytokine receptor and an intracellular signaling domain of a cytokine receptor which is distinct from the cytokine receptor from which the orthogonal cytokine receptor is derived. Upon binding of the orthogonal cytokine, the orthogonal chimeric cytokine receptor activates signaling that is transduced through native cellular elements to provide for a biological activity that mimics the native response of the receptor from which the intracellular signaling domain is derived, but which is specific to an engineered cell expressing the orthogonal chimeric cytokine receptor.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

B. Orthogonal Chimeric Cytokine Receptor/Cytokine Pairs

In one aspect, the present invention provides orthogonal chimeric cytokine receptor/cytokine pairs and methods of use thereof. In some embodiments, the orthogonal chimeric cytokine receptor comprises an extracellular domain of an orthogonal IL-2 receptor (oIL2R) and an intracellular signaling domain of an IL-9 receptor (IL9R). In some embodiments, the orthogonal chimeric cytokine receptor comprises an extracellular domain of an orthogonal IL-2 receptor beta (oIL2Rb) and an intracellular signaling domain of an IL-9 receptor alpha (IL9Ra). The orthogonal chimeric cytokine receptor extracellular domain (i.e., oIL2Rb) specifically binds to a counterpart engineered orthogonal cytokine (i.e., oIL2).

Upon binding the orthogonal IL2 cytokine (oIL2) by the oIL2R extracellular domain, the orthogonal chimeric cytokine receptor activates signaling of the intracellular signaling domain (e.g., IL9R intracellular signaling domain) that is transduced through native cellular elements to provide for a biological activity that mimics the native response of the receptor from which the intracellular signaling domain is derived, but which is specific to an engineered cell expressing the orthogonal chimeric cytokine receptor. The orthogonal chimeric cytokine receptor does not bind to the endogenous counterpart cytokine, including the native counterpart of the orthogonal cytokine (e.g., IL-2), while the orthogonal cytokine (e.g., oIL2) does not bind to any endogenous receptors, including the native counterpart of the orthogonal receptor from which the orthogonal extracellular domain is derived (e.g., IL-2R). In some embodiments, the affinity of the orthogonal cytokine for the orthogonal chimeric cytokine receptor is comparable to the affinity of the native cytokine for the native receptor from which the orthogonal extracellular domain is derived.

Nucleotide and amino acid sequences of exemplary orthogonal cytokines and orthogonal chimeric cytokine receptors of the present invention are provided below.

```
Human ortho-IL2 cDNA
                                                    (SEQ ID NO: 1)
ATGTACAGGATGCAGCTGCTGTCTTGCATCGCCCTGAGCCTGGCCCTGGTGACCAACTCCGCCC

CCACAAGCTCCTCTACCAAGAAGACACAGCTGCAGCTGTCTCAGCTGCTGGTGCTGCTGAAGGC

CATCCTGAACGGCATCAACAATTACAAGAATCCCAAGCTGACCCGCATGCTGACATTCAAGTTT

TATATGCCTAAGAAGGCCACCGAGCTGAAGCACCTGCAGTGTCTGGAGGAGGAGCTGAAGCCAC

TGGAGGAGGTGCTGAACCTGGCCCAGTCCAAGAATTTCCACCTGCGGCCCAGAGACCTGATCTC

TAACATCAATGTGATCGTGCTGGAGCTGAAGGGCAGCGAGACCACCTTCATGTGCGAGTATGCC

GATGAGACCGCCACAATCGTGGAGTTCCTGAATCGGTGGATCACATTTTGTCAGAGCATCATCT

CCACCCTGACATGA

Human ortho-IL2 Protein
                                                    (SEQ ID NO: 2)
MYRMQLLSCIALSLALVINSAPTSSSTKKTQLQLSQLLVLLKAILNGINNYKNPKLTRMLTFKF

YMPKKATELKHLQCLEEELKPLEEVLNLAQSKNFHLRPRDLISNINVIVLELKGSETTFMCEYA

DETATIVEFLNRWITFCQSIISTLT

Human orthoIL2Rb cDNA
                                                    (SEQ ID NO: 3)
ATGGCGGCCCCTGCTCTGTCCTGGCGTCTGCCCCTCCTCATCCTCCTCCTGCCCCTGGCTACCT

CTTGGGCATCTGCAGCGGTGAATGGCACTTCCCAGTTCACATGCTTCTACAACTCGAGAGCCAA

CATCTCCTGTGTCTGGAGCCAAGATGGGGCTCTGCAGGACACTTCCTGCCAAGTCCATGCCTGG

CCGGACAGACGGCGGTGGAACCAAACCTGTGAGCTGCTCCCCGTGAGTCAAGCATCCTGGGCCT

GCAACCTGATCCTCGGAGCCCCAGATTCTCAGAAACTGACCACAGTTGACATCGTCACCCTGAG

GGTGCTGTGCCGTGAGGGGGTGCGATGGAGGGTGATGGCCATCCAGGACTTCAAGCCCTTTGAG

AACCTTCGCCTGATGGCCCCCATCTCCCTCCAAGTTGTCCACGTGGAGACCCACAGATGCAACA

TAAGCTGGGAAATCTCCCAAGCCTCCGACTTCTTTGAAAGACACCTGGAGTTCGAGGCCCGGAC

GCTGTCCCCAGGCCACACCTGGGAGGAGGCCCCCCTGCTGACTCTCAAGCAGAAGCAGGAATGG

ATCTGCCTGGAGACGCTCACCCCAGACACCCAGTATGAGTTTCAGGTGCGGGTCAAGCCTCTGC

AAGGCGAGTTCACGACCTGGAGCCCCTGGAGCCAGCCCCTGGCCTTCAGGACAAAGCCTGCAGC

CCTTGGGAAGGACACCATTCCGTGGCTCGGCCACCTCCTCGTGGGTCTCAGCGGGGCTTTTGGC

TTCATCATCTTAGTGTACTTGCTGATCAACTGCAGGAACACCGGGCCATGGCTGAAGAAGGTCC

TGAAGTGTAACACCCCAGACCCCTCGAAGTTCTTTTCCCAGCTGAGCTCAGAGCATGGAGGAGA

CGTCCAGAAGTGGCTCTCTTCGCCCTTCCCCTCATCGTCCTTCAGCCCTGGCGGCCTGGCACCT

GAGATCTCGCCACTAGAAGTGCTGGAGAGGGACAAGGTGACGCAGCTGCTCCTGCAGCAGGACA

AGGTGCCTGAGCCCGCATCCTTAAGCAGCAACCACTCGCTGACCAGCTGCTTCACCAACCAGGG

TTACTTCTTCTTCCACCTCCCGGATGCCTTGGAGATAGAGGCCTGCCAGGTGTACTTTACTTAC

GACCCCTACTCAGAGGAAGACCCTGATGAGGGTGTGGCCGGGGCACCCACAGGGTCTTCCCCCC

AACCCCTGCAGCCTCTGTCAGGGGAGGACGACGCCTACTGCACCTTCCCCTCCAGGGATGACCT

GCTGCTCTTCTCCCCCAGTCTCCTCGGTGGCCCCAGCCCCCCAAGCACTGCCCCTGGGGGCAGT

GGGGCCGGTGAAGAGAGGATGCCCCCTTCTTTGCAAGAAAGAGTCCCCAGAGACTGGGACCCCC

AGCCCCTGGGGCCTCCCACCCCAGGAGTCCCAGACCTGGTGGATTTTCAGCCACCCCCTGAGCT
```

-continued

```
GGTGCTGCGAGAGGCTGGGGAGGAGGTCCCTGACGCTGGCCCCAGGGAGGGAGTCAGTTTCCCC

TGGTCCAGGCCTCCTGGGCAGGGGGAGTTCAGGGCCCTTAATGCTCGCCTGCCCCTGAACACTG

ATGCCTACTTGTCCCTCCAAGAACTCCAGGGTCAGGACCCAACTCACTTGGTGTGA
```

Human orthoIL2Rb Protein (SEQ ID NO: 4)
```
MAAPALSWRLPLLILLLPLATSWASAAVNGTSQFTCFYNSRANISCVWSQDGALQDTSCQVHAW

PDRRRWNQTCELLPVSQASWACNLILGAPDSQKLTTVDIVTLRVLCREGVRWRVMAIQDFKPFE

NLRLMAPISLQVVHVETHRCNISWEISQASDFFERHLEFEARTLSPGHTWEEAPLLTLKQKQEW

ICLETLTPDTQYEFQVRVKPLQGEFITWSPWSQPLAFRTKPAALGKDTIPWLGHLLVGLSGAFG

FIILVYLLINCRNTGPWLKKVLKCNTPDPSKFFSQLSSEHGGDVQKWLSSPFPSSSFSPGGLAP

EISPLEVLERDKVTQLLLQQDKVPEPASLSSNHSLTSCFTNQGYFFFHLPDALEIEACQVYFTY

DPYSEEDPDEGVAGAPTGSSPOPLOPLSGEDDAYCTFPSRDDLLLFSPSLLGGPSPPSTAPGGS

GAGEERMPPSLQERVPRDWDPQPLGPPTPGVPDLVDFQPPPELVLREAGEEVPDAGPREGVSFP

WSRPPGQGEFRALNARLPLNTDAYLSLQELQGQDPTHLV
```

Human orthoIL2Rb/IL9Ra cDNA (SEQ ID NO: 5)
```
ATGGCCGCCCCCGCCCTGTCTTGGAGACTGCCCCTCCTGATCCTGCTGCTGCCTCTGGCTACAA

GCTGGGCTTCTGCCGCTGTGAACGGCACCAGCCAATTTACCTGCTTCTACAACTCCCGGGCCAA

CATCTCTTGCGTGTGGTCCCAAGACGGCGCCCTGCAAGATACCAGCTGTCAGGTGCACGCCTGG

CCTGATAGACGGAGATGGAACCAGACCTGCGAGCTGCTTCCAGTGTCTCAGGCCAGCTGGGCCT

GTAATTTGATCCTGGGCGCTCCCGACAGCCAGAAACTGACCACCGTGGACATCGTGACCCTGAG

GGTGCTTTGTAGAGAGGGCGTTAGATGGCGGGTGATGGCCATCCAGGATTTCAAACCCTTCGAA

AACCTGAGACTCATGGCCCCAATCAGCCTGCAGGTGGTGCATGTGGAAACACACAGATGCAACA

TCAGCTGGGAGATCAGCCAGGCCAGCGACTTCTTCGAGCGGCACCTGGAATTTGAGGCCAGAAC

CCTGTCCCCAGGCCACACATGGGAAGAGGCCCCCCTGCTGACACTGAAGCAGAAGCAGGAGTGG

ATCTGCCTGGAGACACTGACCCCTGATACACAGTACGAGTTTCAGGTCAGAGTTAAGCCCCTGC

AGGGAGAATTCACCACCTGGTCTCCTTGGAGCCAGCCTCTGGCCTTCAGAACCAAGCCTGCCCA

GAGACAGGGTCCTCTGATTCCTCCTTGGGGCTGGCCCGGCAATACCCTGGTGGCCGTGTCTATC

TTTCTGCTCCTGACAGGCCCCACCTACCTGCTGTTCAAGCTGTCCCCTAGAGTGAAGCGGATCT

TCTACCAGAACGTGCCTAGCCCGGCCATGTTCTTCCAACCTCTGTACAGCGTGCACAACGGCAA

CTTCCAAACCTGGATGGGCGCCCACGGCGCCGGCGTGCTGCTGAGCCAGGACTGCGCCGGCACC

CCTCAGGGCGCACTGGAACCTTGTGTGCAGGAGGCCACAGCCCTGCTGACATGCGGCCCTGCCC

GCCCTTGGAAGAGCGTGGCCCTGGAAGAAGAGCAGGAGGGCCCCGGCACCAGACTGCCTGGAAA

TCTGAGCTCTGAGGACGTGCTGCCTGCTGGCTGTACCGAGTGGCGGGTGCAGACACTGGCTTAT

CTGCCCCAGGAGGACTGGGCCCCTACATCTCTGACTAGACCTGCCCCTCCAGACTCTGAAGGCT

CTAGGTCTAGCAGCAGCAGCAGCAGCAACAACAACAATTACTGCGCCCTGGGCTGCTACGG

CGGATGGCACCTGAGCGCCCTGCCTGGCAACACCCAGAGCAGCGGCCCCATCCCTGCCCTGGCT

TGCGGCCTGTCATGCGACCACCAGGGACTGGAAACCCAGCAGGGCGTGGCTTGGGTCCTGGCCG

GGCACTGCCAGCGGCCTGGACTGCACGAGGATCTGCAAGGAATGCTGCTGCCCAGCGTGCTGAG

CAAGGCCAGAAGCTGGACCTTCTAA
```

Human orthoIL2Rb/IL9Ra Protein (SEQ ID NO: 6)
```
MAAPALSWRLPLLILLLPLATSWASAAVNGTSQFTCFYNSRANISCVWSQDGALQDTSCQVHAW

PDRRRWNQTCELLPVSQASWACNLILGAPDSQKLTTVDIVTLRVLCREGVRWRVMAIQDEKPFE
```

-continued

NLRLMAPISLOVVHVETHRCNISWEISQASDFFERHLEFEARTLSPGHTWEEAPLLTLKQKQEW

ICLETLTPDTQYEFQVRVKPLOGEFTTWSPWSQPLAFRTKPAQRQGPLIPPWGWPGNTLVAVSI

FLLLTGPTYLLFKLSPRVKRIFYONVPSPAMFFOPLYSVHNGNFQTWMGAHGAGVLLSQDCAGT

PQGALEPCVQEATALLTCGPARPWKSVALEEEQEGPGTRLPGNLSSEDVLPAGCTEWRVOTLAY

LPQEDWAPTSLTRPAPPDSEGSRSSSSSSSSNNNNYCALGCYGGWHLSALPGNTQSSGPIPALA

CGLSCDHQGLETQQGVAWVLAGHCORPGLHEDLQGMLLPSVLSKARSWTF

Mouse ortho-IL2 (clone 3A10) cDNA
                                                       (SEQ ID NO: 7)
ATGTATTCAATGCAGCTCGCCTCATGCGTCACCCTCACACTCGTCCTCCTCGTCAACTCAGCCC

CCACCTCTTCACCAACTTCCTCACCAACCAGCTCCTCTACAGCCGAGGCTCAGCAACAACAGCA

GCAGCAGCAGCACCTGGACAACCTGCTGGTGCTGCTGAAGGCCCTGCTGTCTAGGATGGAGAAC

TACAGAAACCTGAAGCTGCCCAGGATGCTGACCTTCAAGTTTTACCTGCCTAAGCAGGCTACAG

AGCTGAAGGACCTGCAGTGCCTGGAGGATGAGCTGGGACCACTGAGGCACGTGCTGGACCTGAC

CCAGAGCAAGTCCTTCCAGCTGGAGGATGCCGAGAACTTTATCTCTAACATCCGCGTGACCGTG

GTGAAGCTGAAGGGAAGCGATAACACATTCGAGTGTCAGTTTGACGATGAGTCCGCTACAGTGG

TGGATTTTCTCAGACGGTGGATTGCCTTTTGCCAGAGCATCATCTCAACTTCCCCTCAGTAA

Mouse ortho-IL2 (clone 3A10) Protein
                                                       (SEQ ID NO: 8)
MYSMQLASCVTLTLVLLVNSAPTSSPTSSPTSSSTAEAQQQQQQQQHLDNLLVLLKALLSRMEN

YRNLKLPRMLTFKFYLPKQATELKDLQCLEDELGPLRHVLDLTQSKSFQLEDAENFISNIRVTV

VKLKGSDNTFECQFDDESATVVDFLRRWIAFCOSIISTSPQ

Mouse orthoIL2Rb (aka o2R) cDNA
                                                       (SEQ ID NO: 9)
ATGGCAACAATCGCTCTCCCTTGGTCTCTCAGTCTCTATGTCTTTCTCCTGCTCCTCGCTACTC

CCTGGGCATCTGCTGCTGTGAAGAACTGCTCCCACCTGGAGTGTTTTTACAACTCTCGCGCTAA

CGTGTCTTGTATGTGGAGCCACGAGGAGGCCCTGAACGTGACCACATGCCACGTGCACGCTAAG

TCCAACCTGAGACACTGGAACAAGACCTGTGAGCTGACACTGGTGCGGCAGGCTAGCTGGGCTT

GCAACCTGATCCTGGGATCCTTCCCTGAGAGCCAGTCCCTGACCTCTGTGGACCTGCTGGATAT

CAACGTGGTGTGCTGGGAGGAGAAGGGCTGGAGGAGAGTGAAGACATGCGACTTTCACCCTTTC

GATAACCTGAGGCTGGTGGCTCCACACTCCCTGCAGGTGCTGCACATCGACACCCAGAGGTGTA

ACATCTCTTGGAAGGTGTCTCAGGTGAGCGACTTCATCGAGCCATACCTGGAGTTCGAGGCTCG

GCGCAGGCTGCTGGGACACTCCTGGGAGGACGCCTCCGTGCTGTCTCTGAAGCAGAGGCAGCAG

TGGCTGTTCCTGGAGATGCTGATCCCCTCTACAAGCTACGAGGTGCAGGTGAGAGTGAAGGCTC

AGCGGAACAACACCGGAACATGGAGCCCCTGGTCCCAGCCTCTGACCTTTAGAACACGGCCTGC

CGATCCAATGAAGGAGATCCTGCCCATGAGCTGGCTGAGATACCTGCTGCTGGTGCTGGGATGC

TTCTCCGGCTTCTTTTCTTGCGTGTACATCCTGGTGAAGTGCCGGTACCTGGGCCCTTGGCTGA

AGACCGTGCTGAAGTGCCACATCCCTGACCCAAGCGAGTTCTTTTCCCAGCTGAGCTCCCAGCA

CGGCGGAGATCTGCAGAAGTGGCTGTCTAGCCCCGTGCCTCTGAGCTTCTTTTCCCCCTCTGGA

CCAGCTCCCGAGATCAGCCCTCTGGAGGTGCTGGACGGCGATTCCAAGGCCGTGCAGCTGCTGC

TGCTGCAGAAGGACTCCGCTCCTCTGCCAAGCCCATCCGGACACTCTCAGGCCAGCTGTTTTAC

CAACCAGGGCTACTTCTTTTTCCACCTGCCTAACGCCCTGGAGATCGAGTCTTGTCAGGTGTAC

TTCACATACGACCCATGCGTGGAGGAGGAGGTGGAGGAGGATGGATCTCGCCTGCCAGAGGGCA

GCCCCCACCCACCTCTGCTGCCTCTGGCCGGAGAGCAGGACGATTACTGCGCTTTTCCACCCAG

-continued

GGACGATCTGCTGCTGTTCTCTCCTAGCCTGTCCACCCCAAACACAGCTTACGGAGGAAGCCGC

GCTCCAGAGGAGAGGTCCCCTCTGTCTCTGCACGAGGGACTGCCAAGCCTGGCTTCCAGGGACC

TGATGGGCCTGCAGCGCCCACTGGAGAGGATGCCAGAGGGCGATGGAGAGGGCCTGTCTGCCAA

CTCCTCTGGCGAGCAGGCTAGCGTGCCAGAGGGAAACCTGCACGGACAGGACCAGGATAGGGGA

CAGGGACCCATCCTGACACTGAATACAGATGCTTACCTCTCACTCCAGGAACTCCAGGCACAGG

ATTCAGTCCACCTCATTTAA

Mouse orthoIL2Rb (aka o2R) Protein
                                                          (SEQ ID NO: 10)
MATIALPWSLSLYVFLLLLATPWASAAVKNCSHLECFYNSRANVSCMWSHEEALNVTTCHVHAK

SNLRHWNKTCELTLVRQASWACNLILGSFPESQSLTSVDLLDINVVCWEEKGWRRVKTCDFHPF

DNLRLVAPHSLQVLHIDTQRCNISWKVSQVSDFIEPYLEFEARRRLLGHSWEDASVLSLKQRQQ

WLFLEMLIPSTSYEVQVRVKAQRNNTGTWSPWSQPLTFRTRPADPMKEILPMSWLRYLLLVLGC

FSGFFSCVYILVKCRYLGPWLKTVLKCHIPDPSEFFSQLSSQHGGDLQKWLSSPVPLSFFSPSG

PAPEISPLEVLDGDSKAVQLLLLQKDSAPLPSPSGHSQASCFTNQGYFFFHLPNALEIESCQVY

FTYDPCVEEEVEEDGSRLPEGSPHPPLLPLAGEQDDYCAFPPRDDLLLFSPSLSTPNTAYGGSR

APEERSPLSLHEGLPSLASRDLMGLQRPLERMPEGDGEGLSANSSGEQASVPEGNLHGQDQDRG

QGPILTLNTDAYLSLQELQAQDSVHLI

Mouse orthoIL2Rb (aka o2R) Extracellular Domain
                                                          (SEQ ID NO: 11)
MATIALPWSLSLYVFLLLLATPWASAAVKNCSHLECFYNSRANVSCMWSHEEALNVTTCHVHAK

SNLRHWNKTCELTLVRQASWACNLILGSFPESQSLTSVDLLDINVVCWEEKGWRRVKTCDFHPF

DNLRLVAPHSLQVLHIDTQRCNISWKVSQVSDFIEPYLEFEARRRLLGHSWEDASVLSLKQRQQ

WLFLEMLIPSTSYEVQVRVKAQRNNTGTWSPWSQPLTFRTRPADPMKE

Mouse orthoIL2Rb (aka o2R) Transmembrane region
                                                          (SEQ ID NO: 12)
ILPMSWLRYLLLVLGCFSGFFSCVYILV Mouse orthoIL2Rb (aka o2R) Intracellular Domain
                                                          (SEQ ID NO: 13)
KCRYLGPWLKTVLKCHIPDPSEFFSQLSSQHGGDLQKWLSSPVPLSFFSPSGPAPEISPLEVLD

GDSKAVQLLLLQKDSAPLPSPSGHSQASCFTNQGYFFFHLPNALEIESCQVYFTYDPCVEEEVE

EDGSRLPEGSPHPPLLPLAGEQDDYCAFPPRDDLLLFSPSLSTPNTAYGGSRAPEERSPLSLHE

GLPSLASRDLMGLQRPLERMPEGDGEGLSANSSGEQASVPEGNLHGQDQDRGQ

GPILTLNTDAYLSLQELQAQDSVHLI

Mouse orthoIL2Rb/IL9Ra (aka o9R) cDNA
                                                          (SEQ ID NO: 14)
ATGGCTACTATCGCTCTGCCTTGGTCCCTCTCACTCTATGTCTTCCTGCTCCTGCTGGCTACAC

CCTGGGCTTCTGCTGCCGTCAAAAACTGCTCCCACCTGGAGTGTTTCTACAACTCTCGCGCCAA

CGTGAGCTGCATGTGGTCCCACGAGGAGGCCCTGAACGTGACCACATGTCACGTGCACGCTAAG

TCCAACCTGAGACACTGGAACAAGACCTGCGAGCTGACACTGGTGCGGCAGGCCTCTTGGGCTT

GTAACCTGATCCTGGGAAGCTTTCCCGAGAGCCAGTCCCTGACCTCCGTGGACCTGCTGGATAT

CAACGTGGTGTGCTGGGAGGAGAAGGGCTGGAGGAGAGTGAAGACATGTGACTTCCACCCATTT

GATAACCTGAGGCTGGTGGCTCCACACAGCCTGCAGGTGCTGCACATCGACACCCAGAGGTGCA

ACATCTCCTGGAAGGTGAGCCAGGTGTCCGATTTCATCGAGCCTTACCTGGAGTTTGAGGCTCG

GCGCAGGCTGCTGGGACACTCCTGGGAGGACGCTTCTGTGCTGAGCCTGAAGCAGCGGCAGCAG

TGGCTGTTCCTGGAGATGCTGATCCCATCTACCAGCTACGAGGTGCAGGTGCGCGTGAAGGCCC

AGAGGAACAACACCGGAACATGGTCCCCCTTGGAGCCAGCCACTGACCTTCCGCACAAGGCCCGC

CGATCCTATGAAGGAGGCTTCTATCCTGGTGGTGGTGCCTATCTTTCTGCTGCTGACAGGCTTC

GTGCACCTGCTGTTTAAGCTGTCTCCAAGACTGAAGCGGATCTTCTACCAGAACATCCCTAGCC

CAGAGGCTTTCTTTCACCCCCTGTACAGCGTGTACCACGGAGACTTTCAGTCCTGGACCGGAGC

TAGAAGGGCTGGACCTCAGGCTAGACAGAACGGAGTGTCTACAAGCTCCGCTGGCAGCGAGTCT

AGCATCTGGGAGGCCGTGGCTACCCTGACATACTCTCCAGCCTGCCCCGTGCAGTTCGCTTGTC

TGAAGTGGGAGGCCACCGCTCCTGGCTTTCCAGGACTGCCAGGAAGCGAGCACGTGCTGCCAGC

TGGATGTCTGGAGCTGGAGGGACAGCCATCCGCTTACCTGCCTCAGGAGGATTGGGCTCCACTG

GGATCTGCTCGGCCCCCTCCACCAGACTCCGATTCTGGATCCTCTGACTACTGCATGCTGGATT

GCTGTGAGGAGTGTCACCTGAGCGCCTTCCCCGGCCACACAGAAAGCCCCGAACTCACCCTCGC

ACAGCCCGTCGCACTCCCAGTCTCCTCCAGAGCATAA

Mouse orthoIL2Rb/IL9Ra (aka o9R) Protein
                                                    (SEQ ID NO: 15)
MATIALPWSLSLYVFLLLLATPWASAAVKNCSHLECFYNSRANVSCMWSHEEALNVTTCHVHAK

SNLRHWNKTCELTLVRQASWACNLILGSFPESQSLTSVDLLDINVVCWEEKGWRRVKTCDFHPF

DNLRLVAPHSLQVLHIDTQRCNISWKVSQVSDFIEPYLEFEARRRLLGHSWEDASVLSLKQRQQ

WLFLEMLIPSTSYEVQVRVKAQRNNTGTWSPWSQPLTFRTRPADPMKEASILVVVPIFLLLTGF

VHLLFKLSPRLKRIFYQNIPSPEAFFHPLYSVYHGDFQSWTGARRAGPQARQNGVSTSSAGSES

SIWEAVATLTYSPACPVQFACLKWEATAPGFPGLPGSEHVLPAGCLELEGQPSAYLPQEDWAPL

GSARPPPPDSDSGSSDYCMLDCCEECHLSAFPGHTESPELTLAQPVALPVSSRA

Mouse orthoIL2Rb/IL9Ra (aka o9R) -
orthoIL2Rb extracellular domain
                                                    (SEQ ID NO: 16)
MATIALPWSLSLYVFLLLLATPWASAAVKNCSHLECFYNSRANVSCMWSHEEALNVTTCHVHAK

SNLRHWNKTCELTLVRQASWACNLILGSFPESQSLTSVDLLDINVVCWEEKGWRRVKTCDFHPF

DNLRLVAPHSLQVLHIDTQRCNISWKVSQVSDFIEPYLEFEARRRLLGHSWEDASVLSLKQRQQ

WLFLEMLIPSTSYEVQVRVKAQRNNTGTWSPWSQPLTERTRPA

Mouse orthoIL2Rb/IL9Ra (aka o9R) - transmembrane
region
                                                    (SEQ ID NO: 17)
ASILVVVPIFLLLTGFVHLLF Mouse orthoIL2Rb/IL9Ra (aka o9R) -
IL9Ra intracellular domain with transmembrane region
                                                    SEQ ID NO: 18)
QRRQGLLVPRWQWSASILVVVPIFLLLTGFVHLLFKLSPRLKRIFYQNIPSPEAFFHPLYSVYH

GDFQSWTGARRAGPQARQNGVSTSSAGSESSIWEAVATLTYSPACPVQFACLKWEATAPGFPGL

PGSEHVLPAGCLELEGQPSAYLPQEDWAPLGSARPPPPDSDSGSSDYCMLDCCEECHLSAFPGH

TESPELTLAQPVALPVSSRA

Mouse orthoIL2Rb/IL4R (aka o4R) Protein
                                                    (SEQ ID NO: 19)
MATIALPWSLSLYVFLLLLATPWASAAVKNCSHLECFYNSRANVSCMWSHEEALNVTTCHVHAK

SNLRHWNKTCELTLVRQASWACNLILGSFPESQSLTSVDLLDINVVCWEEKGWRRVKTCDFHPF

DNLRLVAPHSLQVLHIDTQRCNISWKVSQVSDFIEPYLEFEARRRLLGHSWEDASVLSLKQRQQ

WLFLEMLIPSTSYEVQVRVKAQRNNTGTWSPWSQPLTFRIRPAFQLPLIQRLPLGVTISCLCIP

LFCLFCYFSITKIKKIWWDQIPTPARSPLVAIIIQDAQVPLWDKQTRSQESTKYPHWKTCLDKL

LPCLLKHRVKKKTDFPKAAPTKSLQSPGKAGWCPMEVSRTVLWPENVSVSVVRCMELFEAPVQN

VEEEEDEIVKEDLSMSPENSGGCGFQESQADIMARLTENLFSDLLEAENGGLGQSALAESCSPL

PSGSGQASVSWACLPMGPSEEATCQVTEQPSHPGPLSGSPAQSAPTLACTQVPLVLADNPAYRS

-continued

```
FSDCCSPAPNPGELAPEQQQADHLEEEEPPSPADPHSSGPPMQPVESWEQILHMSVLQHGAAAG

STPAPAGGYQEFVQAVKQGAAQDPGVPGVRPSGDPGYKAFSSLLSSNGIRGDTAAAGTDDGHGG

YKPFQNPVPNQSPSSVPLFTFGLDTELSPSPLNSDPPKSPPECLGLELGLKGGDWVKAPPPADQ

VPKPFGDDLGFGIVYSSLTCHLCGHLKQHHSQEEGGQSPIVASPGCGCCYDDRSPSLGSLSGAL

ESCPEGIPPEANLMSAPKTPSNLSGEGKGPGHSPVPSQTTEVPVGALGIAVS

Mouse orthoIL2Rb/IL7R (aka o7R) Protein
                                            (SEQ ID NO: 20)
MATIALPWSLSLYVFLLLLATPWASAAVKNCSHLECFYNSRANVSCMWSHEEALNVTTCHVHAK

SNLRHWNKTCELTLVRQASWACNLILGSFPESQSLTSVDLLDINVVCWEEKGWRRVKTCDFHPF

DNLRLVAPHSLQVLHIDTQRCNISWKVSQVSDFIEPYLEFEARRRLLGHSWEDASVLSLKQRQQ

WLFLEMLIPSTSYEVQVRVKAQRNNTGTWSPWSQPLTFRTRPAKNQGGWDPVLPSVTILSLESV

FLLVILAHVLWKKRIKPVVWPSLPDHKKTLEQLCKKPKTSLNVSENPESFLDCQIHEVKGVEAR

DEVESFLPNDLPAQPEELETQGHRAAVHSANRSPETSVSPPETVRRESPLRCLARNLSTCNAPP

LLSSRSPDYRDGDRNRPPVYQDLLPNSGNTNVPVPVPQPLPFQSGILIPVSQRQPISTSSVLNQ

EEAYVIMSSFYQNK

Mouse orthoIL2Rb/IL21R (aka o21R) Protein
                                            (SEQ ID NO: 21)
MATIALPWSLSLYVFLLLLATPWASAAVKNCSHLECFYNSRANVSCMWSHEEALNVTTCHVHAK

SNLRHWNKTCELTLVRQASWACNLILGSFPESQSLTSVDLLDINVVCWEEKGWRRVKTCDFHPF

DNLRLVAPHSLQVLHIDTQRCNISWKVSQVSDFIEPYLEFEARRRLLGHSWEDASVLSLKQRQQ

WLFLEMLIPSTSYEVQVRVKAQRNNTGTWSPWSQPLTFRTRPAGEPEAGWDPHMLLLLAVLIIV

LVFMGLKIHLPWRLWKKIWAPVPTPESFFQPLYREHSGNFKKWVNTPFTASSIELVPQSSTITS

ALHLSLYPAKEKKFPGLPGLEEQLECDGMSEPGHWCIIPLAAGQAVSAYSEERDRPYGLVSIDT

VTVGDAEGLCVWPCSCEDDGYPAMNLDAGRESGPNSEDLLLVTDPAFLSCGCVSGSGLRLGGSP

GSLLDRLRLSFAKEGDWTADPTWRTGSPGGGSESEAGSPPGLDMDTFDSGFAGSDCGSPVETDE

GPPRSYLRQWVVRTPPPVDSGAQSS
```

C. Chimeric Antigen Receptors (CARs)

In some embodiments of the invention, the modified immune cell (e.g., T cell) expressing the orthogonal chimeric cytokine receptor is a T cell which has been modified to co-express at least one chimeric antigen receptor (a 'CAR-T' cell).

Antigen Binding Domains

The antigen binding domain of a CAR is an extracellular region of the CAR for binding to a specific target antigen including proteins, carbohydrates, and glycolipids. The antigen binding domain can include any domain that binds one or more antigen(s) and may include, but is not limited to, a monoclonal antibody (mAb), a polyclonal antibody, a synthetic antibody, a bispecific antibody, a human antibody, a humanized antibody, a non-human antibody, a single-domain antibody, a full length antibody or any antigen-binding fragment thereof, a Fab, and a single-chain variable fragment (scFv). In some embodiments, the antigen binding domain comprises an aglycosylated antibody or a fragment thereof or scFv thereof.

In some embodiments, the target antigen recognized by the antigen binding comprises a tumor antigen. Examples of tumor antigens that may be targeted by the antigen binding domain of the CAR include one or more antigens selected from the group including, but not limited to, the CD19, CD20, HER2, NY-ESO-1, MUC1, CD123, FLT3, B7-H3, CD33, IL1RAP, CLL1 (CLEC12A)PSA, CEA, VEGF, VEGF-R2, CD22, ROR1, mesothelin, c-Met, Glycolipid F77, FAP, EGFRvIII, MAGE A3, 5T4, WT1, KG2D ligand, a folate receptor (FRa), and Wnt1 antigens.

As used herein, the term "single-chain variable fragment" or "scFv" is a fusion protein of the variable regions of the heavy (VH) and light (VL) chains of an immunoglobulin (e.g., mouse or human) covalently linked to form a VH::VL heterodimer. The variable heavy (VH) and light (VL) chains are either joined directly or joined by a peptide linker, which connects the N-terminus of the VH with the C-terminus of the VL, or the C-terminus of the VH with the N-terminus of the VL. In some embodiments, the antigen binding domain comprises an scFv having the configuration from N-terminus to C-terminus, VH-linker-VL. In some embodiments, the antigen binding domain comprises an scFv having the configuration from N-terminus to C-terminus, VL-linker-VH. Those of skill in the art would be able to select the appropriate configuration for use in the present invention.

The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/087010, the contents of which are hereby incorporated by reference in their entireties. Various linker sequences are known in the art, including, without limitation, glycine serine (GS) linkers such as $(GS)_n$, $(SG)_n$, $(GSGGS)_n$, $(GGGS)_n$, and $(GGGGS)_n$, where n represents an integer of at least 1. Exemplary linker sequences can comprise amino acid sequences including, without limitation, GGSG, GGSGG, GSGSG, GSGGG, GGGSG, GSSSG, GGGGS, GGGGSGGGGSGGGGSGGGGS and the like. Those of skill in the art would be able to select the appropriate linker sequence for use in the present invention. In one embodiment, an antigen binding domain of the present invention comprises a heavy chain variable region (VH) and a light chain variable region (VL), wherein the VH and VL is separated by the linker sequence.

Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hybridoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chem 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "Fab" refers to a fragment of an antibody structure that binds to an antigen but is monovalent and does not have a Fc portion, for example, an antibody digested by the enzyme papain yields two Fab fragments and an Fc fragment (e.g., a heavy (H) chain constant region; Fc region that does not bind to an antigen).

As used herein, "F(ab')2" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

In some embodiments, the antigen binding domain may be derived from the same species in which the CAR will ultimately be used. For example, for use in humans, the antigen binding domain of the CAR may comprise a human antibody or a fragment thereof. In some embodiments, the antigen binding domain may be derived from a different species in which the CAR will ultimately be used. For example, for use in humans, the antigen binding domain of the CAR may comprise a murine antibody or a fragment thereof, or a humanized murine antibody or a fragment thereof.

In certain embodiments, the antigen binding domain comprises a heavy chain variable region that comprises three heavy chain complementarity determining regions (HCDR1, HCDR2, and HCDR3) and a light chain variable region that comprises three light chain complementarity determining regions (LCDR1, LCDR2, and LCDR3).

Transmembrane Domain

CARs of the present invention may comprise a transmembrane domain that connects the antigen binding domain of the CAR to the intracellular domain of the CAR. The transmembrane domain of the CAR is a region that is capable of spanning the plasma membrane of a cell (e.g., an immune cell or precursor thereof). The transmembrane domain is for insertion into a cell membrane, e.g., a eukaryotic cell membrane. In some embodiments, the transmembrane domain is interposed between the antigen binding domain and the intracellular domain of a CAR.

In some embodiments, the transmembrane domain is naturally associated with one or more of the domains in the CAR. In some embodiments, the transmembrane domain can be selected or modified by one or more amino acid substitutions to avoid binding of such domains to the transmembrane domains of the same or different surface membrane proteins, to minimize interactions with other members of the receptor complex.

The transmembrane domain may be derived either from a natural or a synthetic source. Where the source is natural, the domain may be derived from any membrane-bound or transmembrane protein, e.g., a Type I transmembrane protein. Where the source is synthetic, the transmembrane domain may be any artificial sequence that facilitates insertion of the CAR into a cell membrane, e.g., an artificial hydrophobic sequence. Examples of the transmembrane domain of particular use in this invention include, without limitation, transmembrane domains derived from (i.e. comprise at least the transmembrane region(s) of) the alpha, beta or zeta chain of the T cell receptor, CD28, CD3 epsilon, CD45, CD4, CD5, CD7, CD8, CD9, CD16, CD22, CD33, CD37, CD64, CD80, CD86, CD134 (OX-40), CD137 (4-1BB), CD154 (CD40L), ICOS, CD278, Toll-like receptor 1 (TLR1), TLR2, TLR3, TLR4, TLR5, TLR6, TLR7, TLR8, TLR9 or a transmembrane domain derived from a killer immunoglobulin-like receptor (KIR).

In certain embodiments, the transmembrane domain comprises a transmembrane domain of CD8. In certain embodiments, the transmembrane domain of CD8 is a transmembrane domain of CD8α.

In some embodiments, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

The transmembrane domains described herein can be combined with any of the antigen binding domains described herein, any of the intracellular domains described herein, or any of the other domains described herein that may be included in the CAR.

In some embodiments, the transmembrane domain further comprises a hinge region. The CAR of the present invention may also include a hinge region. The hinge region of the CAR is a hydrophilic region which is located between the antigen binding domain and the transmembrane domain. In some embodiments, this domain facilitates proper protein folding for the CAR. The hinge region is an optional component for the CAR. The hinge region may include a domain selected from Fc fragments of antibodies, hinge regions of antibodies, CH2 regions of antibodies, CH3 regions of antibodies, artificial hinge sequences or combinations thereof. Examples of hinge regions include, without limitation, a CD8a hinge, artificial hinges made of polypeptides which may be as small as, three glycines (Gly), as well as CH1 and CH3 domains of IgGs (such as human IgG4).

In some embodiments, a CAR includes a hinge region that connects the antigen binding domain with the transmembrane domain, which, in turn, connects to the intracellular domain. The hinge region is preferably capable of supporting the antigen binding domain to recognize and bind to the target antigen on the target cells (see, e.g., Hudecek et al., *Cancer Immunol. Res.* (2015) 3(2): 125-135). In some embodiments, the hinge region is a flexible domain, thus allowing the antigen binding domain to have a structure to optimally recognize the specific structure and density of the target antigens on a cell such as tumor cell (Hudecek et al., supra). The flexibility of the hinge region permits the hinge region to adopt many different conformations.

In some embodiments, the hinge region is an immunoglobulin heavy chain hinge region. In some embodiments, the hinge region is a hinge region polypeptide derived from a receptor (e.g., a CD8-derived hinge region). In certain embodiments, the hinge region is a CD8a hinge.

The hinge region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa. In some embodiments, the hinge region can have a length of greater than 5 aa, greater than 10 aa, greater than 15 aa, greater than 20 aa, greater than 25 aa, greater than 30 aa, greater than 35 aa, greater than 40 aa, greater than 45 aa, greater than 50 aa, greater than 55 aa, or more.

Suitable hinge regions can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids. Suitable hinge regions can have a length of greater than 20 amino acids (e.g., 30, 40, 50, 60 or more amino acids).

For example, hinge regions include glycine polymers $(G)_n$, glycine-serine polymers (including, for example, $(GS)_n$, $(GSGGS)_n$ and $(GGGS)_n$, where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see, e.g., Scheraga, *Rev. Computational. Chem.* (1992) 2: 73-142). Exemplary hinge regions can comprise amino acid sequences including, but not limited to, $(GGGGS)_n$, GGSG, GGSGG, GSGSG, GSGGG, GGGSG, GSSSG, GGGGS and the like.

In some embodiments, the hinge region is an immunoglobulin heavy chain hinge region. Immunoglobulin hinge region amino acid sequences are known in the art; see, e.g., Tan et al., *Proc. Natl. Acad. Sci. USA* (1990) 87(1):162-166; and Huck et al., *Nucleic Acids Res.* (1986) 14(4): 1779-1789. As non-limiting examples, an immunoglobulin hinge region can include one of the following amino acid sequences: DKTHT; CPPC; CPEPKSCDTPPPCPR (see, e.g., Glaser et al., *J. Biol. Chem.* (2005) 280:41494-41503); ELKTPLGDTTHT; KSCDKTHTCP; KCCVDCP; KYGPPCP; EPKSCDKTHTCPPCP (human IgG1 hinge); ERKCCVECPPCP (human IgG2 hinge); ELKTPLGDTTH- TCPRCP (human IgG3 hinge); SPNMVPHAHHAQ (human IgG4 hinge); and the like.

The hinge region can comprise an amino acid sequence of a human IgG1, IgG2, IgG3, or IgG4, hinge region. In one embodiment, the hinge region can include one or more amino acid substitutions and/or insertions and/or deletions compared to a wild-type (naturally-occurring) hinge region. For example, His229 of human IgG1 hinge can be substituted with Tyr, so that the hinge region comprises the sequence EPKSCDKTYTCPPCP; see, e.g., Yan et al., *J. Biol. Chem.* (2012) 287: 5891-5897. In one embodiment, the hinge region can comprise an amino acid sequence derived from human CD8, or a variant thereof.

Intracellular Signaling Domain

A CAR of the present invention also includes an intracellular signaling domain. The terms "intracellular signaling domain" and "intracellular domain" are used interchangeably herein. The intracellular signaling domain of the CAR is responsible for activation of at least one of the effector functions of the cell in which the CAR is expressed (e.g., immune cell). The intracellular signaling domain transduces the effector function signal and directs the cell (e.g., immune cell) to perform its specialized function, e.g., harming and/or destroying a target cell.

Examples of an intracellular domain for use in the invention include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

Examples of the intracellular signaling domain include, without limitation, the ζ chain of the T cell receptor complex or any of its homologs, e.g., η chain, FcsRIγ and β chains, MB 1 (Iga) chain, B29 (Ig) chain, etc., human CD3 zeta chain, CD3 polypeptides (Δ, δ and ε), syk family tyrosine kinases (Syk, ZAP 70, etc.), src family tyrosine kinases (Lck, Fyn, Lyn, etc.), and other molecules involved in T cell transduction, such as CD2, CD5 and CD28. In one embodiment, the intracellular signaling domain may be human CD3 zeta chain, FcγRIII, FcsRI, cytoplasmic tails of Fc receptors, an immunoreceptor tyrosine-based activation motif (ITAM) bearing cytoplasmic receptors, and combinations thereof.

In one embodiment, the intracellular signaling domain of the CAR includes any portion of one or more co-stimulatory molecules, such as at least one signaling domain from CD2, CD3, CD8, CD27, CD28, ICOS, 4-1BB, PD-1, any derivative or variant thereof, any synthetic sequence thereof that has the same functional capability, and any combination thereof.

Other examples of the intracellular domain include a fragment or domain from one or more molecules or receptors including, but not limited to, TCR, CD3 zeta, CD3 gamma, CD3 delta, CD3 epsilon, CD86, common FcR gamma, FcR beta (Fc Epsilon RIb), CD79a, CD79b, Fcgamma RIIa, DAP10, DAP12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/

RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

Additional examples of intracellular domains include, without limitation, intracellular signaling domains of several types of various other immune signaling receptors, including, but not limited to, first, second, and third generation T cell signaling proteins including CD3, B7 family costimulatory, and Tumor Necrosis Factor Receptor (TNFR) superfamily receptors (see, e.g., Park and Brentjens, J. Clin. Oncol. (2015) 33(6): 651-653). Additionally, intracellular signaling domains may include signaling domains used by NK and NKT cells (see, e.g., Hermanson and Kaufman, Front. Immunol. (2015) 6: 195) such as signaling domains of NKp30 (B7-H6) (see, e.g., Zhang et al., J. Immunol. (2012) 189(5): 2290-2299), and DAP 12 (see, e.g., Topfer et al., J. Immunol. (2015) 194(7): 3201-3212), NKG2D, NKp44, NKp46, DAP10, and CD3z.

Intracellular signaling domains suitable for use in a CAR of the present invention include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation of the CAR (i.e., activated by antigen and dimerizing agent). In some embodiments, the intracellular signaling domain includes at least one (e.g., one, two, three, four, five, six, etc.) ITAM motifs as described below. In some embodiments, the intracellular signaling domain includes DAP10/CD28 type signaling chains. In some embodiments, the intracellular signaling domain is not covalently attached to the membrane bound CAR, but is instead diffused in the cytoplasm.

Intracellular signaling domains suitable for use in a CAR of the present invention include immunoreceptor tyrosine-based activation motif (ITAM)-containing intracellular signaling polypeptides. In some embodiments, an ITAM motif is repeated twice in an intracellular signaling domain, where the first and second instances of the ITAM motif are separated from one another by 6 to 8 amino acids. In one embodiment, the intracellular signaling domain of the CAR comprises 3 ITAM motifs.

In some embodiments, intracellular signaling domains includes the signaling domains of human immunoglobulin receptors that contain immunoreceptor tyrosine based activation motifs (ITAMs) such as, but not limited to, FcgammaRI, FcgammaRIIA, FcgammaRIIC, FcgammaRIIIA, FcRL5 (see, e.g., Gillis et al., Front. Immunol. (2014) 5:254).

A suitable intracellular signaling domain can be an ITAM motif-containing portion that is derived from a polypeptide that contains an ITAM motif. For example, a suitable intracellular signaling domain can be an ITAM motif-containing domain from any ITAM motif-containing protein. Thus, a suitable intracellular signaling domain need not contain the entire sequence of the entire protein from which it is derived. Examples of suitable ITAM motif-containing polypeptides include, but are not limited to: DAP12, FCER1G (Fc epsilon receptor I gamma chain), CD3D (CD3 delta), CD3E (CD3 epsilon), CD3G (CD3 gamma), CD3Z (CD3 zeta), and CD79A (antigen receptor complex-associated protein alpha chain).

In one embodiment, the intracellular signaling domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). In one embodiment, the intracellular signaling domain is derived from FCER1G (also known as FCRG; Fc epsilon receptor I gamma chain; Fc receptor gamma-chain; fc-epsilon RI-gamma; fcRgamma; fceR1 gamma; high affinity immunoglobulin epsilon receptor subunit gamma; immunoglobulin E receptor, high affinity, gamma chain; etc.). In one embodiment, the intracellular signaling domain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). In one embodiment, the intracellular signaling domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). In one embodiment, the intracellular signaling domain is derived from T-cell surface glycoprotein CD3 gamma chain (also known as CD3G, T-cell receptor T3 gamma chain, CD3-GAMMA, T3G, gamma polypeptide (TiT3 complex), etc.). In one embodiment, the intracellular signaling domain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). In one embodiment, the intracellular signaling domain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). In one embodiment, an intracellular signaling domain suitable for use in a CAR of the present disclosure includes a DAP10/CD28 type signaling chain. In one embodiment, an intracellular signaling domain suitable for use in a CAR of the present disclosure includes a ZAP70 polypeptide. In some embodiments, the intracellular signaling domain includes a cytoplasmic signaling domain of TCR zeta, FcR gamma, FcR beta, CD3 gamma, CD3 delta, CD3 epsilon, CD5, CD22, CD79a, CD79b, or CD66d. In one embodiment, the intracellular signaling domain in the CAR includes a cytoplasmic signaling domain of human CD3 zeta.

While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The intracellular signaling domain includes any truncated portion of the intracellular signaling domain sufficient to transduce the effector function signal.

The intracellular domains described herein can be combined with any of the antigen binding domains described herein, any of the transmembrane domains described herein, or any of the other domains described herein that may be included in a CAR.

In certain embodiments, the intracellular domain comprises a costimulatory domain of 4-1BB. In certain embodiments, the intracellular domain comprises an intracellular domain of CD3ζ or a variant thereof. In certain embodiments, the intracellular domain comprises 4-1BB and CD3ζ domains.

D. T Cell Receptors

In some embodiments of the invention, the modified immune cell (e.g., T cell) expressing the orthogonal chimeric cytokine receptor is an immune cell (e.g., a T cell) which has been modified to co-express at least one T cell receptor (TCR).

In some embodiments, the TCR targets (i.e., has antigenic specificity for) an antigen, for example, a tumor antigen. As used herein, the phrase "having antigenic specificity," or like phrase, means that the TCR can specifically bind to and recognize the antigen, or an epitope thereof.

Natural TCRs are generally hetero dimers. In humans, in 95% of T cells, the TCR comprises an alpha (a) chain and a beta (p) chain (encoded by TRA and TRB, respectively), whereas in 5% of T cells, the TCR comprises gamma and delta (γ/δ) chains (encoded by TRG and TRD, respectively). Natural TCR complexes are an octameric assembly of type-I single-spanning membrane proteins arranged into four dimeric modules: the variable ligand-binding TCRαβ module (in most T cells) (or the TCR 7/6 module) and the three invariant signaling modules CD36c, CD3γc, and CD3ζ dimer. The TCRαβ module binds to pMHC ligands on APC or target cell surfaces, but these proteins lack intrinsic signaling capability and, as such, rely on the signaling modules to transmit information through their cytoplasmic immunoreceptor tyrosine-based activation motifs (ITAMs). See, e.g., Chandler et al. *Int J Mol Sci* (2020) 21:7424, which is incorporated by reference herein. Natural TCRs can be cloned and modified using standard molecular biology and genetic engineering techniques known in the art.

Various engineered TCR forms are also known in the art, including TCR mimic antibodies (Chang et al., *Expert Opin Biol Ther*. (2016) 16(8):979-87), TCR-like CARs and TCR-CARs (Walseng et al., *Sci Rep*. (2017) 7:1-10; Akatsuka et al., *Front Immunol*. (2020) 11:257; Poorebrahim et al., Cancer Gene Ther. (2021) 28(6):581-589. Unlike CARs, TCRs are not restricted to the cell surface antigens, but can detect and bind to the peptides presented by MHC molecules (pMHCs). This feature provides a wide range of potential targets for TCRs such as tumor-specific neoepitopes. Of note, redirection of TCR-based CARs on the highly tumor-specific neoepitopes can prevent "off-tumor" toxicities that are commonly associated with CAR therapies In some embodiments, the TCR is a natural TCR. In some embodiments, the TCR is a modified TCR. In some embodiments, the TCR is an engineered TCR, such as a TCR mimic or antibody-like structure, a CAR-like TCR, or a CAR-TCR. In some embodiments, the TCR is a murine TCR. In some embodiments, the TCR is a human TCR. In some embodiments, the TCR is a hybrid TCR having one or more portions of a human TCR (e.g., a constant portion or a variable portion) and one or more portions of a murine TCR (e.g., a constant portion or a variable portion). Alternatively, the portion can be a few amino acids of a human TCR, such that the TCR, which is mostly murine, is "humanized." Methods of making such hybrid TCRs are known in the art (see, for example, Cohen et al., *Cancer Res*., (2006) 66:8878-8886).

In some embodiments, the TCR targets (i.e., has antigenic specificity for) a gp100 melanoma antigen, e.g., human gp100. In some embodiments, the tumor antigen is gp100. gp100, also known in the art as SILV, SI, SIL, ME20, PMEL17, or D12S53E. gp100, is a protein known to play an important role in regulating mammalian pigmentation (Hoashi et al., *J. Biol. Chem*. (2005) 280:14006-14016) and is known as a cancer antigen expressed by human tumors, including melanoma and colorectal tumors (Tartaglia et al., Vaccine (2001) 19(17-19):2571-5). The amino acid and nucleotide sequences of human gp100 are published in the GenBank database of the National Center for Biotechnology Information (NCBI) as GenBank Accession No. NP_008859 (amino acid sequence) and GenBank Accession No. NM_006928.3 (nucleotide sequence).

TCRs having antigenic specificity for gp100 (i.e., anti-gp100 TCRs) are known in the art, such as the TCRs described in, e.g., US20140219978A1. In some embodiments, the TCR is a pmel-1 TCR. The pmel-1 mouse model was developed as a system to model treatment of malignant melanoma using adoptive cell therapy (ACT) (Overwijk, et al., *J Exp Med*. (2003), 198(4):569-80). The target antigen, pmel-17, is an ortholog of the melanocyte differentiation antigen gp100, which is often overexpressed in human melanomas.

In some embodiments, the TCR targets (i.e., has antigenic specificity for) an NY-ESO-1 antigen. NY-ESO-1 is a cancer-testis antigen overexpressed in synovial sarcoma, myxoid liposarcoma, melanoma and other tumors. In some embodiments, the TCR is an NYESO1-TCR clone 1G4 (Robbins, et al., *J Immunol*, 2008, 180:6116-6131). In some embodiments, the TCR targets an antigen selected from MAGE-A3/A6, MAGE-A10, AFP, PRAME, MART-1, and HPV E6.

E. Nucleic Acids and Expression Vectors

The present disclosure provides (i) nucleic acids encoding an orthogonal chimeric cytokine receptor, (ii) nucleic acids encoding an orthogonal cytokine, and (iii) nucleic acids encoding a CAR and/or a TCR. The nucleic acid of the present disclosure may comprises a nucleic acid sequence (i.e., a polynucleotide sequence) encoding any one of the orthogonal chimeric cytokine receptors, orthogonal cytokines, CARs, and/or TCRs disclosed herein.

In certain embodiments, a nucleic acid of the present disclosure comprises a first polynucleotide sequence and a second polynucleotide sequence. The first and second polynucleotide sequence may be separated by a linker. A linker for use in the present disclosure allows for multiple proteins to be encoded by the same nucleic acid sequence (e.g., a multicistronic or bicistronic sequence), which are translated as a polyprotein that is dissociated into separate protein components. In certain embodiments, the nucleic acid comprises from 5' to 3' the first polynucleotide sequence, the linker, and the second polynucleotide sequence. In certain embodiments, the nucleic acid comprises from 5' to 3' the second polynucleotide sequence, the linker, and the first polynucleotide sequence.

In some embodiments, the linker comprises a nucleic acid sequence that encodes for an internal ribosome entry site (IRES). As used herein, "an internal ribosome entry site" or "IRES" refers to an element that promotes direct internal ribosome entry to the initiation codon, such as ATG, of a protein coding region, thereby leading to cap-independent translation of the gene. Various internal ribosome entry sites are known to those of skill in the art, including, without limitation, IRES obtainable from viral or cellular mRNA sources, e.g., immunogloublin heavy-chain binding protein (BiP); vascular endothelial growth factor (VEGF); fibroblast growth factor 2; insulin-like growth factor; translational initiation factor eIF4G; yeast transcription factors TFIID and HAP4; and IRES obtainable from, e.g., cardiovirus, rhino-virus, aphthovirus, HCV, Friend murine leukemia virus (FrMLV), and Moloney murine leukemia virus (MoMLV). Those of skill in the art would be able to select the appropriate IRES for use in the present invention.

In some embodiments, the linker comprises a nucleic acid sequence that encodes for a self-cleaving peptide. As used herein, a "self-cleaving peptide" or "2A peptide" refers to an oligopeptide that allow multiple proteins to be encoded as polyproteins, which dissociate into component proteins upon translation. Use of the term "self-cleaving" is not intended to imply a proteolytic cleavage reaction. Various self-cleaving or 2A peptides are known to those of skill in the art, including, without limitation, those found in mem-bers of the Picornaviridae virus family, e.g., foot-and-mouth disease virus (FMDV), equine rhinitis A virus (ERAVO, Thosea asigna virus (TaV), and porcine tescho virus-1 (PTV-1); and carioviruses such as Theilovirus and encepha-lomyocarditis viruses. 2A peptides derived from FMDV, ERAV, PTV-1, and TaV are referred to herein as "F2A," "E2A," "P2A," and "T2A," respectively. Those of skill in the art would be able to select the appropriate self-cleaving peptide for use in the present invention.

In some embodiments, a linker further comprises a nucleic acid sequence that encodes a furin cleavage site. Furin is a ubiquitously expressed protease that resides in the trans-golgi and processes protein precursors before their secretion. Furin cleaves at the COOH— terminus of its consensus recognition sequence. Various furin consensus recognition sequences (or "furin cleavage sites") are known to those of skill in the art, including, without limitation, Arg-X1-Lys-Arg or Arg-X1-Arg-Arg, X2-Arg-X1-X3-Arg, and Arg-X1-X1-Arg, such as an Arg-Gln-Lys-Arg, where X1 is any naturally occurring amino acid, X2 is Lys or Arg, and X3 is Lys or Arg. Those of skill in the art would be able to select the appropriate Furin cleavage site for use in the present invention.

In some embodiments, the linker comprises a nucleic acid sequence encoding a combination of a Furin cleavage site and a 2A peptide. Examples include, without limitation, a linker comprising a nucleic acid sequence encoding a Furin cleavage site and F2A, a linker comprising a nucleic acid sequence encoding a Furin cleavage site and E2A, a linker comprising a nucleic acid sequence encoding a Furin cleav-age site and P2A, a linker comprising a nucleic acid sequence encoding a Furin cleavage site and T2A. Those of skill in the art would be able to select the appropriate combination for use in the present invention. In such embodiments, the linker may further comprise a spacer sequence between the Furin cleavage site and the 2A pep-tide. In some embodiments, the linker comprises a Furin cleavage site 5' to a 2A peptide. In some embodiments, the linker comprises a 2A peptide 5' to a Furin cleavage site. Various spacer sequences are known in the art, including, without limitation, glycine serine (GS) spacers (also known as GS linkers) such as (GS)n, (SG)n, (GSGGS)n and (GGGS)n, where n represents an integer of at least 1. Exemplary spacer sequences can comprise amino acid sequences including, without limitation, GGSG, GGSGG, GSGSG, GSGGG, GGGSG, GSSSG, and the like. Those of skill in the art would be able to select the appropriate spacer sequence for use in the present invention.

In some embodiments, a nucleic acid of the present disclosure may be operably linked to a transcriptional con-trol element, e.g., a promoter, and enhancer, etc. Suitable promoter and enhancer elements are known to those of skill in the art.

For expression in a bacterial cell, suitable promoters include, but are not limited to, lacd, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early pro-moter; herpes simplex virus thymidine kinase promoter; early and late SV40 promoters; promoter present in long terminal repeats from a retrovirus; mouse metallothionein-I promoter; and various art-known tissue specific promoters. Suitable reversible promoters, including reversible inducible promoters are known in the art. Such reversible promoters may be isolated and derived from many organisms, e.g., eukaryotes and prokaryotes. Modification of reversible pro-moters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (A1cR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thy-roid promoter systems, ecdysone promoter systems, mife-pristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some embodiments, the promoter is a CD8 cell-specific promoter, a CD4 cell-specific promoter, a neutrophil-spe-cific promoter, or an NK-specific promoter. For example, a CD4 gene promoter can be used; see, e.g., Salmon et al. Proc. Natl. Acad. Sci. USA (1993) 90:7739; and Marodon et al. (2003) Blood 101:3416. As another example, a CD8 gene promoter can be used. NK cell-specific expression can be achieved by use of an NcrI (p46) promoter; see, e.g., Eckelhart et al. Blood (2011) 117:1565.

For expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in Pichia). Selection of the appropriate vector and promoter is well within the level of ordinary skill in the art. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol. (1991) 173(1): 86-93; Alpuche-Aranda et al., Proc. Natl. Acad. Sci. USA (1992) 89(21): 10079-83), a nirB promoter (Harborne et al. Mol. Micro. (1992) 6:2805-2813), and the like (see, e.g., Dunstan et al., Infect. Immun. (1999) 67:5133-5141; McKelvie et al., Vaccine (2004) 22:3243-3255; and Chatfield et al., Biotechnol. (1992) 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al., Infect. Immun. (2002) 70:1087-1096); an rpsM promoter (see, e.g., Valdivia and Falkow Mol. Microbiol. (1996). 22:367); a tet promoter (see, e.g., Hillen, W. and Wissmann, A. (1989) In Saenger, W. and Heinemann, U. (eds), Topics in Molecular and Structural Biology, Protein—Nucleic Acid Interaction. Macmillan, London, UK, Vol. 10, pp. 143-162); an SP6 promoter (see, e.g., Melton et al., Nucl. Acids Res. (1984) 12:7035); and the like. Suitable strong promoters for use in prokaryotes such as *Escherichia coli* include, but are not limited to Trc, Tac, T5, T7, and PLambda. Non-limiting examples of operators for use in bacterial host cells include a lactose promoter operator (LacI repressor protein changes conformation when contacted with lactose, thereby preventing the Lad repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, e.g., deBoer et al., Proc. Natl. Acad. Sci. U.S.A. (1983) 80:21-25).

Other examples of suitable promoters include the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to a simian virus 40 (SV40) early promoter, a mouse mammary tumor virus (MMTV) or human immunodeficiency virus (HIV) long terminal repeat (LTR) promoter, a MoMuLV promoter, an avian leukemia virus promoter, an Epstein-Barr virus immediate early promoter, a Rous sarcoma virus promoter, the EF-1 alpha promoter, as well as human gene promoters such as, but not limited to, an actin promoter, a myosin promoter, a hemoglobin promoter, and a creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., Proc. Natl. Acad. Sci. USA (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. Annual Review of Biochemistry (2006) 567-605; and Tropp, Molecular Biology (2012) (Jones & Bartlett Publishers, Sudbury, Mass.), the disclosures of which are incorporated herein by reference.

In some embodiments, a nucleic acid of the present disclosure further comprises a nucleic acid sequence encoding a CAR inducible expression cassette. In one embodiment, the CAR inducible expression cassette is for the production of a transgenic polypeptide product that is released upon CAR signaling. See, e.g., Chmielewski and Abken, Expert Opin. Biol. Ther. (2015) 15(8): 1145-1154; and Abken, Immunotherapy (2015) 7(5): 535-544. In some embodiments, a nucleic acid of the present disclosure further comprises a nucleic acid sequence encoding a cytokine operably linked to a T-cell activation responsive promoter. In some embodiments, the cytokine operably linked to a T-cell activation responsive promoter is present on a separate nucleic acid sequence. In one embodiment, the cytokine is IL-12.

A nucleic acid of the present disclosure may be present within an expression vector and/or a cloning vector. An expression vector can include a selectable marker, an origin of replication, and other features that provide for replication and/or maintenance of the vector. Suitable expression vectors include, e.g., plasmids, viral vectors, and the like. Large numbers of suitable vectors and promoters are known to those of skill in the art; many are commercially available for generating a subject recombinant construct. The following vectors are provided by way of example, and should not be construed in anyway as limiting: Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest. Opthalmol. Vis. Sci. (1994) 35: 2543-2549; Borras et al., Gene Ther. (1999) 6: 515-524; Li and Davidson, Proc. Natl. Acad. Sci. USA (1995) 92: 7700-7704; Sakamoto et al., H. Gene Ther. (1999) 5: 1088-1097; WO 94/12649, WO 93/03769; WO 93/19191; WO 94/28938; WO 95/11984 and WO 95/00655); adeno-associated virus (see, e.g., Ali et al., Hum. Gene Ther. (1998) 9: 81-86, Flannery et al., Proc. Natl. Acad. Sci. USA (1997) 94: 6916-6921; Bennett et al., Invest. Opthalmol. Vis. Sci. (1997) 38: 2857-2863; Jomary et al., Gene Ther. (1997) 4:683 690, Rolling et al., Hum. Gene Ther. (1999) 10: 641-648; Ali et al., Hum. Mol. Genet. (1996) 5: 591-594; Srivastava in WO 93/09239, Samulski et al., J. Vir. (1989) 63: 3822-3828; Mendelson et al., Virol. (1988) 166: 154-165; and Flotte et al., Proc. Natl. Acad. Sci. USA (1993) 90: 10613-10617); SV40; herpes simplex virus; human immunodeficiency virus (see, e.g., Miyoshi et al., Proc. Natl. Acad. Sci. USA (1997) 94: 10319-23; Takahashi et al., J. Virol. (1999) 73: 7812-7816); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Additional expression vectors suitable for use are, e.g., without limitation, a lentivirus vector, a gamma retrovirus vector, a foamy virus vector, an adeno-associated virus vector, an adenovirus vector, a pox virus vector, a herpes virus vector, an engineered hybrid virus vector, a transposon mediated vector, and the like. Viral vector technology is well known in the art and is described, for example, in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses.

In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In some embodiments, an expression vector (e.g., a lentiviral vector) may be used to introduce the CAR or TCR into an immune cell or precursor thereof (e.g., a T cell). Accordingly, an expression vector (e.g., a lentiviral vector) of the present invention may comprise a nucleic acid encoding for a CAR or a TCR. In some embodiments, the expression vector (e.g., lentiviral vector) will comprise additional elements that will aid in the functional expression of the CAR or TCR encoded therein. In some embodiments, an expression vector comprising a nucleic acid encoding for a CAR or TCR further comprises a mammalian promoter. In one embodiment, the vector further comprises an elongation-factor-1-alpha promoter (EF-1α promoter). Use of an EF-1 promoter may increase the efficiency in expression of downstream transgenes (e.g., a CAR- or TCR-encoding nucleic acid sequence). Physiologic promoters (e.g., an EF-1α promoter) may be less likely to induce integration mediated genotoxicity, and may abrogate the ability of the retroviral vector to transform stem cells. Other physiological promoters suitable for use in a vector (e.g., lentiviral vector) are known to those of skill in the art and may be incorporated into a vector of the present invention. In some embodiments, the vector (e.g., lentiviral vector) further comprises a non-requisite cis acting sequence that may improve titers and gene expression. One non-limiting example of a non-requisite cis acting sequence is the central polypurine tract and central termination sequence (cPPT/CTS) which is important for efficient reverse transcription and nuclear import. Other non-requisite cis acting sequences are known to those of skill in the art and may be incorporated into a vector (e.g., lentiviral vector) of the present invention. In some embodiments, the vector further comprises a posttranscriptional regulatory element. Posttranscriptional regulatory elements may improve RNA translation, improve transgene expression and stabilize RNA transcripts. One example of a posttranscriptional regulatory element is the woodchuck hepatitis virus posttranscriptional regulatory element (WPRE). Accordingly, in some embodiments a vector for the present invention further comprises a WPRE sequence. Various posttranscriptional regulator elements are known to those of skill in the art and may be incorporated into a vector (e.g., lentiviral vector) of the present invention. A vector of the present invention may further comprise additional elements such as a rev response element (RRE) for RNA transport, packaging sequences, and 5' and 3' long terminal repeats (LTRs). The term "long terminal repeat" or "LTR" refers to domains of base pairs located at the ends of retroviral DNAs which comprise U3, R and U5 regions. LTRs generally provide functions required for the expression of retroviral genes (e.g., promotion, initiation and polyadenylation of gene transcripts) and to viral replication. In one embodiment, a vector (e.g., lentiviral vector) of the present invention includes a 3' U3 deleted LTR. Accordingly, a vector (e.g., lentiviral vector) of the present invention may comprise any combination of the elements described herein to enhance the efficiency of functional expression of transgenes. For example, a vector (e.g., lentiviral vector) of the present invention may comprise a WPRE sequence, cPPT sequence, RRE sequence, 5'LTR, 3' U3 deleted LTR' in addition to a nucleic acid encoding for a CAR or a TCR.

Vectors of the present invention may be self-inactivating vectors. As used herein, the term "self-inactivating vector" refers to vectors in which the 3' LTR enhancer promoter region (U3 region) has been modified (e.g., by deletion or substitution). A self-inactivating vector may prevent viral transcription beyond the first round of viral replication. Consequently, a self-inactivating vector may be capable of infecting and then integrating into a host genome (e.g., a mammalian genome) only once, and cannot be passed further. Accordingly, self-inactivating vectors may greatly reduce the risk of creating a replication-competent virus.

In some embodiments, a nucleic acid of the present invention may be RNA, e.g., in vitro synthesized RNA. Methods for in vitro synthesis of RNA are known to those of skill in the art; any known method can be used to synthesize RNA comprising a sequence encoding an orthogonal chimeric cytokine receptor or its corresponding orthogonal cytokine, and/or a CAR or TCR of the present disclosure. Methods for introducing RNA into a host cell are known in the art. See, e.g., Zhao et al. Cancer Res. (2010) 15: 9053. Introducing RNA comprising a nucleotide sequence encoding a CAR or TCR of the present disclosure into a host cell can be carried out in vitro, ex vivo or in vivo. For example, a host cell (e.g., an NK cell, a cytotoxic T lymphocyte, etc.) can be electroporated in vitro or ex vivo with RNA comprising a nucleotide sequence encoding an orthogonal chimeric cytokine receptor or its corresponding orthogonal cytokine, and/or a CAR or TCR of the present disclosure.

In order to assess the expression of a polypeptide or portions thereof, the expression vector to be introduced into a cell may also contain either a selectable marker gene or a reporter gene, or both, to facilitate identification and selection of expressing cells from the population of cells sought to be transfected or infected through viral vectors. In some embodiments, the selectable marker may be carried on a separate piece of DNA and used in a co-transfection procedure. Both selectable markers and reporter genes may be flanked with appropriate regulatory sequences to enable expression in the host cells. Useful selectable markers include, without limitation, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include, without limitation, genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82).

In some embodiments, a nucleic acid of the present disclosure is provided for the production of (i) an orthogonal chimeric cytokine receptor, (ii) an orthogonal cytokine, and/or (iii) a CAR or TCR as described herein, e.g., in a mammalian cell. In some embodiments, a nucleic acid of the present disclosure provides for amplification of the nucleic acid.

Oncolytic Adenoviral Vectors

Oncolytic viruses represent highly promising agents for the treatment of solid tumors, and an oncolytic herpes virus expressing GM-CSF was approved by the US FDA for the therapy of advanced melanoma based on therapeutic benefit demonstrated in a clinical study (Andtbacka R H, et al. Talimogene laherparepvec improves durable response rate in patients with advanced melanoma. J Clin Oncol. 2015; 33(25):2780-2788). Oncolytic adenoviruses (OAds) can be programmed to specifically target, replicate in, and kill cancer cells while sparing normal cells. The release of virus progeny results in an exponential increase of the virus inoculum, which can cause direct tumor debulking while providing danger signals necessary to awaken the immune system (Lichty BD, Breitbach C J, Stojdl D F, Bell J C. Going viral with cancer immunotherapy. Nat Rev Cancer. 2014; 14(8):559-567). Importantly, OAds can be genetically modified to express therapeutic transgenes selectively in the TME (Siurala M, et al. Adenoviral delivery of tumor necrosis factor-α and interleukin-2 enables successful adoptive cell therapy of immunosuppressive melanoma. Mol Ther. 2016; 24(8):1435-1443; Nishio N, et al. Armed oncolytic virus enhances immune functions of chimeric antigen receptor-modified T cells in solid tumors. Cancer Res. 2014; 74(18):5195-5205; Tanoue K, et al. Armed oncolytic adenovirus-expressing PD-L1 mini-body enhances antitumor effects of chimeric antigen receptor T cells in solid tumors. Cancer Res. 2017; 77(8):2040-2051; Rosewell Shaw A, et al. Adenovirotherapy delivering cytokine and checkpoint inhibitor augments CAR T cells against metastatic head and neck cancer. Mol Ther. 2017; 25(11):2440-2451). The feasibility and safety of OAds in human patients have been demonstrated in clinical trials (Kim K H, et al. A phase I clinical trial of Ad5/3-Δ24, a novel serotype-chimeric, infectivity-enhanced, conditionally-replicative adenovirus (CRAd), in patients with recurrent ovarian cancer. Gynecol Oncol. 2013; 130(3):518-524; Ranki T, et al. Phase I study with ONCOS-102 for the treatment of solid tumors—an evaluation of clinical response and exploratory analyses of immune markers. J Immunother Cancer. 2016; 4:17). Their ability to revert tumor immunosuppression while locally expressing therapeutic transgenes provides a rational strategy for combination with adoptive T cell transfer.

In some embodiments, an orthogonal cytokine of the present disclosure, e.g., orthogonal IL-2, is encoded by a nucleic acid sequence which is comprised within an oncolytic adenoviral vector such as a conditionally replicating oncolytic adenoviral vector. One example of a conditionally replicating oncolytic adenoviral vector includes a serotype 5 adenoviral vector (Ad5) with modifications to the early genes E1A and E3 to enable cancer cell-specific replication and transgene expression, respectively. E1A is modified by deleting 24 base pairs of DNA from the CR2 region (aka D24 variant) to yield a virus capable of selectively replicating in cancer cells harboring p16-Rb pathway mutations. The orthogonal cytokine (e.g., oIL2) transgene may be placed in the E3 region. Furthermore, the virus capsid is modified to include a chimeric 5/3 fiber which enables improved transduction efficiency of tumor cells. This construct, Ad5/3-D24-orthoIL2, and its isogenic controls are used in in vitro and in vivo studies to assess the ability of orthogonal cytokine pairs to selectively attract and stimulate lentivirally transduced orthoCAR T cells and/or orthoTCR T cells for improved antitumor efficacy.

F. Modified Immune Cells

The present invention provides modified immune cells or precursors thereof (e.g., a T cell) comprising (i) an orthogonal chimeric cytokine receptor and (ii) at least one CAR. Also provided are modified immune cells or precursor cell thereof comprising one or more nucleic acids encoding (i) an orthogonal chimeric cytokine receptor and (ii) at least one CAR. Accordingly, such modified cells possess the specificity directed by the CAR(s) that is expressed therein. For example, a modified cell of the present disclosure comprising a CAR(s) possesses specificity for one or more antigen(s) on a target cell (e.g., one or more tumor antigen(s) on a cancer cell). In one aspect, the invention provides a method of treating cancer comprising administering (i) modified cells comprising an orthogonal chimeric cytokine receptor and at least one CAR and (ii) an oncolytic adenoviral vector comprising a nucleic acid encoding an orthogonal cytokine to a subject having cancer, thereby treating the cancer.

The present invention additionally provides modified immune cells or precursors thereof (e.g., a T cell) modified to express (i) an orthogonal chimeric cytokine receptor and (ii) at least one T cell receptor (TCR). Also provided are modified immune cells or precursor cell thereof comprising one or more nucleic acids encoding (i) an orthogonal chimeric cytokine receptor and (ii) at least one TCR. Accordingly, such modified cells possess the specificity directed by the TCR(s) that is expressed therein. For example, a modified cell of the present disclosure comprising a TCR(s) possesses specificity for one or more antigen(s) on a target cell (e.g., one or more tumor antigen(s) on a cancer cell). In one aspect, the invention provides a method of treating cancer comprising administering (i) modified cells modified to express an orthogonal chimeric cytokine receptor and at least one TCR and (ii) an oncolytic adenoviral vector comprising a nucleic acid encoding an orthogonal cytokine to a subject having cancer, thereby treating the cancer.

In certain embodiments, the modified cell is a modified immune cell. In certain embodiments, the modified cell is an autologous cell. In certain embodiments, the modified cell is an autologous cell obtained from a human subject. In certain embodiments, the modified cell is a T cell.

G. Methods of Treatment

The modified cells (e.g., T cells) described herein may be included in a composition for immunotherapy. The composition may include a pharmaceutical composition and further include a pharmaceutically acceptable carrier. A therapeutically effective amount of the pharmaceutical composition comprising the modified T cells may be administered.

In one aspect, the invention includes a method for adoptive cell transfer therapy comprising administering to a subject in need thereof a modified T cell of the present invention. In another aspect, the invention includes a method of treating a disease or condition in a subject comprising administering to a subject in need thereof a population of modified T cells. In one aspect, the invention provides a method of treating cancer comprising administering (a) modified cells comprising (i) an orthogonal chimeric cytokine receptor and (ii) at least one CAR, and (b) an oncolytic adenoviral vector comprising a nucleic acid sequence encoding an orthogonal ctyokine to a subject having cancer, wherein the modified cells assume stem cell memory (Tscm) features with improved trafficking and effector function, thereby treating the cancer. In one aspect, the invention provides a method of treating cancer comprising administering (a) modified cells modified to express (i) an orthogonal chimeric cytokine receptor and (ii) at least one TCR, and (b) an oncolytic adenoviral vector comprising a nucleic acid sequence encoding an orthogonal ctyokine to a subject having cancer, wherein the modified cells assume stem cell memory (Tscm) features with improved trafficking and effector function, thereby treating the cancer.

Methods for administration of immune cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338. In some embodiments, the cell therapy, e.g., adoptive T cell therapy is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject has been treated with a therapeutic agent targeting the disease or condition, e.g. the tumor, prior to administration of the cells or composition containing the cells. In some aspects, the subject is refractory or non-responsive to the other therapeutic agent. In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

In some embodiments, the subject is responsive to the other therapeutic agent, and treatment with the therapeutic agent reduces disease burden. In some aspects, the subject is initially responsive to the therapeutic agent, but exhibits a relapse of the disease or condition over time. In some embodiments, the subject has not relapsed. In some such embodiments, the subject is determined to be at risk for relapse, such as at a high risk of relapse, and thus the cells are administered prophylactically, e.g., to reduce the likelihood of or prevent relapse. In some aspects, the subject has not received prior treatment with another therapeutic agent.

In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

The modified immune cells of the present invention can be administered to an animal, preferably a mammal, even more preferably a human, to treat a cancer. In addition, the cells of the present invention can be used for the treatment of any condition related to a cancer, especially a cell-mediated immune response against a tumor cell(s), where it is desirable to treat or alleviate the disease. The types of cancers to be treated with the modified cells or pharmaceutical compositions of the invention include, carcinoma, blastoma, and sarcoma, and certain leukemia or lymphoid malignancies, benign and malignant tumors, and malignancies e.g., sarcomas, carcinomas, and melanomas. Other exemplary cancers include but are not limited breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like. The cancers may be non-solid tumors (such as hematological tumors) or solid tumors. Adult tumors/cancers and pediatric tumors/cancers are also included. In one embodiment, the cancer is a solid tumor or a hematological tumor. In one embodiment, the cancer is a carcinoma. In one embodiment, the cancer is a sarcoma. In one embodiment, the cancer is a leukemia. In one embodiment the cancer is a solid tumor.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

In certain exemplary embodiments, the modified immune cells of the invention are used to treat a myeloma, or a condition related to myeloma. Examples of myeloma or conditions related thereto include, without limitation, light chain myeloma, non-secretory myeloma, monoclonal gammopathy of undetermined significance (MGUS), plasmacytoma (e.g., solitary, multiple solitary, extramedullary plasmacytoma), amyloidosis, and multiple myeloma. In one embodiment, a method of the present disclosure is used to treat multiple myeloma. In one embodiment, a method of the present disclosure is used to treat refractory myeloma. In one embodiment, a method of the present disclosure is used to treat relapsed myeloma.

In certain exemplary embodiments, the modified immune cells of the invention are used to treat a melanoma, or a condition related to melanoma. Examples of melanoma or conditions related thereto include, without limitation, superficial spreading melanoma, nodular melanoma, lentigo maligna melanoma, acral lentiginous melanoma, amelanotic melanoma, or melanoma of the skin (e.g., cutaneous, eye, vulva, vagina, rectum melanoma). In one embodiment, a method of the present disclosure is used to treat cutaneous melanoma. In one embodiment, a method of the present disclosure is used to treat refractory melanoma. In one embodiment, a method of the present disclosure is used to treat relapsed melanoma.

In yet other exemplary embodiments, the modified immune cells of the invention are used to treat a sarcoma, or a condition related to sarcoma. Examples of sarcoma or conditions related thereto include, without limitation, angiosarcoma, chondrosarcoma, Ewing's sarcoma, fibrosarcoma, gastrointestinal stromal tumor, leiomyosarcoma, liposarcoma, malignant peripheral nerve sheath tumor, osteosarcoma, pleomorphic sarcoma, rhabdomyosarcoma, and synovial sarcoma. In one embodiment, a method of the present disclosure is used to treat synovial sarcoma. In one embodiment, a method of the present disclosure is used to treat liposarcoma such as myxoid/round cell liposarcoma, differentiated/dedifferentiated liposarcoma, and pleomorphic liposarcoma. In one embodiment, a method of the present disclosure is used to treat myxoid/round cell liposarcoma. In one embodiment, a method of the present disclosure is used to treat a refractory sarcoma. In one embodiment, a method of the present disclosure is used to treat a relapsed sarcoma.

The cells of the invention to be administered may be autologous, with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, alymph node, an organ, a tumor, and the like.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as CD8$^+$ and CD4$^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as CD4$^+$ to CD8$^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or subtype, or minimum number of cells of the population or sub-type per unit of body weight. Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of CD4$^+$ to CD8$^+$ cells, and/or is based on a desired fixed or minimum dose of CD4$^+$ and/or CD8$^+$ cells.

In certain embodiments, the cells, or individual populations of sub-types of cells, are administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

In some embodiments, the dose of total cells and/or dose of individual sub-populations of cells is within a range of between at or about $1\times10^5$ cells/kg to about $1\times10^{11}$ cells/kg $10^4$ and at or about $10^1$ cells/kilograms (kg) body weight, such as between 105 and $10^6$ cells/kg body weight, for example, at or about $1\times10^5$ cells/kg, $1.5\times10^5$ cells/kg, $2\times10^5$ cells/kg, or $1\times10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^6$ T cells/kg body weight, for example, at or about $1\times10^5$ T cells/kg, $1.5\times10^5$ T cells/kg, $2\times10^5$ T cells/kg, or $1\times10^6$ T cells/kg body weight. In other exemplary embodiments, a suitable dosage range of modified cells for use in a method of the present disclosure includes, without limitation, from about $1\times10^5$ cells/kg to about $1\times10^6$ cells/kg, from about $1\times10^6$ cells/kg to about $1\times10^7$ cells/kg, from about $1\times10^7$ cells/kg about $1\times10^8$ cells/kg, from about $1\times10^8$ cells/kg about $1\times10^9$ cells/kg, from about $1\times10^9$ cells/kg about $1\times10^{10}$ cells/kg, from about $1\times10^{10}$ cells/kg about $1\times10^{11}$ cells/kg. In an exemplary embodiment, a suitable dosage for use in a method of the present disclosure is about $1\times10^8$ cells/kg. In an exemplary embodiment, a suitable dosage for use in a method of the present disclosure is about $1\times10^7$ cells/kg. In other embodiments, a suitable dosage is from about $1\times10^7$ total cells to about $5\times10^7$ total cells. In some embodiments, a suitable dosage is from about $1\times10^8$ total cells to about $5\times10^8$ total cells. In some embodiments, a suitable dosage is from about $1.4\times10^7$ total cells to about $1.1\times10^9$ total cells. In an exemplary embodiment, a suitable dosage for use in a method of the present disclosure is about $7\times10^9$ total cells.

In some embodiments, the cells are administered at or within a certain range of error of between at or about 104 and at or about $10^9$ CD4$^+$ and/or CD8$^+$ cells/kilograms (kg) body weight, such as between $10^5$ and $10^6$ CD4$^+$ and/or CD8$^+$ cells/kg body weight, for example, at or about $1\times10^5$ CD4$^+$ and/or CD8$^+$ cells/kg, $1.5\times10^5$ CD4$^+$ and/or CD8$^+$ cells/kg, $2\times10^5$ CD4$^+$ and/or CD8$^+$ cells/kg, or $1\times10^6$ CD4$^+$ and/or CD8$^+$ cells/kg body weight. In some embodiments, the cells are administered at or within a certain range of error of, greater than, and/or at least about $1\times10^6$, about $2.5\times10^6$, about $5\times10^6$, about $7.5\times10^6$, or about $9\times10^6$ CD4$^+$ cells, and/or at least about $1\times10^6$, about $2.5\times10^6$, about $5\times10^6$, about $7.5\times10^6$, or about $9\times10^6$ CD8+ cells, and/or at least about $1\times10^6$, about $2.5\times10^6$, about $5\times10^6$, about $7.5\times10^6$, or about $9\times10^6$ T cells. In some embodiments, the cells are administered at or within a certain range of error of between about $10^8$ and $10^{12}$ or between about $10^{10}$ and $10^11$ T cells, between about 10' and $10^{12}$ or between about $10^{10}$ and $10^{11}$ CD4$^+$ cells, and/or between about $10^8$ and $10^{12}$ or between about $10^{10}$ and 101 CD8$^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios, for example, in some embodiments, the desired ratio (e.g., ratio of CD4$^+$ to CD8$^+$ cells) is between at or about 5: 1 and at or about 5: 1 (or greater than about 1:5 and less than about 5: 1), or between at or about 1:3 and at or about 3: 1 (or greater than about 1:3 and less than about 3: 1), such as between at or about 2: 1 and at or about 1:5 (or greater than about 1:5 and less than about 2: 1, such as at or about 5: 1, 4.5: 1, 4: 1, 3.5: 1, 3: 1, 2.5: 1, 2: 1, 1.9: 1, 1.8: 1, 17: 1, 1.6: 1, 1.5: 1, 1.4: 1, 1.3: 1, 1.2: 1, 1.1: 1.1: 1, 1:1.1, 1: 1.2, 1: 1.3, 1:1.4, 1: 1.5, 1: 1.6, 1: 1.7, 1: 1.8, 1: 1.9: 1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In some embodiments, a dose of modified cells is administered to a subject in need thereof, in a single dose or multiple doses. In some embodiments, a dose of modified cells is administered in multiple doses, e.g., once a week or every 7 days, once every 2 weeks or every 14 days, once every 3 weeks or every 21 days, once every 4 weeks or every 28 days. In an exemplary embodiment, a single dose of modified cells is administered to a subject in need thereof. In an exemplary embodiment, a single dose of modified cells is administered to a subject in need thereof by rapid intravenous infusion.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2, for example, to enhance persistence. In some embodiments, the methods comprise administration of a chemotherapeutic agent.

In certain embodiments, the modified cells of the invention (e.g., a modified cell comprising (i) an orthogonal chimeric cytokine receptor and (ii) at least one CAR or TCR) may be administered to a subject in combination with an immune checkpoint antibody (e.g., an anti-PD1, anti-CTLA-4, or anti-PDL1 antibody). For example, the modified cell may be administered in combination with an antibody or antibody fragment targeting, for example, PD-1 (programmed death 1 protein). Examples of anti-PD-1 antibodies include, but are not limited to, pembrolizumab (KEYTRUDA®, formerly lambrolizumab, also known as MK-3475), and nivolumab (BMS-936558, MDX-1106, ONO-4538, OPDIVA®) or an antigen-binding fragment thereof. In certain embodiments, the modified cell may be administered in combination with an anti-PD-L1 antibody or antigen-binding fragment thereof. Examples of anti-PD-L1 antibodies include, but are not limited to, BMS-936559, MPDL3280A (TECENTRIQ®, Atezolizumab), and MED14736 (Durvalumab, Imfinzi). In certain embodiments, the modified cell may be administered in combination with an anti-CTLA-4 antibody or antigen-binding fragment thereof. An example of an anti-CTLA-4 antibody includes, but is not limited to, Ipilimumab (trade name Yervoy). Other types of immune checkpoint modulators may also be used including, but not limited to, small molecules, siRNA, miRNA, and CRISPR systems. Immune checkpoint modulators may be administered before, after, or concurrently with the modified cell comprising the CAR or TCR. In certain embodiments, combination treatment comprising an immune checkpoint modulator may increase the therapeutic efficacy of a therapy comprising a modified cell of the present invention.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFNγ, IL-2, and TNF. In some aspects the biological activity is measured by assessing clinical outcome, such as reduction in tumor burden or load.

In certain embodiments, the subject is provided a secondary treatment. Secondary treatments include but are not limited to chemotherapy, radiation, surgery, and medications.

In some embodiments, the subject can be administered a conditioning therapy prior to adoptive cell therapy (e.g., CAR T cell therapy). In some embodiments, the conditioning therapy comprises administering an effective amount of cyclophosphamide to the subject. In some embodiments, the conditioning therapy comprises administering an effective amount of fludarabine to the subject. In preferred embodiments, the conditioning therapy comprises administering an effective amount of a combination of cyclophosphamide and fludarabine to the subject. Administration of a conditioning therapy prior to adoptive cell therapy (e.g., CAR T cell therapy) may increase the efficacy of the adoptive cell therapy. Methods of conditioning patients for T cell therapy are described in U.S. Pat. No. 9,855,298, which is incorporated herein by reference in its entirety.

In some embodiments, a specific dosage regimen of the present disclosure includes a lymphodepletion step prior to the administration of the modified T cells. In an exemplary embodiment, the lymphodepletion step includes administration of cyclophosphamide and/or fludarabine.

In some embodiments, the lymphodepletion step includes administration of cyclophosphamide at a dose of between about 200 mg/m²/day and about 2000 mg/m²/day (e.g., 200 mg/m²/day, 300 mg/m²/day, or 500 mg/m²/day). In an exemplary embodiment, the dose of cyclophosphamide is about 300 mg/m²/day. In some embodiments, the lymphodepletion step includes administration of fludarabine at a dose of between about 20 mg/m²/day and about 900 mg/m²/day (e.g., 20 mg/m²/day, 25 mg/m²/day, 30 mg/m²/day, or 60 mg/m²/day). In an exemplary embodiment, the dose of fludarabine is about 30 mg/m²/day.

In some embodiment, the lymphodepletion step includes administration of cyclophosphamide at a dose of between about 200 mg/m²/day and about 2000 mg/m²/day (e.g., 200 mg/m²/day, 300 mg/m²/day, or 500 mg/m²/day), and fludarabine at a dose of between about 20 mg/m²/day and about 900 mg/m²/day (e.g., 20 mg/m²/day, 25 mg/m²/day, 30 mg/m²/day, or 60 mg/m²/day). In an exemplary embodiment, the lymphodepletion step includes administration of cyclophosphamide at a dose of about 300 mg/m²/day, and fludarabine at a dose of about 30 mg/m²/day.

In an exemplary embodiment, the dosing of cyclophosphamide is 300 mg/m²/day over three days, and the dosing of fludarabine is 30 mg/m²/day over three days.

Dosing of lymphodepletion chemotherapy may be scheduled on Days −6 to −4 (with a −1 day window, i.e., dosing on Days −7 to −5) relative to T cell (e.g., CAR-T, TCR-T, a modified T cell, etc.) infusion on Day 0.

In an exemplary embodiment, for a subject having cancer, the subject receives lymphodepleting chemotherapy including 300 mg/m² of cyclophosphamide by intravenous infusion 3 days prior to administration of the modified T cells. In an exemplary embodiment, for a subject having cancer, the subject receives lymphodepleting chemotherapy including 300 mg/m² of cyclophosphamide by intravenous infusion for 3 days prior to administration of the modified T cells.

In an exemplary embodiment, for a subject having cancer, the subject receives lymphodepleting chemotherapy including fludarabine at a dose of between about 20 mg/m²/day and about 900 mg/m²/day (e.g., 20 mg/m²/day, 25 mg/m²/day, 30 mg/m²/day, or 60 mg/m²/day). In an exemplary embodiment, for a subject having cancer, the subject receives lymphodepleting chemotherapy including fludarabine at a dose of 30 mg/m² for 3 days.

In an exemplary embodiment, for a subject having cancer, the subject receives lymphodepleting chemotherapy including cyclophosphamide at a dose of between about 200 mg/m²/day and about 2000 mg/m²/day (e.g., 200 mg/m²/day, 300 mg/m²/day, or 500 mg/m²/day), and fludarabine at a dose of between about 20 mg/m²/day and about 900 mg/m²/day (e.g., 20 mg/m²/day, 25 mg/m²/day, 30 mg/m²/day, or 60 mg/m²/day). In an exemplary embodiment, for a subject having cancer, the subject receives lymphodepleting chemotherapy including cyclophosphamide at a dose of about 300 mg/m²/day, and fludarabine at a dose of 30 mg/m² for 3 days.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

It is known in the art that one of the adverse effects following infusion of CAR T cells is the onset of immune activation, known as cytokine release syndrome (CRS). CRS is immune activation resulting in elevated inflammatory cytokines. CRS is a known on-target toxicity, development of which likely correlates with efficacy. Clinical and laboratory measures range from mild CRS (constitutional symptoms and/or grade-2 organ toxicity) to severe CRS (sCRS; grade ≥3 organ toxicity, aggressive clinical intervention, and/or potentially life threatening). Clinical features include: high fever, malaise, fatigue, myalgia, nausea, anorexia, tachycardia/hypotension, capillary leak, cardiac dysfunction, renal impairment, hepatic failure, and disseminated intravascular coagulation. Dramatic elevations of cytokines including interferon-gamma, granulocyte macrophage colony-stimulating factor, IL-10, and IL-6 have been shown following CAR T-cell infusion. One CRS signature is elevation of cytokines including IL-6 (severe elevation), IFN-gamma, TNF-alpha (moderate), and IL-2 (mild). Elevations in clinically available markers of inflammation including ferritin and C-reactive protein (CRP) have also been observed to correlate with the CRS syndrome. The presence of CRS generally correlates with expansion and progressive immune activation of adoptively transferred cells. It has been demonstrated that the degree of CRS severity is dictated by disease burden at the time of infusion as patients with high tumor burden experience a more sCRS.

Accordingly, the invention provides for, following the diagnosis of CRS, appropriate CRS management strategies to mitigate the physiological symptoms of uncontrolled inflammation without dampening the antitumor efficacy of the engineered cells (e.g., CAR T cells). CRS management strategies are known in the art. For example, systemic corticosteroids may be administered to rapidly reverse symptoms of sCRS (e.g., grade 3 CRS) without compromising initial antitumor response.

In some embodiments, an anti-IL-6R antibody may be administered. An example of an anti-IL-6R antibody is the Food and Drug Administration-approved monoclonal antibody tocilizumab, also known as atlizumab (marketed as Actemra, or RoActemra). Tocilizumab is a humanized monoclonal antibody against the interleukin-6 receptor (IL-6R). Administration of tocilizumab has demonstrated near-immediate reversal of CRS.

CRS is generally managed based on the severity of the observed syndrome and interventions are tailored as such. CRS management decisions may be based upon clinical signs and symptoms and response to interventions, not solely on laboratory values alone.

Mild to moderate cases generally are treated with symptom management with fluid therapy, non-steroidal anti-inflammatory drug (NSAID) and antihistamines as needed for adequate symptom relief More severe cases include patients with any degree of hemodynamic instability; with any hemodynamic instability, the administration of tocilizumab is recommended. The first-line management of CRS may be tocilizumab, in some embodiments, at the labeled dose of 8 mg/kg IV over 60 minutes (not to exceed 800 mg/dose); tocilizumab can be repeated Q8 hours. If suboptimal response to the first dose of tocilizumab, additional doses of tocilizumab may be considered. Tocilizumab can be administered alone or in combination with corticosteroid therapy. Patients with continued or progressive CRS symptoms, inadequate clinical improvement in 12-18 hours or poor response to tocilizumab, may be treated with high-dose corticosteroid therapy, generally hydrocortisone 100 mg IV or methylprednisolone 1-2 mg/kg. In patients with more severe hemodynamic instability or more severe respiratory symptoms, patients may be administered high-dose corticosteroid therapy early in the course of the CRS. CRS management guidance may be based on published standards (Lee et al. (2019) *Biol BloodMarrow Transplant*, doi.org/10.1016/j.bbmt.2018.12.758; Neelapu et al. (2018) *Nat Rev Clin Oncology*, 15:47; Teachey et al. (2016) *Cancer Discov,* 6(6):664-679).

Features consistent with Macrophage Activation Syndrome (MAS) or Hemophagocytic lymphohistiocytosis (HLH) have been observed in patients treated with CAR-T therapy (Henter, 2007), coincident with clinical manifestations of the CRS. MAS appears to be a reaction to immune activation that occurs from the CRS, and should therefore be considered a manifestation of CRS. MAS is similar to HLH (also a reaction to immune stimulation). The clinical syndrome of MAS is characterized by high grade non-remitting fever, cytopenias affecting at least two of three lineages, and hepatosplenomegaly. It is associated with high serum ferritin, soluble interleukin-2 receptor, and triglycerides, and a decrease of circulating natural killer (NK) activity.

Adoptive cell therapy providing the immune cells described herein engineered to express any of the chimeric orthogonal cytokine receptors described herein together with a CAR has the potential to enhance on-target off-tumor toxicity. As such, it is contemplated herein that the adoptive cell therapy methods (i.e., methods of treating cancer), in certain embodiments, further comprise additional cell engineering strategies (e.g. on/off systems, synthetic circuits) to maximize patient safety (see, e.g., Caliendo, et al., *Front Bioeng Biotechnol.* (2019) 7:43.

In one aspect, the invention includes a method of treating cancer in a subject in need thereof, comprising administering to the subject any one of the modified immune or precursor cells disclosed herein. Yet another aspect of the invention includes a method of treating cancer in a subject in need thereof, comprising administering to the subject a modified immune or precursor cell generated by any one of the methods disclosed herein.

H. Sources of Immune Cells

In certain embodiments, a source of immune cells (e.g. T cells) is obtained from a subject for ex vivo manipulation. Sources of target cells for ex vivo manipulation may also include, e.g., autologous or heterologous donor blood, cord blood, or bone marrow. For example the source of immune cells may be from the subject to be treated with the modified immune cells of the invention, e.g., the subject's blood, the subject's cord blood, or the subject's bone marrow. Non-limiting examples of subjects include humans, dogs, cats, mice, rats, and transgenic species thereof. Preferably, the subject is a human.

Immune cells can be obtained from a number of sources, including blood, peripheral blood mononuclear cells, bone marrow, lymph node tissue, spleen tissue, umbilical cord, lymph, or lymphoid organs. Immune cells are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some aspects, the cells are human cells. With reference to the subject to be treated, the cells may be allogeneic and/or autologous. The cells typically are primary cells, such as those isolated directly from a subject and/or isolated from a subject and frozen.

In certain embodiments, the immune cell is a T cell, e.g., a CD8+ T cell (e.g., a CD8+naïve T cell, central memory T cell, or effector memory T cell), a CD4+ T cell, a natural killer T cell (NKT cells), a regulatory T cell (Treg), a stem cell memory T cell, a lymphoid progenitor cell a hematopoietic stem cell, a natural killer cell (NK cell) or a dendritic cell. In some embodiments, the cells are monocytes or granulocytes, e.g., myeloid cells, macrophages, neutrophils, dendritic cells, mast cells, eosinophils, and/or basophils. In an embodiment, the target cell is an induced pluripotent stem (iPS) cell or a cell derived from an iPS cell, e.g., an iPS cell generated from a subject, manipulated to alter (e.g., induce a mutation in) or manipulate the expression of one or more target genes, and differentiated into, e.g., a T cell, e.g., a CD8+ T cell (e.g., a CD8+ naive T cell, central memory T cell, or effector memory T cell), a CD4+ T cell, a stem cell memory T cell, a lymphoid progenitor cell or a hematopoietic stem cell.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. Among the sub-types and subpopulations of T cells and/or of CD4+ and/or of CD8+ T cells are naive T (TN) cells, effector T cells (TEFF), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In certain embodiments, any number of T cell lines available in the art, may be used.

In some embodiments, the methods include isolating immune cells from the subject, preparing, processing, culturing, and/or engineering them. In some embodiments, preparation of the engineered cells includes one or more culture and/or preparation steps. The cells for engineering as described may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig. In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets. In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some aspects, a washing step is accomplished by tangential flow filtration (TFF) according to the manufacturer's instructions. In some embodiments, the cells are resuspended in a variety of biocompatible buffers after washing. In certain embodiments, components of a blood cell sample are removed and the cells directly resuspended in culture media. In some embodiments, the methods include density-based cell separation methods, such as the preparation of white blood cells from peripheral blood by lysing the red blood cells and centrifugation through a Percoll or Ficoll gradient.

In one embodiment, immune are obtained cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immuno-affinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population. The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In some embodiments, one or more of the T cell populations is enriched for or depleted of cells that are positive for (marker$^+$) or express high levels (marker$^{high}$) of one or more particular markers, such as surface markers, or that are negative for (marker $-$) or express relatively low levels (marker$^{low}$) of one or more markers. For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8+ cells or the T cells, e.g., CD3+ cells) are enriched for (i.e., positively selected for) cells that are positive or expressing high surface levels of CD45RO, CCR7, CD28, CD27, CD44, CD 127, and/or CD62L and/or depleted of (e.g., negatively selected for) cells that are positive for or express high surface levels of CD45RA. In some embodiments, cells are enriched for or depleted of cells positive or expressing high surface levels of CD 122, CD95, CD25, CD27, and/or IL7-Ra (CD 127). In some examples, CD8+ T cells are enriched for cells positive for CD45RO (or negative for CD45RA) and for CD62L. For example, CD3+, CD28+ T cells can be positively selected using CD3/CD28 conjugated magnetic beads (e.g., DYNA-BEADS® M-450 CD3/CD28 T Cell Expander).

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations. In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such sub-populations. In some embodiments, combining TCM-enriched CD8+ T cells and CD4+ T cells further enhances efficacy.

In some embodiments, memory T cells are present in both CD62L+ and CD62L- subsets of CD8+ peripheral blood lymphocytes. PBMC can be enriched for or depleted of CD62L-CD8+ and/or CD62L+CD8+ fractions, such as using anti-CD8 and anti-CD62L antibodies. In some embodiments, a CD4+ T cell population and a CD8+ T cell sub-population, e.g., a sub-population enriched for central memory (TCM) cells. In some embodiments, the enrichment for central memory T (TCM) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8+ population enriched for TCM cells is carried out by depletion of cells expressing CD4, CD 14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD 14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

CD4+T helper cells are sorted into naive, central memory, and effector cells by identifying cell populations that have cell surface antigens. CD4+ lymphocytes can be obtained by standard methods. In some embodiments, naive CD4+T lymphocytes are CD45RO-, CD45RA+, CD62L+, CD4+ T cells. In some embodiments, central memory CD4+ cells are CD62L+ and CD45RO+. In some embodiments, effector CD4+ cells are CD62L- and CD45RO. In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In another embodiment, T cells are isolated from peripheral blood by lysing the red blood cells and depleting the monocytes, for example, by centrifugation through a PER-COLL™ gradient. Alternatively, T cells can be isolated from an umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19, and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° C. per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

In certain embodiments, T regulatory cells (Tregs) can be isolated from a sample. The sample can include, but is not limited to, umbilical cord blood or peripheral blood. In certain embodiments, the Tregs are isolated by flow-cytometry sorting. The sample can be enriched for Tregs prior to isolation by any means known in the art. The isolated Tregs can be cryopreserved, and/or expanded prior to use. Methods for isolating Tregs are described in U.S. Pat. Nos. 7,754,482, 8,722,400, and 9,555,105, and U.S. patent application Ser. No. 13/639,927, contents of which are incorporated herein in their entirety.

I. Expansion of Immune Cells

Whether prior to or after modification of cells to express a CAR or TCR, the cells can be activated and expanded in number using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Publication No. 20060121005. For example, the T cells of the invention may be expanded by contact with a surface having attached thereto an agent that stimulates a CD3/TCR complex associated signal and a ligand that stimulates a co-stimulatory molecule on the surface of the T cells. In particular, T cell populations may be stimulated by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, T cells can be contacted with an anti-CD3 antibody and an anti-CD28 antibody, under conditions appropriate for stimulating proliferation of the T cells. Examples of an anti-CD28 antibody include 9.3, B-T3, XR-CD28 (Diaclone, Besancon, France) and these can be used in the invention, as can other methods and reagents known in the art (see, e.g., ten Berge et al., Transplant Proc. (1998) 30(8): 3975-3977; Haanen et al., J. Exp. Med. (1999) 190(9): 1319-1328; and Garland et al., J. Immunol. Methods (1999) 227(1-2): 53-63).

Expanding T cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-$\alpha$ or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, $\alpha$-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. A cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more. In one embodiment, human T regulatory cells are expanded via anti-CD3 antibody coated KT64.86 artificial antigen presenting cells (aAPCs). Methods for expanding and activating T cells can be found in U.S. Pat. Nos. 7,754,482, 8,722,400, and 9,555,105, contents of which are incorporated herein in their entirety.

In one embodiment, the method of expanding the T cells can further comprise isolating the expanded T cells for further applications. In another embodiment, the method of expanding can further comprise a subsequent electroporation of the expanded T cells followed by culturing. The subsequent electroporation may include introducing a nucleic acid encoding an agent, such as a transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function.

J. Pharmaceutical Compositions and Formulations

Also provided are populations of immune cells of the invention, compositions containing such cells and/or enriched for such cells, such as in which cells expressing the orthogonal chimeric cytokine receptor or coexpressing the orthogonal chimeric cytokine receptor and at least one CAR or TCR make up at least 50%, 60%, 70%, 80%, 90%, 91%, 92%, 93%, 94%, 95%, 96%, 97%, 98%, 99%, or more of the total cells in the composition or cells of a certain type such as T cells or CD8+ or CD4+ cells. Among the compositions are pharmaceutical compositions and formulations for administration, such as for adoptive cell therapy. Also provided are therapeutic methods for administering the cells and compositions to subjects, e.g., patients.

Also provided are compositions including the cells for administration, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Protein Production

DNA encoding mouse and human wild-type and orthogonal IL-2 and wild-type IL-9 was cloned into the insect expression vector pAcGP67-A, which includes a C-terminal 8×HIS tag for affinity purification. DNA encoding mouse serum albumin (MSA) was purchased from Integrated DNA Technologies (IDT) and cloned into pAcGP67-A as a N-terminal fusion. Insect expression DNA constructs were transfected into *Trichoplusia ni* (High Five) cells (Invitrogen)

using the BaculoGold baculovirus expression system (BD Biosciences) for secretion and purified from the clarified supernatant via Ni-NTA followed by size exclusion chromatography with a Superdex-200 column and formulated in sterile Phosphate Buffer Saline (PBS) for injection. Endotoxin was removed using the Proteus NoEndo HC Spin column kit following the manufacturer's recommendations (VivaProducts) and endotoxin removal was confirmed using the Pierce LAL Chromogenic Endotoxin Quantification Kit (ThermoFisher). Proteins were concentrated and stored at −80° C. until ready for use.

Mammalian Expression Vectors cDNA encoding mouse orthogonal IL-2Rβ and geneblock cDNA encoding mouse intracellular domains (ICD) of IL4R, IL7R, IL9R, and IL21R (Integrated DNA Tech) were PCR and ITA cloned into the retroviral vector pMSCV-MCS-IRES-YFP. Human orthogonal IL2Rβ and chimeric orthogonal IL9R were similarly cloned into pMSCV vector Animals Mice were housed under Association for the Assessment and Accreditation of Laboratory Care-approved animal facilities and used under protocols approved by Institutional Animal Care and Use Committee at the University of California, Los Angeles (UCLA), University of Pennsylvania and Stanford University. For experiments conducted at UCLA, C57BL/6J mice were bred and kept in the Radiation Oncology Vivarium; pmel-1 TCR/Thy1.1 transgenic mice (pmel mice) on a C57BL/6 background were obtained from the Jackson Laboratory. For experiments conducted at University of Pennsylvania, C57BL/6J and B6 CD45.1 "Pepboy" mice were purchased from Jackson Labs.

Cell Lines and Cell Culture

The B16-F10 mouse melanoma cell line was purchased from ATCC and cultured with RPMI 1640 with L-glutamine (Fisher Scientific) containing 10% fetal bovine serum (FBS, Omega Scientific), penicillin (100 U/mL, Omega Scientific), streptomycin (100 μg/mL, Omega Scientific), and amphotericin B (0.25 μg/ml, Omega Scientific). The KPC-derived mouse pancreatic cancer cell line PDA7940b was maintained in RPMI 1640 media supplemented with 10% FBS and 1% penicillin/streptomycin. Human melanoma cell lines M407 and M263 were established from patients' biopsies under UCLA IRB approval #11-003254 and maintained in RPMI 1640 media supplemented with 10% FBS and 1% penicillin/streptomycin; M407 cells were stably transduced to express nuclear RFP (nRFP) for use in a live cell imaging assay (Zaretsky, et al., The New England Journal of Medicine, 2016, 375:819-829). T cells derived from C57BL/6 or pmel transgenic mice were cultured in RPMI 1640 with L-glutamine supplemented with 10% FBS (Hyclone Characterized Fetal Bovine Serum), antibiotics, 50 μM 2-mercaptoethanol (Gibco), 1% NEAA, 1% NaPyr, and HEPES. Primary human T cells were cultured in RPMI 1640 with L-glutamine supplemented with 10% FBS (Hyclone Characterized Fetal Bovine Serum), antibiotics, 1% NEAA, 1% NaPyr, and HEPES. HEK293T cells were purchased from ATCC and maintained in DMEM supplemented with 10% FBS, 1× GlutaMax (Gibco) and penicillin and streptomycin. Cell lines were periodically authenticated and also periodically tested for *mycoplasma* infection using *mycoplasma* detection kit (Biotool).

Retrovirus Production

Production of retroviruses encoding orthogonal cytokine receptors has been previously described (Sockolosky et al., *Science* (2018) 359:1037-1042). Briefly, HEK293T cells were seeded at a 3×10⁶ cells per 10 cm tissue culture dish and allowed to adhere overnight. Cells were transfected with a 1.5:1 ratio of pMSCV retroviral vector to pCL-Eco packaging vector using X-tremeGENE HP (Roche), Turbofect (ThermoFisher) or TransIT Reagent (Thermofisher) and cultured overnight in DMEM with 5% FBS. After 24 h, media was replaced with fresh DMEM with 5% FBS and cultured for an additional 24 h. Media was collected, clarified via centrifugation, and flash frozen in liquid nitrogen for storage at −80° C. Cells were replenished with fresh DMEM with 5% FBS, and cultured for an additional 24 h, and retroviral supernatant was collected and stored as described. To generate retrovirus for transduction of pmel and human T cells, the same procedure was used with the following variations: 18 h after transfection, media was replaced DMEM with 10% FBS containing 20 mM HEPES and 10 mM Sodium Butyrate and incubated for 8 h. Media was then replaced with DMEM with 10% FBS containing 20 mM HEPES and no sodium butyrate and incubated overnight. The next day, the media was collected and filtered through a 0.45 m filter. If not used immediately, virus was frozen at −80° C. for later use. Retroviruses encoding chimeric antigen receptors were produced as previously described (Watanabe et al., *JCI Insight* (2018) 3(7):e99573). Briefly, Plat-E packaging cells (Cell Biolabs) were transfected with pMSGV vectors using Lipofectamine 2000 (ThermoFisher). Culture media was replaced 24 h later and after an additional 24 h the media was collected, clarified by centrifugation, and passed through a 0.45 m filter before storage at −80° C.

Adenovirus Construction and Purification

Replication-deficient E1/E3-deleted adenovirus vectors Ad5-CMV-oIL2 (Ad-oIL2) and Ad5-CMV-Null (Ad-Null) were constructed using AdEasy™ XL Adenoviral Vector System (Agilent). Mouse orthogonal IL-2 clone 3A10 cDNA was synthesized (GenScript) with 5' KpnI and 3' HindIII restriction sites and subcloned into the multiple cloning site of pShuttle-CMV (Addgene). pAdEasy-1-containing BJ5183-AD-1 *E. coli* cells were transformed with PmeI-linearized pShuttle-CMV-oIL2 for homologous recombination. Resulting recombinant Ad plasmid was sequence-verified and expanded in XL10-Gold Ultracompetent cells before Pac-linearization and transfection into HEK293T cells. High-titer adenoviruses were purified by cesium chloride (CsCl$_2$) gradient centrifugation after multiple rounds of amplification. CsCl$_2$ was exchanged to A195 buffer (Evans et al., *J Pharm Sci* (2004) 93:2458-2475) with Amicon Ultra-15 centrifugal filter units (Millipore). Viral titer (VP/ml) was determined spectrophotometrically (Nanodrop, ThermoFisher).

Activation, Retroviral Transduction and Sorting of Primary Mouse T Cells

Viral transduction of C57BL/6-derived mouse T cells was previously described (Sockolosky et al., *Science* (2018) 359:1037-1042). In brief, 12-well tissue culture plates were coated overnight with 2.5 µg/ml solution of anti-mouse CD3E (clone 145-2C11, Biolegend) in sterile PBS. Single cell suspensions were prepared from spleens and lymph nodes of 6-8 week old C57BL/6J mice by dissociation through a 70 µm cell strainer followed by RBC lysis in ACK lysis buffer (Gibco). Cells were resuspended in mouse T cell media containing 100 IU/ml recombinant mouse IL-2 and activated with plate bound anti-mouse CD3ε and soluble anti-mouse CD28 (5 ug/ml, clone 37.51, BioXCell) for 24 h. Activated mouse T cells were transduced via spinfection using retroviral supernatants containing polybrene (10 ug/ml) and 100 IU/ml mIL-2 at 2600 rpm, 90' at 32° C. Viral supernatant was replaced with fresh mouse T cell media containing 100 IU/ml IL-2 and cultured for 24 h. Cells were harvested off the place via gentle pipetting and resuspended at 1×10$^6$/ml in fresh T cell media containing 100 IU/ml IL-2 and expanded overnight at 37° C. prior to further downstream cellular assays.

For retroviral transduction of pmel T cells, splenocytes from the 5-10 week old pmel mice were harvested one to three days prior to transduction and activated with 50 U/mL murine IL-2 (Peprotech) and 1 µg/mL murine gp100 peptide (Anaspec). One day prior to transduction, six-well tissue culture plates were coated with Retronectin (Takara) and placed in a 4° C. refrigerator overnight. The following day, plates were blocked with 0.5% FBS in PBS for 30 mins and washed with PBS. Viral supernatant (2 mL) was added to each well and spun at 2000 g for 2 h. Activated pmel T cells (3×10$^6$) were added to each well with 50 U/mL murine IL-2 and spun at 2000 g for 10 minutes and then cultured at 37° C. for 18-24 hours. Then, viable transduced cells were sorted based on expression of YFP and exclusion of 7-AAD using an Aria II cell sorter (BD Biosciences), and rested overnight prior to use in downstream in vitro or in vivo assays.

Retroviral transduction of mouse CAR T cells was previously described (Watanabe et al., *JCI Insight* (2018) 3(7):e99573). Briefly, primary donor CD45.1 mouse splenocytes were enriched for CD3+ cells by magnetic bead separation (Stemcell Technologies). T cells were activated with mouse CD3/CD28 Dynabeads (ThermoFisher) in the presence of 50 U/ml recombinant human IL-2 (Peprotech) for 48 h before spinfection on retronectin-coated (Takara Bio) plates. Cell were harvested for in vitro assays or intravenous injection 2 days after spinfection.

Activation, Retroviral Transduction and Sorting of Primary Human T Cells

Primary human peripheral blood mononuclear cells (PBMCs) isolated from a healthy human donor leukapheresis were thawed and rested overnight prior to activation for two days with anti-human CD3/28 magnetic Dynabeads (ThermoFisher) and human IL-2 (500 U/mL). T cells were co-transduced for 48 h on six-well plates coated with Retronectin (Takara) and loaded with 1 mL/well of each retrovirus (encoding ho2R and NYESO1-TCR clone 1G4 or ho9R and NYESO1-TCR clone 1G4) by spinfection. Activated and transduced cells were collected and beads were removed by placing on an EasySep cell separation magnet for 2 minutes. Cells were stained with anti-human Vβ13.1 PE antibody (Beckman Coulter, recognizes the f chain of the NYESO1-TCR clone 1G4), and 7-AAD live/dead dye prior to cell sorting based on expression of YFP, Vβ13.1, and exclusion of 7-AAD using an Aria II cell sorter (BD Biosciences).

Phosphoflo Signaling Assay

Actively growing primary mouse or human T cells were rested in RPMI-C lacking IL-2 for 24 h prior to signaling assays. Cells were plated in ultra-low binding 96-well round bottom plate in 50 µl warm RPMI-C media. Cells were subsequently stimulated by addition of 50 µl solution of serial dilutions of recombinant cytokines for 20' at 37° C., and the reaction was terminated by fixation with 1.5% PFA for 15' at room temperature (RT) with agitation. Cells were washed and permeabilized with 150 µl ice-cold 100% methanol for 60' on ice or stored at −80° C. overnight. Cells were washed with FACS buffer prior to staining with Alexa647 labeled anti-STAT5 pY694 (BD Biosciences), anti-STAT3 (BD Biosciences), or anti-STAT1 (Cell Signaling), diluted 1:100 in FACS buffer and incubated for 1 h at 4° C. in the dark. Cells were washed and analyzed on a CytoFlex (Beckman Coulter). Data represent the mean fluorescence intensity (MFI), and points were fit to a log (agonist) vs. dose response model using Prism 8.4 (Graph-Pad).

Western Blot

IL-2 and FBS-starved CAR T cells were stimulated for 20 minutes with cytokines and lysed with ice-cold RIPA buffer supplemented with protease/phosphatase inhibitor cocktail (Halt, ThermoFisher) to extract protein. 30 μg of total protein was loaded into SDS-PAGE gels (NuPage Bis-Tris, ThermoFisher) and subsequently transferred to PVDF membranes (Immobilon-FL, Millipore). Detection of pSTAT1/pSTAT3/pSTAT5 and GAPDH was performed with respective primary antibodies followed by IRDye-labelled secondary antibodies or HRP-linked secondary antibodies. Membranes were imaged on Odyssey CLx (LI-COR Biosciences).

Mouse T Cell Proliferation Assay

Actively growing primary mouse T cells were rested in RPMI-C lacking IL2 for 48 h prior to labeling with Cell-Tracer Violet (CTV, ThermoFisher). Labeled cells were seeded at 50,000 T cells/well in 50 μl in a 96-well round bottom plate. Serial dilutions of MSA-oIL2 (50 μl) were added to a total volume of 100 μl and cultured for 2 days at 37° C. On day 2, freshly diluted cytokine (100 l) was added to the cells and cultured for an additional 2 days. On day 4, CTV labeled cell proliferation was evaluated by FACS using the CytoFlex. Live cell gates based on FSC and SSC.

CAR T cell proliferation was assessed by seeding 50,000 cells/well in a round-bottom 96-well plate in the presence of MSA-oIL2 or MSA-IL2. On Day 2, cells were fed with fresh media and cytokines. Daily cell counts were acquired by staining an aliquot of cells with Calcein AM viability dye (ThermoFisher) and analyzed on the Celigo Image Cytometer (Nexcelom Bioscience).

Cytokine Assays

For Luminex assays, transduced CAR T cells were incubated in round-bottom 96-well plates (50,000 cells/well in 200 μl) in triplicates for 4 days in the presence of cytokines after which supernatants were analyzed with Th1/Th2/Th9/Th17/Th22/Treg Cytokine 17-Plex Mouse ProcartaPlex™ Panel (ThermoFisher). A Cytokine Bead Array (BD Biosciences) was used to individually measure IFNγ from supernatant of B16-F10 coculture with pmel T cells according to manufacturer's instructions. oIL-2 expression from PDA7940b cells (10,000 cells/well, 96 well plate) was evaluated by mouse IL-2 ELISA (Abcam) in cell culture supernatants at various timepoints following infection with Ad-Null or Ad-oIL2 (100 VP/cell). In vivo expression was assessed by injecting PBS, Ad-Null or Ad-oIL2 (1e9 VP/tumor) into PDA7940b tumors and harvesting 72 h later. Tumors were dissociated by three freeze-thaw cycles and homogenates were analyzed for mouse IL-2 by ELISA. Terminal blood was collected by cardiac puncture and processed to serum by centrifugation. IL-2 concentrations were normalized to total protein content.

Real-Time Cell Killing Assays

PDA7940b tumor cells were seeded at 10,000 cells/well of a 96-well xCELLigence E-Plate (Agilent). 24 h later, transduced CAR T cells pre-incubated 48 h in the presence of oIL-2 were added at 2:1 ratio and target cell index was recorded every 15 minutes in the Real-Time Cell Analysis (RTCA) Analyzer (Agilent). T cell killing of B16-F10 cell lines transduced with a nuclear localizing RFP were previously described (Kalbasi et al., *Science Translational Medicine* (2020) 12:eabb0152). Briefly, B16-F10-RFP+ cells pulsed with 100 ng/mL of IFNγ 18 h were plated in a flat bottom 96-well plate in triplicate at 5,000 cells per well for IncuCyte Live Cell Analysis (Essen Bioscience). Pmel T cells (o2R or o9R, pre-treated with MSA-IL2 or MSA-oIL2 for 48 h) were added at 2:1 effector to target ratio and two phase-contrast and fluorescent images were obtained of each well every 2 h using the IncuCyte live imaging system and quantified by percentage confluence. Human T cell repetitive killing assay was also conducted using IncuCyte Live Cell Analysis. Human melanoma cells (nRFP-M407, $5\times10^5$) were plated per well in six-well plates. Untransduced or co-transduced human T cells (cotransduced with either ho2R/NYESO1-TCR or ho9R/NYESO1-TCR, and preincubated for 48 h with MSA-hoIL2) were added in duplicate at 1:1 effector:target ratio. Every 72 h, melanoma cells (nRFP-M407, $5\times10^5$) were added to each well; orthogonal cytokine (MSA-hoIL2) was replenished 24 h prior to every tumor rechallenge In Vivo Tumor Studies For in vivo B16-F10 tumor growth experiments, early passage cell lines were used (less than ten passages). B16-F10 cells ($5\times10^5$) were injected subcutaneously in the right flank of C57BL/6 mice. Where indicated, mice were lymphodepleted with 500 cGy of total body irradiation one day prior to adoptive transfer of T cells. T cells were adoptively transferred approximately seven days after tumor inoculation, or when tumors became palpable. Specifically, $5\times10^6$ sorted T cells were resuspended in 50 μl of PBS per mouse and administered via retroorbital injection. Where indicated, mice received treatment with cytokines: mouse serum albumin (MSA)-bound murine IL-2 (MSA-IL2) or MSA orthogonal IL2 (MSA-oIL2) (25,000 units per day, intraperitoneal) for 5 consecutive days starting on the day of adoptive transfer. Tumor size (length×width) was monitored with calipers three times a week and volume was calculated as (length×width$^2$)/2). Peripheral blood (10 μL) was harvested at specified time points from tail vein for quantification of adoptively transferred pmel T cells by flow cytometry. Mice were euthanized when the total tumor volume exceeded 2000 mm$^3$.

Syngeneic PDA tumor model has been previously described (Watanabe et al., *JCI Insight* (2018) 3(7):e99573). Briefly, established subcutaneous PDA7940b tumors were treated intratumorally with control virus Ad-Null (1e9 VP/injection) or Ad-oIL2 (1e9 VP/injection) in 50 μl PBS on Days 0 and 4. CAR T cells (5e6 live CAR-positive cells) were administered via tail vein injection on Day 1 in 200 μl PBS. Cyclophosphamide preconditioning was performed on Day −1 by intraperitoneal injection (120 mg/kg). Tumor dimensions were measured with digital calipers and volumes were calculated as follows: volume=(length×width$^2$)/2. Cured mice were rechallenged with PDA7940b cells by subcutaneous injection into the opposite flank and tumor size was recorded 24 days later by caliper measurement. Age-matched naïve mice were injected identically and served as control for tumor growth.

Immunophenotyping by Flow and Mass Cytometry

For in vitro immunophenotyping of orthogonal cytokine receptor transduced T cells, sorted T cells were plated with equipotent doses of MSA-oIL2 or MSA-IL2 in triplicates. After 48 h, T-cells were collected and surface-stained. For in vivo assessments, peripheral blood was obtained via tail vein sampling at indicated time points. At the time of necropsy, spleens were crushed and washed with PBS over a 70 μm cell strainer to collect splenocytes. Splenocytes and peripheral blood samples were treated with ACK Lysis Buffer prior to antibody staining.

B16 tumors were minced and dissociated using a murine tumor dissociation kit (Miltenyi Biotec) and a gentleMACS Octo Dissociator (Miltenyi Biotec). Cells were then resuspended in PBS and filtered through a 70 μm cell strainer to obtain single cell suspensions.

Cells were stained with antibodies at 4° C. for 30 minutes in phosphate-buffered saline (PBS), 5% fetal bovine serum, and 2 mM EDTA. Antibodies are listed in FIG. 20. 7-AAD viability dye was used to distinguish live cells from dead cells. Cells were analyzed by flow cytometry using a LSR-Fortessa (BD Biosciences). Data was analyzed using the FlowJo software (version 10, BD Biosciences).

PDA7940b tumors were excised, weighed, minced with scalpels and dissociated using an enzyme cocktail consisting of hyaluronidase (2.5 U/ml), DNAse (50 U/ml), Collagen Type I/II/JV (75 U/ml, 35 U/ml, 75 U/ml, respectively) in RPMI 1640 supplemented with 1% penicillin/streptomycin. CD45-positive cells were isolated from single-cell tumor suspensions with CD45 (TIL) MicroBeads according to manufacturer's instructions (Miltenyi Biotec) and stored in liquid nitrogen. Quantification of tumor-infiltrating CAR T cells was performed using CountBright Beads (ThermoFisher) and normalized to tumor weight.

For mass cytometry, cells were first fixed with 1.6% PFA for 5 mins at room temperature. Cells were washed with 10 mL of MaxPar Cell Staining Buffer (Fluidigm) and spun at 970×g at 4° C. for 10 minutes. Next, the cells were resuspended in the surface antibody cocktail for 30 mins at RT. Cells were washed with 5 mL of PBS and resuspended in 1 mL of ice-cold methanol for 15 minutes on ice. Cells were again washed with MaxPar Cell Staining Buffer and stained with the intracellular antibody cocktail for 30 minutes at RT. Finally, cells were washed with 10 mL MaxPar Cell Staining Buffer and stained with the intercalating solution (Cell-ID™ Intercalator-Ir, cat #201192B) at a 1:6000 dilution in Maxpar Fix and Perm Buffer with 1.6% PFA (Fluidigm cat #201067) overnight at 4° C. Data was acquired using the Fluidigm® Helios™ (San Francisco, CA) mass cytometer. Analysis was performed using Omiq (San Francisco, CA) based on arcsinh scaled data gated on live, singlet CD45+ leukocytes or CD8+ T cells. Cells were embedded in two-dimensional visualization using opt-SNE and clustered using FlowSOM with elbow metaclustering using Euclidean distances. Differentially abundant clusters were determined using edgeR with a p-value significance threshold of 0.05 and log(fold change)≥1. Graphs were generated using the R package ggplot.

Intracellular Cytokine Staining

Human co-transduced T cells (either ho2R/NYESO1-TCR or ho9R/NYESO1-TCR) were harvested from repetitive tumor challenge coculture 72 h after the most recent tumor challenge and 24 h after orthogonal cytokine had been replenished in culture media. T cells ($1×10^5$) were cultured in a 96-well plate with anti-human CD3/CD28 Dynabeads (ThermoFisher) or melanoma cells at 1:1 effector:target ratio (nRFP-M407 or M263) in the presence of brefeldin A and monensin. After 4 h, cells were surface stained for 30 mins at RT, fixed and permeabilized for intracellular cytokine staining for 30 min at RT. For intracellular cytokine staining of enriched CD45+ TILs from PDA740b tumors, cells were stimulated for 6 h with Cell Activation Cocktail (with Brefeldin A) (Biolegend), fixed/permeabilized in Cyto-Fast™ Fix/Perm Buffer Set (Biolegend) and stained with an anti-IFNγ antibody. Cells were washed and analyzed by flow cytometry using a LSRII (BD Biosciences). Data was analyzed using the FlowJo software (version 10, BD Biosciences Multiplex Immunohistochemistry Formalin-fixed and paraffin-embedded tumor specimens were cut in 4 μm thick sections onto glass slides for staining. The tyramid signal amplification (TSA)-based Opal method was used in this study for immunofluorescence (IF) staining (Opal Polaris 7-Color Automation IHC Kit; Akoya Biosciences, Marlborough, MA, USA; Catalogue No. NEL871001KT). The Opal fluorophores were used at a 1 in 150 dilution, as per manufacturer's recommendation. A fluorescent single-plex was performed for each biomarker and compared to the appropriate chromogenic single-plex to assess staining performance. Once each target was optimized with single-plex staining, the Opal 6 multiplexed assay was used to perform multiplex staining of slides. Primary antibodies were applied to mouse spleen specimens as controls at optimized concentrations previously determined for single-plex staining of control tissues. Staining was performed using the BOND RX system (Leica Biosystems). The sequence of antibodies for multiplex staining was: Foxp3 (opal 480), CD4 (opal 520), PD-1 (opal 570), CD8 (opal 620), and CD3 (opal 690). Staining was performed after 20 minutes of heat-induced antigen retrieval using Bond Epitope Retrieval Solution 2 (Leica Biosystems). Antibodies are listed in FIG. 20 and were at 1:200 dilution with 1 hour incubation. All fluorescently-labeled slides were counterstained with DAPI and scanned on the Vectra Polaris (Akoya Biosciences) at 20× magnification using appropriate exposure times. The data from the multispectral camera were analyzed by the imaging InForm software (Akoya Biosciences) and quantification was performed using HALO image analysis software (Indica Labs).

Histopathology, Clinical Chemistry and RNA ISH

Animals were euthanized by means of $CO_2$ asphyxiation. Immediately after death, blood (n=3 per group) was collected by cardiac puncture into Microvette tubes (Sarstedt) and allowed to clot in RT for 30 min before centrifugation at 12,000 g for 10 min. Serum was stored at −80° C. before analysis. Cytokine levels in sera were measured with the Mouse 25-plex Cytokine Panel (IDEXX Bioanalytics). Serum levels of Ca, P, K, and uric acid were measured with a custom clinical chemistry panel (IDEXX Bioanalytics).

Complete necropsy with macroscopic post-mortem examination was performed on all animals and the following organs/tissues were sampled and fixed in 10% neutral buffered formalin for histopathological examination: head and brain, lumbar spinal cord, skin from the dorsal region, auricles, quadriceps femoralis, sternum, salivary glands, larynx and trachea, esophagus, lungs, heart, GI tract, mesenteric ligament, pancreas, liver and gall bladder, reproductive tract, kidneys, urinary bladder, any organ/tissue showing macroscopic lesion/s. The weights of liver, right kidney, left kidney, and heart were recorded before fixation. Formalin-fixed tissues samples were trimmed according to the RITA guidelines (1, 2, 3) and then routinely processed for paraffin embedding, sectioning and H&E staining. The resulting slides were analyzed by a board-certified veterinary pathologist blinded to experimental design.

Distribution of mesothelin expression and CAR T cell infiltration in the meninges were investigated by means of multiplex fluorescent RNA in situ hybridization (RNAscope® Multiplex Fluorescent Assay, ACD Bio) including a custom probe designed against the murine retrovirus used to transduce T cells with CAR and ortho-receptors. The assay was performed on formalin-fixed and paraffin-embedded brain section. Whole slide imaging on the resulting fluorescently labeled sections was performed using the Aperio VERSA 200 slide scanner (Leica Biosystems). CAR T cells and mesothelin-positive cells were finally counted using object counting tool included in the Aperio ImageScope software (Leica Biosystems).

RNA Sequencing and Analysis

Figure 7A:
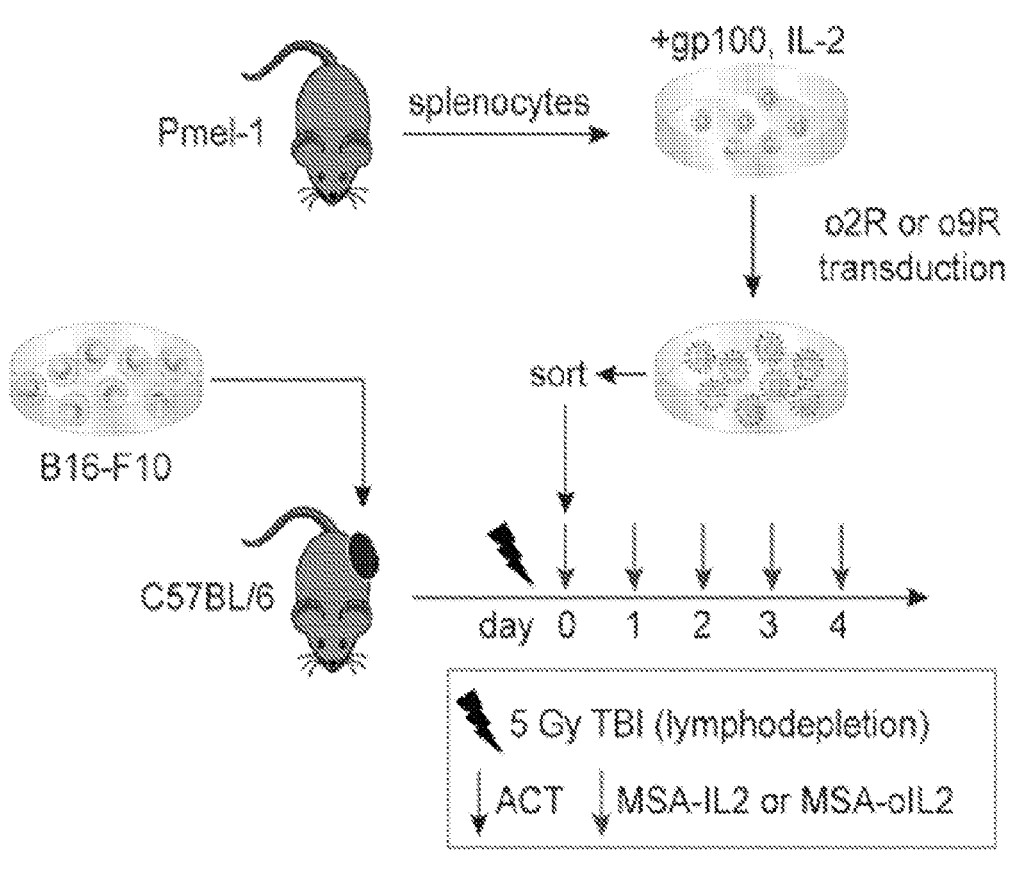
Figure 7B:
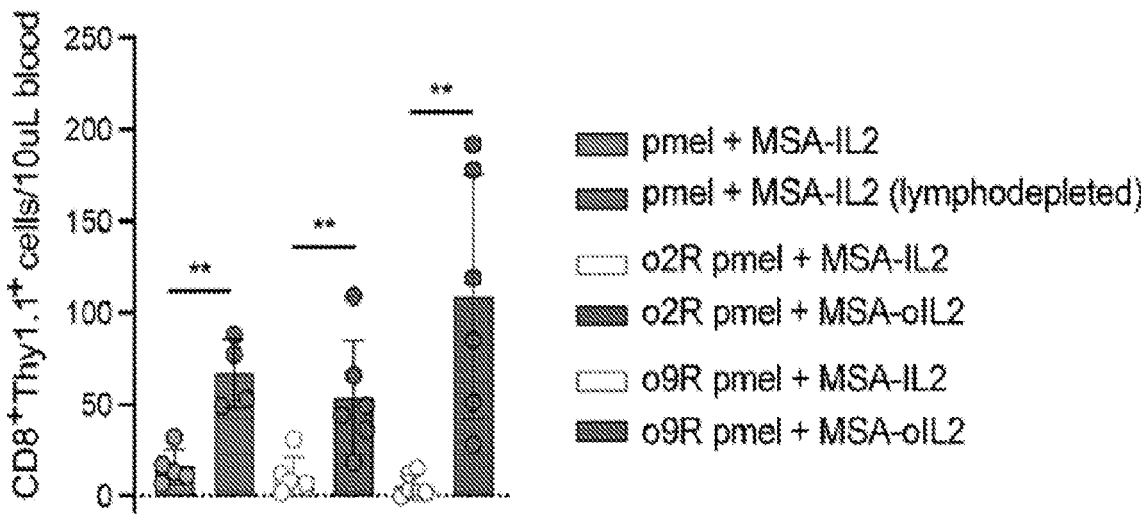
Figures 7C, 7D, 7E, 7F:
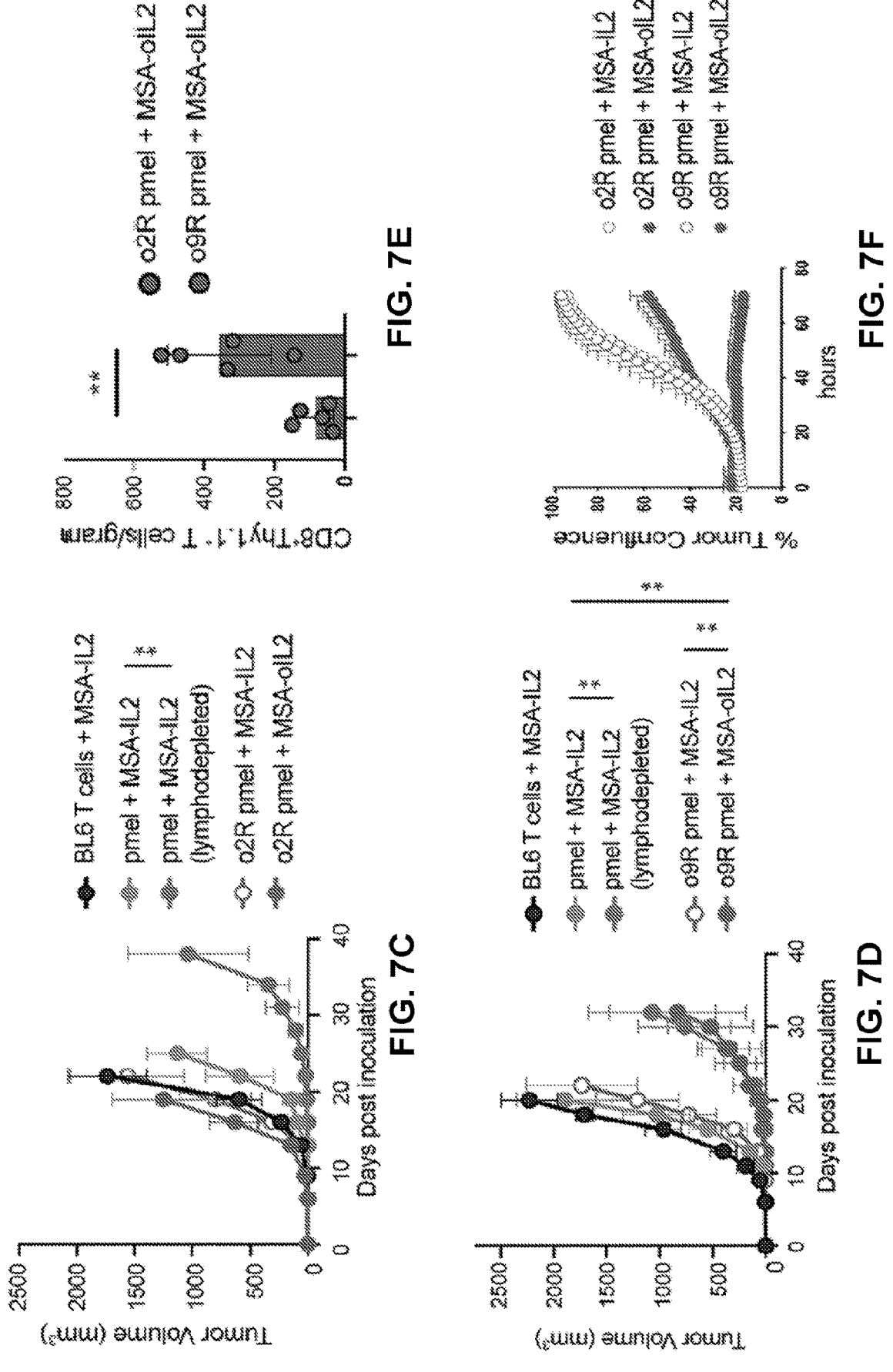
Figures 7H, 7I:
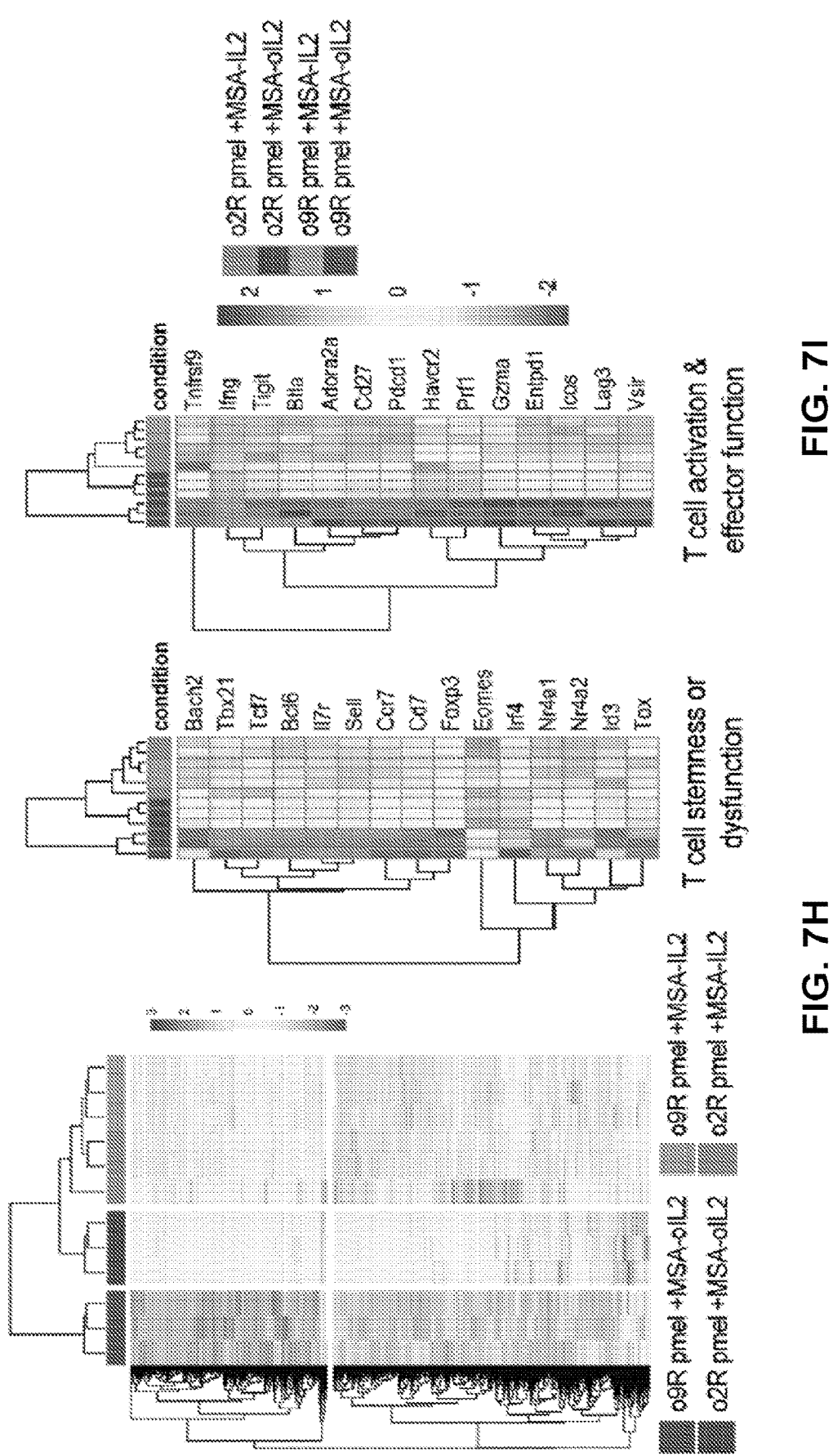
Figure 7J:
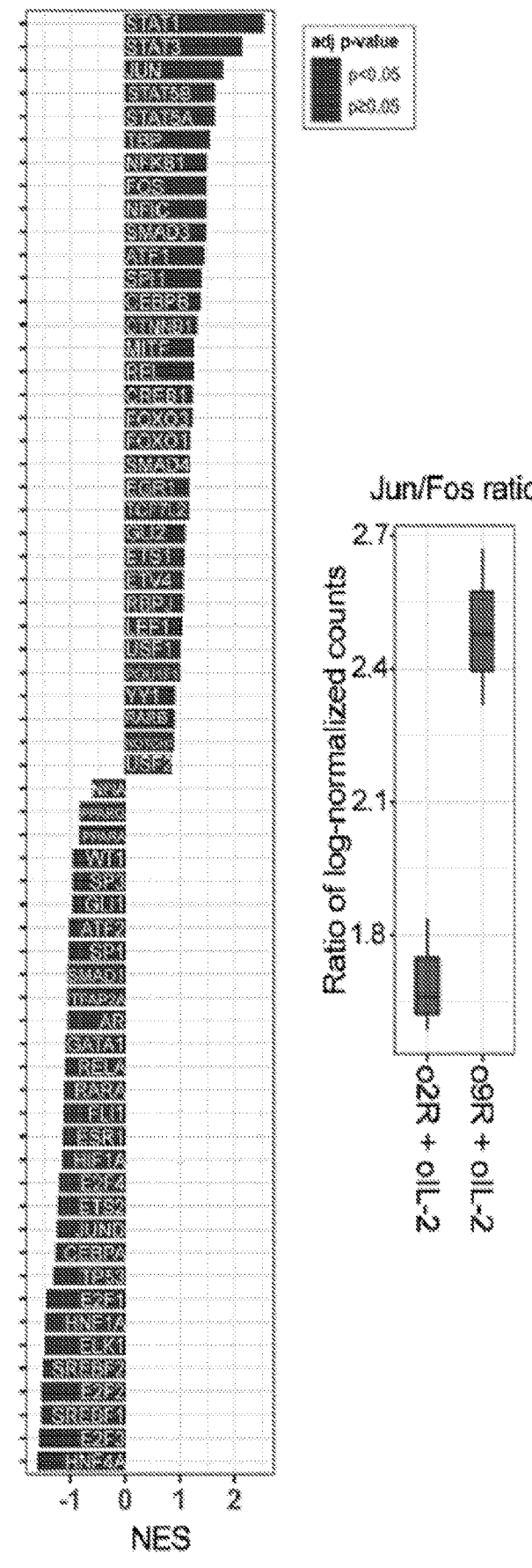

For in vitro experiments described in FIGS. 7H-7J, o2R and o9R pmel T cells were stimulated with 5 μM oIL-2 or 0.05 μM oIL-2 for 48 h. RNA was extracted using the RNeasy mini kit (Qiagen). RNA sequencing (RNAseq) libraries were prepared using the KAPA mRNA stranded library preparation kit, according to the manufacturer's recommendations. Libraries were pooled and sequenced on the Illumina HiSeq3000 platform (50 bp single-end reads). Reads were aligned to the mouse reference genome (mm9/GRCm38) using HISAT2 (v2.0.4) (Kim et al., *Nature Biotechnology* (2019) 37:907-915). Gene expression was quantified using HTSeq-counts (v0.6.1) (Anders et al., *Bioinformatics* (2015) 31:166-169). Differential expression analysis was performed using DESeq2 (Love et al., *Genome Biol* (2014) 15:550), and subsequent gene set enrichment analysis was performed using the fgsea (Sergushichev et al., bioRxiv, 060012 (2016)) and msigdbr (Liberzon et al., *Cell Systems* (2015) 1:417-425). R packages, specifically on the TFactS annotated gene set (Essaghir et al., *Nucleic Acids Res* (2010) 38:e120), and visualized using the ggplot2 R package. Differentially expressed genes were filtered to those with an adjusted p-value of less than 0.01 and a log 2(fold change)≥1. Gene expression was visualized using the normalized gene expression (calculated using the r log transform from DESeq2 and scaled by row) using the pheatmap R package. Principal component analysis and sample-to-sample heatmaps were generated using the R functions prcomp and dist, respectively.

Figure 13G:
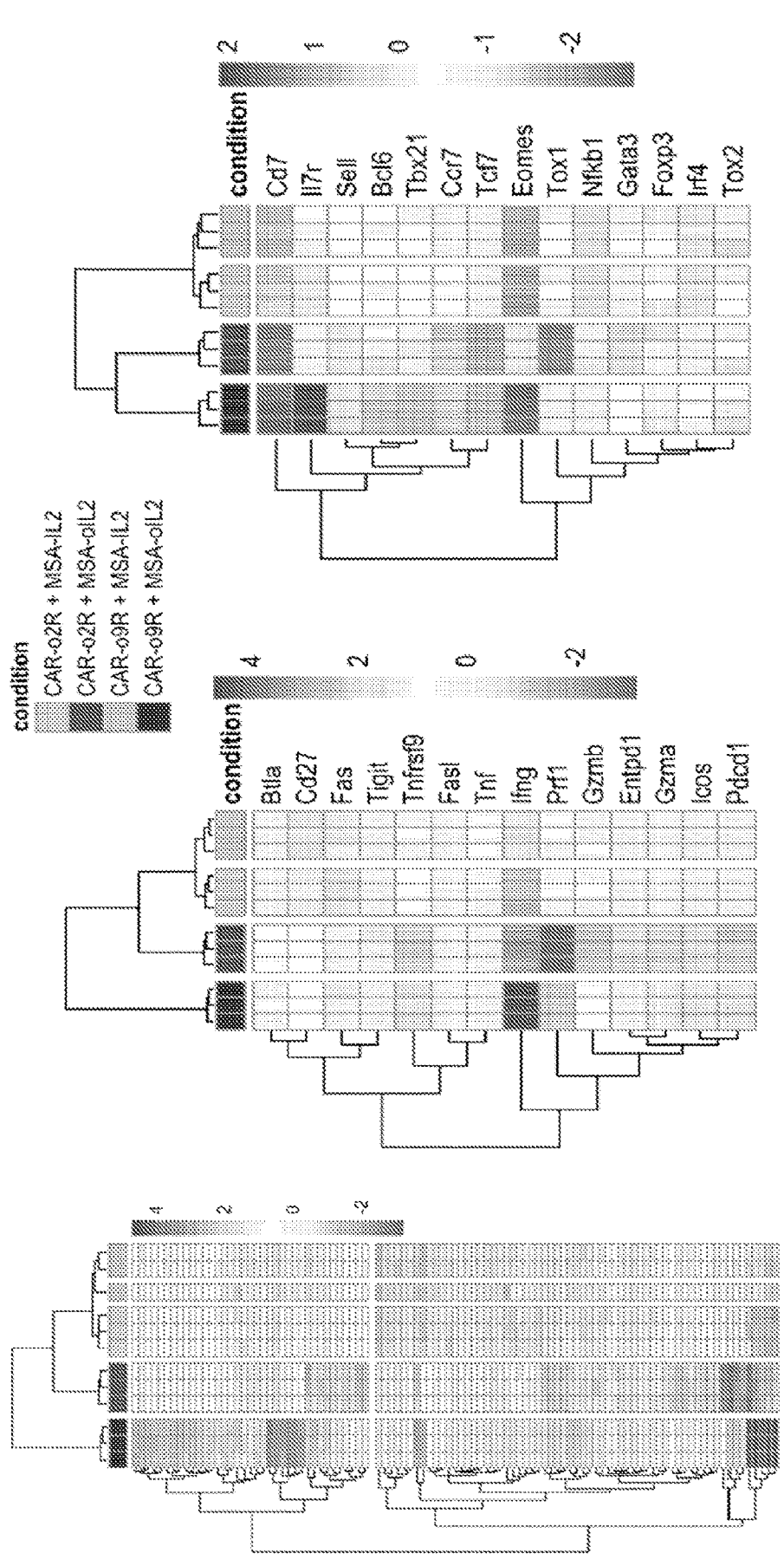

For in vitro experiments described in FIG. 13G, CAR-o2R and CAR-o9R cells were stimulated for 48 h with MSA-oIL2 or MSA-IL2 and total RNA was extracted using the RNeasy mini kit (Qiagen). RNA expression was analyzed using the nCounter Mouse Immunology Panel (Nanostring Technologies). Analysis was performed as described above.

FIG. 20 provides a table of reagents used in the experiments described herein.

The results of the the experiments are now described.

Example 1: Synthetic IL-9 Receptor Signaling Endows T Cells with a Combination of Stem Cell Memory and Effector Antitumor Activity Synthetic receptor signaling has the potential to endow adoptively transferred T cells with new functions that overcome major barriers in the treatment of solid tumors, including the need for conditioning chemotherapy. Here, chimeric receptors that have an orthogonal IL-2 receptor (o2R) extracellular domain fused with the intracellular domain (ICD) of receptors for common γ-chain (γc) cytokines IL-4, IL-7, IL-9 and IL-21 were designed such that the orthogonal IL-2 cytokine elicits the corresponding γc cytokine signal. Of these, T cells signaling through the chimeric orthogonal IL-2R-ECD/IL-9-ICD receptor (o9R) are distinguished by concomitant activation of STAT1, STAT3 and STAT5 and assume characteristics of stem cell memory (Tscm) and effector T cells. o9R T cells have superior anti-tumor efficacy in two recalcitrant syngeneic murine solid tumor models of melanoma and pancreatic cancer and were effective even in the absence of conditioning lymphodepletion. Therefore, by repurposing IL-9R signaling using a chimeric orthogonal cytokine-receptor, T cells gain new functions resulting in improved antitumor activity for hard-to-treat solid tumors.

Adoptively transferred gene engineered T cell therapies have demonstrated significant antitumor activity in patients with hematopoietic malignancies, but have limited benefit in patients with solid tumors (Rosenberg and Restifo, Science (2015) 348:62-68). One major limitation is the poor in vivo expansion and persistence of adoptively transferred T cells, necessitating lymphodepleting conditioning chemotherapy—a toxic regimen that limits patient eligibility (Goff et al., *J Clin Oncol*. (2016) 34:2389-2397; Dudley et al., *J Clin Oncol*. (2008) 26:5233-5239; Dutcher et al., *Journal for Immuno Therapy of Cancer* (2014) 2:26). Even those T cells that do expand and persist become terminally differentiated and dysfunctional (Philip et al., Nature (2017) 545:452-456; Schietinger et al., *Immunity* (2016) 45:389-401). Synthetic cytokine receptor signaling could reprogram T cells with a stem-like phenotype, becoming able to overcome these limitations and exhibit superior antitumor activity in mouse models and humans (Gattinoni et al., *Nature Reviews Cancer* (2012) 12:671-684; Krishna et al., *Science* (2020) 370:1328-1334). Previously, therapeutic manipulations to select or expand stem-like T cells were limited to the cell manufacturing phase and could not be made in vivo.

An orthogonal cytokine receptor is a mutant form of the native cytokine receptor that selectively binds to a mutant form of the native cytokine. This orthogonal cytokine-receptor pair is mutually exclusive from the native cytokine-receptor pair. Thus, orthogonal cytokine receptors, when transduced into T cells and then stimulated by their corresponding orthogonal cytokine, provide a means to selectively and biologically manipulate adoptively transferred cells in vivo. This was recently demonstrated with the use of an orthogonal mouse IL-2 cytokine-receptor pair (oIL2 and o2R) (Sockolosky et al., *Science* (2018) 359:1037-1042) for in vivo modulation of adoptively transferred T cells for cancer immunotherapy, as IL-2R signaling potently stimulates T cell survival, expansion, and enhanced anti-tumor function.

Figure 1A:
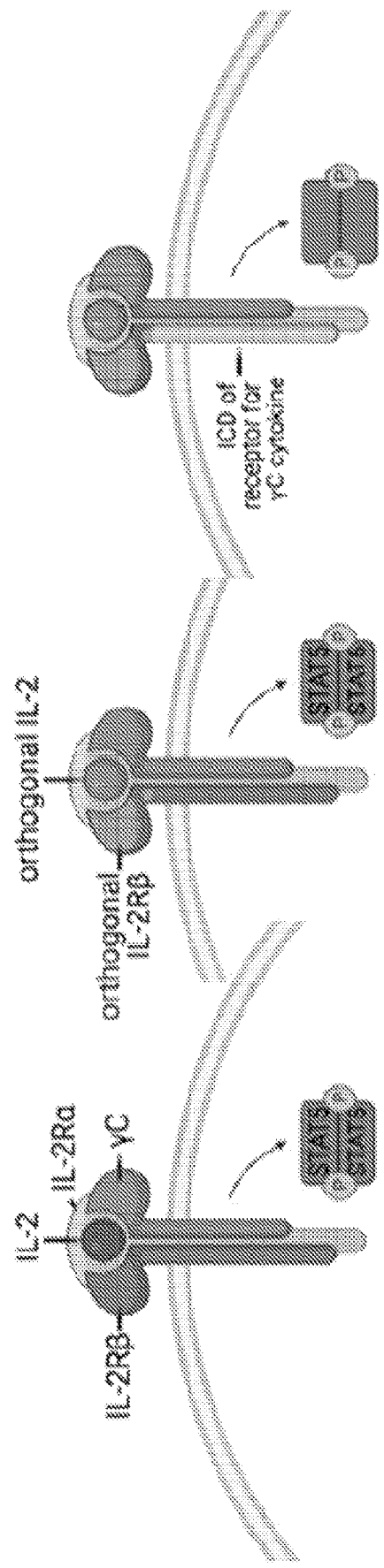
FIG. 1A-FIG. 1G illustrate the finding that a chimeric orthogonal IL-2 receptor unveils properties of IL-9R signaling in T cells.

The orthogonal mouse IL-2 receptor (o2R) consists of the IL-2Rβ chain with a modified extracellular domain that selectively binds oIL-2 (clone 3A10), but not wildtype IL-2 (FIG. 1A). Likewise, oIL-2 cannot bind the wildtype IL-2 receptor. To signal, both orthogonal and wildtype IL-2 receptor cooperate with the wildtype γc. Employing the modular nature of the oIL-2 system, we wished to explore the potential functional and therapeutic utility of other members of the γc cytokine receptor family, some of which confer favorable features upon anti-tumor T cells (Dwyer et al., *Frontiers in Immunology* (2019) 10:263; Leonard et al., *Immunity* (2019) 50:832-850).

Figure 1B:
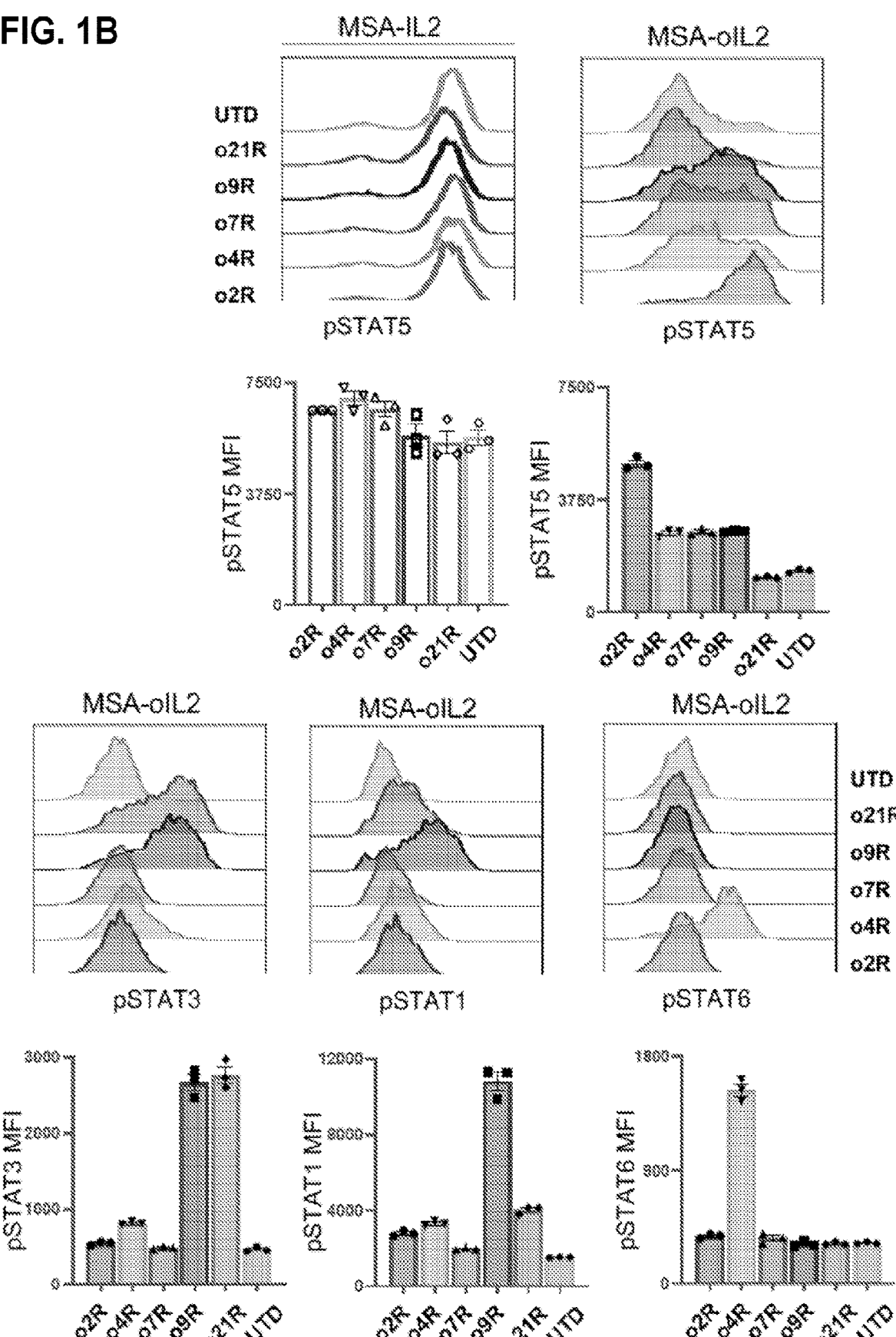

To do so, the intracellular domain (ICD) of o2R was replaced with the ICD of receptors for γc cytokines IL-4, IL-7, IL-9 and IL-21, to create chimeric orthogonal receptors containing the mouse oIL-2 binding extracellular domain (ECD) fused to the intracellular domain of each γc cytokine family receptor (ICD) (FIG. 1A, SEQ ID NOs: 15, 19, 20, 21). Importantly, activated primary T cells retrovirally transduced to express chimeric orthogonal receptors (YFP+) retained wildtype IL-2-induced STAT5 phosphorylation (FIG. 1B, left panel).

Stimulation of chimeric orthogonal receptors with mouse serum albumin-bound oIL-2 (MSA-oIL2, clone 3A10) resulted in phospho-STAT signaling patterns (FIG. 1B), consistent with known wildtype signaling through each respective γc cytokine (Leonard, et al., *Immunity, 2019,*

Figure 1C:
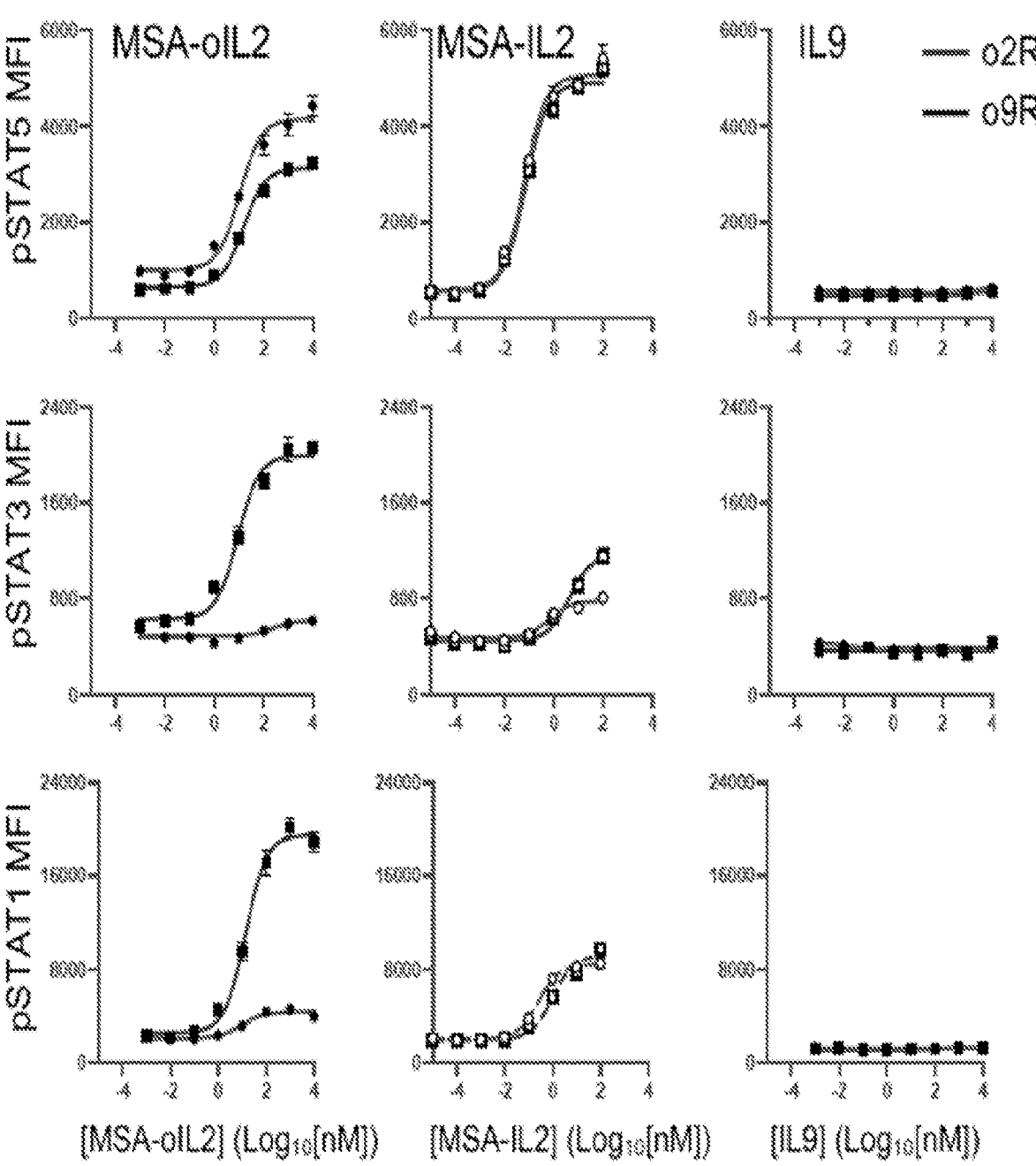
Figure 2:
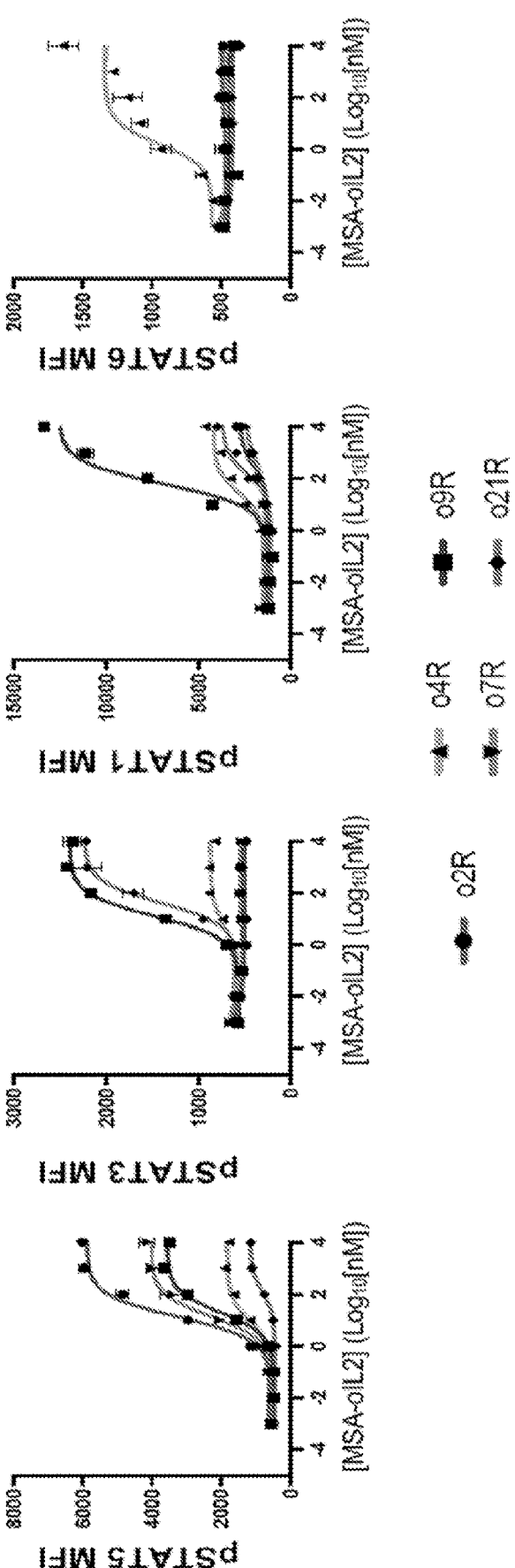
FIG. 2 illustrates pSTAT signaling dose response curves of orthoIL2Rβ ICD chimeric receptor expressing T cells stimulated with MSA-orthoIL2 for 20'. Data are shown as mean fluorescence+/−SEM, n=3.

50:832-850; Demoulin, et al., *Mol Cell Biol.,* 1996, 16:4710-4716). Signaling through o9R generated potent phosphorylation of STAT1, STAT3 and STAT5, a profile distinct from signaling through o2R, o4R, o7R, and o21R (FIG. 1B, FIG. 2), and consistent with known signaling through wildtype IL-9 receptor (CD129) (Demoulin, et al., *J Biol. Chem.,* 1999, 274:25855-25861). o9R signaling was dose-dependent and specific to MSA-oIL2 (FIG. 1C).

The IL-9 receptor, IL9R (also known as CD129), is a less-studied member of ye cytokine receptor family that is naturally expressed by mast cells, memory B cells, innate lymphoid cells, and hematopoietic progenitors (Demoulin, et al., *Mol Cell Biol.,* 1996, 16:4710-4716; Knoops et al., *Growth Factors* (2004) 22:207-215; Bauer, et al., *J Biol Chem.,* (1998) 273: 9255-9260; Takatsuka et al., *Nature Immunology* (2018) 19:1025-1034; Townsend et al., *Immunity* (2000) 13:573-583; Williams et al., *Blood* (1990) 76:906-911; Turner et al., *J Exp Med* (2013) 210:2951-2965). While T cell subsets that produce IL-9 have been described (Lu et al., *J Clin Invest* (2012) 122:4160-4171; Lu et al., *Proc Natl Acad Sci USA* (2014) 111:2265; Purwar et al., *Nat Med* (2012) 18:1248-1253; Liu et al., *Nat Commun.* (2020) 11:5902; Schanz, et al., *J Immunother Cancer* (2021) 9), the effects of IL-9R signaling on T cells are not well characterized (Elyaman et al., *Proc Natl Acad Sci USA* (2009) 106:12885-12890; Nowak et al., *J Exp Med* (2009) 206:1653-1660; Li et al., *Eur J Immunol* (2011) 41:2197-2206; Houssiau et al., *J Immunol* (1993) 150:2634-2640; Louahed et al., *J Immunol* (1995) 154:5061-5070; Lehrnbecher et al., *Cytokine* (1994) 6:279-284). For example, it has been documented that naïve T cells are insensitive to IL-9 and T cell development is unimpaired in IL-9 deficient mice, suggesting that IL-9 is not a critical natural cytokine in T cell biology (Townsend et al., *Immunity* (2000) 13:573-583; Houssiau et al., *J Immunol* (1993) 150:2634-2640; de Heusch, et al., *Eur J Immunol* (2020) 50:1034-1043).

Figures 3A, 3B, 3C:
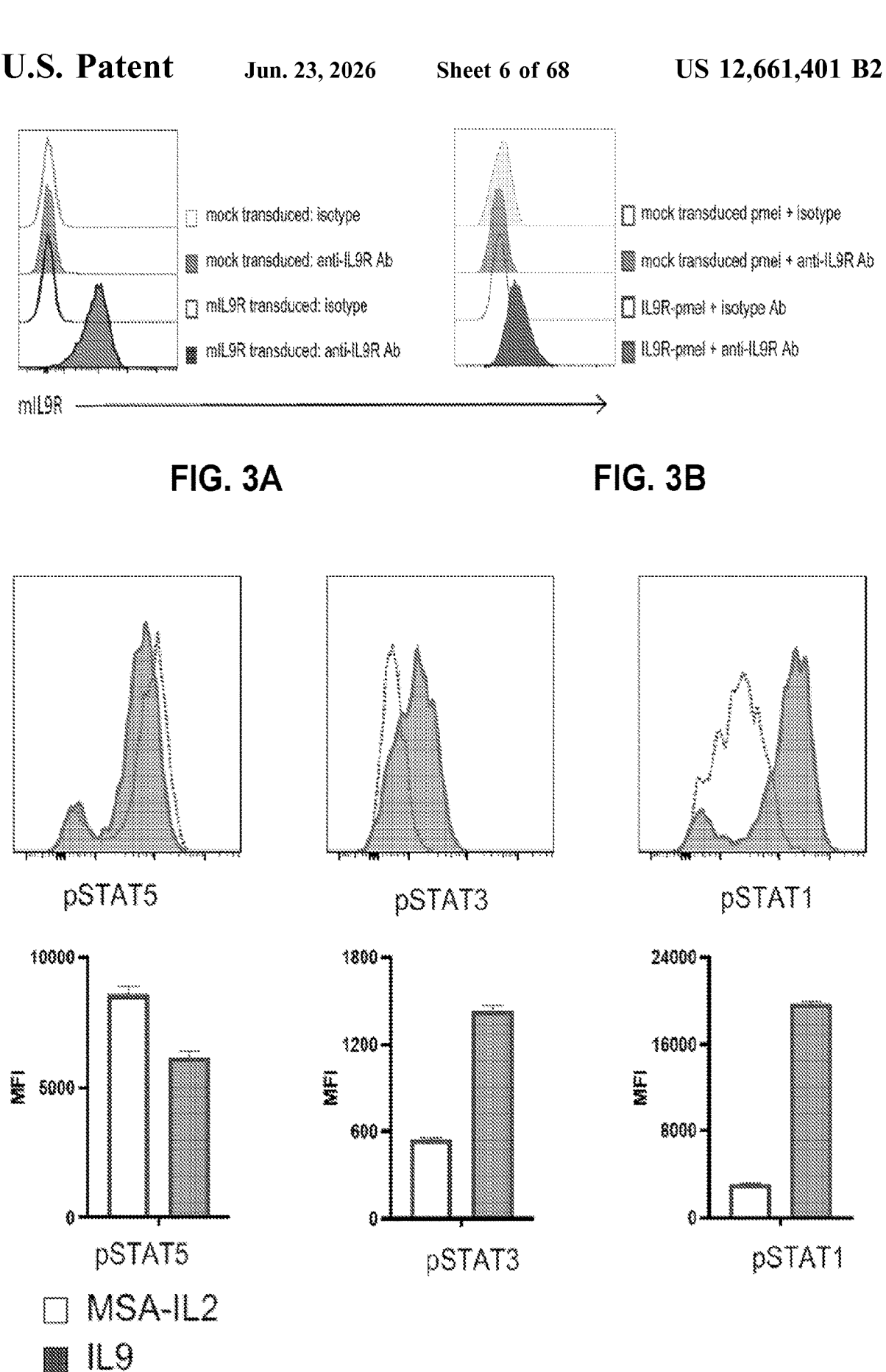
FIG. 3A-FIG. 3D provide data related to expression and pSTAT signaling of mIL9R.
Figure 3D:
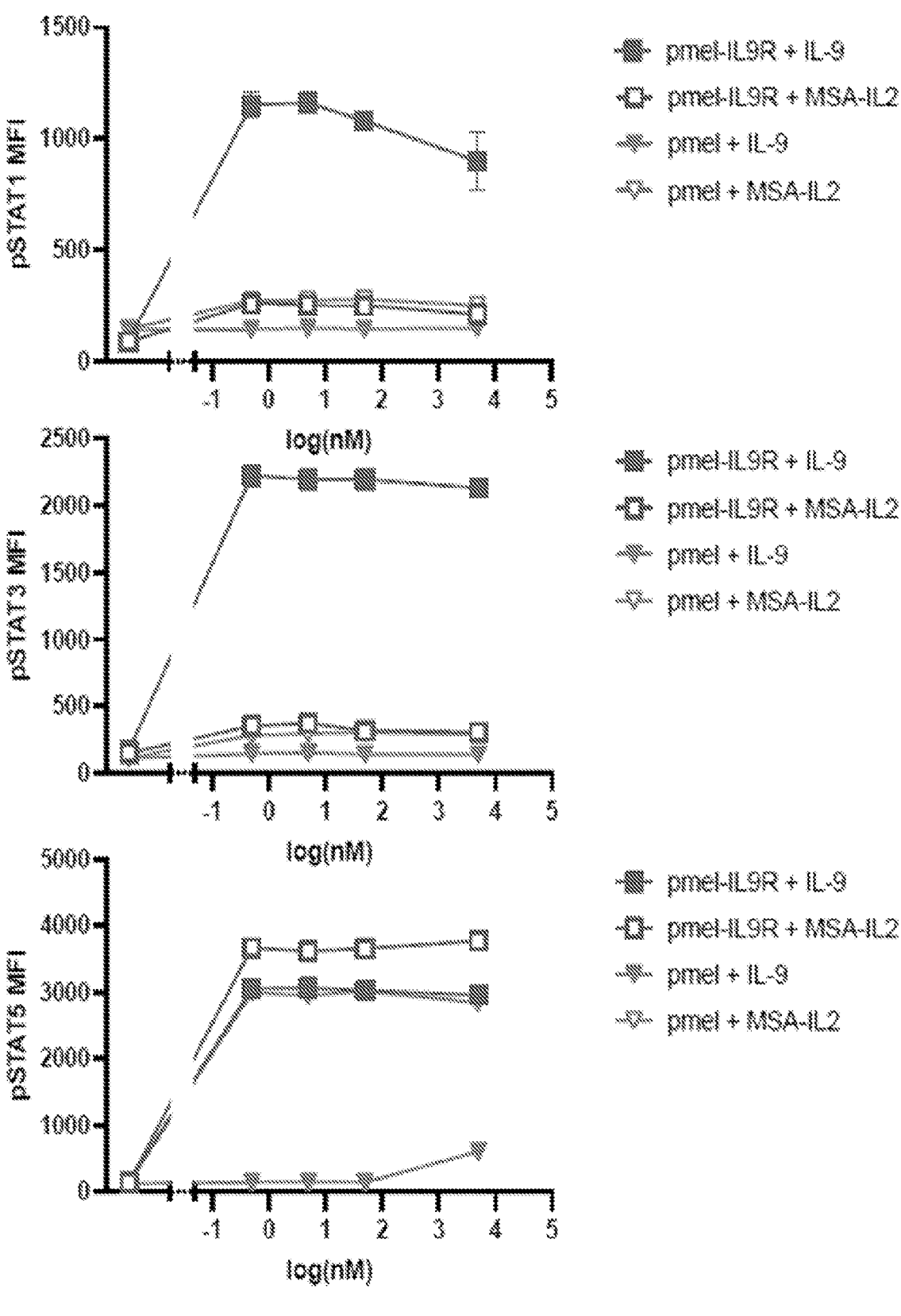

In the present study, activated mouse T cells did not support IL-9 signaling (FIG. 1C) due to the absence of IL-9R expression (FIG. 3A-FIG. 3B), underscoring the unorthodoxy of o9R signaling in these cells (Nowak et al., *J Exp Med* (2009) 206:1653-1660; Druez et al., *J Immunol* (1990) 145:2494-2499; Cosmi et al., *Blood* (2004) 103: 3117-3121). To test whether o9R signaling is a bona fide mimic of wildtype IL-9R signaling, the wildtype IL-9R was overexpressed in mouse T cells from both C57BL/6 and transgenic pmel mice (FIG. 3A-FIG. 3B). Activation of the wildtype IL-9R by IL-9 resulted in a similar STAT1, STAT3 and STAT5 phosphorylation profile observed in response to o9R signaling (FIG. 3C-FIG. 3D).

Figure 4A:
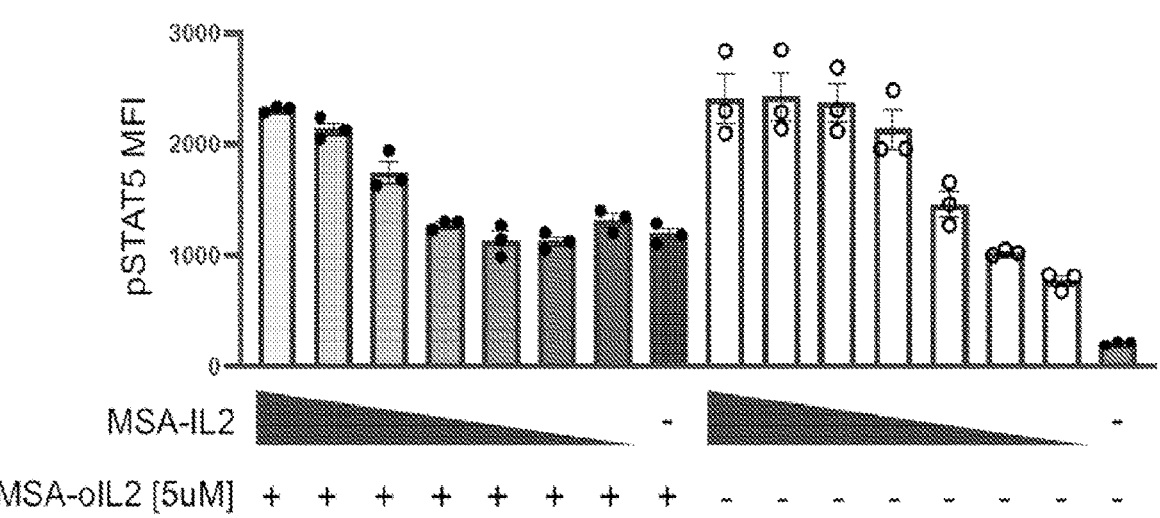
FIG. 4A-FIG. 4C provided date related to pSTAT signaling in o9R expressing C57BL/6 T cells treated with 10-fold dose titration of MSA-IL2 (starting at 100 nM) in the absence (open) or presence of MSA-oIL2 [5 μM] (filled) for 20'. Data shown as mean fluorescence+/−SEM, n=3, YFP(+) gated.
Figure 4B:
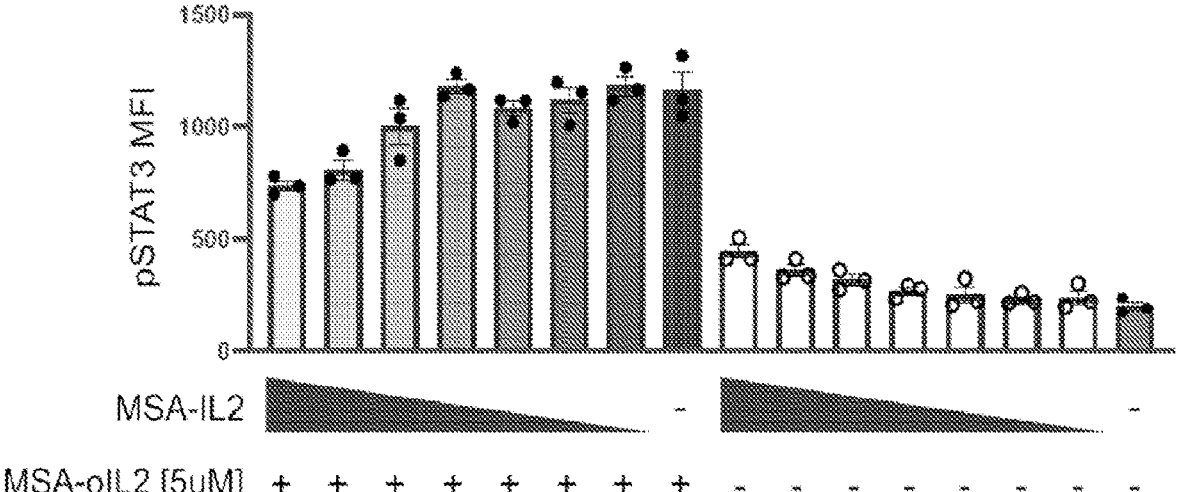
Figure 4C:
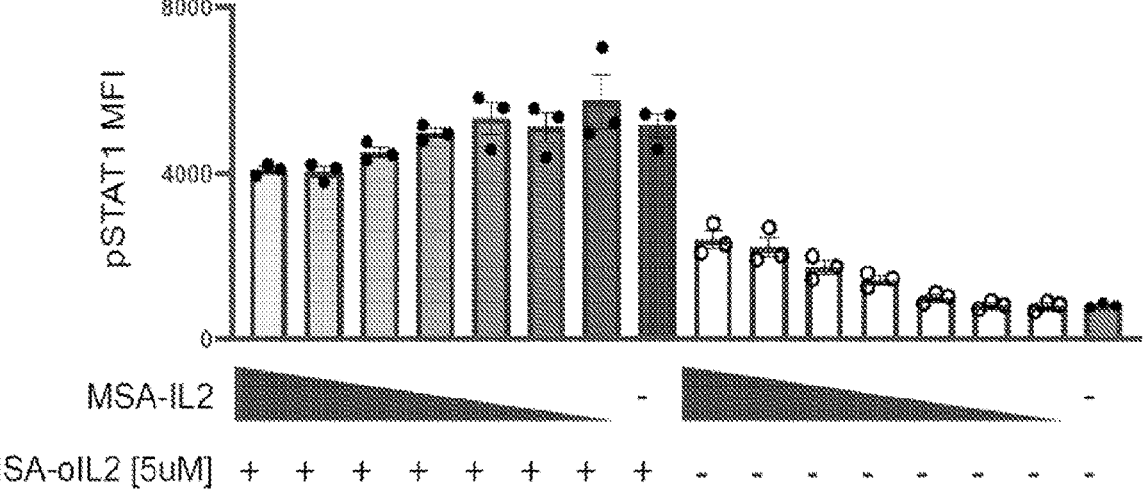

Since o9R cells also express the endogenous wildtype IL-2Rβ, we evaluated the competition between native and orthogonal signaling. Co-exposure to saturating doses of MSA-oIL2 did not affect peak pSTAT5 phosphorylation by MSA-IL2 in o9R T cells (FIG. 4A). Increasing doses of MSA-IL2, however, partially mitigate MSA-oIL2 induction of pSTAT1 and pSTAT3 in o9R T cells (FIG. 4B-FIG. 4C). Still, the unique signaling program of o9R T cells remained active even at saturating doses of MSA-IL2.

Next, the effects of signaling through the different orthogonal receptors on memory phenotype of T cells was examined. It was observed that T cells signaling through o9R (as well as o21R) enriched for a CD62L+ population and higher expression of Fas and Sca-1 consistent with a $T_{SCM}$ phenotype, a subset known for its superior anti-tumor activity in models of adoptive cell therapy (ACT) and in patients with cancer (FIGS. 1D-1F)(Krishna et al., *Science* (2020) 370, 1328-1334; Gattinoni et al., *J Clin Invest* (2005)

Figures 1D, 1E, 1F, 1G:
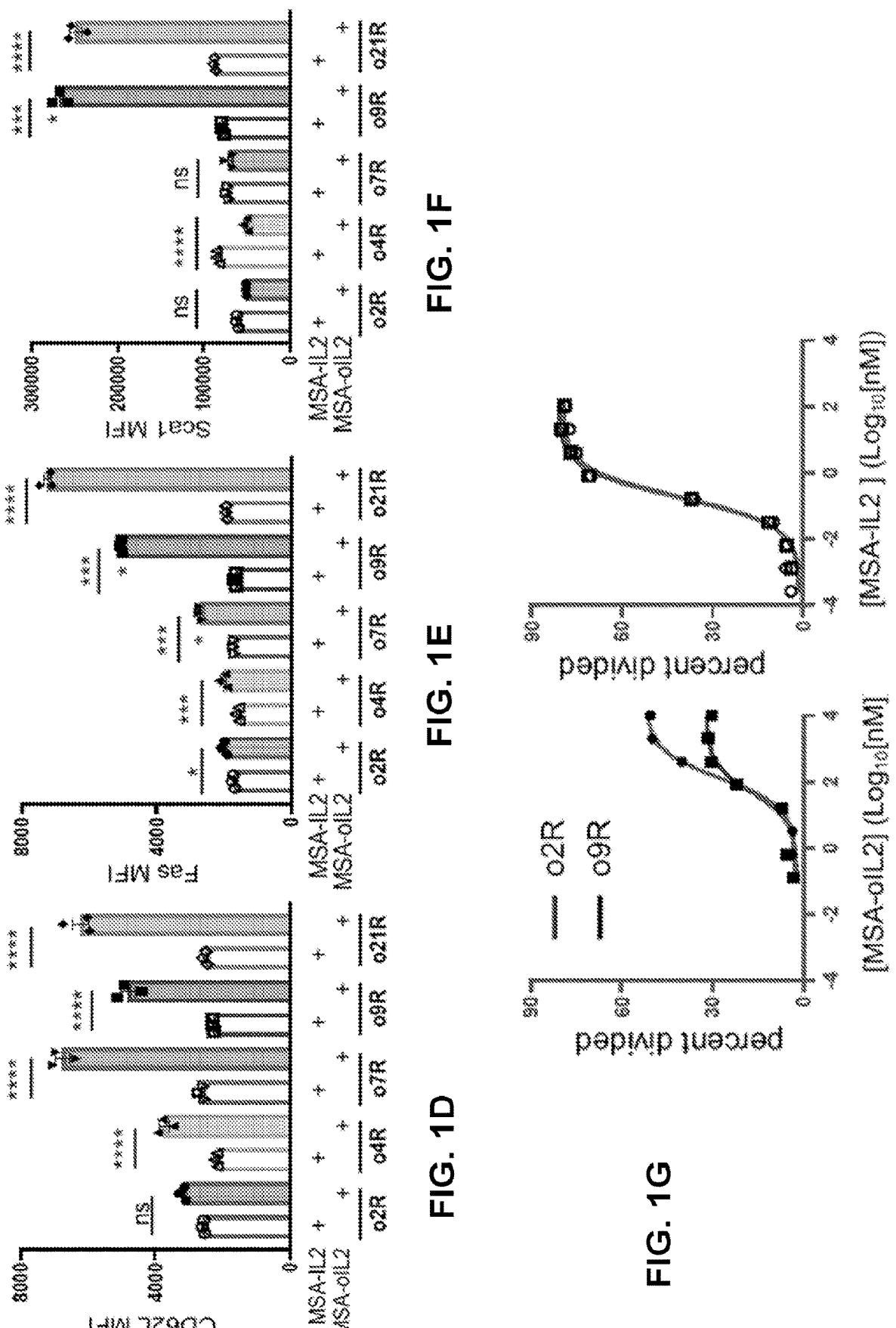
Figure 5A:
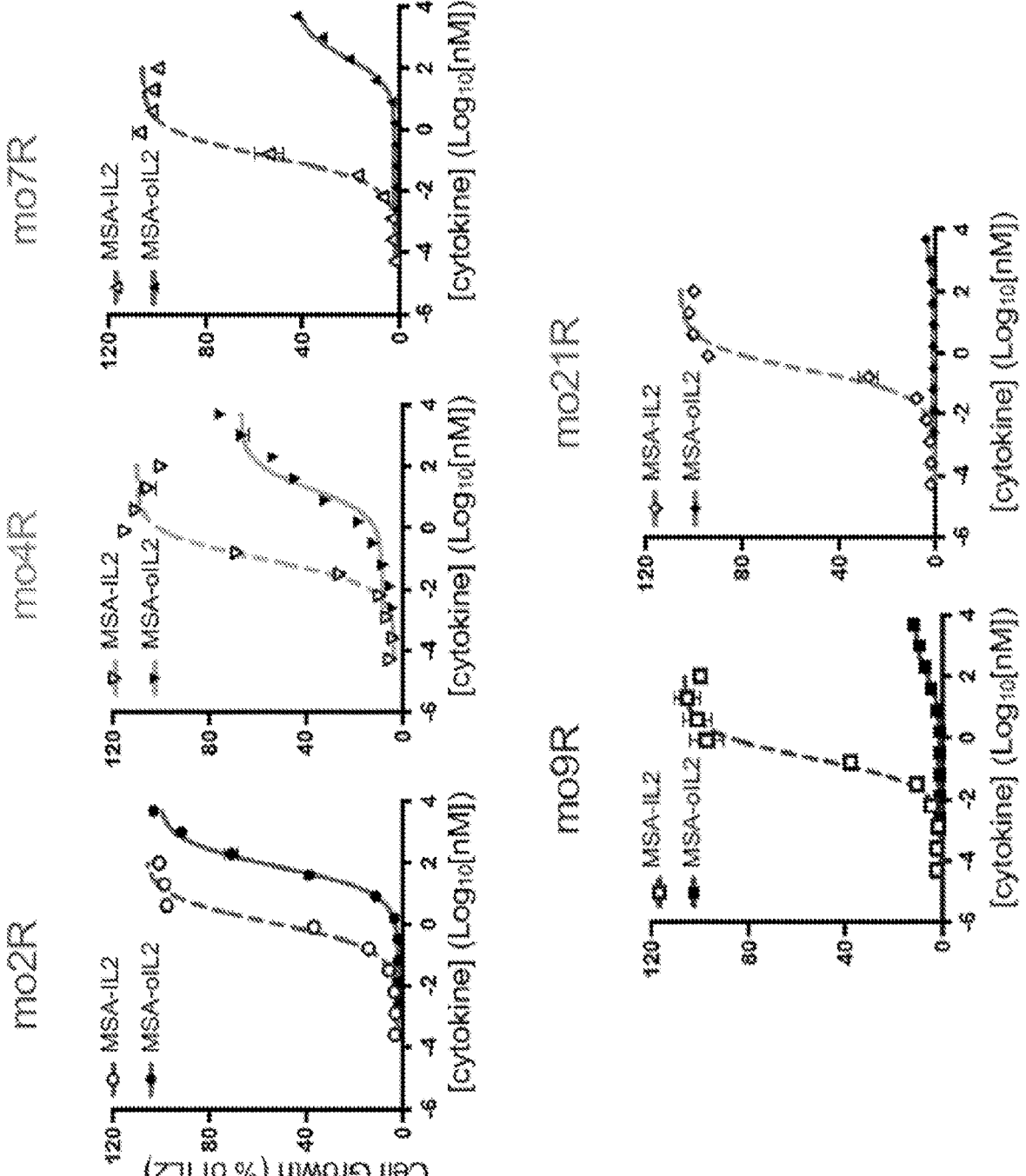
Figure 5B:
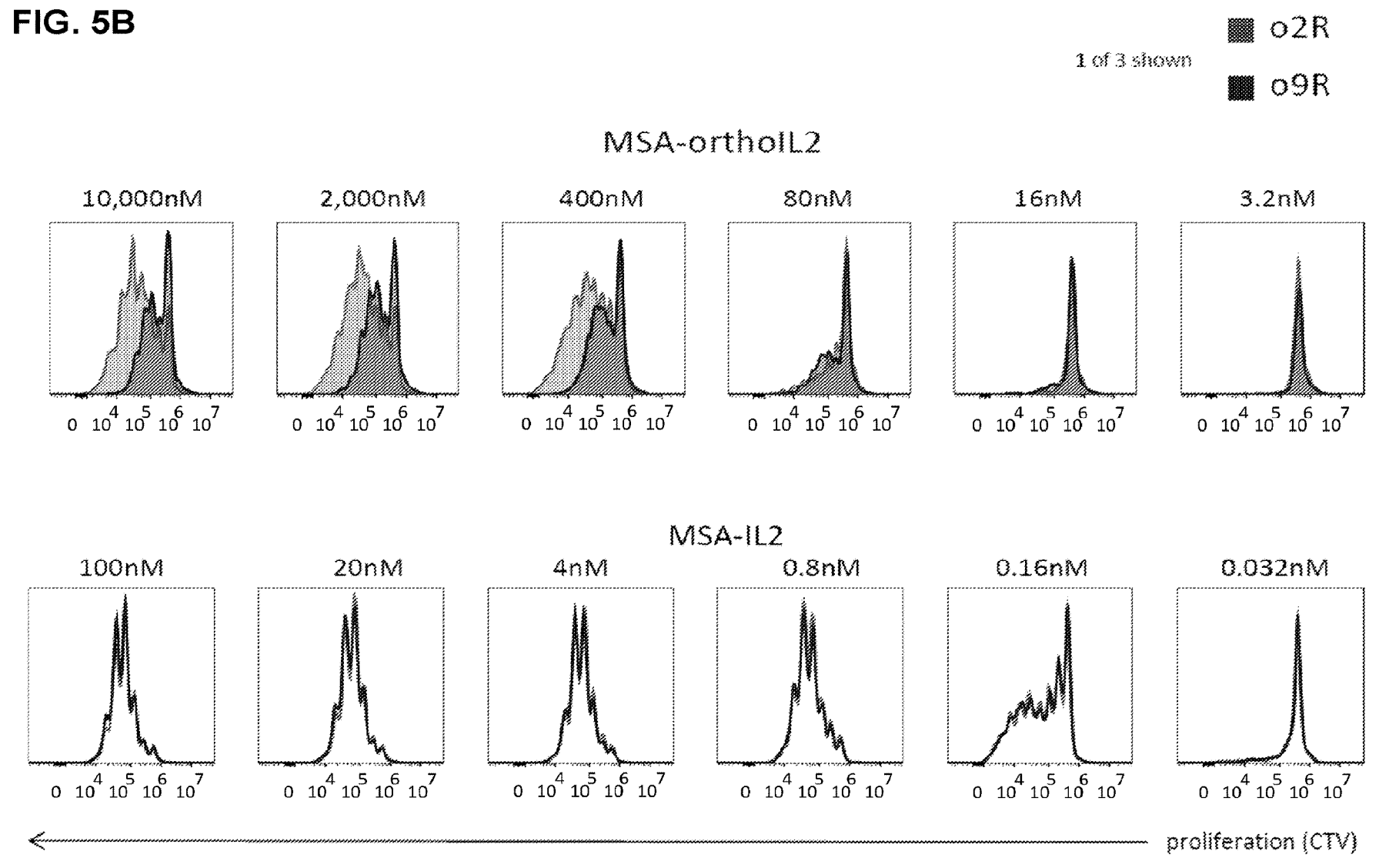

115:1616-1626; Hinrichs et al., *Proc Natl Acad Sci USA* (2009) 106:17469-17474; Klebanoff et al., *Proc Natl Acad Sci USA* (2005) 102:9571-9576). o9R T cells also proliferated less, and underwent less cell division than o2R expressing T cells, even at concentrations of MSA-oIL2 saturating for STAT5 phosphorylation (FIG. 1G and FIG. 5A-FIG. 5B). The limited proliferation was orthogonal-receptor specific, as o9R and o2R T cells responded equally to wildtype IL-2. Among the orthogonal receptors, only o21R (which also signals through STAT3) resulted in less proliferation than o9R (FIG. 5A).

Figure 6A:
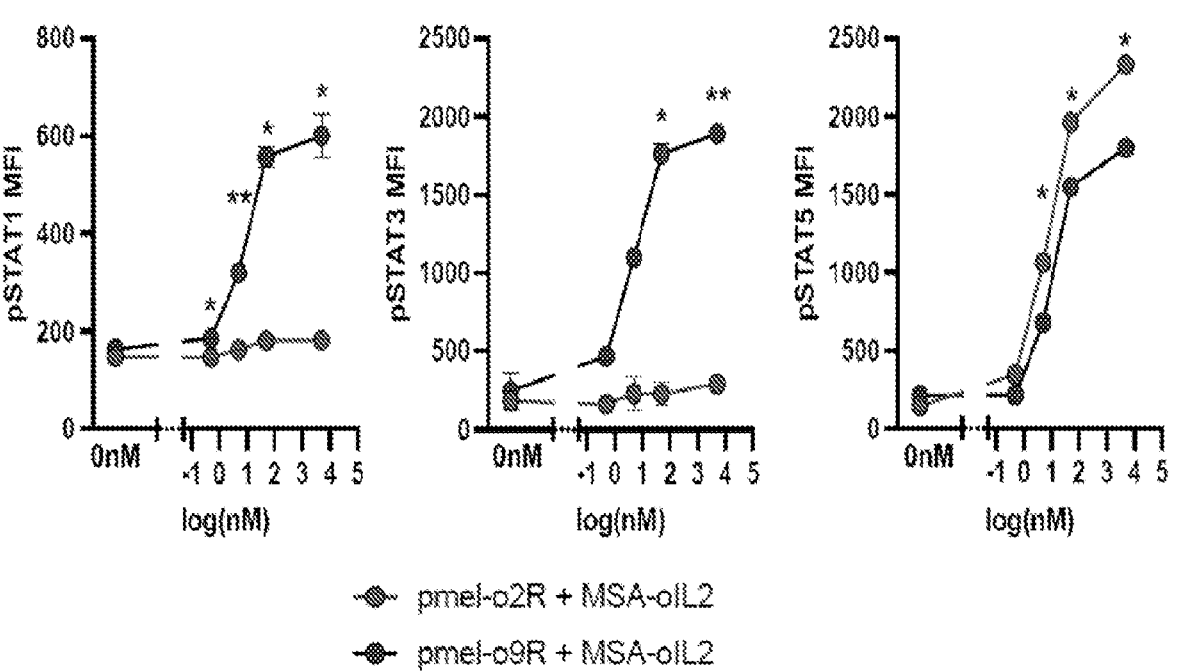
FIG. 6A-FIG. 6B illustrates signaling and proliferation of o2R and o9R pmel T cells.
Figure 6B:
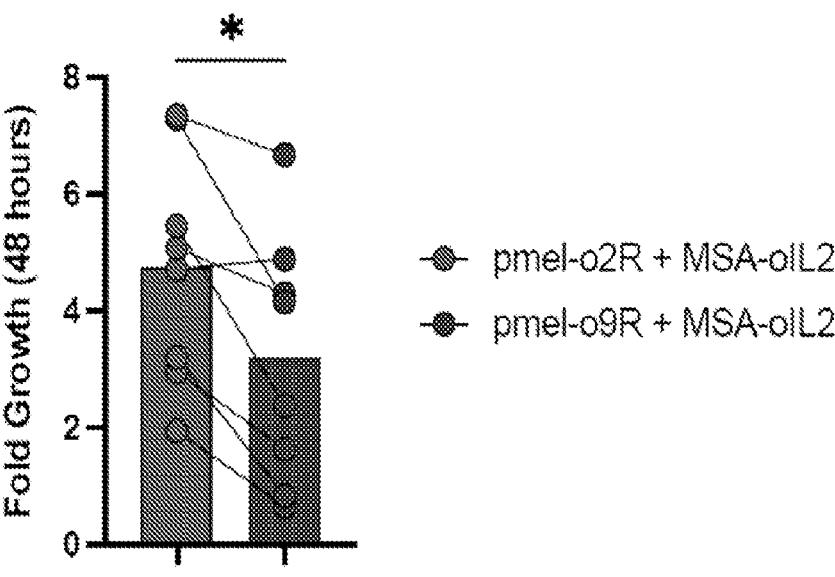

Given the unique STAT signaling profile, its lesser-known status among the γc cytokine receptor family, and acquisition of $T_{SCM}$ features, the impact of o9R signaling in vivo was studied using mouse models of ACT for solid tumors. First, an ACT model was used employing T cells from transgenic pmel mice, which express an endogenous TCR specific for gp100, a melanocytic antigen overexpressed in B16 melanoma (Overwijk et al., *J Exp Med* (2003) 198: 569-580). Given the benefits and efficacy of o2R in this model (Sockolosky et al., *Science* (2018) 359:1037-1042), the protocol was modified to be more stringent and to omit the lymphodepleting radiotherapy, a conditioning regimen which potentiates ACT by inducing homeostatic proliferation of adoptively transferred T cells through γc cytokine signaling (Surh et al., *Immunity* (2008) 29:848-862). B16 tumor-bearing C57BL/6 mice were treated intravenously with pmel T cells retrovirally transduced with either o2R or o9R, and treated with either MSA-IL2 or MSA-oIL2 (FIG. 7A). Similar to the profile of o2R and o9R T cells from C57BL/6 mice, MSA-oIL2 activated phosphorylation of STAT1, STAT3, and STAT5 in o9R pmel T cells, but only STAT5 in o2R pmel T cells (FIG. 6A). o9R pmel T cells also proliferated less than o2R pmel T cells (FIG. 6B).

Figure 8A:
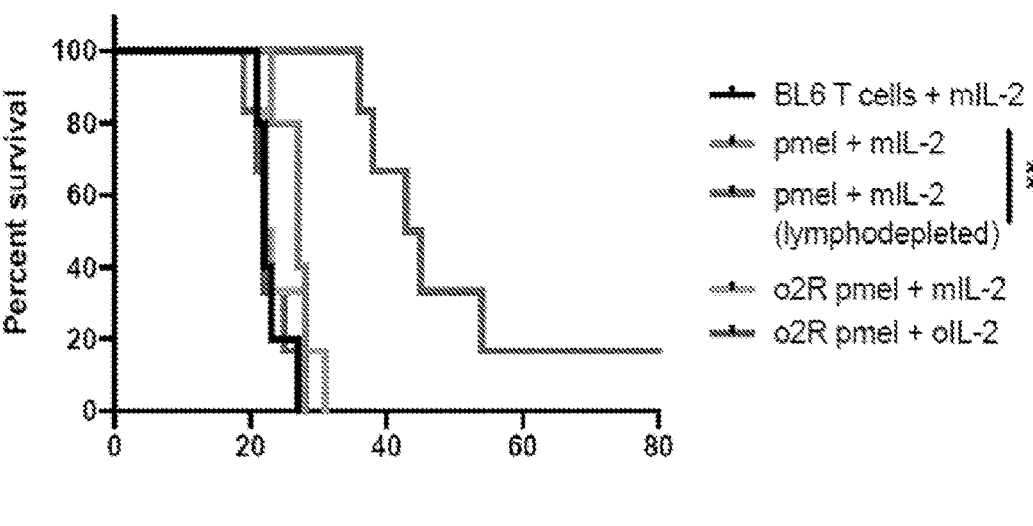
FIG. 8A-FIG. 8C illustrates antitumor efficacy of o2R and o9R pmel T cells in lymphodepleted and lymphoreplete settings.
Figure 8B:
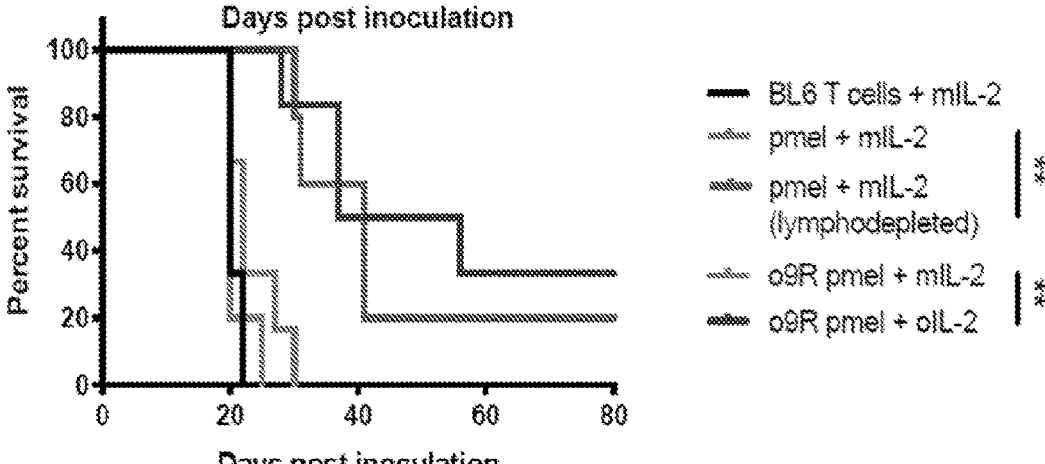
Figure 8C:
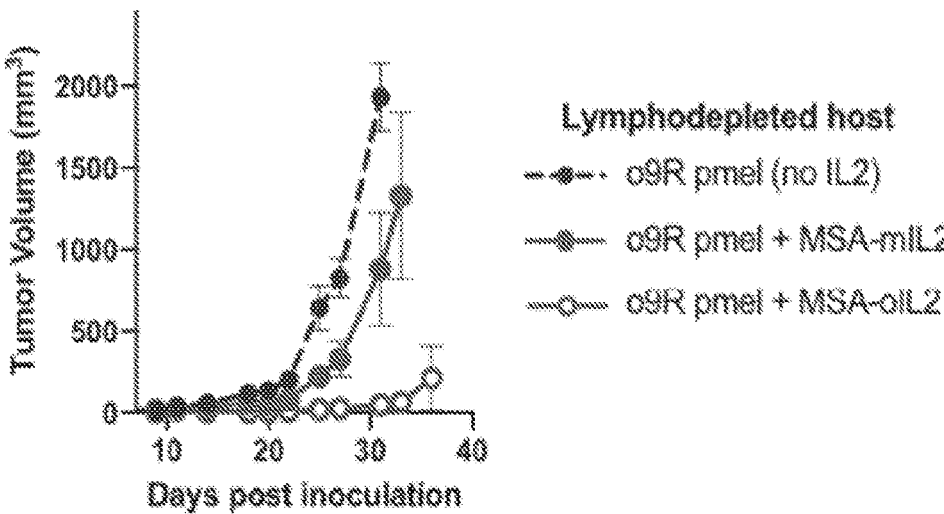

In the absence of lymphodepletion, a greater frequency of o2R and o9R pmel T cells was observed in the peripheral blood 7 days after ACT in mice treated with oIL-2 compared to mice treated with MSA-IL2 (FIG. 7B). Although both o2R and o9R pmel T cells expanded in the absence of lymphodepletion, more consistent anti-tumor effects and prolonged survival were observed in this model with o9R pmel T cells treated with MSA-oIL2 (FIG. 7C, FIG. 7D, FIG. 8A, FIG. 8B), achieving anti-tumor effects comparable to pmel T cells in lymphodepleted mice. The superior anti-tumor efficacy of o9R pmel T cells, despite its weaker proliferative signal, was also observed in lymphodepleted mice treated with MSA-oIL2 (FIG. 8C).

Figure 9A:
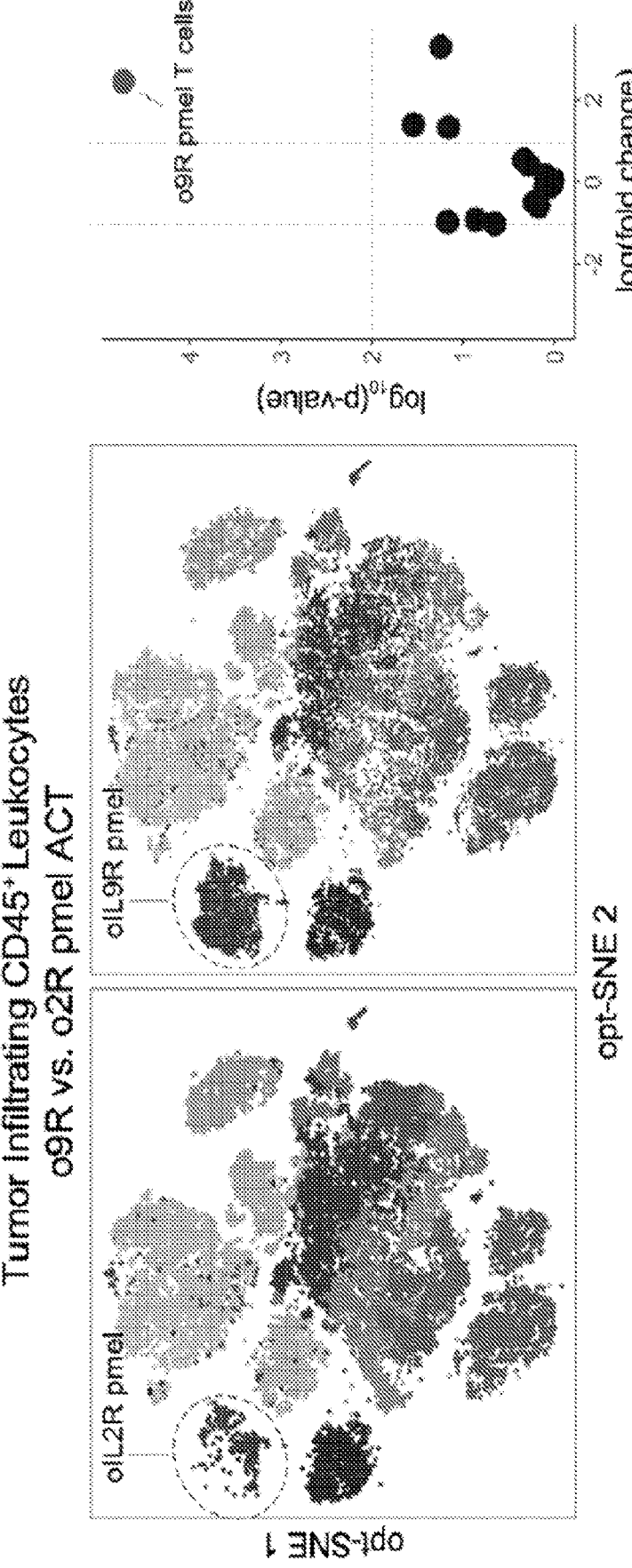
Figure 9B:
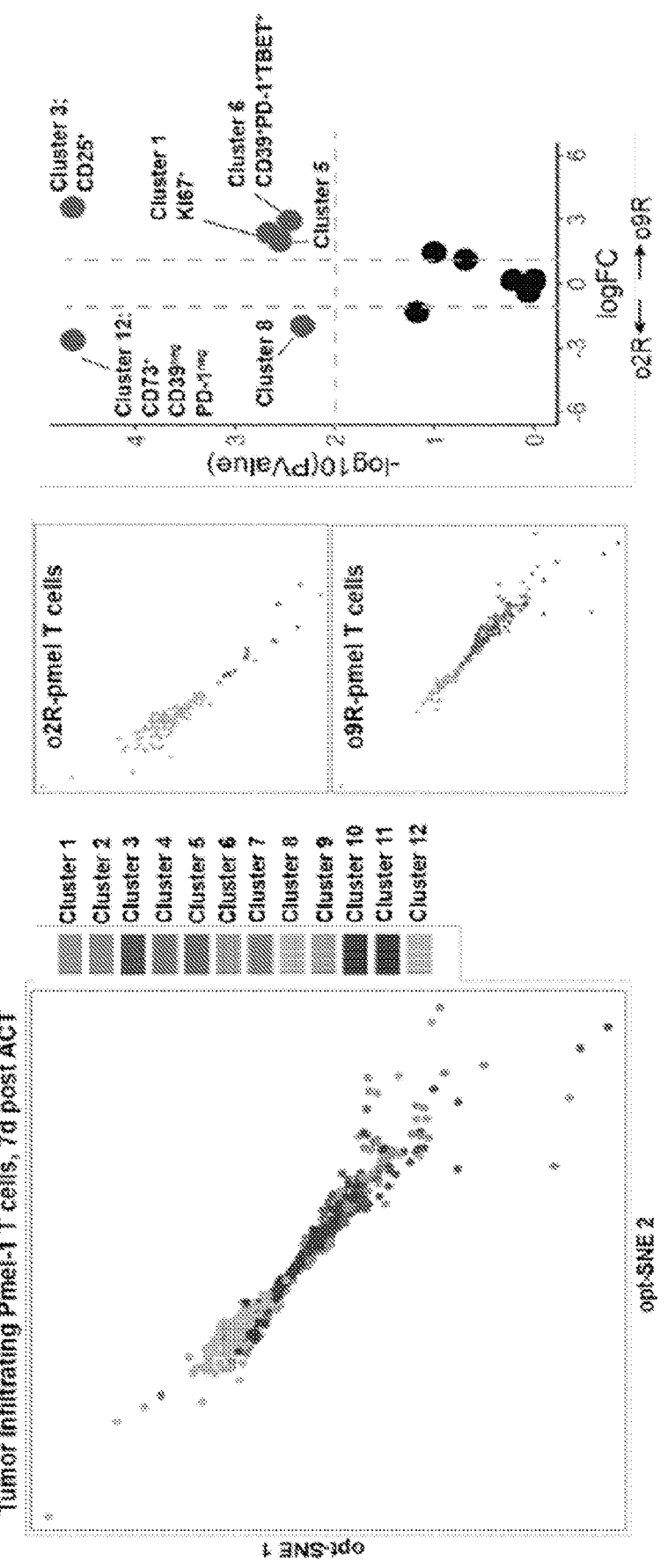

These results suggested that factors beyond selective expansion underlie the enhanced anti-tumor effects of o9R pmel T cells. Greater tumor infiltration by o9R pmel T cells compared to o2R pmel T cells was observed 5 days after ACT in mice treated with MSA-oIL2 (FIG. 7E). Using CyTOF, 18 tumor-infiltrating CD45+ leukocyte population clusters were identified 7 days after ACT with o2R and o9R pmel T cells and MSA-oIL2. Among these, the dominant distinguishing feature based on differential abundance analysis was the presence of a cluster corresponding to pmel T cells, which was highly enriched in o9R treated mice (8.9% vs 1.6% of tumor infiltrating CD45+ cells; FIG. 9A). Among tumor-infiltrating pmel T cells, o9R pmel T cells were enriched for clusters associated with T cell activation, including a cluster co-expressing CD39, PD-1 and TBET, while o2R pmel T cells were enriched for a cluster expressing CD73 and lacking PD-1 and CD39 expression (FIG. 9B).

Superior tumor infiltration of o9R pmel T cells was corroborated by infiltration of CD3+CD8+ and CD8+PD1+

Figure 9C:
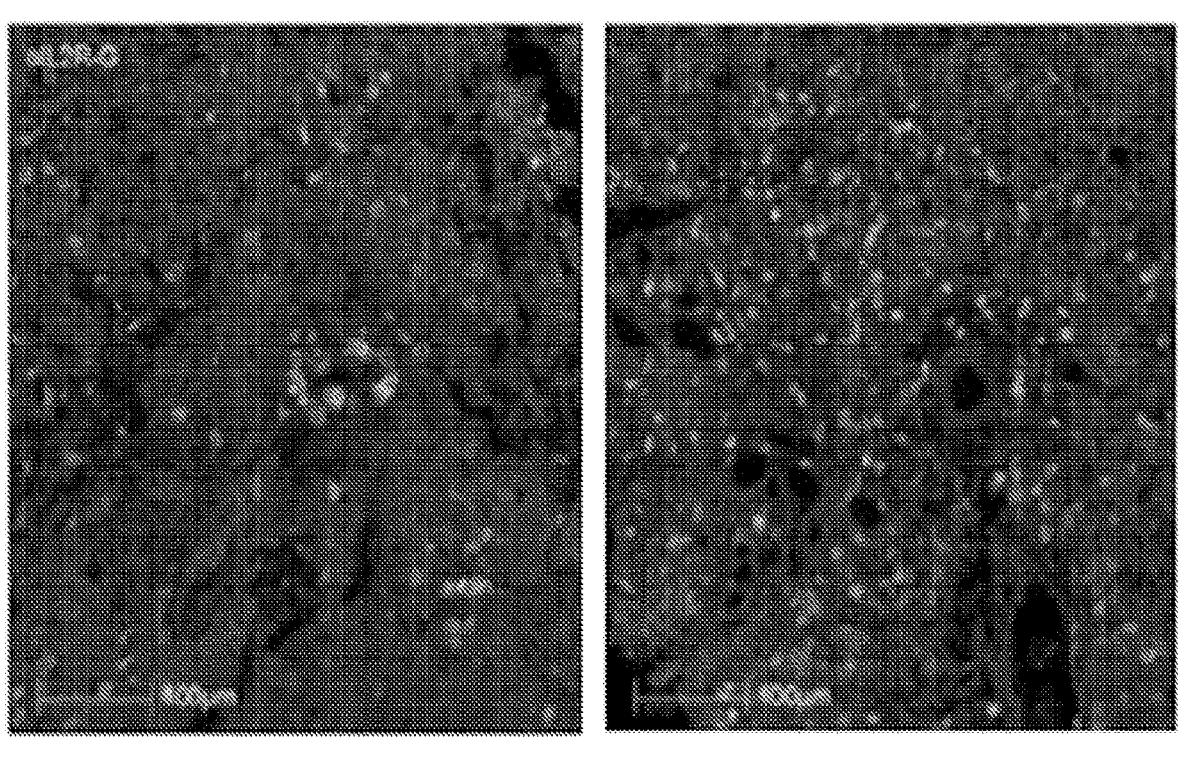
Figure 9D:
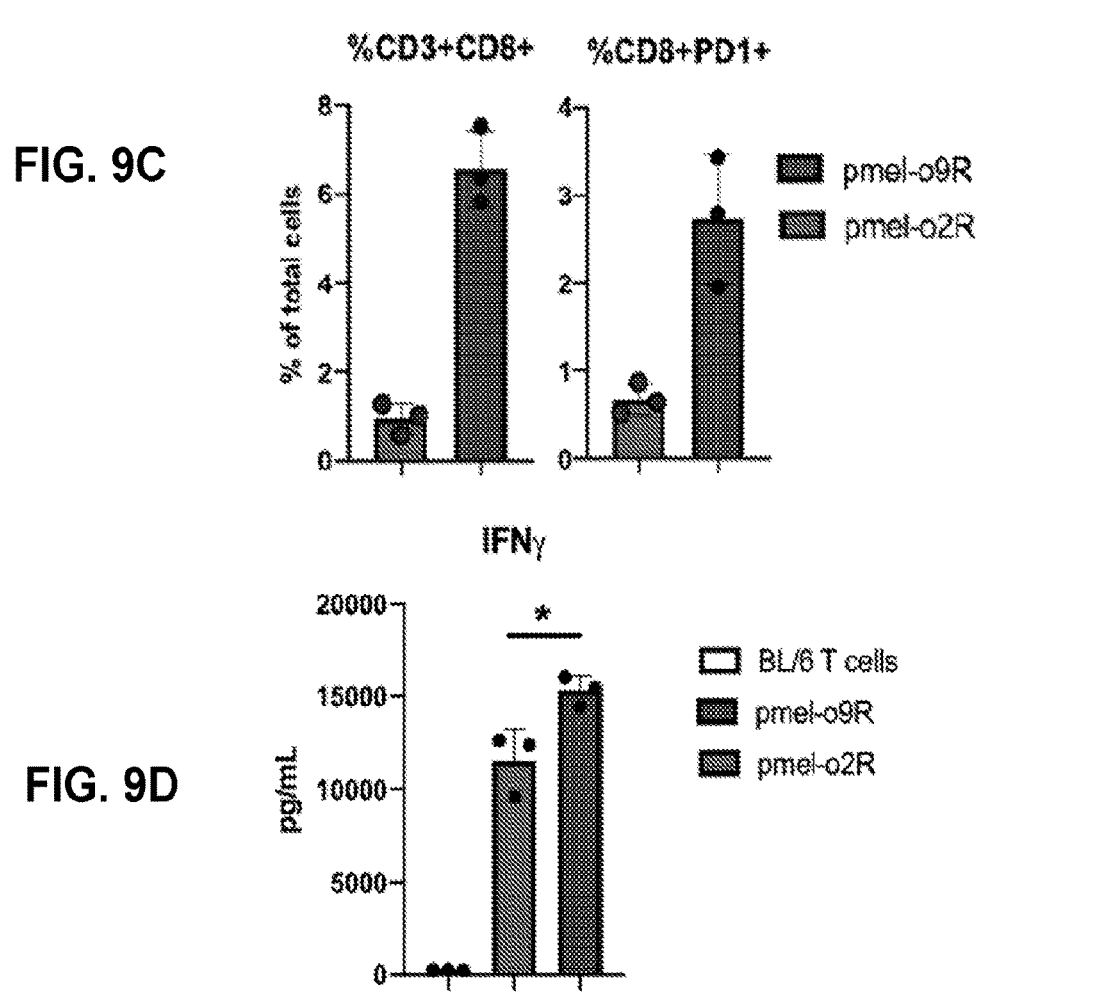

T cells by multiplex immunohistochemistry (FIG. 9C). In addition to improved tumor infiltration, o9R pmel T cells demonstrated superior cytolytic capacity compared to their o2R counterparts (FIG. 7F) and higher IFNγ production in response to tumor cells in vitro (FIG. 9D).

Next, the biological program responsible for the improved infiltration, effector function, and in vivo efficacy of o9R pmel T cells was investigated. In vitro exposure (48 h) to MSA-oIL2 resulted in drastically divergent phenotypes by high-dimensional mass cytometry; eight of 14 clusters were differentially abundant between o2R and o9R pmel T cells (FIG. 7G). Consistent with data from FIGS. 1D, 1E, and 1F using T cells from C57BL/6 mice, o9R pmel T cells acquired markers of a stem cell memory ($T_{SCM}$) phenotype (Sca-1, CD127, Fas and CD62L) (FIG. 7G, FIG. 10), while o2R pmel T cells acquired markers of terminal differentiated effectors (CD44, EOMES and Tbet) (FIG. 7G). These effects of o9R signaling were consistent with the effects of wildtype IL-9R signaling, as a $T_{SCM}$ phenotype was also observed in pmel T cells transduced with wildtype IL-9R and exposed to wildtype IL-9 (FIG. 10).

Compared to o2R pmel T cells, a bulk population of o9R pmel T cells exposed to MSA-oIL2 undergo striking global bidirectional transcriptomic changes, as identified by RNA-seq of sorted pmel T cells 48 h after exposure to MSA-oIL2 or MSA-IL2 in vitro (FIG. 7H, FIG. 11). These changes induced by o9R signaling further support the acquisition of a $T_{SCM}$ phenotype, as illustrated by enrichment of genes including Tcf7, Ccr7, Cd127, Sell, and Bach2 (FIG. 7I). However, simultaneous enrichment of genes classically associated with effector function (Ifng, Gzma, Prf1) and T cell activation (Pdcd1, Icos, Entpd1, Lag3, Havcr2), traditionally excluded from the $T_{SCM}$ phenotype, were also observed (FIG. 7I). This may represent a novel hybrid phenotype or the simultaneous presence of heterogeneous subpopulations unique to o9R signaling in T cells. The induction of granzyme A by IL-9R activation has been reported to be dependent on concomitant activation of STAT1 and STAT3, a characteristic of o9R signaling distinct from o2R, o4R, o7R and o21R signaling (Demoulin, et al., *J Biol. Chem.,* 1999, 274:25855-25861).

A transcriptomic analysis of transcription factor pathway enrichment revealed a significant (p<0.05) enrichment of genes associated with the AP-1 transcription factor JUN, in addition to expected transcription factors STAT1 and STAT3 (FIG. 7J). This was accompanied by an increased in the ratio of Jun to Fos expression, a feature of tumor-specific T cells resistant to tumor-induced exhaustion (Lynn et al., *Nature* (2019) 576:293-300). In parallel, o9R signaling downregulates genes associated with T cell exhaustion or dysfunction, including Nr4a1 and Tox, both of which mediate dysfunction of anti-tumor T cells (FIG. 7I) (Chen et al., *Nature* (2019) 567:530-534; Seo et al., *Proc Natl Acad Sci USA* (2019) 116:12410-12415; Khan et al., *Nature* (2019) 571: 211-218; Scott et al., *Nature* (2019) 571:270-274).

To examine the in vivo activity of the o9R signaling program, CD62L expression on adoptively transferred T cells was examined. CD62L expression was higher among adoptively transferred o9R pmel versus o2R pmel T cells in the draining lymph nodes and spleens of tumor-bearing mice treated with MSA-oIL2 one and five days after ACT (FIG. 12). No difference in CD62L expression was observed in tumors, where antigen-specific T cell activation likely predominates.

To further investigate o9R signaling in the context of CAR-based ACT, an immunotherapy-resistant model of pancreatic cancer expressing mesothelin was used. Vectored delivery was chosen as the source of oIL-2 for in vivo CAR T cell studies (FIG. 13A) to ensure high tumor concentrations of oIL-2 (clone 3A10) in the tumor and to evaluate the impact of o9R signaling on T cell dysfunction in the tumor microenvironment. This model provided a contrast to pmel studies where effects of o9R signaling program were most observed in peripheral tissues. oIL-2 production from the adenoviral vector (Ad-oIL2) was assessed in vitro in PDA7940b cells (FIG. 13A, bottom left) and in vivo by intratumoral injection (FIG. 13A, bottom right), confirming tumor-restricted oIL-2 expression with no cytokine detected in the peripheral blood.

Primary mouse T cells were transduced with retroviruses encoding a second-generation anti-mouse mesothelin CAR together with the orthogonal receptors to generate CAR-o2R and CAR-o9R T cells (FIG. 14A-FIG. 14B). Stimulation of CAR-o9R T cells with MSA-oIL2 resulted in phosphorylation of STAT1, STAT3, and to a lesser degree, STAT5. This was distinct from the STAT5 phosphorylation profile of CAR-o2R T cells treated with MSA-oIL2 (FIG. 13B). Unlike CAR-o2R cells, CAR-o9R cells did not expand in response to oIL-2 (FIG. 15A).

Despite the proliferative advantage of CAR-o2R cells, CAR-o9R cells demonstrated superior anti-tumor efficacy in vitro in clearing the mesothelin-positive pancreatic ductal adenocarcinoma (PDA) cell line PDA7940b, derived from spontaneous tumors arising in KPC (LSL-Kras$^{G12D/+}$; LSL-Trp53$^{R72H/+}$; Pdx-1-Cre) mice (FIG. 13C).

Similar to the pmel model, CAR-o9R cells preserved a TSCM phenotype (CD44$^{lo}$CD62L$^{hi}$Fas$^+$) while CAR-o2R cells shifted towards a central memory/effector phenotype (CD44$^{hi}$CD62L$^{hi}$Fas−) observed in cells stimulated with mIL-2 (FIG. 13D-FIG. 13E and FIG. 15B). Although phenotypically appearing as $T_{SCM}$, CAR-o9R T cells secrete higher levels of IFNγ, TNFα, IL-2, IL-9, IL-10, IL-18, IL-22 and IL-23 than CAR-o2R cells in response to oIL-2 (FIG. 13F). This diverse cytokine profile mirrors the complex transcriptomic signature of o9R pmel T cells, which was validated in CAR-o9R T cells using the nCounter Mouse Immunology Panel (FIG. 13G). Genes associated with effector functions (Ifng, Prf1, Gzmb, Gzma) and T cell activation (Pdcd1, Icos, Entpd1) were upregulated in CAR-o9R cells along with a shift toward T cell stemness (upregulation of Il7r, Sell, and Bcl6 and downregulation of Eomes, Tox1).

Figure 13H:
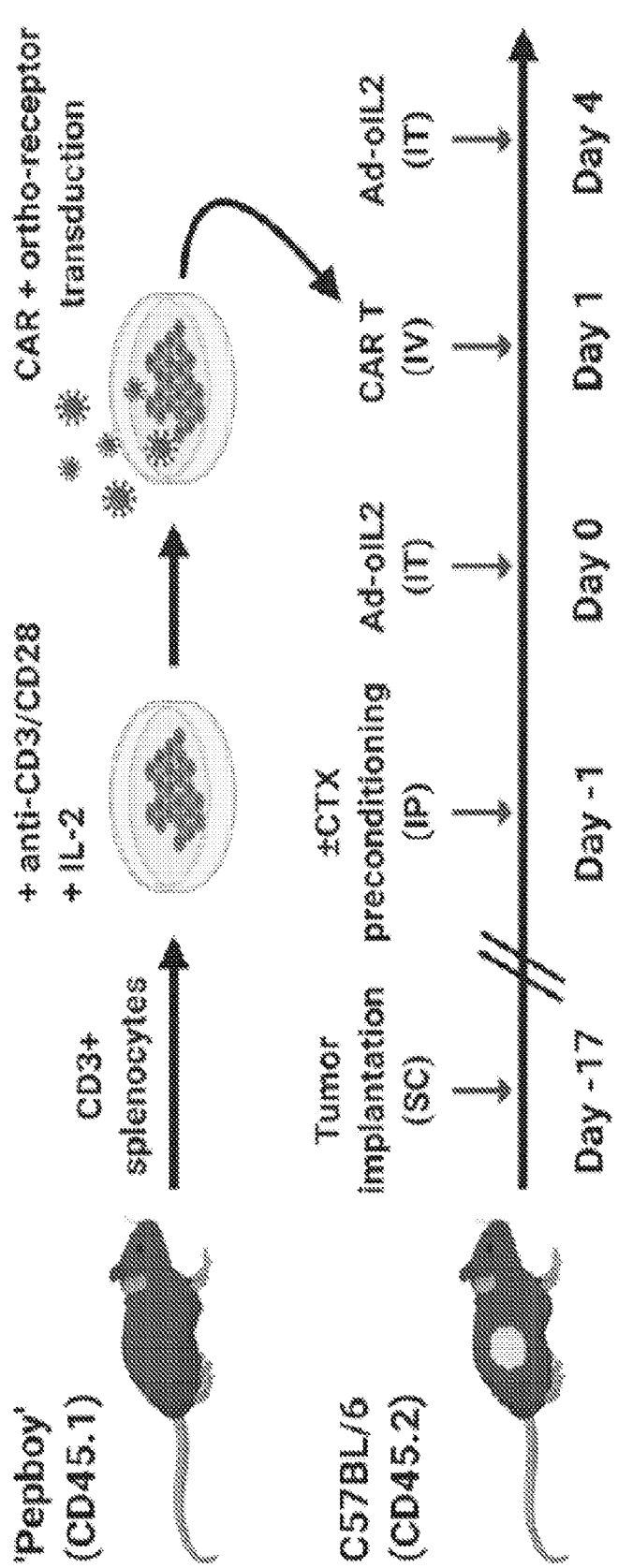
Figure 13I:
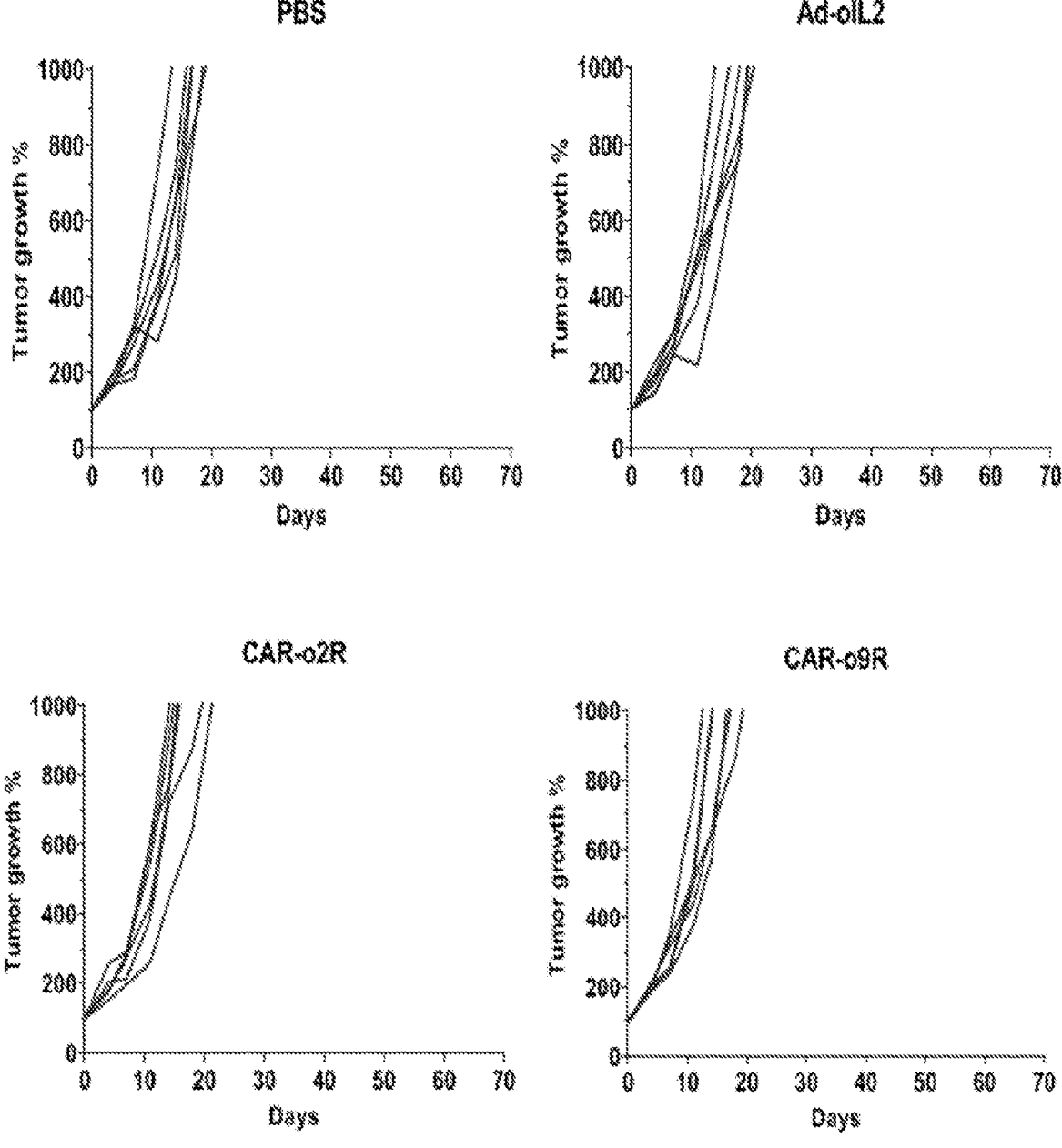

The syngeneic in vivo model used to evaluate antitumor properties of CAR-o2R and CAR-o9R cells utilizes two immunocompetent mouse strains differing in CD45 alleles (CD45.1 versus CD45.2) to enable discrimination of adoptively transferred (donor) T cells from endogenous (host) T cells (FIG. 13H). In this model, treatment of mice with established subcutaneous PD7940b tumors with either Ad-oIL2 or CAR-o2R/CAR-o9R is ineffective in controlling rapidly growing tumors (FIG. 13I). The experimental monotherapies showed no improvement over mock treatment (PBS injection), highlighting the recalcitrant nature of the tumor model.

Figure 13J:
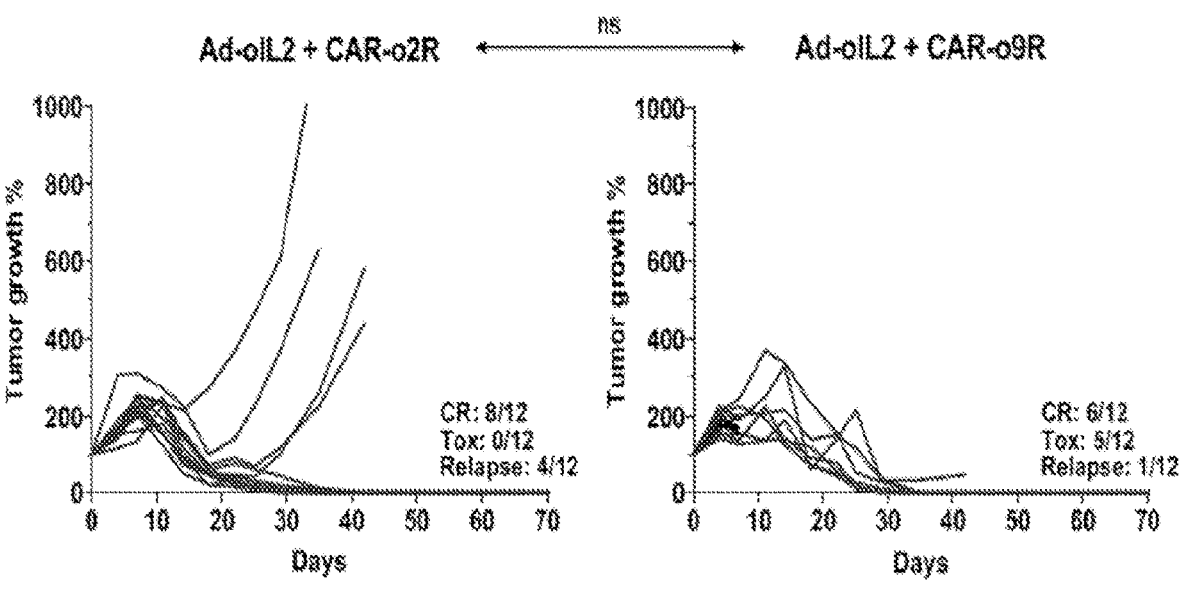
Figure 13K:
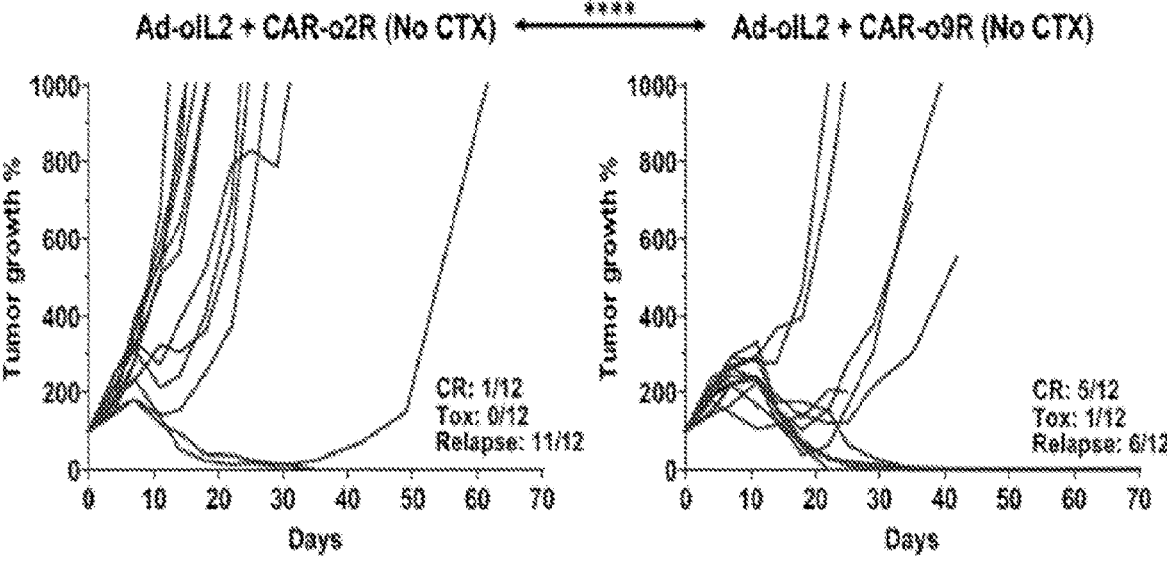

Still, combination therapy with Ad-oIL2 plus CAR-o2R or Ad-oIL2 plus CAR-o9R resulted in a robust antitumor response clearing tumors in 8 of 12 animals (67% CR) and 6 of 12 animals (50% CR), respectively (FIG. 13J). Early toxicity was observed in the Ad-oIL2 plus CAR-o9R group as 40% of mice (5 of 12) died by Day 10, but notably, fewer tumor relapses were seen in surviving animals in the Ad-oIL2 plus CAR-o9R group (1 of 7) as opposed to 4 of 12 mice succumbing to relapse in the Ad-oIL2 plus CAR-o2R group.

Figure 16B:
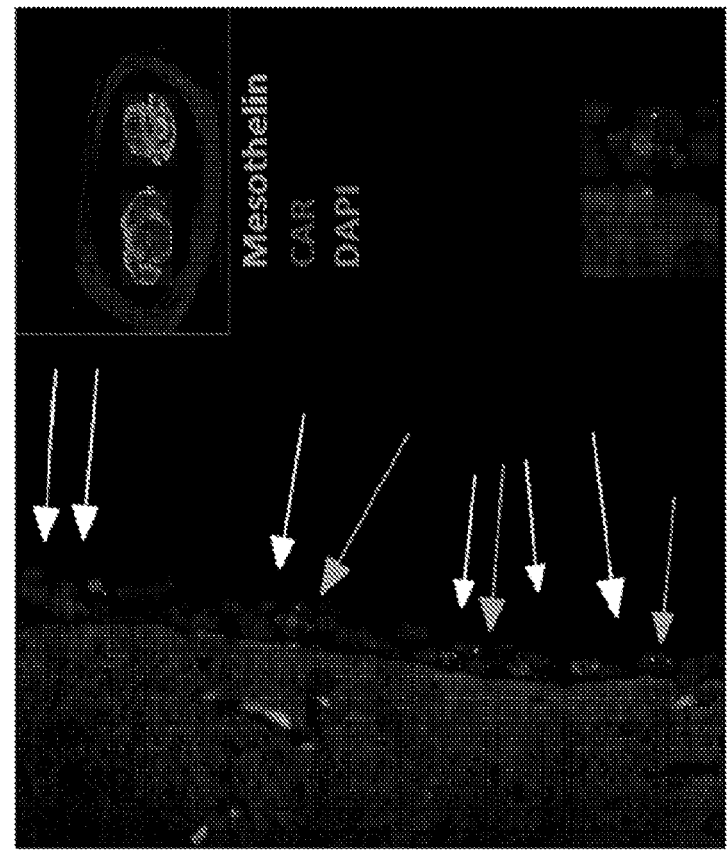
Figure 16A:
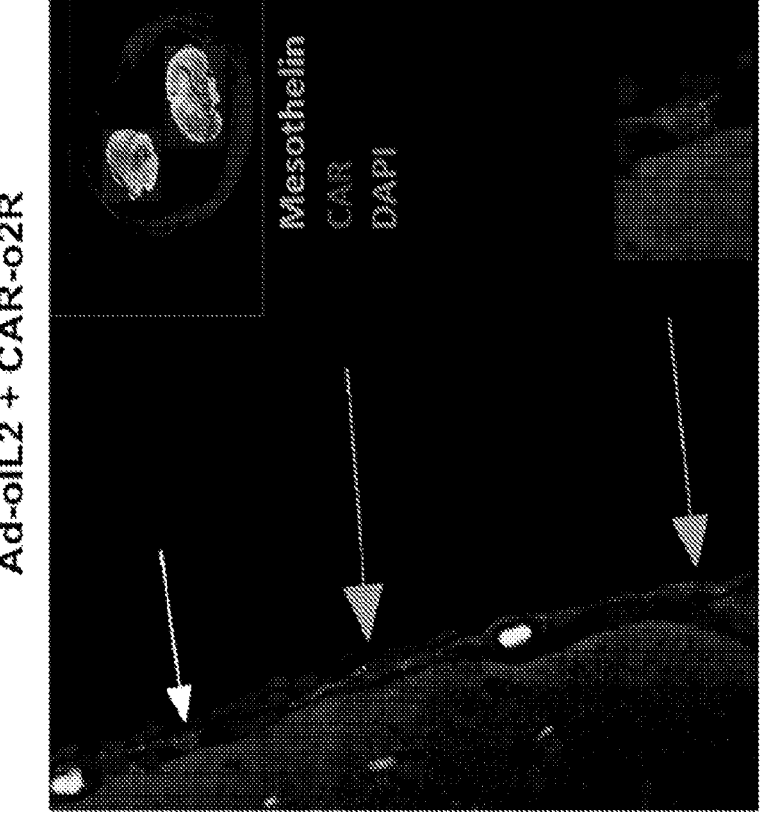
Figure 16D:
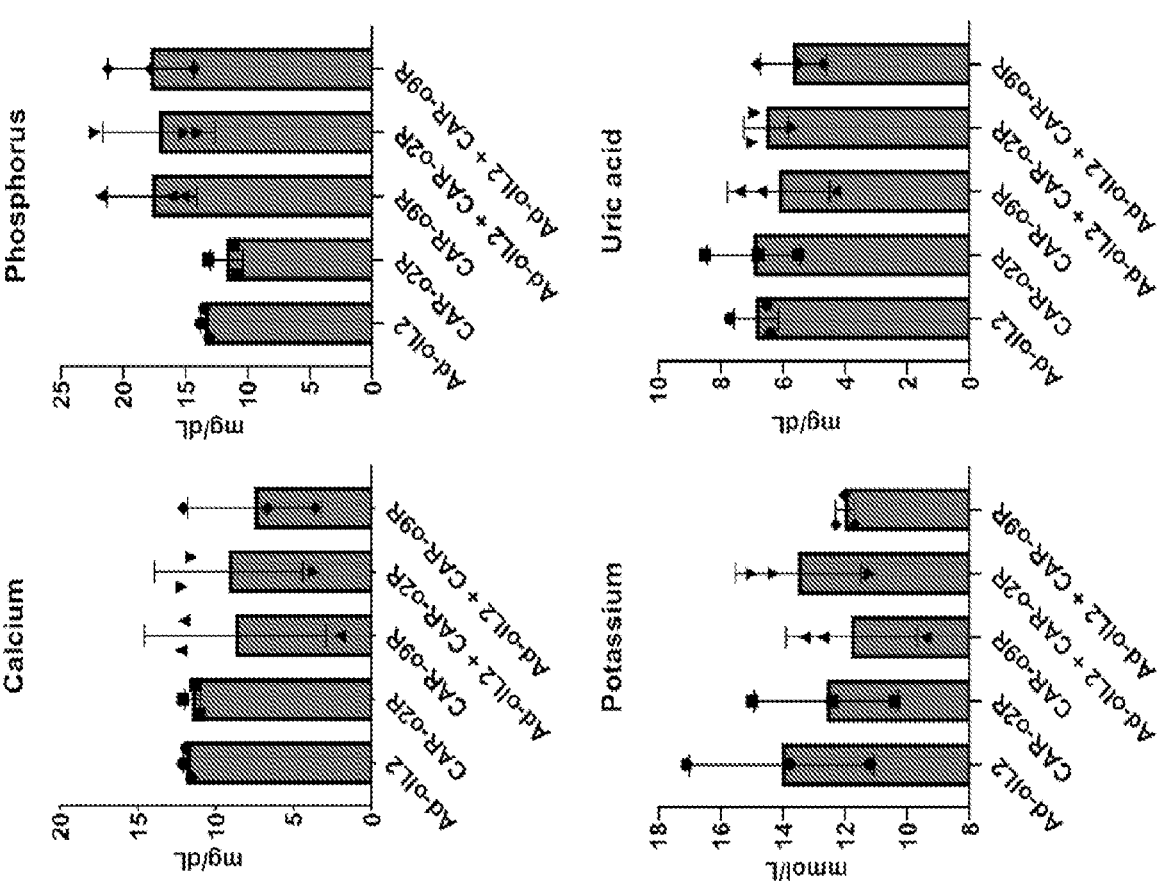
Figure 16C:
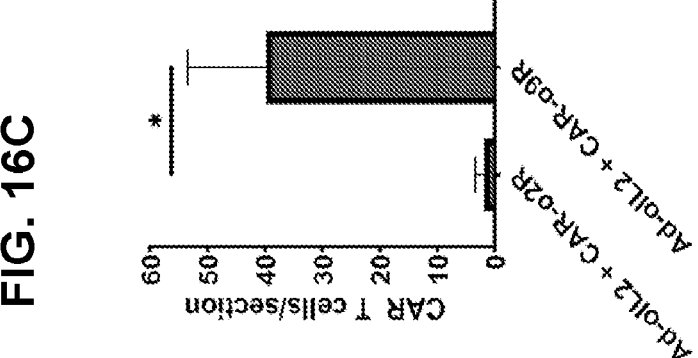
Figure 16E:
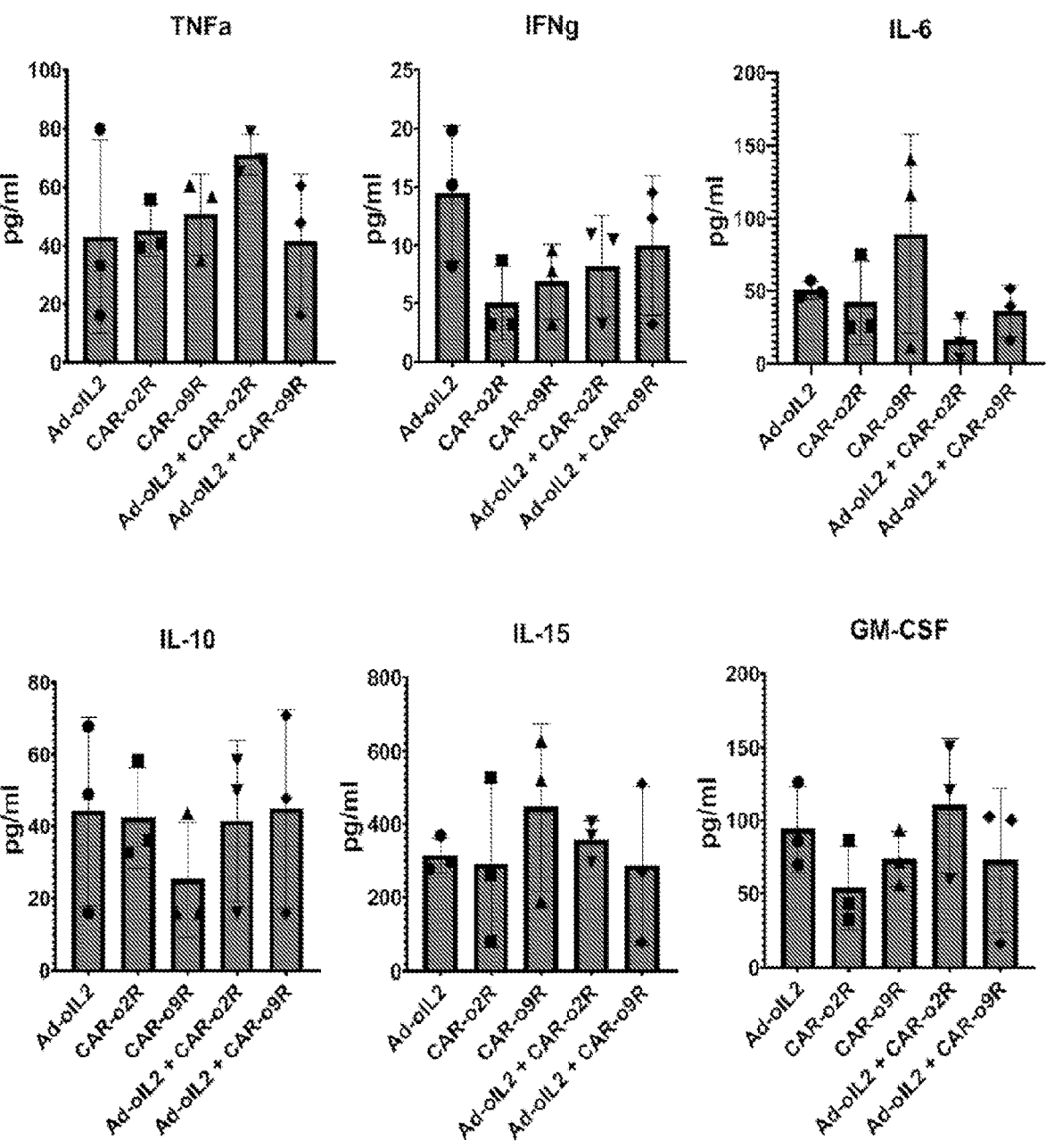

The toxicity of Ad-oIL2 plus CAR-o9R in lymphode-pleted mice was characterized by clinical signs (tremor, delirium, seizures) of immune effector cell-associated neu-rotoxicity syndrome (ICANS). RNA in situ hybridization (RNA ISH) analysis of mice with ICANS revealed CAR T cell infiltration in the meningeal layers of the brain where mesothelin-expressing meningeal cells were also detected (FIG. 16A-FIG. 16B). Significantly more meningeal-infil-trating CAR T cells were observed in Ad-oIL2 plus CAR-o9R group versus Ad-oIL2 plus CAR-o2R, suggesting an association between CAR-driven on-target off-tumor activ-ity and the observed ICANS (FIG. 16C). Serum analyses did not show evidence of cytokine release syndrome (CRS) or tumor lysis syndrome (TLS) (FIG. 16D-FIG. 16E). Based on these findings and the absence of similar toxicities in the pmel model, the observed ICANS appears to be specific to the CAR specificity and not inherent to o9R engineered T cells. Still, the translation of o9R signaling to CAR T cells must consider potential added on-target off-tumor toxicity, and may require additional engineering strategies (e.g. on/off systems, synthetic circuits) to maximize patient safety.

Figure 13L:
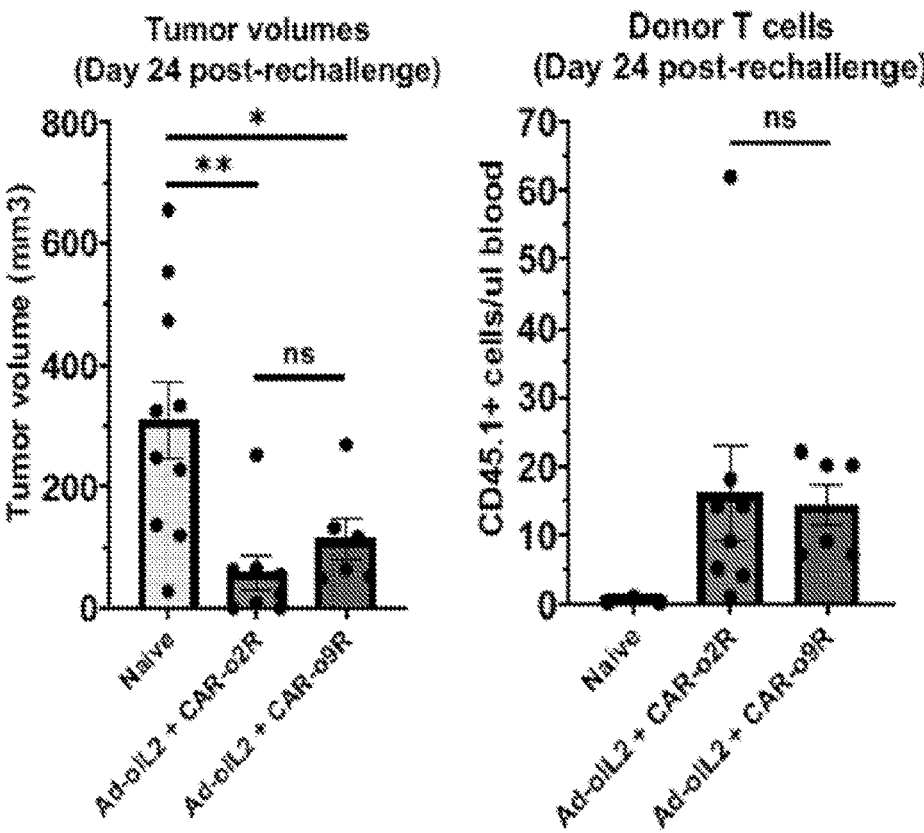

In the absence of cyclophosphamide preconditioning, superiority of Ad-oIL2 (3A10) plus CAR-o9R over Ad-oIL2 (3A10) plus CAR-o2R was more evident as suggested by complete response rates of 42% (5 of 12) and 8.3% (1 of 12), respectively (FIG. 13K), as well as prolonged survival (FIG. 17A), since only 1 of 12 mice in the Ad-oIL2 plus CAR-o9R exhibited toxicity in the absence of preconditioning. Effi-cacy was dependent on orthogonal receptor expression on T cells and oIL-2 expression via Ad-oIL2, as CAR T cells without o2R had no antitumor effects in combination with Ad-oIL2 (FIG. 17B), and control virus Ad-Null failed to potentiate CAR-o2R therapy (FIG. 17C). When rechal-lenged with PDA7940b, tumor growth was significantly controlled in animals previously cured with combination treatment compared with naïve animals (FIG. 13L). Meso-thelin knockout tumor cells (PDA7940b$^{MSLN}$–) were gen-erated by CRISPR/Cas9 technology (FIG. 21) and subse-quently implanted to previously cured mice (FIG. 22). On day 24, these tumors were smaller in cured mice compared with naïve mice, indicating induction of tumor antigen (=epitope) spreading. CD45.1+ donor T cells were detected in the peripheral blood of animals 24 days after rechallenge and 94 days after initial infusion, suggesting that in vivo oIL-2 stimulation enables long-term persistence of CAR-o2R/CAR-o9R T cells in immunocompetent mice.

Figure 13M:
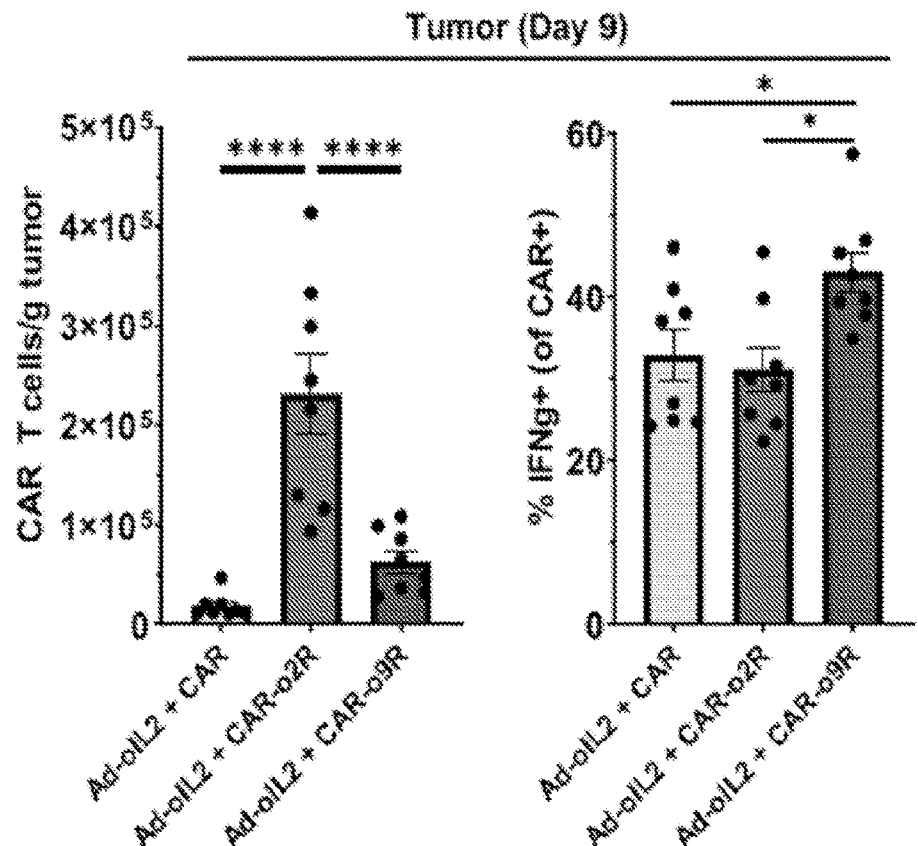

Next, the impact of Ad-oIL2 on the intratumoral quantity and quality of tumor-infiltrating CAR-o9R or CAR-o2R T cells was examined. In contrast to the pmel model, fewer CAR-o9R than CAR-o2R T cells were observed in the tumor 8 days after ACT (FIG. 13M). Given that o9R signaling program is not active in the periphery in the Ad-oIL2 model, the contrasting tumor-infiltration results were not surprising. Of the tumor-infiltrating CAR T cells, a higher frequency of CAR-o9R cells expressed IFNγ (FIG. 13M), suggesting that superior intratumoral function, rather than tumor infiltration, drives anti-tumor efficacy of CAR-o9R T cells in this model.

Figures 18A, 18B:
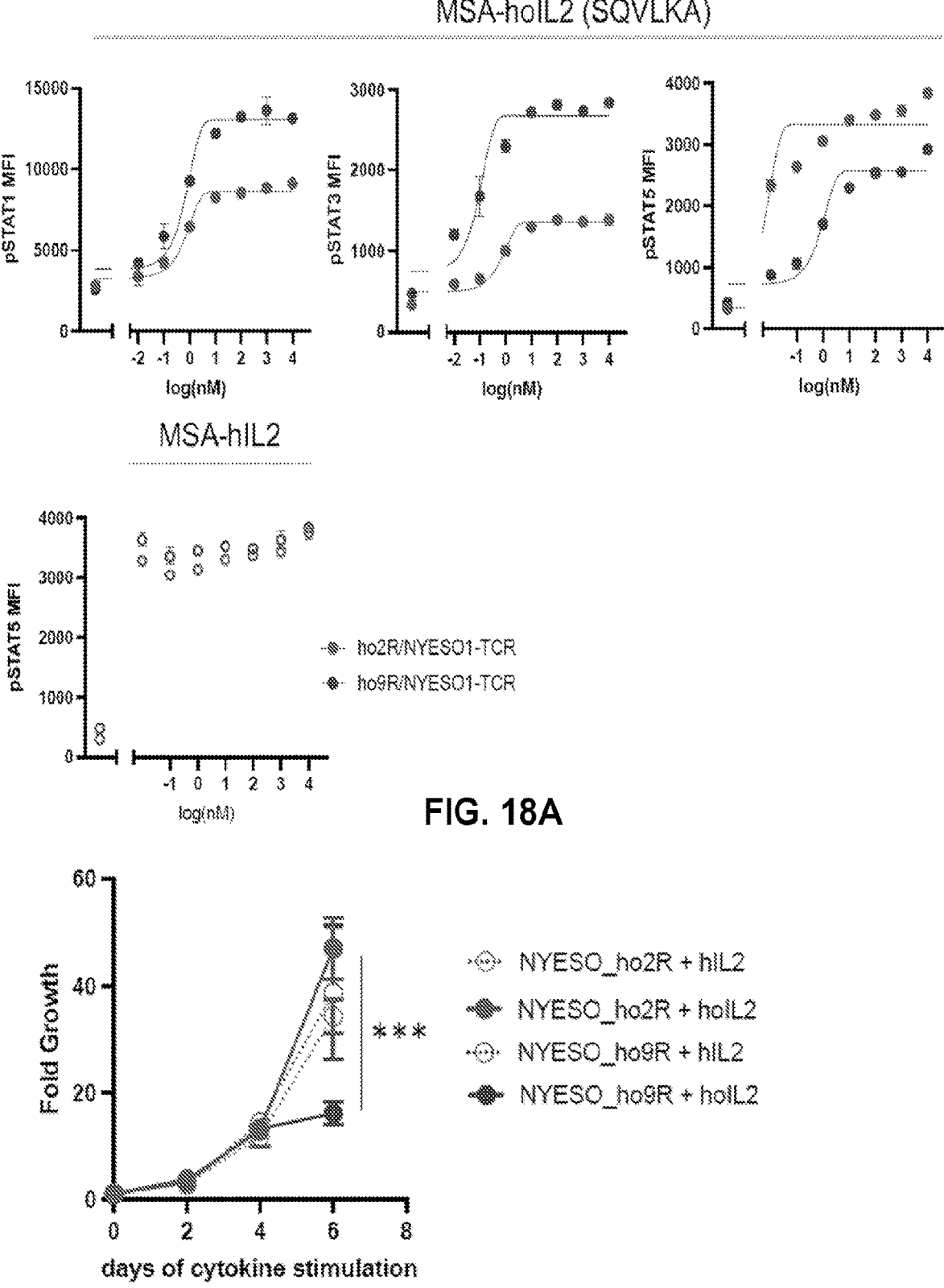

To evaluate the translational potential for o9R signaling, human orthogonal IL-2R$ (ho2R) and human orthogonal chimeric IL-2Rβ/IL-9R (ho9R) were generated (SEQ ID NOs: 4 and 6). Human T cells were retrovirally transduced with vectors encoding either ho2R or ho9R (each also containing YFP), as well as a vector encoding a T cell receptor specific for NY-ESO-1 in the context of HLA*0201 (NYESO1-TCR clone 1G4)(Robbins, et al., *J Immunol,* 2008, 180:6116-6131). NY-ESO-1 is a cancer-testis antigen overexpressed in synovial sarcoma, myxoid liposarcoma, melanoma and other tumors. Transduced T cells sorted based on expression of the NYESO1-TCR and YFP (FIG. 19A) were exposed to MSA-bound human orthogonal IL-2 (MSA-hoIL2) or wildtype IL-2 (MSA-hIL2). Consistent with observations in the mouse system, human T cells signaling through ho9R activate pSTAT1, pSTAT3 and pSTAT5 signaling, whereas human T cells signaling through ho2R primarily activate pSTAT5 signaling (FIG. 18A). Human T cells expressing ho2R or ho9R phosphorylate STAT5 equally after exposure to MSA-hIL2 (FIG. 18A, far right panel), indicating that native IL-2-STAT5 signaling through the endogenous γc is not differentially impacted by orthogonal receptor expression.

Figure 18C:
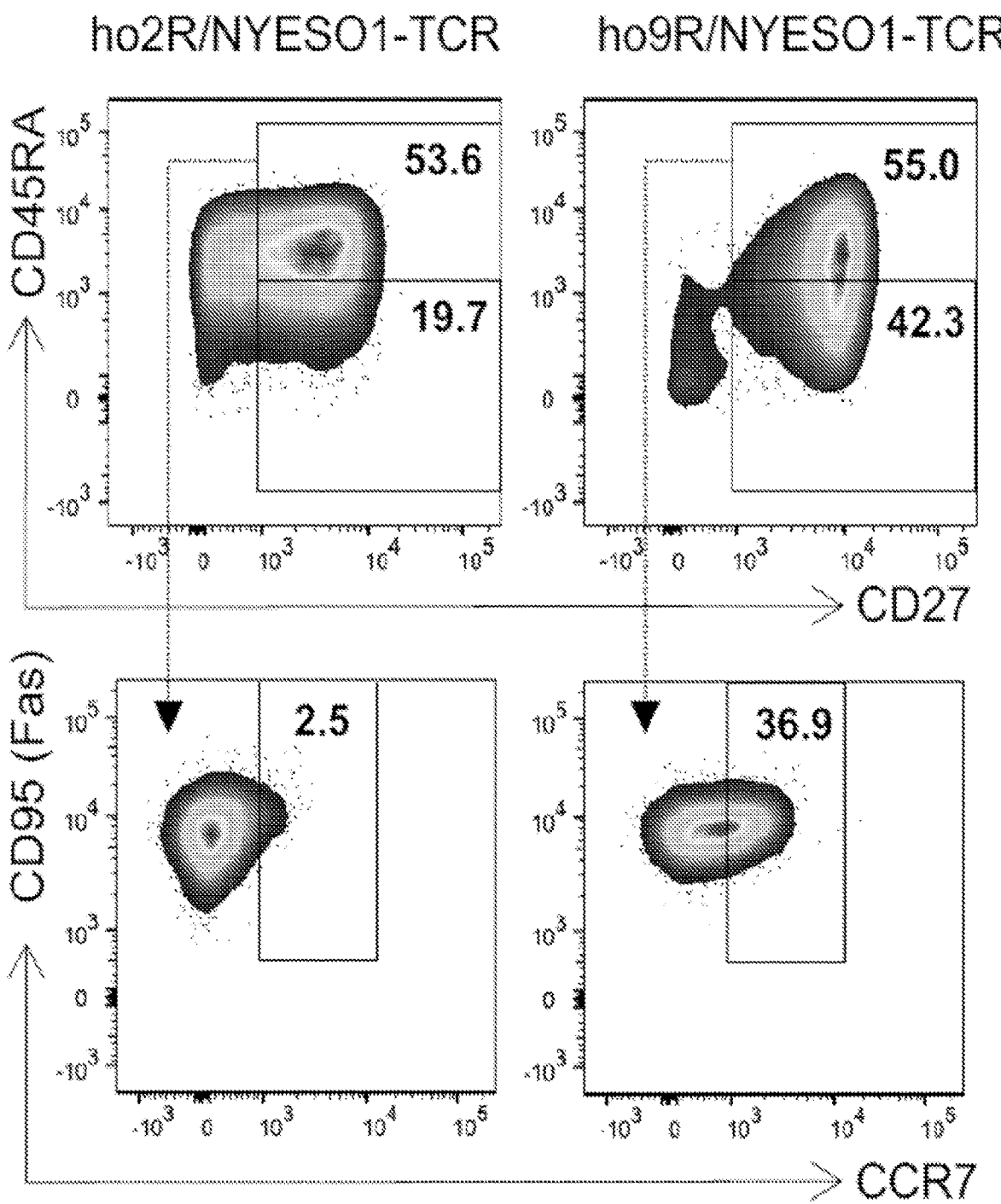
Figure 18C:
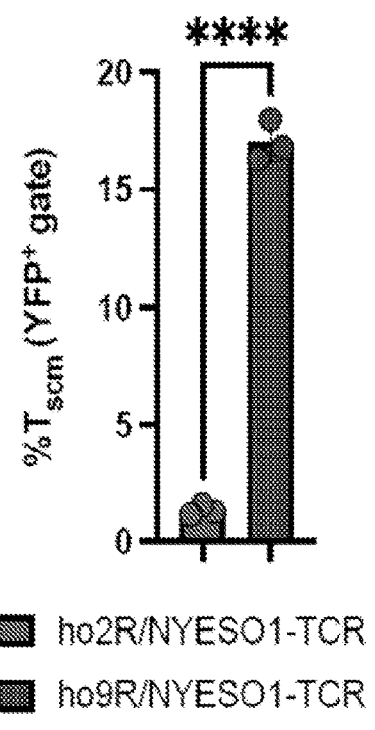
Figure 19A:
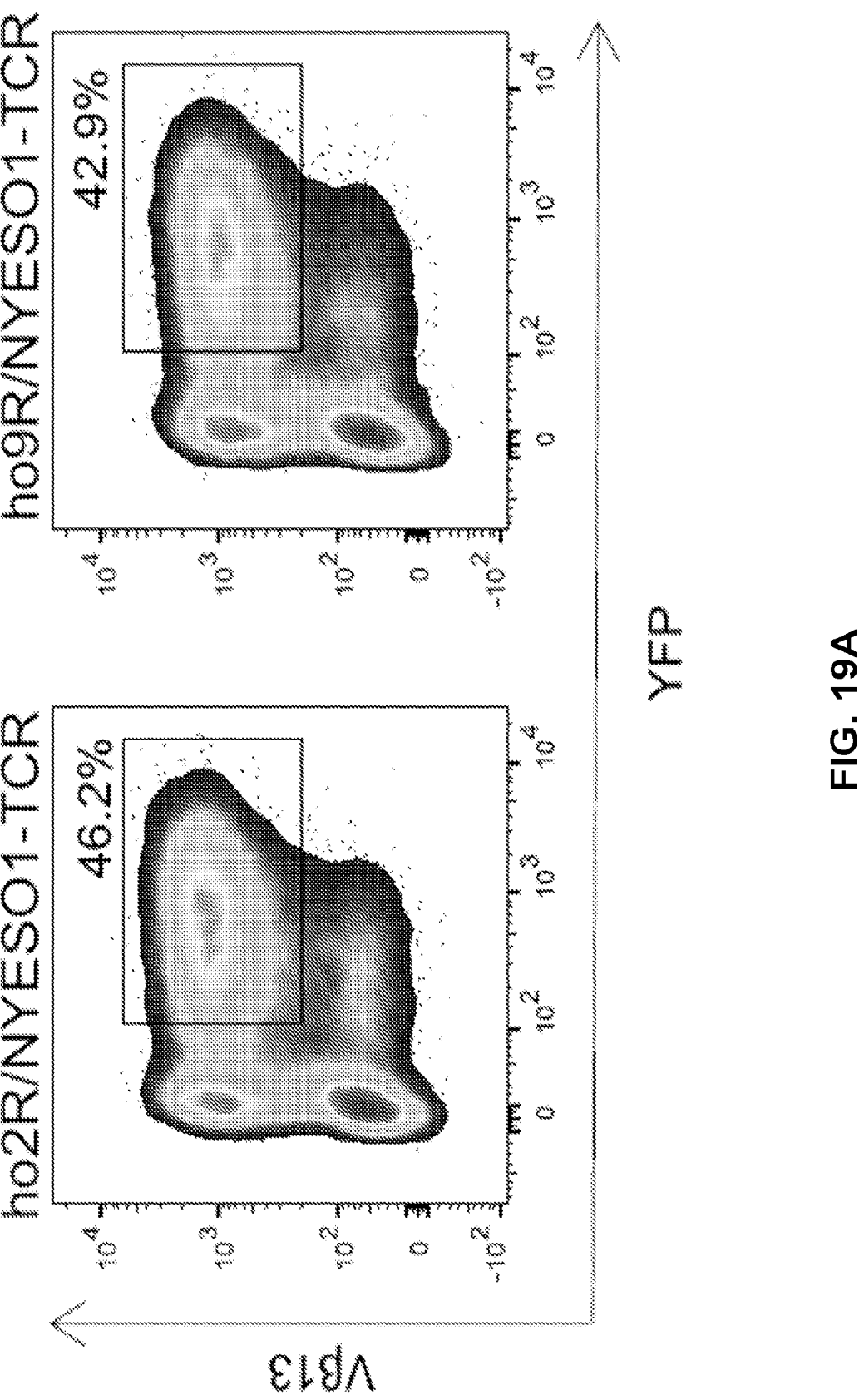
Figure 19B:
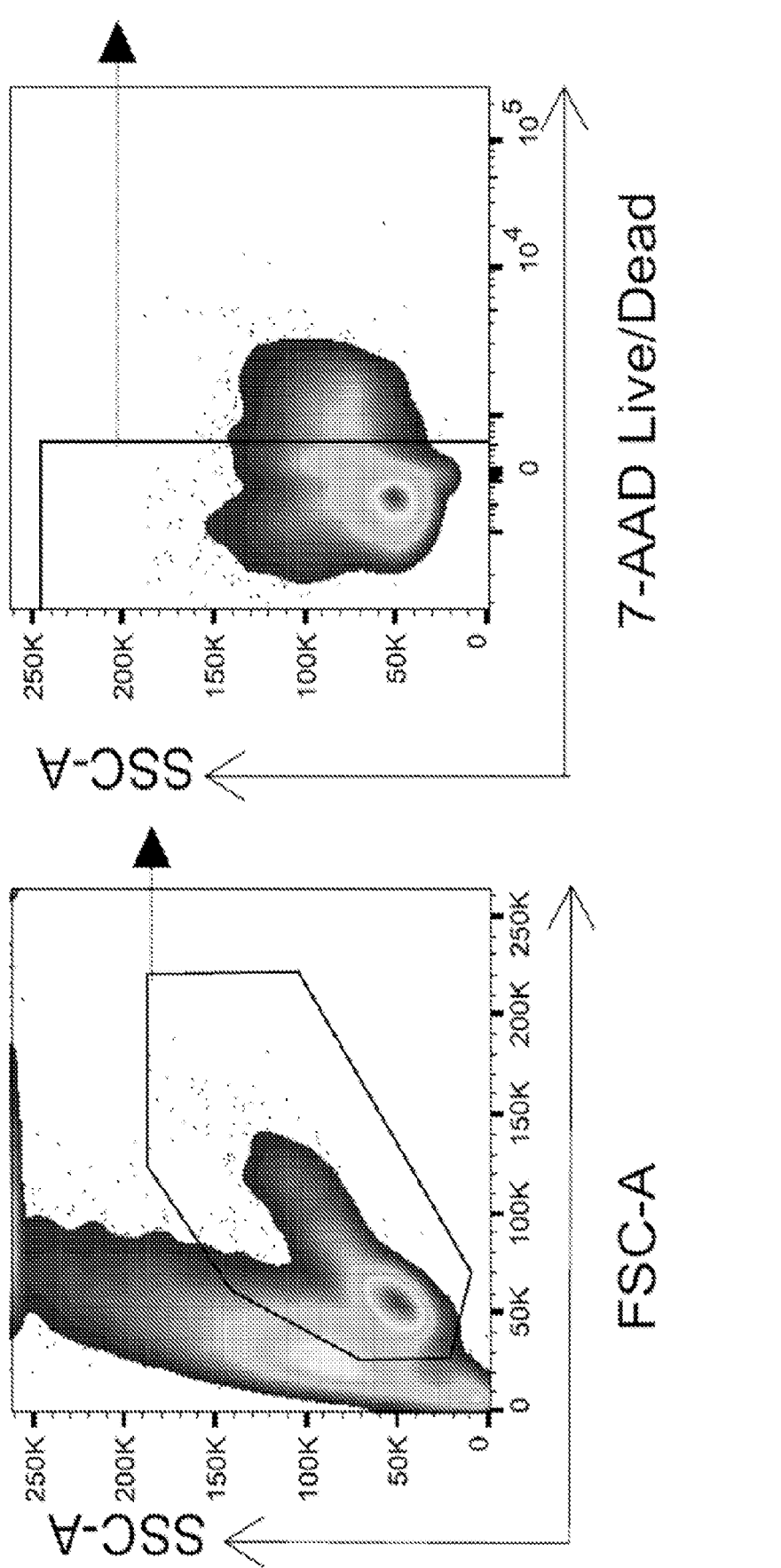
Figure 19B:
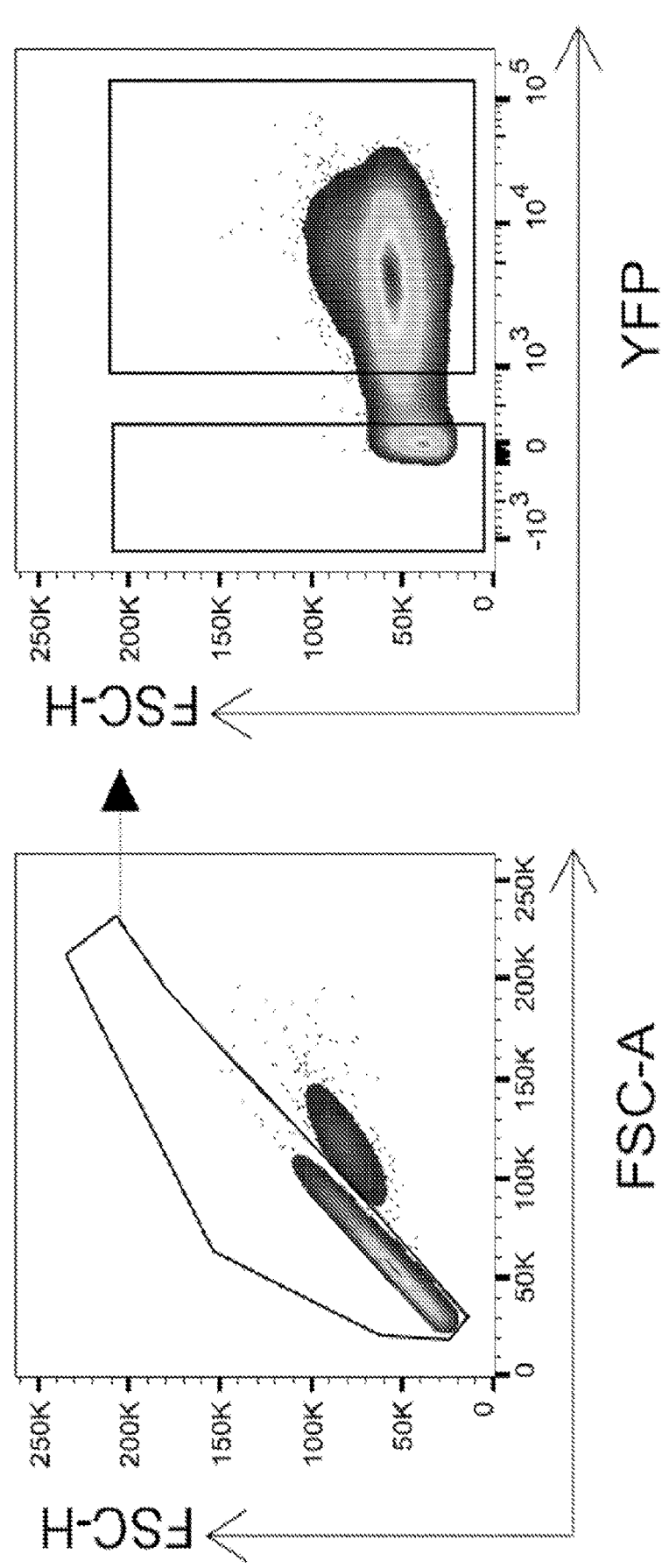
Figures 19C, 19D:
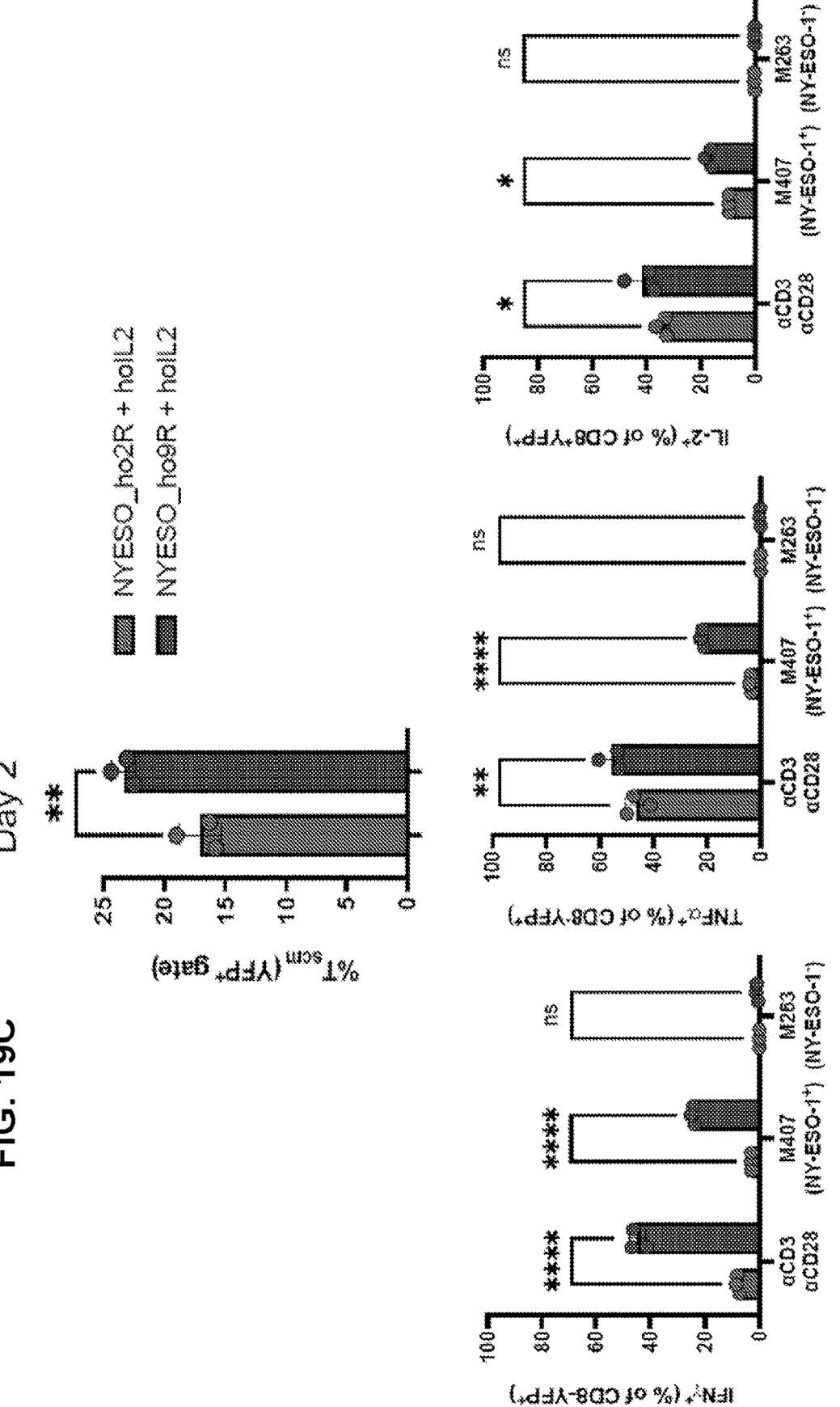

Also similar to the mouse system, ho9R signaling resulted in a weaker proliferative signal than ho2R or wildtype IL-2 signaling (FIG. 18B). Compared to ho2R/NYESO1-TCR T cells, ho9R/NYESO1-TCR T cells enrich for a population of $T_{SCM}$ cells (CD45RA+CD27+CCR7+CD95+) after 2 and 6 days in culture with MSA-hoIL2 (FIG. 19B-FIG. 19C, and FIG. 18C). And despite the reduced proliferation of ho9R/NYESO1-TCR T cells between days 2 and 6 in culture, an expansion was observed of $T_{SCM}$ and central memory ($T_{CM}$, CD45RA-CD27+CCR7+CD95+) cells by absolute quantity (not merely enrichment).

Figure 18D:
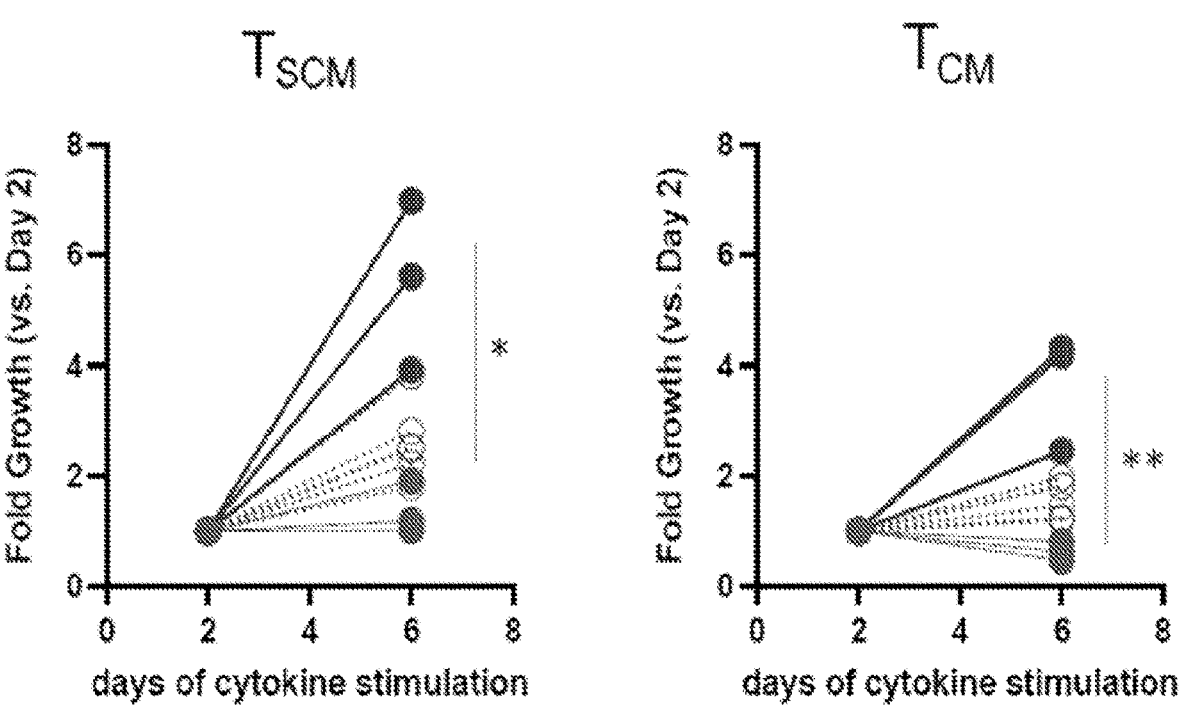
Figure 18E:
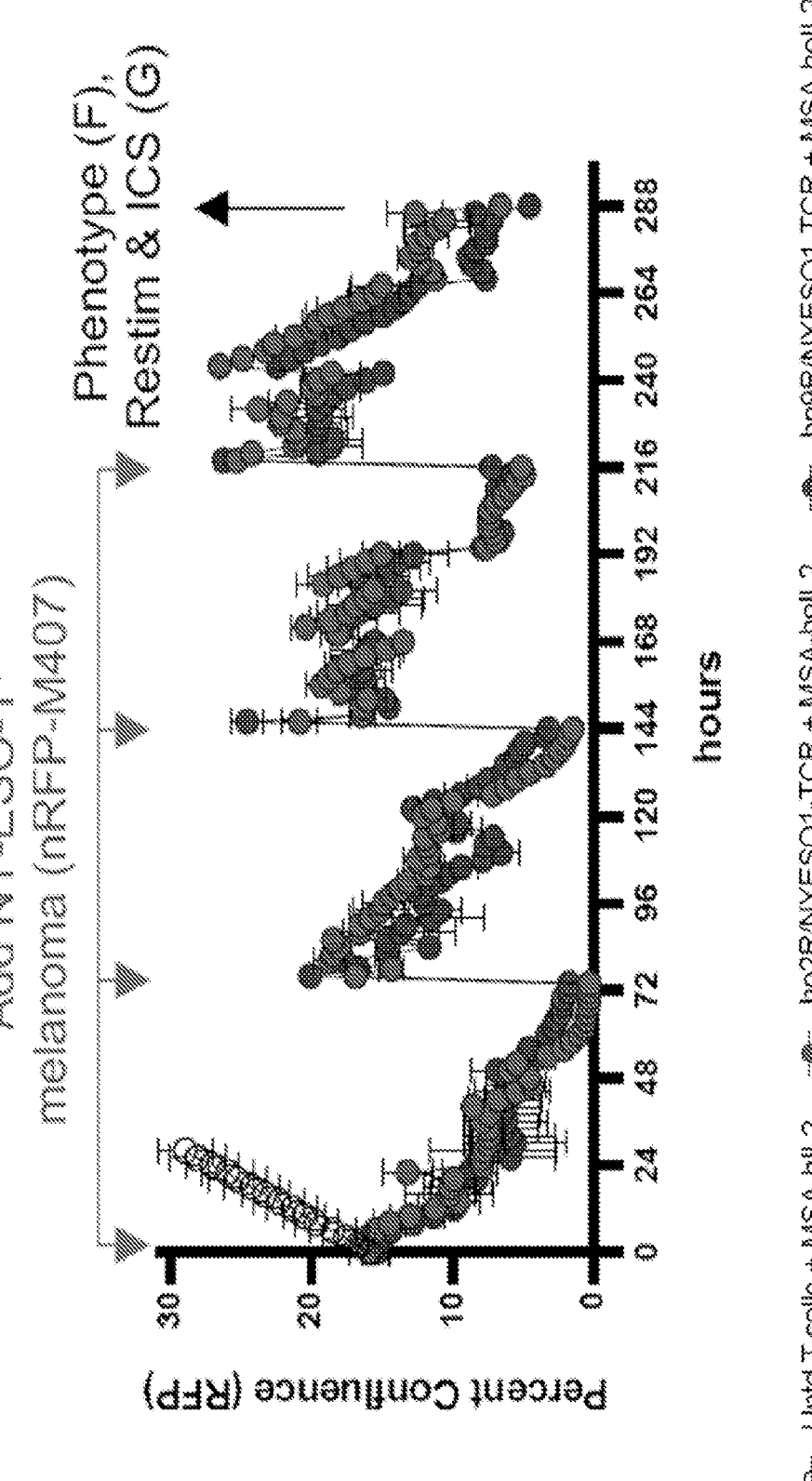
Figure 18F:
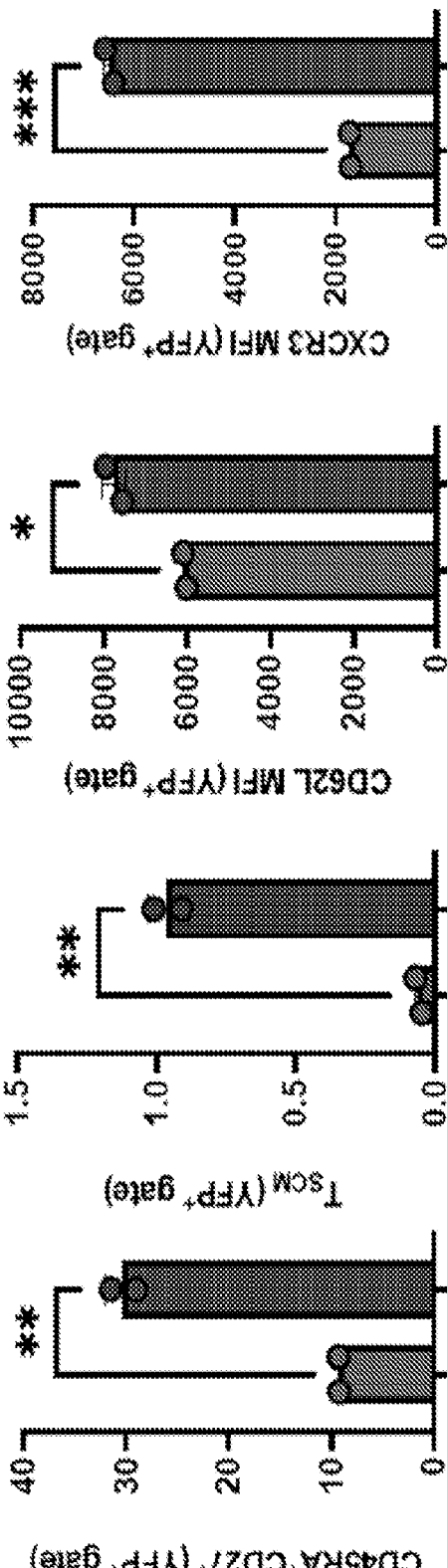
Figure 18G:
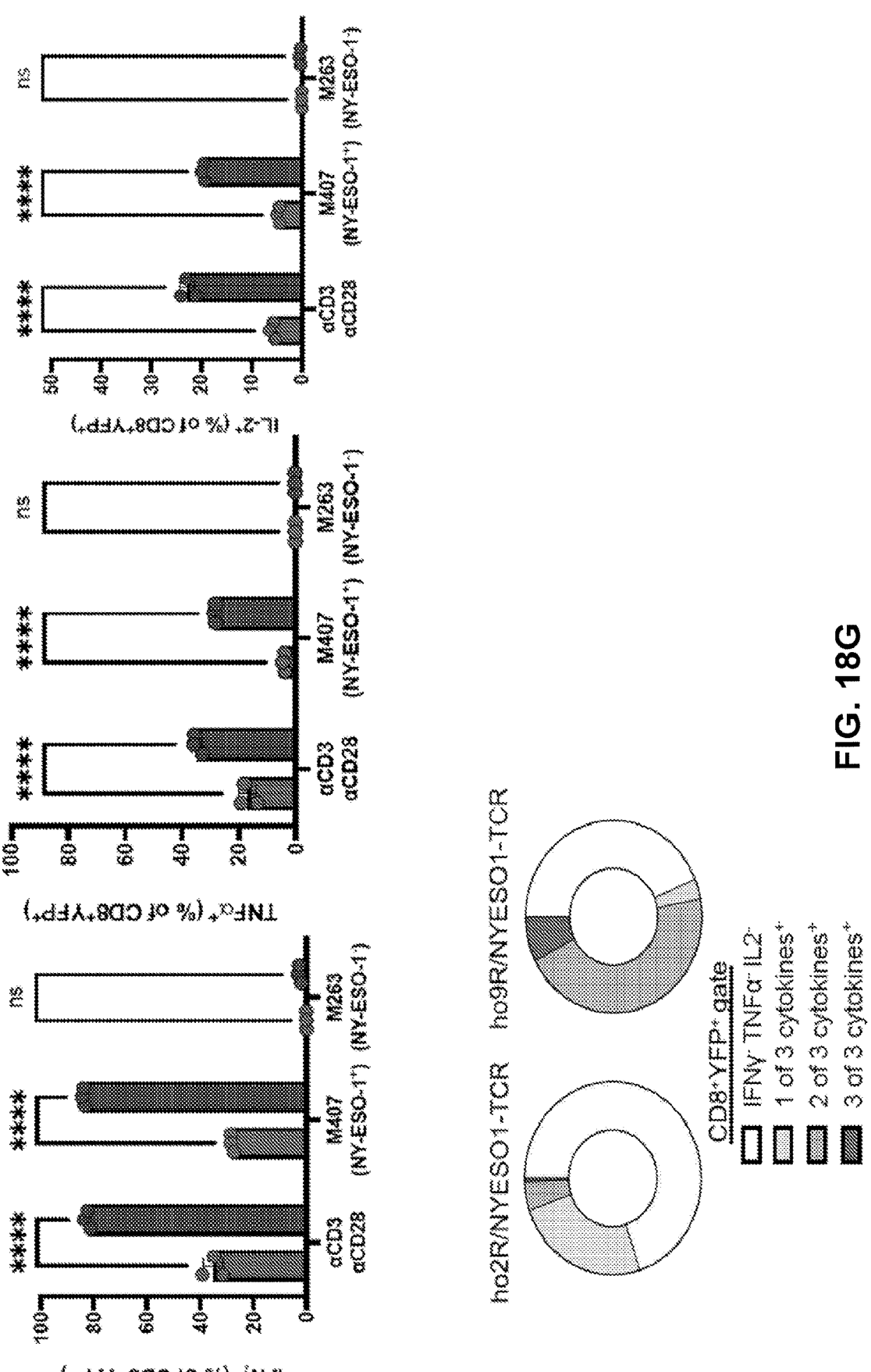

The difference in T cell phenotype between ho9R/NYESO1-TCR and ho2R/NYESO1-TCR T cells persisted even after four antigen-specific challenges with an HLA*0201+NY-ESO-1+ human melanoma tumor cell line, nRFP-M407, in the presence of MSA-hoIL2 (FIG. 18E-FIG. 18F). Compared to ho2R/NYESO1 T cells, ho9R/NYESO1 T cells retained a greater frequency of CD45RA+CD27+ and TSCM cells, and expressed higher levels of CD62L and CXCR3 (FIG. 18D). Repetitively stimulated ho9R/NYESO1 T cells expressed more IFNγ, TNFα, and IL-2 and exhibited greater polyfunctionality when exposed to either activating CD3/CD28 beads or a cognate melanoma cell line (nRFP-M407) (FIG. 18G and FIG. 19D). These findings were antigen-specific, as they were not observed in response to non-cognate melanoma cell line M263 (HLA*0201-NY-ESO-1-).

Additionally, human orthoIL-2 was cloned into Ad5/3-D24 oncolytic adenoviral vector and shown to overexpress in vitro. A549 cells were infected with Ad5/3-D24-hoIL2 or isogenic control virus Ad5/3-D24 or mock-infected. 96 hours post-infection, 50 μl of cell culture supernatant was collected and analyzed by human IL-2 ELISA (FIG. 23A). Next, fiber-chimeric oncolytic adenovirus Ad5/3-D24-hoIL2 encoding human orthoIL-2 was purified via CsCl$_2$ gradient (FIG. 23B). Virus-infected A549 cells were har-vested 48 hours post-infection by scraping from 11 confluent T150 cell culture flasks followed by 3 freeze/thaw cycles to release the virus particles. The supernatant was clarified by 2 rounds of ultracentrifugation over cesium chloride (CsCl) gradients. Red arrow indicates the band containing intact virus particles that are collected with needle and syringe by puncturing the side of the tube. CsCl was removed by 2 rounds of buffer exchange in 15 ml ultrafiltration units.

The human orthogonal IL-2Rβ (ho2R) and human orthogonal chimeric IL-2Rβ/IL-9R (ho9R) were next shown to co-express with a PSMA-retargeted CAR in human T cells. 1e5 primary human T cells (1:1 ratio of CD4/CD8) were infected with increasing dilutions of lentiviral vectors encoding PSMA28z CAR and human orthogonal receptor, either full-length orthoIL2Rb receptor (FIG. 24A) or chi-meric orthoIL2Rb/IL9Ra switch receptor (FIG. 24B). Co-expression was evaluated by flow cytometry and demonstrated 48 hours post-infection.

In conclusion, the orthogonal IL-2 cytokine-receptor platform enables redirection of signaling through modular replacement of the orthogonal IL-2Rβ ICD with ICDs of receptors for other γc cytokines. Here, unexpectedly, specific in vivo stimulation of o9R signaling in TCR- and CAR-based tumor-specific T cells by the orthogonal IL-2 ligand 3A10 resulted in improved antitumor activity in two immunotherapy refractory solid tumor models, and retained robust activity in a more stringent setting without lymphodepletion. This benefit was mediated by leveraging the γc to reroute the IL-2 signaling message through the IL-9Ra ICD, resulting in concomitant activation STAT1, STAT3 and STAT5. Conveyed in T cells, the signaling message of IL-9Ra resulted in a unique phenotype that merges beneficial functional characteristics of stem cell memory and effector T cells, to provide improved in vivo antitumor activity.

Enumerated Embodiments

The following enumerated embodiments are provided, the numbering of which is not to be construed as designating levels of importance.

Embodiment 1 provides a system for selective activation of a receptor in a cell, the system comprising: (a) a modified immune cell comprising (i) an orthogonal chimeric cytokine receptor, and (ii) at least one chimeric antigen receptor (CAR), and (b) an oncolytic adenoviral vector comprising a nucleic acid sequence encoding an orthogonal IL2 cytokine, wherein the orthogonal chimeric cytokine receptor comprises an extracellular domain of an orthogonal IL2 receptor (oIL2R) and an intracellular signaling domain of a cytokine receptor that is not IL2R.

Embodiment 2 provides the system of embodiment 1, wherein the extracellular domain of an oIL2R is an extracellular domain of an orthogonal IL2 receptor beta (oIL2Rb).

Embodiment 3 provides the system of embodiment 1 or 2, wherein the intracellular signaling domain of the orthogonal chimeric cytokine receptor comprises an IL9R intracellular signaling domain.

Embodiment 4 provides the system of any one of embodiments 1-3, wherein the IL9R intracellular signaling domain is an IL9R-alpha (IL9Ra) intracellular signaling domain.

Embodiment 5 provides the system of any one of the preceding embodiments, wherein the CAR comprises an antigen binding domain, a transmembrane domain, and an intracellular domain.

Embodiment 6 provides the system of any one of the preceding embodiments, wherein the antigen binding domain is selected from the group consisting of a full length antibody or antigen-binding fragment thereof, a Fab, a single-chain variable fragment (scFv), or a single-domain antibody.

Embodiment 7 provides the system of any one of the preceding embodiments, wherein the antigen binding domain targets a tumor antigen.

Embodiment 8 provides the system of any one of the preceding embodiments, wherein the tumor antigen is selected from the group consisting of CD19, CD20, HER2, NY-ESO-1, MUC1, CD123, FLT3, B7-H3, CD33, IL1RAP, CLL1 (CLEC12A)PSA, CEA, VEGF, VEGF-R2, CD22, ROR1, mesothelin, c-Met, Glycolipid F77, FAP, EGFRvIII, MAGE A3, 5T4, WT1, KG2D ligand, a folate receptor (FRa), and Wnt1 antigens.

Embodiment 9 provides the system of any one of the preceding embodiments, wherein the antigen binding domain is an scFv.

Embodiment 10 provides the system of any one of the preceding embodiments, wherein the antigen binding domain is an anti-mesothelin scFv.

Embodiment 11 provides the system of any one of the preceding embodiments, wherein the intracellular domain of the CAR comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS, NKG2C, and B7-H3 (CD276), or a variant thereof, or an intracellular domain derived from a killer immunoglobulin-like receptor (KIR).

Embodiment 12 provides the system of any one of the preceding embodiments, wherein the intracellular domain of the CAR comprises an intracellular signaling domain of a protein selected from the group consisting of a human CD3 zeta chain (CD3ζ), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof.

Embodiment 13 provides the system of any one of the preceding embodiments, wherein: (a) the orthogonal chimeric cytokine receptor comprises an extracellular domain of an oIL2Rb and an intracellular signaling domain of an IL9Ra, and (b) the CAR comprises an anti-mesothelin antigen binding domain.

Embodiment 14 provides a method of treating cancer in a subject comprising: (a) administering to the subject an effective amount of a modified immune cell or precursor thereof (a population of modified immune cells) comprising (i) an orthogonal chimeric cytokine receptor, and (ii) at least one CAR, and (b) administering to the subject an oncolytic adenoviral vector comprising a nucleic acid sequence encoding an orthogonal IL2 cytokine; wherein the orthogonal chimeric cytokine receptor comprises an extracellular domain of an orthogonal IL2 receptor (oIL2R) and an intracellular signaling domain of a cytokine receptor that is not IL2R.

Embodiment 15 provides the method of embodiment 14, wherein the extracellular domain of an oIL2R is an extracellular domain of an orthogonal IL2 receptor beta (oIL2Rb).

Embodiment 16 provides the method of embodiment 14 or 15, wherein the intracellular signaling domain of the orthogonal chimeric cytokine receptor comprises an IL9R intracellular signaling domain.

Embodiment 17 provides the method of any one of the preceding embodiments, wherein the IL9R intracellular signaling domain is an IL9R-alpha (IL9Ra) intracellular signaling domain.

Embodiment 18 provides the method of any one of the preceding embodiments, wherein the CAR comprises an antigen binding domain, a transmembrane domain, and an intracellular domain.

Embodiment 19 provides the method of any one of the preceding embodiments, wherein the antigen binding domain is selected from the group consisting of a full length antibody or antigen-binding fragment thereof, a Fab, a single-chain variable fragment (scFv), or a single-domain antibody.

Embodiment 20 provides the method of any one of the preceding embodiments, wherein the antigen binding domain targets a tumor antigen.

Embodiment 21 provides the method of any one of the preceding embodiments, wherein the tumor antigen is selected from the group consisting of CD19, CD20, HER2, NY-ESO-1, MUC1, CD123, FLT3, B7-H3, CD33, IL1RAP, CLL1 (CLEC12A)PSA, CEA, VEGF, VEGF-R2, CD22, ROR1, mesothelin, c-Met, Glycolipid F77, FAP, EGFRvIII, MAGE A3, 5T4, WT1, KG2D ligand, a folate receptor (FRa), and Wnt1 antigens.

Embodiment 22 provides the method of any one of the preceding embodiments, wherein the antigen binding domain is an scFv.

Embodiment 23 provides the method of any one of the preceding embodiments, wherein the antigen binding domain is an anti-mesothelin scFv.

Embodiment 24 provides the method of any one of the preceding embodiments, wherein the intracellular domain of the CAR comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS, NKG2C, and B7-H3 (CD276), or a variant thereof, or an intracellular domain derived from a killer immunoglobu-lin-like receptor (KIR).

Embodiment 25 provides the method of any one of the preceding embodiments, wherein the intracellular domain of the CAR comprises an intracellular signaling domain of a protein selected from the group consisting of a human CD3 zeta chain (CD3ζ), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof.

Embodiment 26 provides the method of any one of the preceding embodiments, wherein: (a) the orthogonal chime-ric cytokine receptor comprises an extracellular domain of an oIL2Rb and an intracellular signaling domain of an IL9Ra, and (b) the CAR comprises an anti-mesothelin antigen binding domain.

Embodiment 27 provides the method of any one of the preceding embodiments, wherein the population of modified immune cells assume stem cell memory (Tscm) features with improved trafficking and effector function, thereby treating the cancer.

Embodiment 28 provides the method of any one of the preceding embodiments, wherein administering the vector comprises intratumoral injection.

Embodiment 29 provides the method of any one of the preceding embodiments, wherein the cancer is selected from the group consisting of pancreatic cancer and melanoma.

Embodiment 30 provides the method of embodiment 29, wherein the pancreatic cancer is pancreatic ductal adeno-carcinoma.

Embodiment 31 provides a system for selective activation of a receptor in a cell, the system comprising: (a) a modified immune cell engineered to express: (i) an orthogonal chi-meric cytokine receptor, and (ii) at least one T cell receptor (TCR), and (b) an oncolytic adenoviral vector comprising a nucleic acid sequence encoding an orthogonal IL2 cytokine, wherein the orthogonal chimeric cytokine receptor com-prises an extracellular domain of an orthogonal IL2 receptor (oIL2R) and an intracellular signaling domain of a cytokine receptor that is not IL2R.

Embodiment 32 provides the system embodiment 31, wherein the extracellular domain of an oIL2R is an extra-cellular domain of an orthogonal IL2 receptor beta (oIL2Rb).

Embodiment 33 provides the system embodiment embodiment 31 or 32, wherein the intracellular signaling domain of the orthogonal chimeric cytokine receptor com-prises an IL9R intracellular signaling domain.

Embodiment 34 provides the system of any one of embodiments 31-33, wherein the IL9R intracellular signal-ing domain is an IL9R-alpha (IL9Ra) intracellular signaling domain.

Embodiment 35 provides the system of any one of embodiments 31-34, wherein the TCR targets a tumor antigen.

Embodiment 36 provides the system of any one of embodiments 31-35, wherein the TCR targets a gp100 melanoma antigen or NYESO1.

Embodiment 37 provides the system of any one of embodiments 31-36, wherein the TCR is a pmel-1 TCR or an NYESO1-specific TCR.

Embodiment 38 provides the system of any one of embodiments 31-37, wherein: (a) the orthogonal chimeric cytokine receptor comprises an extracellular domain of an oIL2Rb and an intracellular signaling domain of an IL9Ra, and (b) the TCR is a pmel-1 TCR or an NYESO1-specific TCR.

Embodiment 39 provides a method of treating cancer in a subject comprising: (a) administering to the subject an effective amount of a modified immune cell or precursor thereof (a population of modified immune cells) modified to express (i) an orthogonal chimeric cytokine receptor, and (ii) at least one T cell receptor (TCR), and (b) administering to the subject an oncolytic adenoviral vector comprising a nucleic acid sequence encoding an orthogonal IL2 cytokine; wherein the orthogonal chimeric cytokine receptor com-prises an extracellular domain of an orthogonal IL2 receptor (oIL2R) and an intracellular signaling domain of a cytokine receptor that is not IL2R.

Embodiment 40 provides the method of embodiment 39, wherein the extracellular domain of an oIL2R is an extra-cellular domain of an orthogonal IL2 receptor beta (oIL2Rb).

Embodiment 41 provides the method of embodiment 39 or 40, wherein the intracellular signaling domain of the orthogonal chimeric cytokine receptor comprises an IL9R intracellular signaling domain.

Embodiment 42 provides the method of any one of embodiments 39-41, wherein the IL9R intracellular signal-ing domain is an IL9R-alpha (IL9Ra) intracellular signaling domain.

Embodiment 43 provides the method of any one of embodiments 39-42, wherein the TCR targets a tumor antigen.

Embodiment 44 provides the method of any one of embodiments 39-43, wherein the TCR targets a gp100 melanoma antigen or NYESO1.

Embodiment 45 provides the method of any one of embodiments 39-44, wherein the TCR is a pmel-1 TCR or an NYESO1-specific TCR.

Embodiment 46 provides the method of any one of embodiments 39-45, wherein: (a) the orthogonal chimeric cytokine receptor comprises an extracellular domain of an oIL2Rb and an intracellular signaling domain of an IL9Ra, and (b) the TCR is a pmel-1 TCR or an NYESO1-specific TCR.

Embodiment 47 provides the method of any one of embodiments 39-46, wherein the population of modified immune cells assume stem cell memory (Tscm) features with improved trafficking and effector function, thereby treating the cancer.

Embodiment 48 provides the method of any one of embodiments 39-47, wherein administering the vector comprises intratumoral injection.

Embodiment 49 provides the method of any one of embodiments 39-48, wherein the cancer is selected from the group consisting of pancreatic cancer and melanoma.

Embodiment 50 provides the method of embodiment 49, wherein the pancreatic cancer is pancreatic ductal adenocarcinoma.

OTHER EMBODIMENTS

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

---

What is claimed:

1. A system for selective activation of a receptor in a cell, the system comprising:
   (a) a modified immune cell comprising
      (i) an orthogonal chimeric cytokine receptor, and
      (ii) at least one chimeric antigen receptor (CAR), and
   (b) an oncolytic adenoviral vector comprising a nucleic acid sequence encoding an orthogonal IL2 cytokine,
      wherein the orthogonal chimeric cytokine receptor comprises an extracellular domain of an orthogonal IL2 receptor (oIL2R) and an intracellular signaling domain of a cytokine receptor that is not IL2R;
      further wherein the CAR comprises an antigen binding domain, a transmembrane domain, and an intracellular domain, optionally wherein the antigen binding domain targets a tumor antigen.

2. The system of claim 1, wherein:
   (a) the extracellular domain of an oIL2R is an extracellular domain of an orthogonal IL2 receptor beta (oIL2Rb); and/or
   (b) the intracellular signaling domain of the orthogonal chimeric cytokine receptor comprises an IL9R intracellular signaling domain, optionally wherein the IL9R intracellular signaling domain is an IL9R-alpha (IL9Ra) intracellular signaling domain.

3. The system of claim 1, wherein:
   (a) the orthogonal chimeric cytokine receptor comprises an extracellular domain of an oIL2Rb and an intracellular signaling domain of an IL9Ra, and
   (b) the CAR comprises an anti-mesothelin antigen binding domain.

4. A method of treating cancer in a subject in need thereof, the method comprising:
   (a) administering to the subject an effective amount of a modified immune cell or precursor thereof (a population of modified immune cells) comprising:
      (i) an orthogonal chimeric cytokine receptor, and
      (ii) at least one chimeric antigen receptor (CAR), and
   (b) administering to the subject an oncolytic adenoviral vector comprising a nucleic acid sequence encoding an orthogonal IL2 cytokine;
      wherein the orthogonal chimeric cytokine receptor comprises an extracellular domain of an orthogonal IL2 receptor (oIL2R) and an intracellular signaling domain of a cytokine receptor that is not IL2R;
      further wherein the CAR comprises an antigen binding domain, a transmembrane domain, and an intracellular domain, optionally wherein the antigen binding domain targets a tumor antigen.

5. The method of claim 4, wherein:
   (a) the extracellular domain of an oIL2R is an extracellular domain of an orthogonal IL2 receptor beta (oIL2Rb); and/or
   (b) the intracellular signaling domain of the orthogonal chimeric cytokine receptor comprises an IL9R intracellular signaling domain, optionally wherein the IL9R intracellular signaling domain is an IL9R-alpha (IL9Ra) intracellular signaling domain.

6. The method of claim 4, wherein:
   (a) the orthogonal chimeric cytokine receptor comprises an extracellular domain of an oIL2Rb and an intracellular signaling domain of an IL9Ra, and
   (b) the CAR comprises an anti-mesothelin antigen binding domain.

7. The method of claim 4, wherein the population of modified immune cells assume stem cell memory (Tscm) features with improved trafficking and effector function, thereby treating the cancer.

8. The method of claim 4, wherein administering the vector comprises intratumoral injection.

9. The method of claim 4, wherein the cancer is selected from the group consisting of pancreatic cancer and melanoma.

10. The method of claim 9, wherein the pancreatic cancer is pancreatic ductal adenocarcinoma.

11. A system for selective activation of a receptor in a cell, the system comprising:

(a) a modified immune cell engineered to express:

(i) an orthogonal chimeric cytokine receptor, and (ii) at least one T cell receptor (TCR), and (b) an oncolytic adenoviral vector comprising a nucleic acid sequence encoding an orthogonal IL2 cytokine, wherein the orthogonal chimeric cytokine receptor comprises an extracellular domain of an orthogonal IL2 receptor (oIL2R) and an intracellular signaling domain of a cytokine receptor that is not IL2R;

optionally wherein the TCR targets a tumor antigen.

12. The system of claim 11, wherein:

(a) the extracellular domain of an oIL2R is an extracellular domain of an orthogonal IL2 receptor beta (oIL2Rb); and/or (b) the intracellular signaling domain of the orthogonal chimeric cytokine receptor comprises an IL9R intracellular signaling domain, optionally wherein the IL9R intracellular signaling domain is an IL9R-alpha (IL9Ra) intracellular signaling domain.

13. The system of claim 11, wherein:

(a) the orthogonal chimeric cytokine receptor comprises an extracellular domain of an oIL2Rb and an intracellular signaling domain of an IL9Ra, and (b) the TCR is a pmel-1 TCR or an NYESO1-specific TCR.

14. A method of treating cancer in a subject in need thereof, the method comprising:

(a) administering to the subject an effective amount of a modified immune cell or precursor thereof (a population of modified immune cells) modified to express:

(i) an orthogonal chimeric cytokine receptor, and (ii) at least one T cell receptor (TCR), and (b) administering to the subject an oncolytic adenoviral vector comprising a nucleic acid sequence encoding an orthogonal IL2 cytokine;

wherein the orthogonal chimeric cytokine receptor comprises an extracellular domain of an orthogonal IL2 receptor (oIL2R) and an intracellular signaling domain of a cytokine receptor that is not IL2R;

optionally wherein the TCR targets a tumor antigen.

15. The method of claim 14, wherein:

(a) the extracellular domain of an oIL2R is an extracellular domain of an orthogonal IL2 receptor beta (oIL2Rb); and/or (b) the intracellular signaling domain of the orthogonal chimeric cytokine receptor comprises an IL9R intracellular signaling domain, optionally wherein the IL9R intracellular signaling domain is an IL9R-alpha (IL9Ra) intracellular signaling domain.

16. The method of claim 14, wherein:

(a) the orthogonal chimeric cytokine receptor comprises an extracellular domain of an oIL2Rb and an intracellular signaling domain of an IL9Ra, and (b) the TCR is a pmel-1 TCR or an NYESO1-specific TCR.

17. The method of claim 14, wherein the population of modified immune cells assume stem cell memory (Tscm) features with improved trafficking and effector function, thereby treating the cancer.

18. The method of claim 14, wherein administering the vector comprises intratumoral injection.

19. The method of claim 14, wherein the cancer is selected from the group consisting of pancreatic cancer and melanoma.

20. The method of claim 19, wherein the pancreatic cancer is pancreatic ductal adenocarcinoma.

* * * * *